(12) United States Patent
Felber et al.

(10) Patent No.: US 8,715,964 B2
(45) Date of Patent: May 6, 2014

(54) EXPRESSION OF IL-12 FAMILY HETERODIMERS

(75) Inventors: Barbara K. Felber, Rockville, MD (US); George N. Pavlakis, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 407 days.

(21) Appl. No.: 12/992,077

(22) PCT Filed: May 11, 2009

(86) PCT No.: PCT/US2009/043481
§ 371 (c)(1),
(2), (4) Date: Feb. 9, 2011

(87) PCT Pub. No.: WO2009/140206
PCT Pub. Date: Nov. 19, 2009

(65) Prior Publication Data
US 2011/0166210 A1   Jul. 7, 2011

Related U.S. Application Data

(60) Provisional application No. 61/052,239, filed on May 11, 2008, provisional application No. 61/052,916, filed on May 13, 2008.

(51) Int. Cl.
*C12P 21/04* (2006.01)

(52) U.S. Cl.
USPC .......................................................... 435/70.3

(58) Field of Classification Search
None
See application file for complete search history.

(56) References Cited

U.S. PATENT DOCUMENTS

| | | | |
|---|---|---|---|
| 5,830,451 | A | 11/1998 | Devergne et al. |
| 5,965,726 | A | 10/1999 | Pavlakis et al. |
| 5,972,596 | A | 10/1999 | Pavlakis et al. |
| 6,174,666 | B1 | 1/2001 | Pavlakis et al. |
| 6,291,664 | B1 | 9/2001 | Pavlakis et al. |
| 6,414,132 | B1 | 7/2002 | Pavlakis et al. |
| 6,794,498 | B2 | 9/2004 | Pavlakis et al. |
| 2006/0160147 | A1 | 7/2006 | Vandenbroeck et al. |
| 2011/0166210 | A1* | 7/2011 | Felber et al. ................ 514/44 R |

FOREIGN PATENT DOCUMENTS

| | | |
|---|---|---|
| WO | WO 98/17814 A | 4/1998 |
| WO | WO 99/47679 A | 9/1999 |
| WO | WO 99/60135 A | 11/1999 |
| WO | WO 2007/084342 A | 7/2007 |
| WO | WO 2007/084364 A | 7/2007 |

OTHER PUBLICATIONS

Gascón, S., et al., "Dual-promoter lentiviral for constitutive and regulated gene expression in neurons," *J. Neurosci Methods*, vol. 168(1), pp. 104-112 (Feb. 15, 2008, Epub Sep. 29, 2007)
Jordan, M., et al., "Transient Expression of a Soluble and Secreted Form of Heterodimeric T-Cell Receptor in HEK-293," *New Developments and New Applications in Animal Cell Technology*, pp. 121-123 (1998).
Lee, Y-L., et al., "Construction of Vectors Expressing Bioactive Heterodimeric and Single-Chain Murine Interleukin-12 for Gene Therapy," *Human Gene Therapy*, vol. 9(4), pp. 457-465 (Mar. 1, 1998).
Li, J., et la., "A comparative study of different vector designs for the mammalian expression of recombinant IgG antibodies," *Journal of Immunological Methods*, vol. 318, pp. 113-124 (2007).
Li, J., et al., "Analysis of IgG heavy chain to light chain ration with mutant Encephalomyocarditis virus internal ribosome entry site," *Protein Engineering, Design & Selection*, vol. 20(10), pp. 491-496 (2007).
Liu, W., et al., "A balanced expression of two chains of heterodimer protein, the human interleukin-12, improves high-level expression of the protein in CHO cells," , *Biochemical and Biophysical Research and Communications*, vol. 313(2), pp. 287-293 (Jan. 9, 2004).
Meier, T., et al., "Cloning, expression, purification, and characterization of the human Class la phosphoinositide 3-kinase isoforms," *Protein Expression and Purification*, vol. 35, pp. 218-224 (2004).
Schlatter, S., et al., "On the Optimal Ratio of Heavy to Light Chain Genes for Efficient Recombinant Antibody Production by CHO Cells," *Biotechnol. Prog.*, vol. 21, pp. 122-133 (2005).
Urano, J., et al., "Reconstitution of Yeast Farnesyltransferase from Individually Purified Subunits," *Methods in Molecular Biology: Protein Lipidation Protocols*, vol. 116, pp. 145-159 (1997).

* cited by examiner

*Primary Examiner* — Michael Burkhart
(74) *Attorney, Agent, or Firm* — Kilpatrick Townsend & Stockton LLP

(57) ABSTRACT

The present invention provides methods of improving the levels and stability of expression of interleukin-12 family cytokine polypeptides by expressing the alpha and beta subunits of the polypeptides at their determined relative molar ratios that increase the levels and stability of expression of the heterodimer, e.g., in comparison to heterodimer expressed at an equimolar ratio.

9 Claims, 21 Drawing Sheets

FIG. 2

FIG. 6

FIG. 10

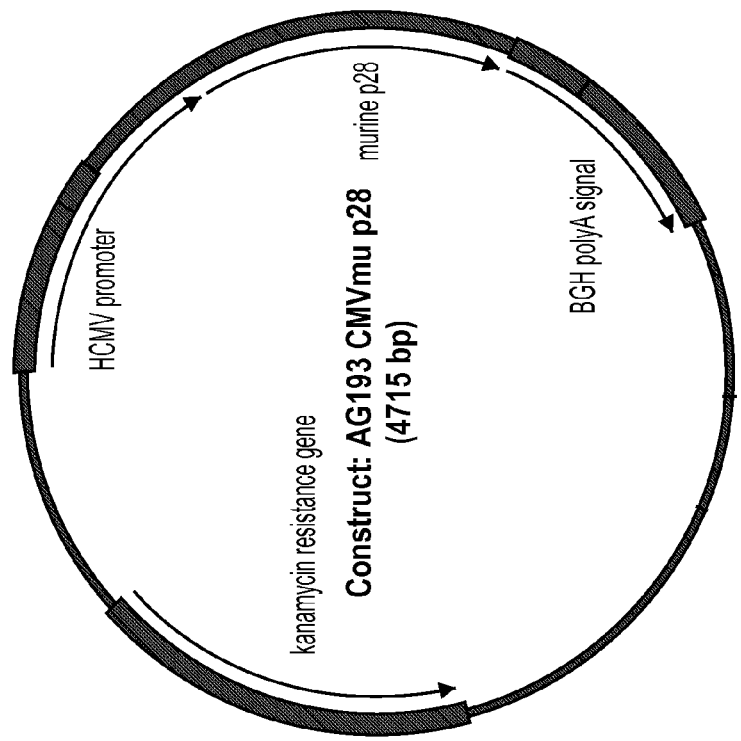
FIG. 14

FIG. 16

FIG. 18

FIG. 19

SEQUENCE LISTING

<160> NUMBER OF SEQ ID NOS: 34

<210> SEQ ID NO 1
<211> LENGTH: 6293
<212> TYPE: DNA
<213> ORGANISM: Artificial Sequence
<220> FEATURE:
<223> OTHER INFORMATION: synthetic dual-promoter expression vector
      plasmid AG181 for human IL-12 heterodimer expression with
      human cytomegalovirus (CMV) promoter

<400> SEQUENCE: 1
cctggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240

```
tagtaacgcc aatagggact ttccattgac gtcaatgggt ggagtattta cggtaaactg      300
cccacttggc agtacatcaa gtgtatcata tgccaagtac gccccctatt gacgtcaatg      360
atggtaaatg gcccgcctgg cattatgccc agtacatgac cttatgggac tttcctactt      420
ggcagtacat ctacgtatta gtcatcgcta ttaccatggt gatgcggttt tggcagtaca      480
tcaatgggcg tggatagcgg tttgactcac ggggatttcc aagtctccac cccattgacg      540
tcaatgggag tttgttttgg caccaaaatc aacgggactt tccaaaatgt cgtaacaact      600
ccgccccatt gacgcaaatg ggcggtaggc gtgtacggtg ggaggtctat ataagcagag      660
ctcgtttagt gaaccgtcag atcgcctgga cgccatcc acgctgtttt gacctccata       720
gaagacaccg ggaccgatcc agcctccgcg gccgcgcgtc gaggaatttc gagaagaaat      780
gtgccaccag cagctggtca tcagctggtt cagcctcgtt ttcctcgcct cgccgctggt      840
cgccatatgg gagctcaaga aggacgtata cgtggtggag ctggactggt accccgacgc      900
gccgggcgag atggtcgtcc tgacgtgcga cacgccggag gaggacggca tcacgtggac      960
gctggaccag tccagcgagg tcctcggctc cggcaagacg ctgacgatcc aggtcaagga     1020
gttcggcgac gcgggccagt acacgtgcca aagggcggc gaggtcctga gccactccct      1080
cctcctgcta cacaagaagg aggacgggat ctggagcacg acatcctca aggaccagaa      1140 ggagccgaag aacaagacct tcctgcgctg cgaggcgaag aattactcgg ccggttcac      1200 gtgctggtgg ctcaccacga tcagcacgga cctgacgttc tcggtcaagt cgtcgcgggg     1260
ctcgtcggac ccccaggggg tgacctgcgc gcggcgacg ctgtcggcgg agcgggtgcg      1320
gggcgacaac aaggagtacg agtactcggt cgagtgccag gaggactcgg cgtgcccggc     1380
ggcggaggag tcgctgccga tcgaggtgat ggtcgacgcg gtccacaagc tgaagtacga     1440
gaactacacg tcgtcgttct tcatccggga catcatcaag ccggaccgc cgaagaacct      1500 gcagctgaag ccgctgaaga actcgcggca ggtcgaggtc tcgtgggagt acccggacac     1560
gtggtcgacg ccgcactcgt acttctcgct gacgttctgc gtccaagtgc agggcaagtc     1620
gaagcgggag aagaaggacc gggtgttcac cgacaagacg agcgcgacgg tgatctgccg     1680
gaagaacgcg tcgatctcgg tgcgggcgca ggaccggtac tactcgtcgt cgtggtcgga     1740
gtgggcgtcg gtgccgtgca gctagaccta ggggcgcgcc agatctgata tcggatctgc     1800
tgtgccttct agttgccagc catctgttgt ttgcccctcc ccgtgccttc cttgaccct      1860 ggaaggtgcc actcccactg tcctttccta ataaaatgag gaaattgcat cgcattgtct     1920
gagtaggtgt cattctattc tggggggtgg ggtggggcag acagcaagg gggaggattg      1980 ggaagacaat agcaggcatg ctggggatgc ggtgggctct atgggtaccc aggtgctgaa     2040
gaattgaccc ggttcctcct gggccagaaa gaagcaggca catccccttc tctgtgacac     2100
accctgtcca cgcccctggt tcttagttcc agccccactc ataggacact catagctcag     2160
gagggctccg ccttcaatcc cacccgctaa agtacttgga cggtctctc cctccctcat      2220 cagcccacca aaccaaacct agcctccaag agtgggaaga attaaagca agataggcta      2280 ttaagtgcag agggagagaa aatgcctcca acatgtgagg aagtaatgag agaaatcata     2340
gaatttcttc cgcttcctcg ctcactgact cgctgcgctc ggtcgttcgg ctgcggcgag     2400
cggtatcagc tcactcaaag gcggtaatac ggttatccac agaatcaggg gataacgcag     2460
gaaagaacat gtgagcaaaa ggccagcaaa aggccaggaa ccgtaaaaag gccgcgttgc     2520
tggcgttttt ccataggctc cgcccccctg acgagcatca aaaaatcga cgctcaagtc     2580 agaggtggcg aaacccgaca ggactataaa gataccaggc gtttccccct ggaagctccc     2640
```

```
tcgtgcgctc tcctgttccg accctgccgc ttaccggata cctgtccgcc tttctcccct    2700
cgggaagcgt ggcgctttct catagctcac gctgtaggta tctcagttcg gtgtaggtcg    2760
ttcgctccaa gctgggctgt gtgcacgaac cccccgttca gcccgaccgc tgcgccttat    2820
ccggtaacta tcgtcttgag tccaacccgg taagacacga cttatcgcca ctggcagcag    2880
ccactggtaa caggattagc agagcgaggt atgtaggcgg tgctacagag ttcttgaagt    2940
ggtggcctaa ctacggctac actagaagaa cagtatttgg tatctgcgct ctgctgaagc    3000
cagttacctt cggaaaaaga gttggtagct cttgatccgg caaacaaacc accgctggta    3060
gcggtggttt ttttgtttgc aagcagcaga ttacgcgcag aaaaaaagga tctcaagaag    3120
atcctttgat cttttctacg gggtctgacg ctcagtggaa cgaaaactca cgttaaggga    3180
ttttggtcat gagattatca aaaggatct cacctagat ccttttaaat taaaaatgaa    3240
gttttaaatc aatctaaagt atatatgagt aaacttggtc tgacagttac caatgcttaa    3300
tcagtgaggc acctatctca gcgatctgtc tatttcgttc atccatagtt gcctgactcg    3360
gggggggggg gcgctgaggt ctgcctcgtg aagaaggtgt tgctgactca taccaggcct    3420
gaatcgcccc atcatccagc cagaaagtga gggagccacg gttgatgaga gctttgttgt    3480
aggtggacca gttggtgatt ttgaactttt gctttgccac ggaacggtct gcgttgtcgg    3540
gaagatgcgt gatctgatcc ttcaactcag caaaagttcg atttattcaa caaagccgcc    3600
gtcccgtcaa gtcagcgtaa tgctctgcca gtgttacaac caattaacca attctgatta    3660
gaaaaactca tcgagcatca aatgaaactg caatttattc atatcaggat tatcaatacc    3720
atattttga aaaagccgtt tctgtaatga aggagaaaac tcaccgaggc agttccatag    3780
gatggcaaga tcctggtatc ggtctgcgat tccgactcgt ccaacatcaa tacaacctat    3840
taatttcccc tcgtcaaaaa taaggttatc aagtgagaaa tcaccatgag tgacgactga    3900
atccggtgag aatggcaaaa gcttatgcat ttctttccag acttgttcaa caggccagcc    3960
attacgctcg tcatcaaaat cactcgcatc aaccaaaccg ttattcattc gtgattgcgc    4020
ctgagcgaga cgaaatacgc gatcgctgtt aaaaggacaa ttacaaacag gaatcgaatg    4080
caaccggcgc aggaacactg ccagcgcatc aacaatattt tcacctgaat caggatattc    4140
ttctaatacc tggaatgctg ttttcccggg gatcgcagtg gtgagtaacc atgcatcatc    4200
aggagtacgg ataaaatgct tgatggtcgg aagaggcata aattccgtca gccagtttag    4260
tctgaccatc tcatctgtaa catcattggc aacgctacct ttgccatgtt cagaaacaa    4320
ctctggcgca tcgggcttcc catacaatcg atagattgtc gcacctgatt gcccgacatt    4380
atcgcgagcc catttatacc catataaatc agcatccatg ttggaattta atcgcggcct    4440
cgagcaagac gtttcccgtt gaatatggct cataacaccc cttgtattac tgtttatgta    4500
agcagacagt tttattgttc atgatgatat ttttatct tgtgcaatgt aacatcagag    4560
attttgagac acaacgtgga tcatccagac atgataagat acattgatga gtttggacaa    4620
accacaacta gaatgcagtg aaaaaaatgc tttatttgtg aaatttgtga tgctattgct    4680
ttatttgtaa ccattataag ctgcaataaa caagttaaca acaacaattg cattcattt    4740
atgtttcagg ttcaggggga ggtgtgggag gttttttaaa gcaagtaaaa cctctacaaa    4800
tgtggtatgg ctgattatga tcgtcgagga tccggcgccg gtttcgcgtc gatatcttac    4860
gaagcgttca ggtacgacat caccccggtcg atcgtcaccg cccggatccg gaaagcgtgc    4920
agcaggatgc agagcttgat cttcgtcttg tagaagtccg gctcctcgag cgacgacttc    4980
tgcggcaccg tctcgctgtt gaagttgagc gcctgcatga gctcgtcgat caccgccagc    5040
```

-continued

```
atgttctggt cgaggaagat ctgccgcttc gggtccatca gcagcttcgc gttcatcgtc   5100
ttgaactcca cctggtacat cttcaggtcc tcgtagatcg acgacaggca cagcgccatc   5160
atgaacgacg tcttccgcga cgccaggcac gacccgttcg tgatgaacga cgtctccctc   5220
gagttcaggc acgactcgtt cttcgtcagc tccagcggca ggcacgcctc caccgtgctg   5280
gtcttgtcct tcgtgatgtc ctcgtggtcg atctcctcgc tcgtgcacgg gtagaactcc   5340
agcgtctgcc gcgccttctg cagcatgttc gacaccgccc gcagcaggtt ctggctgtgg   5400
tgcaggcacg ggaacatccc cgggtccggc gtcgccaccg gcaggttccg cgccaggctc   5460
aggtggtcga gcaggaccag cgtcgccacg agcagcaggg agcgcgccgg gcacatttct   5520
ttctagaaac gtcgacagat ccaaacgctc ctccgacgtc cccaggcaga atggcggttc   5580
cctaaacgag cattgcttat atagacctcc cattaggcac gcctaccgcc catttacgtc   5640
aatggaacgc ccatttgcgt cattgcccct ccccattgac gtcaatgggg atgtacttgg   5700
cagccatcgc gggccattta ccgccattga cgtcaatggg agtactgcca atgtaccctg   5760
gcgtacttcc aatagtaatg tacttgccaa gttactatta atagatattg atgtactgcc   5820
aagtgggcca tttaccgtca ttgacgtcaa taggggggcgt gagaacggat atgaatgggc   5880
aatgagccat cccattgacg tcaatggtgg gtggtcctat tgacgtcaat gggcattgag   5940
ccaggcgggc catttaccgt aattgacgtc aatgggggag cgccatata cgtcaatagg   6000 accgcccata tgacgtcaat aggtaagacc atgaggccct tcgtctcgc gcgtttcggt   6060 gatgacggtg aaaacctctg acacatgcag ctcccggaga cggtcacagc ttgtctgtaa   6120
gcggatgccg ggagcagaca gcccgtcag ggcgcgtcag cgggtgttgg cgggtgtcgg   6180
ggctggctta actatgcggc atcagagcag attgtactga gagtgcacca tatgcggtgt   6240
gaaataccgc acagatgcgt aaggagaaaa taccgcatca gattggctat tgg          6293
```

<210> SEQ ID NO 2
<211> LENGTH: 6293
<212> TYPE: DNA
<213> ORGANISM: Artificial Sequence
<220> FEATURE:
<223> OTHER INFORMATION: synthetic dual-promoter expression vector
    plasmid AG183 for human IL-12 heterodimer expression with
    simian cytomegalovirus (CMV) promoter

<400> SEQUENCE: 2

```
cctggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccgtcag atcgcctgga gacgccatcc acgctgtttt gacctccata    720
gaagacaccg ggaccgatcc agcctccgcg ggcgcgcgtc gaggaattcg ctagaaagaa    780
```

```
atgtgcccgg cgcgctccct gctgctcgtg gcgacgctgg tcctgctcga ccacctgagc    840
ctggcgcgga acctgccggt ggcgacgccg gacccgggga tgttcccgtg cctgcaccac    900
agccagaacc tgctgcgggc ggtgtcgaac atgctgcaga aggcgcggca gacgctggag    960
ttctacccgt gcacgagcga ggagatcgac cacgaggaca tcacgaagga caagaccagc   1020
acggtggagg cgtgcctgcc gctggagctg acgaagaacg agtcgtgcct gaactcgagg   1080
gagacgtcgt tcatcacgaa cgggtcgtgc ctggcgtcgc ggaagacgtc gttcatgatg   1140
gcgctgtgcc tgtcgtcgat ctacgaggac ctgaagatgt accaggtgga gttcaagacg   1200
atgaacgcga agctgctgat ggacccgaag cggcagatct tcctcgacca gaacatgctg   1260
gcggtgatcg acgagctcat gcaggcgctc aacttcaaca gcgagacggt gccgcagaag   1320
tcgtcgctcg aggagccgga cttctacaag acgaagatca agctctgcat cctgctgcac   1380
gctttccgga tccgggcggt gacgatcgac cgggtgatgt cgtacctgaa cgcttcgtaa   1440
gatatcgacg cgccagatct gatatcggat ctgctgtgcc ttctagttgc cagccatctg   1500
ttgtttgccc ctccccgtg ccttccttga ccctggaagg tgccactccc actgtccttt   1560
cctaataaaa tgaggaaatt gcatcgcatt gtctgagtag gtgtcattct attctggggg   1620
gtggggtggg gcaggacagc aagggggagg attgggaaga caatagcagg catgctgggg   1680
atgcggtggg ctctatgggt acccaggtgc tgaagaattg accggttcc tcctgggcca   1740 gaaagaagca ggcacatccc cttctctgtg acacaccctg tccacgcccc tggttcttag   1800
ttccagcccc actcatagga cactcatagc tcaggagggc tccgccttca atcccacccg   1860
ctaaagtact tggagcggtc tctccctccc tcatcagccc accaaaccaa acctagcctc   1920
caagagtggg aagaaattaa agcaagatag gctattaagt gcagagggag agaaaatgcc   1980
tccaacatgt gaggaagtaa tgagagaaat catagaattt cttccgcttc ctcgctcact   2040
gactcgctgc gctcggtcgt tcggctgcgg cgagcggtat cagctcactc aaaggcggta   2100
atacggttat ccacagaatc aggggataac gcaggaaaga acatgtgagc aaaaggccag   2160
caaaaggcca ggaaccgtaa aaaggccgcg ttgctggcgt ttttccatag gctccgcccc   2220
cctgacgagc atcacaaaaa tcgacgctca agtcagaggt ggcgaaaccc gacaggacta   2280
taaagatacc aggcgtttcc ccctggaagc tccctcgtgc gctctcctgt tccgaccctg   2340
ccgcttaccg gatacctgtc cgcctttctc ccttcgggaa gcgtggcgct ttctcatagc   2400
tcacgctgta ggtatctcag ttcggtgtag gtcgttcgct ccaagctggg ctgtgtgcac   2460
gaaccccccg ttcagcccga ccgctgcgcc ttatccggta actatcgtct tgagtccaac   2520
ccggtaagac acgacttatc gccactggca gcagccactg gtaacaggat tagcagagcg   2580
aggtatgtag gcggtgctac agagttcttg aagtggtggc ctaactacgg ctacactaga   2640
agaacagtat ttggtatctg cgctctgctg aagccagtta ccttcggaaa aagagttggt   2700
agctcttgat ccggcaaaca aaccaccgct ggtagcggtg gtttttttgt ttgcaagcag   2760
cagattacgc gcagaaaaaa aggatctcaa gaagatcctt tgatcttttc tacggggtct   2820
gacgctcagt ggaacgaaaa ctcacgttaa gggattttgg tcatgagatt atcaaaaagg   2880
atcttcacct agatcctttt aaattaaaaa tgaagtttta aatcaatcta agtatatat   2940 gagtaaactt ggtctgacag ttaccaatgc ttaatcagtg aggcacctat ctcagcgatc   3000
tgtctatttc gttcatccat agttgcctga ctcgggggg ggggcgctg aggtctgcct   3060 cgtgaagaag gtgttgctga ctcataccag gcctgaatcg ccccatcatc cagccagaaa   3120
gtgagggagc cacggttgat gagagctttg ttgtaggtgg accagttggt gattttgaac   3180
```

```
ttttgctttg ccacggaacg gtctgcgttg tcgggaagat gcgtgatctg atccttcaac    3240
tcagcaaaag ttcgatttat tcaacaaagc cgccgtcccg tcaagtcagc gtaatgctct    3300
gccagtgtta caaccaatta accaattctg attagaaaaa ctcatcgagc atcaaatgaa    3360
actgcaattt attcatatca ggattatcaa taccatattt ttgaaaaagc cgtttctgta    3420
atgaaggaga aaactcaccg aggcagttcc ataggatggc aagatcctgg tatcggtctg    3480
cgattccgac tcgtccaaca tcaatacaac ctattaattt cccctcgtca aaaataaggt    3540
tatcaagtga gaaatcacca tgagtgacga ctgaatccgg tgagaatggc aaaagcttat    3600
gcatttcttt ccagacttgt tcaacaggcc agccattacg ctcgtcatca aaatcactcg    3660
catcaaccaa accgttattc attcgtgatt gcgcctgagc gagacgaaat acgcgatcgc    3720
tgttaaaagg acaattacaa acaggaatcg aatgcaaccg cgcaggaac actgccagcg    3780
catcaacaat attttcacct gaatcaggat attcttctaa tacctggaat gctgttttcc    3840
cggggatcgc agtggtgagt aaccatgcat catcaggagt acggataaaa tgcttgatgg    3900
tcggaagagg cataaattcc gtcagccagt ttagtctgac catctcatct gtaacatcat    3960
tggcaacgct acctttgcca tgtttcagaa acaactctgg cgcatcgggc ttcccataca    4020
atcgatagat tgtcgcacct gattgcccga cattatcgcg agcccattta tacccatata    4080
aatcagcatc catgttggaa tttaatcgcg gcctcgagca agacgtttcc cgttgaatat    4140
ggctcataac accccttgta ttactgttta tgtaagcaga cagttttatt gttcatgatg    4200
atatatttt atcttgtgca atgtaacatc agagattttg agacacaacg tggatcatcc    4260
agacatgata agatacattg atgagtttgg acaaaccaca actagaatgc agtgaaaaaa    4320
atgctttatt tgtgaaattt gtgatgctat tgctttattt gtaaccatta taagctgcaa    4380
taaacaagtt aacaacaaca attgcattca ttttatgttt caggttcagg gggaggtgtg    4440
ggaggttttt taaagcaagt aaaacctcta caaatgtggt atggctgatt atgatcgtcg    4500
aggatccggc gccggtttga tccggcgcgc cctaggtct agctgcacgg caccgacgcc    4560
cactccgacc acgacgacga gtagtaccgg tcctgcgccc gcaccgagat cgacgcgttc    4620
ttccggcaga tcaccgtcgc gctcgtcttg tcggtgaaca cccggtcctt cttctcccgc    4680
ttcgacttgc cctgcacttg gacgcagaac gtcagcgaga agtacgagtg cggcgtcgac    4740
cacgtgtccg ggtactccca cgagacctcg acctgccgcg agttcttcag cggcttcagc    4800
tgcaggttct tcggcgggtc cggcttgatg atgtcccgga tgaagaacga cgacgtgtag    4860
ttctcgtact tcagcttgtg gaccgcgtcg accatcacct cgatcggcag cgactcctcc    4920
gccgccgggc acgccgagtc ctcctggcac tcgaccgagt actcgtactc cttgttgtcg    4980
cccgcaccc gctccgccga cagcgtcgcc gcgccgcagg tcacccctg ggggtccgac    5040
gagccccgcg acgacttgac cgagaacgtc aggtccgtgc tgatcgtggt gagccaccag    5100
cacgtgaacc ggcccgagta attcttcgcc tcgcagcgca ggaaggtctt gttcttcggc    5160
tccttctggt ccttgaggat gtccgtgctc cagatcccgt cctccttctt gtgtagcagg    5220
aggagggagt ggctcaggac ctcgccgccc ttgtggcacg tgtactggcc cgcgtcgccg    5280
aactccttga cctggatcgt cagcgtcttg ccggagccga ggacctcgct ggactggtcc    5340
agcgtccacg tgatgccgtc ctcctccggc gtgtcgcacg tcaggacgac catctcgccc    5400
ggcgcgtcgg ggtaccagtc cagctccacc acgtatacgt ccttcttgag ctcccatatg    5460
gcgaccagcg gcgaggcgag gaaaacgagg ctgaaccagc tgatgaccag ctgctggtgg    5520
cacatttctt ctcgacagat ccaaacgctc ctccgacgtc cccaggcaga atggcggttc    5580
```

| | |
|---|---:|
| cctaaacgag cattgcttat atagacctcc cattaggcac gcctaccgcc catttacgtc | 5640 |
| aatgaacgc ccatttgcgt cattgcccct ccccattgac gtcaatgggg atgtacttgg | 5700 |
| cagccatcgc gggccattta ccgccattga cgtcaatggg agtactgcca atgtaccctg | 5760 |
| gcgtacttcc aatagtaatg tacttgccaa gttactatta atagatattg atgtactgcc | 5820 |
| aagtgggcca tttaccgtca ttgacgtcaa taggggcgt gagaacggat atgaatgggc | 5880 |
| aatgagccat cccattgacg tcaatggtgg gtggtcctat tgacgtcaat gggcattgag | 5940 |
| ccaggcgggc catttaccgt aattgacgtc aatgggggag gcgccatata cgtcaatagg | 6000 |
| accgcccata tgacgtcaat aggtaagacc atgaggccct tcgtctcgc gcgtttcggt | 6060 |
| gatgacggtg aaaacctctg acacatgcag ctcccggaga cggtcacagc ttgtctgtaa | 6120 |
| gcggatgccg ggagcagaca gcccgtcag ggcgcgtcag cgggtgttgg cgggtgtcgg | 6180 |
| ggctggctta actatgcggc atcagagcag attgtactga gagtgcacca tatgcggtgt | 6240 |
| gaaataccgc acagatgcgt aaggagaaaa taccgcatca gattggctat tgg | 6293 |

```
<210> SEQ ID NO 3
<211> LENGTH: 6281
<212> TYPE: DNA
<213> ORGANISM: Artificial Sequence
<220> FEATURE:
<223> OTHER INFORMATION: synthetic dual-promoter expression vector
      plasmid AG157 for rhesus IL-12 heterodimer expression with
      human cytomegalovirus (CMV) promoter

<400> SEQUENCE: 3
```

| | |
|---|---:|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg gcggtaggc gtgtacggtg gaggtctat ataagcagag | 660 |
| ctcgtttagt gaaccgtcag atcgcctgga cgccatcc acgctgtttt gacctccata | 720 |
| gaagacaccg ggaccgatcc agcctccgcg gcgcgcgtc gaggaattaa acctcgagaa | 780 |
| gaaatgtgcc accagcagct ggtgatcagc tggttcagcc tggtgttcct ggccagcccc | 840 |
| ctgatggcca tctgggagct gaagaaggac gtatacgtgg tggagctgga ctggtatccc | 900 |
| gacgcgcctg gcgagatggt ggtgctgacc tgcgacaccc ccgaggagga cggcatcacc | 960 |
| tggaccctgg accagagcgg cgaagtgctg gcagcggca agaccctgac gatccaggtc | 1020 |
| aaggagttcg gcgacgccgg ccagtacacc tgccacaagg cggcgaggc cctgagccac | 1080 |
| agcctgctgc tgctgcacaa gaaggaggac gggatctgga gcaccgacgt gctgaaggac | 1140 |
| cagaaggagc ccaagaacaa gaccttcctg cgctgcgagg ccaagaatta cagcggccgg | 1200 |
| ttcacctgtt ggtggctgac caccatcagc accgacctga ccttcagcgt gaagagcagc | 1260 |
| agaggcagca gcaaccccca gggcgtgacc tgtggcgccg tgaccctgag cgccgagaga | 1320 |

```
gtgagaggcg acaacaagga gtacgagtac agcgtggagt gccaggagga cagcgcctgc    1380
cctgccgccg aggagagact gcccatcgaa gtgatggtgg acgccatcca caagctgaag    1440
tacgagaact acaccagctc cttcttcatc cgggacatca tcaagcccga ccccccaag     1500 aacctgcagc tgaagcccct gaagaacagc aggcaggtgg aagtgagctg ggagtacccc    1560
gacacctgga gcacccctca cagctacttc agcctgacct tctgcatcca agtgcagggc    1620
aagagcaagc gggagaagaa ggaccggatc ttcaccgata agaccagcgc caccgtgatc    1680
tgccggaaga acgccagctt cagcgtgcag gcccaggaca gatactacag cagcagctgg    1740
agcgagtggg ccagcgtgcc ttgcagctga tgaacctagg ggcgcgccag atctgatatc    1800
ggatctgctg tgccttctag ttgccagcca tctgttgttt gcccctcccc cgtgccttcc    1860
ttgaccctgg aaggtgccac tcccactgtc ctttcctaat aaaatgagga aattgcatcg    1920
cattgtctga gtaggtgtca ttctattctg gggggtgggg tggggcagga cagcaagggg    1980
gaggattggg aagacaatag caggcatgct ggggatgcgg tgggctctat gggtacccag    2040
gtgctgaaga attgacccgg ttcctcctgg gccagaaaga agcaggcaca tcccttctc    2100 tgtgacacac cctgtccacg cccctggttc ttagttccag ccccactcat aggacactca    2160
tagctcagga gggctccgcc ttcaatccca cccgctaaag tacttggagc ggtctctccc    2220
tccctcatca gcccaccaaa ccaaacctag cctccaagag tgggaagaaa ttaaagcaag    2280
ataggctatt aagtgcagag ggagagaaaa tgcctccaac atgtgaggaa gtaatgagag    2340
aaatcataga atttcttccg cttcctcgct cactgactcg ctgcgctcgg tcgttcggct    2400
gcggcgagcg gtatcagctc actcaaaggc ggtaatacgg ttatccacag aatcaggga    2460 taacgcagga aagaacatgt gagcaaaagg ccagcaaaag gccaggaacc gtaaaaaggc    2520
cgcgttgctg gcgtttttcc ataggctccg ccccctgac gagcatcaca aaaatcgacg    2580
ctcaagtcag aggtggcgaa acccgacagg actataaaga taccaggcgt ttccccctgg    2640
aagctccctc gtgcgctctc ctgttccgac cctgccgctt accggatacc tgtccgcctt    2700
tctcccttcg ggaagcgtgg cgctttctca tagctcacgc tgtaggtatc tcagttcggt    2760
gtaggtcgtt cgctccaagc tgggctgtgt gcacgaaccc cccgttcagc ccgaccgctg    2820
cgccttatcc ggtaactatc gtcttgagtc aacccggta agacacgact tatcgccact    2880
ggcagcagcc actggtaaca ggattagcag agcgaggtat gtaggcggtg ctacagagtt    2940
cttgaagtgg tggcctaact acggctacac tagaagaaca gtatttggta tctgcgctct    3000
gctgaagcca gttaccttcg gaaaaagagt ggtagctct tgatccggca acaaaccac     3060 cgctggtagc ggtggttttt ttgtttgcaa gcagcagatt acgcgcagaa aaaaggatc    3120 tcaagaagat cctttgatct tttctacggg gtctgacgct cagtggaacg aaaactcacg    3180
ttaagggatt ttggtcatga gattatcaaa aaggatcttc acctagatcc ttttaaatta    3240
aaaatgaagt tttaaatcaa tctaaagtat atatgagtaa acttggtctg acagttacca    3300
atgcttaatc agtgaggcac ctatctcagc gatctgtcta tttcgttcat ccatagttgc    3360
ctgactcggg gggggggggc gctgaggtct gcctcgtgaa gaaggtgttg ctgactcata    3420
ccaggcctga atcgccccat catccagcca gaaagtgagg gagccacggt tgatgagagc    3480
tttgttgtag gtggaccagt tggtgatttt gaacttttgc tttgccacgg aacggtctgc    3540
gttgtcggga agatgcgtga tctgatcctt caactcagca aaagttcgat ttattcaaca    3600
aagccgccgt cccgtcaagt cagcgtaatg ctctgccagt gttacaacca attaccaat    3660 tctgattaga aaaactcatc gagcatcaaa tgaaactgca atttattcat atcaggatta    3720
```

```
tcaataccat attttttgaaa aagccgtttc tgtaatgaag gagaaaactc accgaggcag    3780
ttccatagga tggcaagatc ctggtatcgg tctgcgattc cgactcgtcc aacatcaata    3840
caacctatta atttcccctc gtcaaaaata aggttatcaa gtgagaaatc accatgagtg    3900
acgactgaat ccggtgagaa tggcaaaagc ttatgcattt ctttccagac ttgttcaaca    3960
ggccagccat tacgctcgtc atcaaaatca ctcgcatcaa ccaaaccgtt attcattcgt    4020
gattgcgcct gagcgagacg aaatacgcga tcgctgttaa aaggacaatt acaaacagga    4080
atcgaatgca accggcgcag gaacactgcc agcgcatcaa caatattttc acctgaatca    4140
ggatattctt ctaatacctg gaatgctgtt ttcccgggga tcgcagtggt gagtaaccat    4200
gcatcatcag gagtacggat aaaatgcttg atggtcggaa gaggcataaa ttccgtcagc    4260
cagtttagtc tgaccatctc atctgtaaca tcattggcaa cgctaccttt gccatgtttc    4320
agaaacaact ctggcgcatc gggcttccca tacaatcgat agattgtcgc acctgattgc    4380
ccgacattat cgcgagccca tttatacccca tataaatcag catccatgtt ggaatttaat    4440
cgcggcctcg agcaagacgt ttcccgttga atatggctca taacaccccct tgtattactg    4500 tttatgtaag cagacagttt tattgttcat gatgatatat ttttatcttg tgcaatgtaa    4560
catcagagat tttgagacac aacgtggatc atccagacat gataagatac attgatgagt    4620
ttggacaaac cacaactaga atgcagtgaa aaaaatgctt tatttgtgaa atttgtgatg    4680
ctattgcttt atttgtaacc attataagct gcaataaaca agttaacaac aacaattgca    4740 ttcatttttat gtttcaggtt caggggggagg tgtgggaggt tttttaaagc aagtaaaacc    4800
tctacaaatg tggtatggct gattatgatc gtcgaggatc atcttatcag ctggcgttca    4860
ggtagctcat cactctgtcg atggtcacgg ccctgatccg gaaggcgtgc agcaggatgc    4920
acagcttgat cttggtcttg tagaagtcgg gctcctccag gctgctcttc tgaggcacgg    4980
tctcgctgtt gaagttcagg gcctgcatca gctcgtcgat cacgcccagg atgttctggt    5040
ccaggaagat ctgcctcttg ggtccctca gcagcttggc gttcatggtc ttgaactcca    5100
cctggtacat cttcaggtcc tcgtagatgc tcctcaggca cagggccatc atgaaggagg    5160
tctttctgct ggccaggcag ctgccgttgg tgatgaagct ggtctccctc gagttcaggc    5220
acgactcgtt cttgatcagc tccagcggca ggcacgcctc caccgtgctg gtcttgtcct    5280
tcgtgatgtc ctcgtggtcg atctcctcgc tcgtgcacgg gtagaactcc aggatctgcc    5340
gcgccttctg cagcgtgttc gacgccgcct tcagcaggtt ctggctgtgg tgcaggcacg    5400
ggaacatctc cggtcccggg gtcgccaccg acaggttccg cgccaggctc aggtagtcga    5460
gcaggaccag cgtcgccacg agcagcaggg agcgcgccgg gcacatttct ttctagacgt    5520
cgacagatcc aaaacgctcct ccgacgtccc caggcagaat ggcggttccc taaacgagca    5580
ttgcttatat agacctccca ttaggcacgc ctaccgccca tttacgtcaa tggaacgccc    5640
atttgcgtca ttgcccctcc ccattgacgt caatggggat gtacttggca gccatcgcgg    5700
gccatttacc gccattgacg tcaatgggag tactgccaat gtaccctggc gtacttccaa    5760
tagtaatgta cttgccaagt tactattaat agatattgat gtactgccaa gtgggccatt    5820
taccgtcatt gacgtcaata ggggggcgtga gaacggatat gaatgggcaa tgagccatcc    5880
cattgacgtc aatggtgggt ggtcctattg acgtcaatgg gcattgagcc aggcgggcca    5940
tttaccgtaa ttgacgtcaa tggggggaggc gccatatacg tcaataggac cgcccatatg    6000
acgtcaatag gtaagaccat gaggcccttt cgtctcgcgc gtttcggtga tgacggtgaa    6060
aacctctgac acatgcagct cccggagacg gtcacagctt gtctgtaagc ggatgccggg    6120
```

-continued

| | |
|---|---|
| agcagacaag cccgtcaggg cgcgtcagcg ggtgttggcg ggtgtcgggg ctggcttaac | 6180 |
| tatgcggcat cagagcagat tgtactgaga gtgcaccata tgcggtgtga aataccgcac | 6240 |
| agatgcgtaa ggagaaaata ccgcatcaga ttggctattg g | 6281 |

<210> SEQ ID NO 4
<211> LENGTH: 6281
<212> TYPE: DNA
<213> ORGANISM: Artificial Sequence
<220> FEATURE:
<223> OTHER INFORMATION: synthetic dual-promoter expression vector plasmid AG159 for rhesus IL-12 heterodimer expression with simian cytomegalovirus (CMV) promoter

<400> SEQUENCE: 4

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg gaggtctat ataagcagag | 660 |
| ctcgtttagt gaaccgtcag atcgcctgga gacgccatcc acgctgtttt gacctccata | 720 |
| gaagacaccg ggaccgatcc agcctccgcg gccgcgcgtc gaggaattcg ctagaaagaa | 780 |
| atgtgcccgg cgcgctccct gctgctcgtg gcgacgctgg tcctgctcga ctacctgagc | 840 |
| ctggcgcgga acctgtcggt ggcgacccct ggaccggaga tgttcccgtg cctgcaccac | 900 |
| agccagaacc tgctgaaggc ggcgtcgaac acgctgcaga aggcgcggca gatcctggag | 960 |
| ttctacccgt gcacgagcga ggagatcgac cacgaggaca tcacgaagga caagaccagc | 1020 |
| acggtggagg cgtgcctgcc gctggagctg atcaagaacg agtcgtgcct gaactcgagg | 1080 |
| gagaccagct tcatcaccaa cggcagctgc ctggccagca aaagacctc cttcatgatg | 1140 |
| gccctgtgcc tgaggagcat ctacgaggac ctgaagatgt accaggtgga gttcaagacc | 1200 |
| atgaacgcca agctgctgag ggaccccaag aggcagatct tcctggacca gaacatcctg | 1260 |
| ggcgtgatcg acgagctgat gcaggccctg aacttcaaca gcgagaccgt gcctcagaag | 1320 |
| agcagcctgg aggagcccga cttctacaag accaagatca agctgtgcat cctgctgcac | 1380 |
| gccttccgga tcaggccgt gaccatcgac agagtgatga ctacctgaa cgccagctga | 1440 |
| taagatatcg gatctatcgg atctgctgtg ccttctagtt gccagccatc tgttgtttgc | 1500 |
| ccctcccccg tgccttcctt gaccctggaa ggtgccactc ccactgtcct ttcctaataa | 1560 |
| aatgaggaaa ttgcatcgca ttgtctgagt aggtgtcatt ctattctggg gggtggggtg | 1620 |
| gggcaggaca gcaaggggga ggattggaa acaatagca ggcatgctgg ggatgcggtg | 1680 |
| ggctctatgg gtacccaggt gctgaagaat tgacccggtt cctcctgggc cagaaagaag | 1740 |
| caggcacatc cccttctctg tgacacaccc tgtccacgcc cctggttctt agttccagcc | 1800 |
| ccactcatag gacactcata gctcaggagg gctccgcctt caatcccacc cgctaaagta | 1860 |

```
cttggagcgg tctctccctc cctcatcagc ccaccaaacc aaacctagcc tccaagagtg   1920
ggaagaaatt aaagcaagat aggctattaa gtgcagaggg agagaaaatg cctccaacat   1980
gtgaggaagt aatgagagaa atcatagaat ttcttccgct tcctcgctca ctgactcgct   2040
gcgctcggtc gttcggctgc ggcgagcggt atcagctcac tcaaaggcgg taatacggtt   2100
atccacagaa tcaggggata acgcaggaaa gaacatgtga gcaaaaggcc agcaaaaggc   2160
caggaaccgt aaaaaggccg cgttgctggc gtttttccat aggctccgcc ccctgacga   2220 gcatcacaaa aatcgacgct caagtcagag gtggcgaaac ccgacaggac tataaagata   2280
ccaggcgttt ccccctggaa gctccctcgt gcgctctcct gttccgaccc tgccgcttac   2340
cggatacctg tccgcctttc tcccttcggg aagcgtggcg ctttctcata gctcacgctg   2400
taggtatctc agttcggtgt aggtcgttcg ctccaagctg ggctgtgtgc acgaaccccc   2460
cgttcagccc gaccgctgcg ccttatccgg taactatcgt cttgagtcca acccggtaag   2520
acacgactta tcgccactgg cagcagccac tggtaacagg attagcagag cgaggtatgt   2580
aggcggtgct acagagttct tgaagtggtg gcctaactac ggctacacta agaacagt    2640 atttggtatc tgcgctctgc tgaagccagt taccttcgga aaagagttg gtagctcttg    2700 atccggcaaa caaaccaccg ctggtagcgg tggtttttt gtttgcaagc agcagattac    2760
gcgcagaaaa aaaggatctc aagaagatcc tttgatcttt tctacggggt ctgacgctca   2820
gtggaacgaa aactcacgtt aagggatttt ggtcatgaga ttatcaaaaa ggatcttcac   2880
ctagatcctt ttaaattaaa aatgaagttt taaatcaatc taaagtatat atgagtaaac   2940
ttggtctgac agttaccaat gcttaatcag tgaggcacct atctcagcga tctgtctatt   3000
tcgttcatcc atagttgcct gactcggggg gggggggcgc tgaggtctgc ctcgtgaaga   3060
aggtgttgct gactcatacc aggcctgaat cgccccatca tccagccaga aagtgaggga   3120
gccacggttg atgagagctt tgttgtaggt ggaccagttg gtgattttga acttttgctt   3180
tgccacggaa cggtctgcgt tgtcgggaag atgcgtgatc tgatccttca actcagcaaa   3240
agttcgattt attcaacaaa gccgccgtcc cgtcaagtca gcgtaatgct ctgccagtgt   3300
tacaaccaat taaccaattc tgattagaaa aactcatcga gcatcaaatg aaactgcaat   3360
ttattcatat caggattatc aataccatat ttttgaaaaa gccgtttctg taatgaagga   3420
gaaaactcac cgaggcagtt ccataggatg caagatcct ggtatcggtc tgcgattccg    3480
actcgtccaa catcaataca acctattaat ttccctcgt caaaaataag gttatcaagt    3540
gagaaatcac catgagtgac gactgaatcc ggtgagaatg gcaaaagctt atgcatttct   3600
ttccagactt gttcaacagg ccagccatta cgctcgtcat caaaatcact cgcatcaacc   3660
aaaccgttat tcattcgtga ttgcgcctga gcgagacgaa atacgcgatc gctgttaaaa   3720
ggacaattac aaacaggaat cgaatgcaac cggcgcagga acactgccag cgcatcaaca   3780
atattttcac ctgaatcagg atattcttct aatacctgga atgctgtttt cccgggatc    3840 gcagtggtga gtaaccatgc atcatcagga gtacggataa aatgcttgat ggtcggaaga   3900
ggcataaatt ccgtcagcca gtttagtctg accatctcat ctgtaacatc attggcaacg   3960
ctacctttgc catgtttcag aaacaactct ggcgcatcgg gcttcccata caatcgatag   4020
attgtcgcac ctgattgccc gacattatcg cgagcccatt tatacccata taatcagca    4080 tccatgttgg aatttaatcg cggcctcgag caagacgttt cccgttgaat atggctcata   4140
acaccccttg tattactgtt tatgtaagca gacagttta ttgttcatga tgatatattt     4200
ttatcttgtg caatgtaaca tcagagattt tgagacacaa cgtggatcat ccagacatga   4260
```

-continued

```
taagatacat tgatgagttt ggacaaacca caactagaat gcagtgaaaa aaatgcttta    4320
tttgtgaaat ttgtgatgct attgctttat ttgtaaccat tataagctgc aataaacaag    4380
ttaacaacaa caattgcatt cattttatgt ttcaggttca gggggaggtg tgggaggttt    4440
tttaaagcaa gtaaaacctc tacaaatgtg gtatggctga ttatgatcgt cgaggatccg    4500
gcgccggttt cgcgccccta ggttcatcag ctgcaaggca cgctggccca ctcgctccag    4560
ctgctgctgt agtatctgtc ctgggcctgc acgctgaagc tggcgttctt ccggcagatc    4620
acggtggcgc tggtcttatc ggtgaagatc cggtccttct tctcccgctt gctcttgccc    4680
tgcacttgga tgcagaaggt caggctgaag tagctgtgag gggtgctcca ggtgtcgggg    4740
tactcccagc tcacttccac ctgcctgctg ttcttcaggg gcttcagctg caggttcttg    4800
gggggtcgg gcttgatgat gtcccggatg aagaaggagc tggtgtagtt ctcgtacttc    4860
agcttgtgga tggcgtccac catcacttcg atgggcagtc tctcctcggc ggcagggcag    4920
gcgctgtcct cctggcactc cacgctgtac tcgtactcct tgttgtcgcc tctcactctc    4980
tcggcgctca gggtcacggc gccacaggtc acgccctggg ggttgctgct gcctctgctg    5040
ctcttcacgc tgaaggtcag gtcggtgctg atggtggtca gccaccaaca ggtgaaccgg    5100
ccgctgtaat tcttggcctc gcagcgcagg aaggtcttgt tcttgggctc cttctggtcc    5160
ttcagcacgt cggtgctcca gatcccgtcc tccttcttgt gcagcagcag caggctgtgg    5220
ctcagggcct cgccgccctt gtggcaggtg tactggccgg cgtcgccgaa ctccttgacc    5280
tggatcgtca gggtcttgcc gctgccagc acttcgccgc tctggtccag ggtccaggtg    5340
atgccgtcct cctcggggt gtcgcaggtc agcaccacca tctcgccagg cgcgtcggga    5400
taccagtcca gctccaccac gtatacgtcc ttcttcagct cccagatggc catcaggggg    5460
ctggccagga acaccaggct gaaccagctg atcaccagct gctggtggca catttcttct    5520
cgacagatcc aaacgctcct ccgacgtccc caggcagaat ggcggttccc taaacgagca    5580
ttgcttatat agacctccca ttaggcacgc ctaccgccca tttacgtcaa tggaacgccc    5640
atttgcgtca ttgcccctcc ccattgacgt caatggggat gtacttggca gccatcgcgg    5700
gccatttacc gccattgacg tcaatgggag tactgccaat gtaccctggc gtacttccaa    5760
tagtaatgta cttgccaagt tactattaat agatattgat gtactgccaa gtgggccatt    5820
taccgtcatt gacgtcaata gggggcgtga gaacggatat gaatgggcaa tgagccatcc    5880
cattgacgtc aatggtgggt ggtcctattg acgtcaatgg cattgagcc aggcgggcca    5940
tttaccgtaa ttgacgtcaa tggggaggc gccatatacg tcaataggac cgcccatatg    6000
acgtcaatag gtaagaccat gaggcccttt cgtctcgcgc gtttcggtga tgacggtgaa    6060
aacctctgac acatgcagct cccggagacg gtcacagctt gtctgtaagc ggatgccggg    6120
agcagacaag cccgtcaggg cgcgtcagcg ggtgttggcg ggtgtcgggg ctggcttaac    6180
tatgcggcat cagagcagat tgtactgaga gtgcaccata tgcggtgtga ataccgcac    6240
agatgcgtaa ggagaaaata ccgcatcaga ttggctattg g                       6281
```

<210> SEQ ID NO 5
<211> LENGTH: 4592
<212> TYPE: DNA
<213> ORGANISM: Artificial Sequence
<220> FEATURE:
<223> OTHER INFORMATION: synthetic expression vector plasmid AG177 for human IL-23 p19 alpha subunit expression

<400> SEQUENCE: 5

```
cctggccatt gcatacgttg tatccatatc ataatatgta catttatatt ggctcatgtc      60
```

```
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg ggaggtctat ataagcagag     660
ctcgtttagt gaaccgtcag atcgcctgga gacgccatcc acgctgtttt gacctccata     720
gaagacaccg gaccgatcc agcctccgcg ggcgcgcgtc gactctagaa agaaatgctg      780
gggagccgcg cggtcatgct gctcttgctg ctcccctgga cggcccaggg ccgggcggtg     840
cccgggggct cgagcccggc ctggacgcag tgccagcagc tcagccagaa gctctgcacc     900
ctggcctggt cggcccaccc gctcgtgggc cacatggacc tccgggagga gggcgacgag     960
gagacgacca acgacgtccc ccacatccag tgcggcgacg gctgcgaccc ccagggcctc     1020
cgggacaact cgcagttctg cctgcagcgc atccaccagg gcctgatctt ctacgagaag     1080
ctgctcggct cggacatctt cacggggag ccgtcgctgc tcccggacag cccggtgggc     1140
cagctccacg cctccctcct gggcctctcg caacttctgc aaccggaggg ccaccactgg     1200
gagacgcagc agatcccgag cctctcgccc agccagccgt ggcagcggct cctgctcaga     1260
ttcaagatct gcgctccct ccaagccttc gtggcggtcg ccgcccgggt cttcgcccac      1320
ggcgcggcca ccctgagccc ctgataagat atcggatcca gatctgctgt gccttctagt     1380
tgccagccat ctgttgtttg cccctccccc gtgccttcct gaccctggaa ggtgccact     1440 cccactgtcc tttcctaata aaatgaggaa attgcatcgc attgtctgag taggtgtcat     1500
tctattctgg ggggtggggt ggggcaggac agcaagggg aggattggga agacaatagc      1560
aggcatgctg gggatgcggt gggctctatg ggtacccagg tgctgaagaa ttgacccggt     1620
tcctcctggg ccagaaagaa gcaggcacat ccccttctct gtgacacacc ctgtccacgc     1680
ccctggttct tagttccagc cccactcata ggacactcat agctcaggag ggctccgcct     1740
tcaatcccac ccgctaaagt acttggagcg gtctctccct ccctcatcag cccaccaaac     1800
caaacctagc ctccaagagt gggaagaaat taaagcaaga taggctatta agtgcagagg     1860
gagagaaaat gcctccaaca tgtgaggaag taatgagaga atcatagaa tttcttccgc       1920 ttcctcgctc actgactcgc tgcgctcggt cgttcggctg cggcgagcgg tatcagctca     1980
ctcaaaggcg gtaatacggt tatccacaga atcagggat aacgcaggaa agaacatgtg      2040
agcaaaaggc cagcaaaagg ccaggaaccg taaaaaggcc gcgttgctgg cgttttccca    2100
taggctccgc cccctgacg agcatcacaa aaatcgacg tcaagtcaga ggtggcgaaa       2160
cccgacagga ctataaagat accaggcgtt ccccctgga agctccctcg tgcgctctcc      2220
tgttccgacc ctgccgctta ccggatacct gtccgccttt ctcccttcgg gaagcgtggc     2280
gctttctcat agctcacgct gtaggtatct cagttcggtg taggtcgttc gctccaagct     2340
gggctgtgtg cacgaacccc ccgttcagcc cgaccgctgc gccttatccg gtaactatcg     2400
tcttgagtcc aacccggtaa gacacgactt atcgccactg gcagcagcca ctggtaacag     2460
```

```
gattagcaga gcgaggtatg taggcggtgc tacagagttc ttgaagtggt ggcctaacta    2520
cggctacact agaagaacag tatttggtat ctgcgctctg ctgaagccag ttaccttcgg    2580
aaaaagagtt ggtagctctt gatccggcaa acaaaccacc gctggtagcg gtggttttt    2640 tgtttgcaag cagcagatta cgcgcagaaa aaaaggatct caagaagatc ctttgatctt    2700
ttctacgggg tctgacgctc agtggaacga aaactcacgt taagggattt tggtcatgag    2760
attatcaaaa aggatcttca cctagatcct tttaaattaa aaatgaagtt ttaaatcaat    2820
ctaaagtata tatgagtaaa cttggtctga cagttaccaa tgcttaatca gtgaggcacc    2880
tatctcagcg atctgtctat ttcgttcatc catagttgcc tgactcgggg ggggggggcg    2940
ctgaggtctg cctcgtgaag aaggtgttgc tgactcatac caggcctgaa tcgccccatc    3000
atccagccag aaagtgaggg agccacggtt gatgagagct ttgttgtagg tggaccagtt    3060
ggtgattttg aacttttgct ttgccacgga acggtctgcg ttgtcgggaa gatgcgtgat    3120
ctgatccttc aactcagcaa aagttcgatt tattcaacaa agccgccgtc ccgtcaagtc    3180
agcgtaatgc tctgccagtg ttacaaccaa ttaaccaatt ctgattagaa aaactcatcg    3240
agcatcaaat gaaactgcaa tttattcata tcaggattat caataccata ttttgaaaa    3300 agccgtttct gtaatgaagg agaaaactca ccgaggcagt tccataggat ggcaagatcc    3360
tggtatcggt ctgcgattcc gactcgtcca acatcaatac aacctattaa tttcccctcg    3420 tcaaaataa ggttatcaag tgagaaatca ccatgagtga cgactgaatc cggtgagaat    3480
ggcaaaagct tatgcatttc tttccagact tgttcaacag gccagccatt acgctcgtca    3540
tcaaaatcac tcgcatcaac caaccgttta ttcattcgtg attgcgcctg agcgagacga    3600
aatacgcgat cgctgttaaa aggacaatta caaacaggaa tcgaatgcaa ccggcgcagg    3660
aacactgcca gcgcatcaac aatattttca cctgaatcag gatattcttc taatacctgg    3720
aatgctgttt tcccggggat cgcagtggtg agtaaccatg catcatcagg agtacggata    3780
aaatgcttga tggtcggaag aggcataaat tccgtcagcc agtttagtct gaccatctca    3840
tctgtaacat cattggcaac gctacctttg ccatgtttca gaaacaactc tggcgcatcg    3900
ggcttcccat acaatcgata gattgtcgca cctgattgcc cgacattatc gcgagcccat    3960 ttataccccat ataaatcagc atccatgttg gaatttaatc gcggcctcga gcaagacgtt    4020
tcccgttgaa tatggctcat aacacccctt gtattactgt ttatgtaagc agacagtttt    4080
attgttcatg atgatatatt tttatcttgt gcaatgtaac atcagagatt ttgagacaca    4140
acgtggcttt ccccccccccc ccattattga agcatttatc agggttattg tctcatgagc    4200
ggatacatat ttgaatgtat ttagaaaaat aaacaaatag gggttccgcg cacatttccc    4260
cgaaaagtgc cacctgacgt ctaagaaacc attattatca tgacattaac ctataaaaat    4320
aggcgtatca cgaggccctt tcgtctcgcg cgtttcggtg atgacggtga aaacctctga    4380
cacatgcagc tcccggagac ggtcacagct tgtctgtaag cggatgccgg gagcagacaa    4440
gcccgtcagg gcgcgtcagc gggtgttggc gggtgtcggg gctggcttaa ctatgcggca    4500
tcagagcaga ttgtactgag agtgcaccat atgcggtgtg aaataccgca cagatgcgta    4560
aggagaaaat accgcatcag attggctatt gg                                 4592
```

<210> SEQ ID NO 6
<211> LENGTH: 5611
<212> TYPE: DNA
<213> ORGANISM: Artificial Sequence
<220> FEATURE:
<223> OTHER INFORMATION: synthetic expression vector plasmid AG180 for human IL-12 p40 beta subunit expression

<400> SEQUENCE: 6

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatggag tttgttttgg caccaaaatc aacgggactt tccaaaatgt cgtaacaact     600
ccgccccatt gacgcaaatg gcggtaggc gtgtacggtg ggaggtctat ataagcagag     660
ctcgtttagt gaaccgtcag atcgcctgga cgccatcc acgctgtttt gacctccata     720
gaagacaccg ggaccgatcc agcctccgcg gcgcgcgtc gaggaatttc gagaagaaat     780
gtgccaccag cagctggtca tcagctggtt cagcctcgtt ttcctcgcct cgccgctggt     840
cgccatatgg gagctcaaga aggacgtata cgtggtggag ctggactggt accccgacgc     900
gccgggcgag atggtcgtcc tgacgtgcga cacgccggag gaggacggca tcacgtggac     960
gctggaccag tccagcgagg tcctcggctc cggcaagacg ctgacgatcc aggtcaagga    1020
gttcggcgac gcgggccagt acacgtgcca aagggcggc gaggtcctga gccactccct    1080
cctcctgcta cacaagaagg aggacgggat ctggagcacg acatcctca aggaccagaa    1140
ggagccgaag aacaagacct tcctgcgctg cgaggcgaag aattactcgg gccggttcac    1200
gtgctggtgg ctcaccacga tcagcacgga cctgacgttc tcggtcaagt cgtcgcgggg    1260
ctcgtcggac ccccagggg tgacctgcgg cgcggcgacg ctgtcggcg agcgggtgcg    1320
gggcgacaac aaggagtacg agtactcggt cgagtgccag gaggactcgg cgtgcccggc    1380
ggcggaggag tcgctgccga tcgaggtgat ggtcgacgcg gtccacaagc tgaagtacga    1440
gaactacacg tcgtcgttct tcatccggga catcatcaag ccggaccccgc cgaagaacct    1500
gcagctgaag ccgctgaaga actcgcggca ggtcgaggtc tcgtgggagt acccggacac    1560
gtggtcgacg ccgcactcgt acttctcgct gacgttctgc gtccaagtgc agggcaagtc    1620
gaagcgggag aagaaggacc gggtgttcac cgacaagacg agcgcgacgg tgatctgccg    1680
gaagaacgcg tcgatctcgg tgcgggcgca ggaccggtac tactcgtcgt cgtggtcgga    1740
gtgggcgtcg gtgccgtgca gctagaccta ggggcgcgcc agatctgata tcggatctgc    1800
tgtgccttct agttgccagc catctgttgt ttgcccctcc ccgtgccttc ccttgaccct    1860
ggaaggtgcc actcccactg tcctttccta ataaaatgag gaaattgcat cgcattgtct    1920
gagtaggtgt cattctattc tggggggtgg ggtggggcag gacagcaagg gggaggattg    1980
ggaagacaat agcaggcatg ctggggatgc ggtgggctct atgggtaccc aggtgctgaa    2040
gaattgaccc ggttcctcct gggccagaaa gaagcaggca catcccttc tctgtgacac    2100
accctgtcca cgccctggt tcttagttcc agccccactc ataggacact catagctcag    2160
gagggctccg ccttcaatcc caccgctaa agtacttgga gcggtctctc cctccctcat    2220
cagcccacca aaccaaacct agcctccaag agtgggaaga aattaaagca agataggcta    2280
```

| | |
|---|---|
| ttaagtgcag agggagagaa aatgcctcca acatgtgagg aagtaatgag agaaatcata | 2340 |
| gaatttcttc cgcttcctcg ctcactgact cgctgcgctc ggtcgttcgg ctgcggcgag | 2400 |
| cggtatcagc tcactcaaag gcggtaatac ggttatccac agaatcaggg gataacgcag | 2460 |
| gaaagaacat gtgagcaaaa ggccagcaaa aggccaggaa ccgtaaaaag gccgcgttgc | 2520 |
| tggcgttttt ccataggctc cgcccccctg acgagcatca aaaaatcga cgctcaagtc | 2580 |
| agaggtggcg aaacccgaca ggactataaa gataccaggc gtttccccct ggaagctccc | 2640 |
| tcgtgcgctc tcctgttccg accctgccgc ttaccggata cctgtccgcc tttctccctt | 2700 |
| cgggaagcgt ggcgctttct catagctcac gctgtaggta tctcagttcg gtgtaggtcg | 2760 |
| ttcgctccaa gctgggctgt gtgcacgaac cccccgttca gcccgaccgc tgcgccttat | 2820 |
| ccggtaacta tcgtcttgag tccaacccgg taagacacga cttatcgcca ctggcagcag | 2880 |
| ccactggtaa caggattagc agagcgaggt atgtaggcgg tgctacagag ttcttgaagt | 2940 |
| ggtggcctaa ctacggctac actagaagaa cagtatttgg tatctgcgct ctgctgaagc | 3000 |
| cagttacctt cggaaaaaga gttggtagct cttgatccgg caaacaaacc accgctggta | 3060 |
| gcggtggttt ttttgtttgc aagcagcaga ttacgcgcag aaaaaaagga tctcaagaag | 3120 |
| atcctttgat cttttctacg gggtctgacg ctcagtggaa cgaaaactca cgttaaggga | 3180 |
| ttttggtcat gagattatca aaaaggatct cacctagat cctttttaaat taaaaatgaa | 3240 |
| gttttaaatc aatctaaagt atatatgagt aaacttggtc tgacagttac caatgcttaa | 3300 |
| tcagtgaggc acctatctca gcgatctgtc tatttcgttc atccatagtt gcctgactcg | 3360 |
| ggggggggg gcgctgaggt ctgcctcgtg aagaaggtgt tgctgactca taccaggcct | 3420 |
| gaatcgcccc atcatccagc cagaaagtga gggagccacg gttgatgaga gctttgttgt | 3480 |
| aggtggacca gttggtgatt tgaactttt gctttgccac ggaacggtct gcgttgtcgg | 3540 |
| gaagatgcgt gatctgatcc ttcaactcag caaaagttcg atttattcaa caaagccgcc | 3600 |
| gtcccgtcaa gtcagcgtaa tgctctgcca gtgttacaac caattaacca attctgatta | 3660 |
| gaaaaactca tcgagcatca aatgaaactg caatttattc atatcaggat tatcaatacc | 3720 |
| atatttttga aaaagccgtt tctgtaatga aggagaaaac tcaccgaggc agttccatag | 3780 |
| gatggcaaga tcctggtatc ggtctgcgat tccgactcgt ccaacatcaa tacaacctat | 3840 |
| taatttcccc tcgtcaaaaa taaggttatc aagtgagaaa tcaccatgag tgacgactga | 3900 |
| atccggtgag aatggcaaaa gcttatgcat ttctttccag acttgttcaa caggccagcc | 3960 |
| attacgctcg tcatcaaaat cactcgcatc aaccaaaccg ttattcattc gtgattgcgc | 4020 |
| ctgagcgaga cgaaatacgc gatcgctgtt aaaaggacaa ttacaaacag gaatcgaatg | 4080 |
| caaccggcgc aggaacactg ccagcgcatc aacaatattt tcacctgaat caggatattc | 4140 |
| ttctaatacc tggaatgctg ttttcccggg gatcgcagtg gtgagtaacc atgcatcatc | 4200 |
| aggagtacga taaaatgct tgatggtcgg aagaggcata aattccgtca gccagtttag | 4260 |
| tctgaccatc tcatctgtaa catcattggc aacgctacct ttgccatgtt tcagaaacaa | 4320 |
| ctctggcgca tcgggcttcc catacaatcg atagattgtc gcacctgatt gcccgacatt | 4380 |
| atcgcgagcc catttatacc catataaatc agcatccatg ttggaattta atcgcggcct | 4440 |
| cgagcaagac gtttcccgtt gaatatggct cataacaccc cttgtattac tgtttatgta | 4500 |
| agcagacagt tttattgttc atgatgatat atttttatct tgtgcaatgt aacatcagag | 4560 |
| attttgagac acaacgtgga tcatccagac atgataagat acattgatga gtttggacaa | 4620 |
| accacaacta gaatgcagtg aaaaaaatgc tttatttgtg aaatttgtga tgctattgct | 4680 |

-continued

| | |
|---|---|
| ttatttgtaa ccattataag ctgcaataaa caagttaaca acaacaattg cattcatttt | 4740 |
| atgtttcagg ttcaggggga ggtgtgggag gttttttaaa gcaagtaaaa cctctacaaa | 4800 |
| tgtggtatgg ctgattatga tcgtcgagga tccggcgccg gtttaaacgt cgacagatcc | 4860 |
| aaacgctcct ccgacgtccc caggcagaat ggcggttccc taaacgagca ttgcttatat | 4920 |
| agacctccca ttaggcacgc ctaccgccca tttacgtcaa tggaacgccc atttgcgtca | 4980 |
| ttgcccctcc ccattgacgt caatgggat gtacttggca gccatcgcgg gccatttacc | 5040 |
| gccattgacg tcaatgggag tactgccaat gtaccctggc gtacttccaa tagtaatgta | 5100 |
| cttgccaagt tactattaat agatattgat gtactgccaa gtgggccatt taccgtcatt | 5160 |
| gacgtcaata ggggcgtga gaacggatat gaatgggcaa tgagccatcc cattgacgtc | 5220 |
| aatggtgggt ggtcctattg acgtcaatgg gcattgagcc aggcgggcca tttaccgtaa | 5280 |
| ttgacgtcaa tgggggaggc gccatatacg tcaataggac cgcccatatg acgtcaatag | 5340 |
| gtaagaccat gaggcccttt cgtctcgcgc gtttcggtga tgacggtgaa aacctctgac | 5400 |
| acatgcagct cccggagacg gtcacagctt gtctgtaagc ggatgccggg agcagacaag | 5460 |
| cccgtcaggg cgcgtcagcg ggtgttggcg ggtgtcgggg ctggcttaac tatgcggcat | 5520 |
| cagagcagat tgtactgaga gtgcaccata tgcggtgtga ataccgcac agatgcgtaa | 5580 |
| ggagaaaata ccgcatcaga ttggctattg g | 5611 |

<210> SEQ ID NO 7
<211> LENGTH: 6194
<212> TYPE: DNA
<213> ORGANISM: Artificial Sequence
<220> FEATURE:
<223> OTHER INFORMATION: synthetic dual-promoter expression vector
plasmid AG184 with human cytomegalovirus (CMV) promoter for human
IL-12 p40 beta subunit expression and simian CMV promoter for
human IL-23 p19 alpha subunit expression

<400> SEQUENCE: 7

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg ggaggtctat ataagcagag | 660 |
| ctcgtttagt gaaccgtcag atcgcctgga gacgccatcc acgctgtttt gacctccata | 720 |
| gaagacaccg ggaccgatcc agcctccgcg ggcgcgcgtc gaggaatttc gagaagaaat | 780 |
| gtgccaccag cagctggtca tcagctggtt cagcctcgtt ttcctcgcct cgccgctggt | 840 |
| cgccatatgg gagctcaaga aggacgtata cgtggtggag ctggactggt accccgacgc | 900 |
| gccgggcgag atggtcgtcc tgacgtgcga cacgccggag gaggacggca tcacgtggac | 960 |
| gctgaccag tccagcgagg tcctcggctc cggcaagacg ctgacgatcc aggtcaagga | 1020 |
| gttcggcgac gcgggccagt acacgtgcca caagggcggc gaggtcctga gccactccct | 1080 |

```
cctcctgcta cacaagaagg aggacgggat ctggagcacg gacatcctca aggaccagaa      1140
ggagccgaag aacaagacct tcctgcgctg cgaggcgaag aattactcgg gccggttcac      1200
gtgctggtgg ctcaccacga tcagcacgga cctgacgttc tcggtcaagt cgtcgcgggg      1260
ctcgtcggac ccccagggg  tgacctgcgg cgcggcgacg ctgtcggcgg agcgggtgcg      1320
gggcgacaac aaggagtacg agtactcggt cgagtgccag gaggactcgg cgtgcccggc      1380
ggcggaggag tcgctgccga tcgaggtgat ggtcgacgcg gtccacaagc tgaagtacga      1440 gaactcacg  tcgtcgttct tcatccggga catcatcaag ccggacccgc cgaagaacct      1500
gcagctgaag ccgctgaaga actcgcggca ggtcgaggtc tcgtgggagt acccggacac      1560
gtggtcgacg ccgcactcgt acttctcgct gacgttctgc gtccaagtgc agggcaagtc      1620
gaagcgggag aagaaggacc gggtgttcac cgacaagacg agcgcgacgg tgatctgccg      1680
gaagaacgcg tcgatctcgg tgcgggcgca ggaccggtac tactcgtcgt cgtggtcgga      1740
gtgggcgtcg gtgccgtgca gctagaccta ggggcgcgcc agatctgata tcggatctgc      1800
tgtgccttct agttgccagc catctgttgt ttgcccctcc cccgtgcctt ccttgaccct      1860
ggaaggtgcc actcccactg tccttttccta ataaaatgag gaaattgcat cgcattgtct      1920
gagtaggtgt cattctattc tggggggtgg ggtggggcag gacagcaagg gggaggattg      1980
ggaagacaat agcaggcatg ctgggatgc  ggtgggctct atgggtaccc aggtgctgaa      2040
gaattgaccc ggttcctcct gggccagaaa gaagcaggca catcccttc  tctgtgacac      2100 accctgtcca cgccctgt  tcttagttcc agccccactc ataggacact catagctcag      2160
gagggctccg ccttcaatcc cacccgctaa agtacttgga gcggtctctc cctccctcat      2220
cagcccacca aaccaaacct agcctccaag agtgggaaga aattaaagca agataggcta      2280
ttaagtgcag agggagagaa aatgcctcca acatgtgagg aagtaatgag agaaatcata      2340
gaatttcttc cgcttcctcg ctcactgact cgctgcgctc ggtcgttcgg ctgcggcgag      2400
cggtatcagc tcactcaaag gcggtaatac ggttatccac agaatcaggg gataacgcag      2460
gaaagaacat gtgagcaaaa ggccagcaaa aggccaggaa ccgtaaaaag gccgcgttgc      2520
tggcgttttt ccataggctc cgcccccctg acgagcatca caaaaatcga cgctcaagtc      2580
agaggtggcg aaacccgaca ggactataaa gataccaggc gtttccccct ggaagctccc      2640
tcgtgcgctc tcctgttccg accctgccgc ttaccggata cctgtccgcc tttctccctt      2700
cgggaagcgt ggcgctttct catagctcac gctgtaggta tctcagttcg gtgtaggtcg      2760
ttcgctccaa gctgggctgt gtgcacgaac cccccgttca gcccgaccgc tgcgccttat      2820
ccggtaacta tcgtcttgag tccaacccgg taagacacga cttatcgcca ctggcagcag      2880
ccactggtaa caggattagc agagcgaggt atgtaggcgg tgctacagag ttcttgaagt      2940
ggtggcctaa ctacggctac actagaagaa cagtatttgg tatctgcgct ctgctgaagc      3000
cagttacctt cggaaaaaga gttggtagct cttgatccgg caaacaaacc accgctggta      3060
gcggtggttt ttttgtttgc aagcagcaga ttacgcgcag aaaaaaagga tctcaagaag      3120
atcctttgat cttttctacg gggtctgacg ctcagtggaa cgaaaactca cgttaaggga      3180
ttttggtcat gagattatca aaaaggatct tcacctagat ccttttaaat taaaaatgaa      3240
gttttaaatc aatctaaagt atatatgagt aaacttggtc tgacagttac caatgcttaa      3300
tcagtgaggc acctatctca gcgatctgtc tatttcgttc atccatagtt gcctgactcg      3360 ggggggggg  gcgctgaggt ctgcctcgtg aagaaggtgt tgctgactca taccaggcct      3420
gaatcgcccc atcatccagc cagaaagtga gggagccacg gttgatgaga gctttgttgt      3480
```

```
aggtggacca gttggtgatt ttgaactttt gctttgccac ggaacggtct gcgttgtcgg   3540
gaagatgcgt gatctgatcc ttcaactcag caaaagttcg atttattcaa caaagccgcc   3600
gtcccgtcaa gtcagcgtaa tgctctgcca gtgttacaac caattaacca attctgatta   3660
gaaaaactca tcgagcatca aatgaaactg caatttattc atatcaggat tatcaatacc   3720 atattttga aaaagccgtt tctgtaatga aggagaaaac tcaccgaggc agttccatag   3780
gatggcaaga tcctggtatc ggtctgcgat tccgactcgt ccaacatcaa tacaacctat   3840
taatttcccc tcgtcaaaaa taaggttatc aagtgagaaa tcaccatgag tgacgactga   3900
atccggtgag aatggcaaaa gcttatgcat ttctttccag acttgttcaa caggccagcc   3960
attacgctcg tcatcaaaat cactcgcatc aaccaaaccg ttattcattc gtgattgcgc   4020
ctgagcgaga cgaaatacgc gatcgctgtt aaaaggacaa ttacaaacag gaatcgaatg   4080
caaccggcgc aggaacactg ccagcgcatc aacaatattt tcacctgaat caggatattc   4140
ttctaatacc tggaatgctg ttttcccggg gatcgcagtg gtgagtaacc atgcatcatc   4200
aggagtacgg ataaaatgct tgatggtcgg aagaggcata aattccgtca gccagtttag   4260
tctgaccatc tcatctgtaa catcattggc aacgctacct ttgccatgtt tcagaaacaa   4320
ctctggcgca tcgggcttcc catacaatcg atagattgtc gcacctgatt gcccgacatt   4380
atcgcgagcc catttatacc catataaatc agcatccatg ttggaattta atcgcggcct   4440
cgagcaagac gtttcccgtt gaatatggct cataacaccc cttgtattac tgtttatgta   4500
agcagacagt tttattgttc atgatgatat attttatct tgtgcaatgt aacatcagag   4560
attttgagac acaacgtgga tcatccagac atgataagat acattgatga gtttggacaa   4620
accacaacta gaatgcagtg aaaaaaatgc tttatttgtg aaatttgtga tgctattgct   4680
ttatttgtaa ccattataag ctgcaataaa caagttaaca acaacaattg cattcatttt   4740
atgtttcagg ttcaggggga ggtgtgggag gttttttaaa gcaagtaaaa cctctacaaa   4800
tgtggtatgg ctgattatga tcgtcgagga tccgatatct tatcaggggc tcagggtggc   4860
cgcgccgtgg gcgaagaccc gggcggcgac cgccacgaag gcttggaggg agcgcaagat   4920
cttgaatctg agcaggagcc gctgccacgg ctggctgggc gagaggctcg ggatctgctg   4980
cgtctcccag tggtggccct ccggttcag aagttgcgag aggcccagga gggaggcgtg   5040
gagctggccc accgggctgt ccgggagcag cgacggctcc cccgtgaaga tgtccgagcc   5100
gagcagcttc tcgtagaaga tcaggccctg gtggatgcgc tgcaggcaga actgcgagtt   5160
gtcccggagg ccctgggggt cgcagccgtc gccgcactgg atgtggggga cgtcgttggt   5220
cgtctcctcg tcgccctcct cccggaggtc catgtggccc acgagcgggt gggccgacca   5280
ggccagggtg cagagcttct ggctgagctg ctggcactgc gtccaggccg ggctcgagcc   5340
cccgggcacc gccgggccct gggccgtcca ggggagcagc aagagcagca tgaccgcgcg   5400
gctccccagc atttctttct agagtcaaac gtcgacagat ccaaacgctc ctccgacgtc   5460
cccaggcaga atggcggttc cctaaacgag cattgcttat atagacctcc cattaggcac   5520
gcctaccgcc catttacgtc aatggaacgc ccatttgcgt cattgcccct ccccattgac   5580
gtcaatgggg atgtacttgg cagccatcgc gggccattta ccgcattga cgtcaatggg   5640 agtactgcca atgtaccctg gcgtacttcc aatagtaatg tacttgccaa gttactatta   5700
atagatattg atgtactgcc aagtgggcca tttaccgtca ttgacgtcaa taggggggcgt   5760 gagaacggat atgaatgggc aatgagccat cccattgacg tcaatggtgg gtggtcctat   5820
tgacgtcaat gggcattgag ccaggcgggc catttaccgt aattgacgtc aatggggag   5880
```

-continued

| | |
|---|---|
| gcgccatata cgtcaatagg accgcccata tgacgtcaat aggtaaagac catgaggccc | 5940 |
| tttcgtctcg cgcgtttcgg tgatgacggt gaaaacctct gacacatgca gctcccggag | 6000 |
| acggtcacag cttgtctgta agcggatgcc gggagcagac aagcccgtca gggcgcgtca | 6060 |
| gcgggtgttg gcgggtgtcg gggctggctt aactatgcgg catcagagca gattgtactg | 6120 |
| agagtgcacc atatgcggtg tgaaataccg cacagatgcg taaggagaaa ataccgcatc | 6180 |
| agattggcta ttgg | 6194 |

<210> SEQ ID NO 8
<211> LENGTH: 4715
<212> TYPE: DNA
<213> ORGANISM: Artificial Sequence
<220> FEATURE:
<223> OTHER INFORMATION: synthetic expression vector plasmid AG193 for murine IL-27 p28 alpha subunit expression

<400> SEQUENCE: 8

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg gaggtctat ataagcagag | 660 |
| ctcgtttagt gaaccgtcag atcgcctgga gacgccatcc acgctgtttt gacctccata | 720 |
| gaagacaccg gaccgatcc agcctccgcg ggcgcgcgtc gacaagaaat gggccaggtc | 780 |
| accggggacc tcgggtggcg cctgtcgctc ctgctcctgc cctcctcct ggtccaagcg | 840 |
| gggagctggg gcttccccac ggatcccctg agcctccagg agctgcgcag ggagttcacc | 900 |
| gtcagcctgt acctcgcccg gaagctgctc tccgaggtcc agggctacgt ccacagcttc | 960 |
| gccgagtcgc gcctgcccgg cgtgaacctg gacctcctgc ccctgggcta ccacctcccc | 1020 |
| aacgtctccc tgacgttcca gcctggcac cacctctccg actccgagcg cctctgcttc | 1080 |
| ctcgccacca cgctccggcc gttcccggcc atgctgggcg gctggggac caggggacc | 1140 |
| tggaccagct ccgagaggga gcagctgtgg gccatgaggc tggacctccg ggacctgcac | 1200 |
| aggcacctcc gcttccaagt cctggccgcg ggcttcaagt gctccaagga ggaggacgac | 1260 |
| aaggaggaag aggaagagga ggaagaagag gaaaagaagc tgcccctcgg ggccctgggc | 1320 |
| ggccccaacc aggtgtcctc ccaagtgtcc tggcccagc tgctctacac ctaccagctc | 1380 |
| ctccactccc tggagctggt cctgagccgg gcggtgcggg acctgctcct gctgtccctg | 1440 |
| ccccggcgcc cgggctcggc ctgggactcc aatgatcta aagatctgc tgtgccttct | 1500 |
| agttgccagc catctgttgt ttgcccctcc cccgtgcctt ccttgaccct ggaaggtgcc | 1560 |
| actcccactg tccttcccta ataaaatgag gaaattgcat cgcattgtct gagtaggtgt | 1620 |
| cattctattc tggggggtgg ggtggggcag gacagcaagg gggaggattg ggaagacaat | 1680 |

```
agcaggcatg ctggggatgc ggtgggctct atgggtaccc aggtgctgaa gaattgaccc    1740
ggttcctcct gggccagaaa gaagcaggca catcccttc tctgtgacac accctgtcca    1800
cgcccctggt tcttagttcc agccccactc ataggacact catagctcag gagggctccg    1860
ccttcaatcc cacccgctaa agtacttgga gcggtctctc cctccctcat cagcccacca    1920
aaccaaacct agcctccaag agtgggaaga aattaaagca agataggcta ttaagtgcag    1980
agggagagaa aatgcctcca acatgtgagg aagtaatgag agaaatcata gaatttcttc    2040
cgcttcctcg ctcactgact cgctgcgctc ggtcgttcgg ctgcggcgag cggtatcagc    2100
tcactcaaag gcggtaatac ggttatccac agaatcaggg gataacgcag gaaagaacat    2160
gtgagcaaaa ggccagcaaa aggccaggaa ccgtaaaaag gccgcgttgc tggcgttttt    2220
ccataggctc cgccccctg acgagcatca caaaatcga cgctcaagtc agaggtggcg    2280
aaacccgaca ggactataaa gataccaggc gtttccccct ggaagctccc tcgtgcgctc    2340
tcctgttccg accctgccgc ttaccggata cctgtccgcc tttctccctt cgggaagcgt    2400
ggcgctttct catagctcac gctgtaggta tctcagttcg gtgtaggtcg ttcgctccaa    2460
gctgggctgt gtgcacgaac cccccgttca gcccgaccgc tgcgccttat ccggtaacta    2520
tcgtcttgag tccaacccgg taagacacga cttatcgcca ctggcagcag ccactggtaa    2580
caggattagc agagcgaggt atgtaggcgg tgctacagag ttcttgaagt ggtggcctaa    2640
ctacggctac actagaagaa cagtatttgg tatctgcgct ctgctgaagc cagttacctt    2700
cggaaaaaga gttggtagct cttgatccgg caaacaaacc accgctggta gcggtggttt    2760
ttttgtttgc aagcagcaga ttacgcgcag aaaaaaagga tctcaagaag atcctttgat    2820
cttttctacg gggtctgacg ctcagtggaa cgaaaactca cgttaaggga ttttggtcat    2880
gagattatca aaaaggatct tcacctagat ccttttaaat taaaaatgaa gttttaaatc    2940
aatctaaagt atatatgagt aaacttggtc tgacagttac caatgcttaa tcagtgaggc    3000
acctatctca gcgatctgtc tatttcgttc atccatagtt gcctgactcg gggggggggg    3060
gcgctgaggt ctgcctcgtg aagaaggtgt tgctgactca taccaggcct gaatcgcccc    3120
atcatccagc cagaaagtga gggagccacg gttgatgaga ctttgttgt aggtggacca    3180
gttggtgatt ttgaacttt gctttgccac ggaacggtct gcgttgtcgg gaagatgcgt    3240
gatctgatcc ttcaactcag caaaagttcg atttattcaa caaagccgcc gtcccgtcaa    3300
gtcagcgtaa tgctctgcca gtgttacaac caattaacca attctgatta gaaaaactca    3360
tcgagcatca aatgaaactg caatttattc atatcaggat tatcaatacc atatttttga    3420
aaaagccgtt tctgtaatga aggagaaaac tcaccgaggc agttccatag gatggcaaga    3480
tcctggtatc ggtctgcgat tccgactcgt ccaacatcaa tacaacctat aatttcccc    3540
tcgtcaaaaa taaggttatc aagtgagaaa tcaccatgag tgacgactga atccggtgag    3600
aatgcaaaa gcttatgcat ttctttccag acttgttcaa caggccagcc attacgctcg    3660
tcatcaaaat cactcgcatc aaccaaaccg ttattcattc gtgattgcgc ctgagcgaga    3720
cgaaatacgc gatcgctgtt aaaaggacaa ttacaaacag gaatcgaatg caaccggcgc    3780
aggaacactg ccagcgcatc aacaatattt tcacctgaat caggatattc ttctaatacc    3840
tggaatgctg ttttcccggg gatcgcagtg gtgagtaacc atgcatcatc aggagtacgg    3900
ataaaatgct tgatggtcgg aagaggcata aattccgtca gccagtttag tctgaccatc    3960
tcatctgtaa catcattggc aacgctacct ttgccatgtt tcagaaacaa ctctggcgca    4020
tcgggcttcc catacaatcg atagattgtc gcacctgatt gcccgacatt atcgcgagcc    4080
```

-continued

| | |
|---|---|
| catttatacc catataaatc agcatccatg ttggaattta atcgcggcct cgagcaagac | 4140 |
| gtttcccgtt gaatatggct cataacaccc cttgtattac tgtttatgta agcagacagt | 4200 |
| tttattgttc atgatgatat attttttatct tgtgcaatgt aacatcagag attttgagac | 4260 |
| acaacgtggc tttccccccc cccccattat tgaagcattt atcagggtta ttgtctcatg | 4320 |
| agcggataca tatttgaatg tatttagaaa aataaacaaa taggggttcc gcgcacattt | 4380 |
| ccccgaaaag tgccacctga cgtctaagaa accattatta tcatgacatt aacctataaa | 4440 |
| aataggcgta tcacgaggcc ctttcgtctc gcgcgtttcg gtgatgacgg tgaaaacctc | 4500 |
| tgacacatgc agctcccgga gacggtcaca gcttgtctgt aagcggatgc cgggagcaga | 4560 |
| caagcccgtc agggcgcgtc agcgggtgtt ggcgggtgtc ggggctggct taactatgcg | 4620 |
| gcatcagagc agattgtact gagagtgcac catatgcggt gtgaaatacc gcacagatgc | 4680 |
| gtaaggagaa ataccgcat cagattggct attgg | 4715 |

<210> SEQ ID NO 9
<211> LENGTH: 4713
<212> TYPE: DNA
<213> ORGANISM: Artificial Sequence
<220> FEATURE:
<223> OTHER INFORMATION: synthetic expression vector plasmid AG194 for
      murine IL-27 Epstein-Barr virus-induced gene 3 (EBI3) beta subunit
      expression

<400> SEQUENCE: 9

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg ggaggtctat ataagcagag | 660 |
| ctcgtttagt gaaccgtcag atcgcctgga gacgccatcc acgctgtttt gacctccata | 720 |
| gaagacaccg ggaccgatcc agcctccgcg gcacgtgaag aaatgtcgaa gctcctgttc | 780 |
| ctgagcctgg cgctctgggc cagccgctcg cggggtata ccgagacggc gctcgtggcc | 840 |
| ctgagccagc ccgggtgca gtgccacgcc tcgcgctacc ccgtggccgt ggactgctcc | 900 |
| tggaccccgc tgcaagcgcc caactccacc aggtccacgt ccttcatcgc cacgtaccgg | 960 |
| ctcggcgtgg ccacccagca gcagagccag ccctgcctgc agcggagccc ccaggcctcc | 1020 |
| cgctgcacca tccccgacgt gcacctgttc tccacggtgc cctacatgct caacgtcacg | 1080 |
| gcggtgcacc cgggcggcgc cagcagcagc ctcctggcct tcgtggcgga gcggatcatc | 1140 |
| aagccggacc cgcggaggg cgtgcgcctg cgcacgcgg gccagcgcct gcaggtgctc | 1200 |
| tggcaccccc cggcctcctg gccctcccg gacatcttct cgctcaagta ccgcctccgc | 1260 |
| taccggcgcc gaggcgcctc ccacttccgc caagtcggcc ccatcgaggc cacgaccttc | 1320 |
| accctccgga actcgaagcc ccacgccaag tactgcatcc aggtgtcggc gcaggacctc | 1380 |

```
accgactacg ggaagcccag cgactggagc ctcccggggc aggtcgagag cgctccccac    1440
aagccctaat gagaattcgc ggatatcggt taacggatcc agatctgctg tgccttctag    1500
ttgccagcca tctgttgttt gcccctcccc cgtgccttcc ttgaccctgg aaggtgccac    1560
tcccactgtc ctttcctaat aaaatgagga aattgcatcg cattgtctga gtaggtgtca    1620
ttctattctg gggggtgggg tggggcagga cagcaagggg gaggattggg aagacaatag    1680
caggcatgct ggggatgcgg tgggctctat gggtacccag gtgctgaaga attgacccgg    1740
ttcctcctgg gccagaaaga agcaggcaca tccccttctc tgtgacacac cctgtccacg    1800
cccctggttc ttagttccag ccccactcat aggacactca tagctcagga gggctccgcc    1860
ttcaatccca cccgctaaag tacttggagc ggtctctccc tccctcatca gcccaccaaa    1920
ccaaacctag cctccaagag tgggaagaaa ttaaagcaag ataggctatt aagtgcagag    1980
ggagagaaaa tgcctccaac atgtgaggaa gtaatgagag aaatcataga atttcttccg    2040
cttcctcgct cactgactcg ctgcgctcgg tcgttcggct gcggcgagcg gtatcagctc    2100
actcaaaggc ggtaatacgg ttatccacag aatcagggga taacgcagga aagaacatgt    2160
gagcaaaagg ccagcaaaag gccaggaacc gtaaaaaggc cgcgttgctg gcgttttttcc    2220 ataggctccg ccccccctgac gagcatcaca aaaatcgacg ctcaagtcag aggtggcgaa    2280
acccgacagg actataaaga taccaggcgt ttccccctgg aagctccctc gtgcgctctc    2340
ctgttccgac cctgccgctt accggatacc tgtccgcctt tctcccttcg ggaagcgtgg    2400
cgctttctca tagctcacgc tgtaggtatc tcagttcggt gtaggtcgtt cgctccaagc    2460
tgggctgtgt gcacgaaccc cccgttcagc ccgaccgctg cgccttatcc ggtaactatc    2520
gtcttgagtc caacccggta agacacgact tatcgccact ggcagcagcc actggtaaca    2580
ggattagcag agcgaggtat gtaggcggtg ctacagagtt cttgaagtgg tggcctaact    2640
acggctacac tagaagaaca gtatttggta tctgcgctct gctgaagcca gttaccttcg    2700
gaaaaagagt tggtagctct tgatccggca aacaaaccac cgctggtagc ggtggttttt    2760
ttgtttgcaa gcagcagatt acgcgcagaa aaaaaggatc tcaagaagat cctttgatct    2820
tttctacggg gtctgacgct cagtggaacg aaaactcacg ttaagggatt ttggtcatga    2880
gattatcaaa aaggatcttc acctagatcc ttttaaatta aaaatgaagt tttaaatcaa    2940
tctaaagtat atatgagtaa acttggtctg acagttacca atgcttaatc agtgaggcac    3000
ctatctcagc gatctgtcta tttcgttcat ccatagttgc ctgactcggg gggggggggc    3060
gctgaggtct gcctcgtgaa gaaggtgttg ctgactcata ccaggcctga atcgccccat    3120
catccagcca gaaagtgagg gagccacggt tgatgagagc tttgttgtag gtggaccagt    3180
tggtgatttt gaacttttgc tttgccacgg aacggtctgc gttgtcggga agatgcgtga    3240
tctgatcctt caactcagca aaagttcgat ttattcaaca agccgccgt cccgtcaagt    3300 cagcgtaatg ctctgccagt gttacaacca attaaccaat tctgattaga aaaactcatc    3360
gagcatcaaa tgaaactgca atttattcat atcaggatta tcaataccat atttttgaaa    3420
aagccgtttc tgtaatgaag gagaaaactc accgaggcag ttccatagga tggcaagatc    3480
ctggtatcgg tctgcgattc cgactcgtcc aacatcaata caacctatta atttcccctc    3540
gtcaaaaata aggttatcaa gtgagaaatc accatgagtg acgactgaat ccggtgagaa    3600
tggcaaaagc ttatgcattt cttttccagac ttgttcaaca ggccagccat tacgctcgtc    3660
atcaaaatca ctcgcatcaa ccaaaccgtt attcattcgt gattgcgcct gagcgagacg    3720
aaatacgcga tcgctgttaa aaggacaatt acaaacagga atcgaatgca accggcgcag    3780
```

```
gaacactgcc agcgcatcaa caatattttc acctgaatca ggatattctt ctaatacctg    3840
gaatgctgtt ttcccgggga tcgcagtggt gagtaaccat gcatcatcag gagtacggat    3900
aaaatgcttg atggtcggaa gaggcataaa ttccgtcagc cagtttagtc tgaccatctc    3960
atctgtaaca tcattggcaa cgctaccttt gccatgtttc agaaacaact ctggcgcatc    4020
gggcttccca tacaatcgat agattgtcgc acctgattgc ccgacattat cgcgagccca    4080
tttataccca tataaatcag catccatgtt ggaatttaat cgcggcctcg agcaagacgt    4140
ttcccgttga atatggctca taacacccct tgtattactg tttatgtaag cagacagttt    4200
tattgttcat gatgatatat ttttatcttg tgcaatgtaa catcagagat tttgagacac    4260
aacgtggctt tccccccccc cccattattg aagcatttat cagggttatt gtctcatgag    4320
cggatacata tttgaatgta tttagaaaaa taaacaaata ggggttccgc gcacatttcc    4380
ccgaaaagtg ccacctgacg tctaagaaac cattattatc atgacattaa cctataaaaa    4440
taggcgtatc acgaggccct ttcgtctcgc gcgtttcggt gatgacggtg aaaacctctg    4500
acacatgcag ctcccggaga cggtcacagc ttgtctgtaa gcggatgccg ggagcagaca    4560
agcccgtcag ggcgcgtcag cgggtgttgg cgggtgtcgg ggctggctta actatgcggc    4620
atcagagcag attgtactga gagtgcacca tatgcggtgt gaaataccgc acagatgcgt    4680
aaggagaaaa taccgcatca gattggctat tgg                                4713
```

<210> SEQ ID NO 10
<211> LENGTH: 5908
<212> TYPE: DNA
<213> ORGANISM: Artificial Sequence
<220> FEATURE:
<223> OTHER INFORMATION: synthetic dual-promoter expression vector plasmid AG205 with human cytomegalovirus (CMV) promoter for murine IL-27 p28 alpha subunit expression and simian CMV promoter for murine IL-27 Epstein-Barr virus-induced gene 3 (EBI3) beta subunit expression

<400> SEQUENCE: 10

```
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg ggaggtctat ataagcagag     660
ctcgtttagt gaaccgtcag atcgcctgga gacgccatcc acgctgtttt gacctccata     720
gaagacaccg ggaccgatcc agcctccgcg gccgcgcgtc gaggaattcg ctagtcgaca     780
agaaatgggc caggtcaccg gggacctcgg gtggcgcctg tcgctcctgc tcctgcccct     840
cctcctggtc caagcgggga gctgggcttc cccacggat cccctgagcc tccaggagct     900
gcgcagggag ttcaccgtca gcctgtacct cgcccggaag ctgctctccg aggtccaggg     960
ctacgtccac agcttcgccg agtcgcgcct gcccggcgtg aacctggacc tcctgcccct    1020
```

```
gggctaccac ctcccccaacg tctccctgac gttccaagcc tggcaccacc tctccgactc   1080
cgagcgcctc tgcttcctcg ccaccacgct ccggccgttc ccggccatgc tgggcgggct   1140
ggggacccag gggacctgga ccagctccga gagggagcag ctgtgggcca tgaggctgga   1200
cctccgggac ctgcacaggc acctccgctt ccaagtcctg gccgcgggct tcaagtgctc   1260
caaggaggag gaggacaagg aggaagagga agaggaggaa gaagaggaaa agaagctgcc   1320
cctcggggcc ctgggcggcc ccaaccaggt gtcctcccaa gtgtcctggc cccagctgct   1380
ctacacctac cagctcctcc actccctgga gctggtcctg agccgggcgg tgcgggacct   1440
gctcctgctg tccctgcccc ggcgcccggg ctcggcctgg gactcctaat gatctagaag   1500
atctgatatc ggatctgctg tgccttctag ttgccagcca tctgttgttt gcccctcccc   1560
cgtgccttcc ttgaccctgg aaggtgccac tcccactgtc ctttcctaat aaaatgagga   1620
aattgcatcg cattgtctga gtaggtgtca ttctattctg gggggtgggg tggggcagga   1680
cagcaagggg gaggattggg aagacaatag caggcatgct ggggatgcgg tgggctctat   1740
gggtacccag gtgctgaaga attgacccgg ttcctcctgg gccagaaaga agcaggcaca   1800
tccccttctc tgtgacacac cctgtccacg ccccctggttc ttagttccag ccccactcat   1860
aggacactca tagctcagga gggctccgcc ttcaatccca cccgctaaag tacttggagc   1920
ggtctctccc tccctcatca gcccaccaaa ccaaacctag cctccaagag tgggaagaaa   1980
ttaaagcaag ataggctatt aagtgcagag ggagagaaaa tgcctccaac atgtgaggaa   2040
gtaatgagag aaatcataga atttcttccg cttcctcgct cactgactcg ctgcgctcgg   2100
tcgttcggct gcggcgagcg gtatcagctc actcaaaggc ggtaatacgg ttatccacag   2160
aatcagggga taacgcagga agaacatgt gagcaaaagg ccagcaaaag gccaggaacc   2220
gtaaaaaggc cgcgttgctg gcgttttttcc ataggctccg ccccccctgac gagcatcaca   2280 aaaatcgacg ctcaagtcag aggtggcgaa acccgacagg actataaaga taccaggcgt   2340
ttccccctgg aagctccctc gtgcgctctc ctgttccgac cctgccgctt accggatacc   2400
tgtccgcctt tctcccttcg ggaagcgtgg cgctttctca tagctcacgc tgtaggtatc   2460
tcagttcggt gtaggtcgtt cgctccaagc tgggctgtgt gcacgaaccc cccgttcagc   2520
ccgaccgctg cgccttatcc ggtaactatc gtcttgagtc aacccggta agacacgact   2580 tatcgccact ggcagcagcc actggtaaca ggattagcag agcgaggtat gtaggcggtg   2640
ctacagagtt cttgaagtgg tggcctaact acggctacac tagaagaaca gtatttggta   2700
tctgcgctct gctgaagcca gttaccttcg gaaaaagagt ggtagctctt gatccggca   2760 aacaaaccac cgctggtagc ggtggttttt tgtttgcaa gcagcagatt acgcgcagaa   2820
aaaaaggatc tcaagaagat cctttgatct ttctacggg gtctgacgct cagtggaacg   2880
aaaactcacg ttaagggatt ttggtcatga gattatcaaa aaggatcttc acctagatcc   2940
ttttaaatta aaaatgaagt tttaaatcaa tctaaagtat atatgagtaa acttggtctg   3000
acagttacca atgcttaatc agtgaggcac ctatctcagc gatctgtcta tttcgttcat   3060
ccatagttgc ctgactcggg ggggggggc gctgaggtct gcctcgtgaa gaaggtgttg   3120
ctgactcata ccaggcctga atcgccccat catccagcca gaaagtgagg gagccacggt   3180
tgatgagagc tttgttgtag gtggaccagt tggtgatttt gaacttttgc tttgccacgg   3240
aacggtctgc gttgtcggga agatgcgtga tctgatcctt caactcagca aaagttcgat   3300
ttattcaaca aagccgccgt cccgtcaagt cagcgtaatg ctctgccagt gttacaacca   3360
attaaccaat tctgattaga aaaactcatc gagcatcaaa tgaaactgca atttattcat   3420
```

```
atcaggatta tcaataccat attttttgaaa aagccgtttc tgtaatgaag gagaaaactc    3480
accgaggcag ttccatagga tggcaagatc ctggtatcgg tctgcgattc cgactcgtcc    3540
aacatcaata caacctatta atttccctc gtcaaaaata aggttatcaa gtgagaaatc    3600
accatgagtg acgactgaat ccggtgagaa tggcaaaagc ttatgcattt ctttccagac    3660
ttgttcaaca ggccagccat tacgctcgtc atcaaaatca ctcgcatcaa ccaaaccgtt    3720
attcattcgt gattgcgcct gagcgagacg aaatacgcga tcgctgttaa aaggacaatt    3780
acaaacagga atcgaatgca accggcgcag gaacactgcc agcgcatcaa caatatttc    3840 acctgaatca ggatattctt ctaataccctg gaatgctgtt ttcccgggga tcgcagtggt    3900
gagtaaccat gcatcatcag gagtacggat aaaatgcttg atggtcggaa gaggcataaa    3960
ttccgtcagc cagtttagtc tgaccatctc atctgtaaca tcattggcaa cgctacctttt    4020 gccatgtttc agaaacaact ctggcgcatc gggcttccca tacaatcgat agattgtcgc    4080
acctgattgc ccgacattat cgcgagccca tttatacccca tataaatcag catccatgtt    4140
ggaatttaat cgcggcctcg agcaagacgt ttcccgttga atatggctca taacacccct    4200
tgtattactg tttatgtaag cagacagttt tattgttcat gatgatatat ttttatcttg    4260
tgcaatgtaa catcagagat tttgagacac aacgtggatc atccagacat gataagatac    4320
attgatgagt ttggacaaac cacaactaga atgcagtgaa aaaaatgctt tatttgtgaa    4380
atttgtgatg ctattgcttt atttgtaacc attataagct gcaataaaca agttaacaac    4440
aacaattgca ttcattttat gtttcaggtt caggggagg tgtgggaggt ttttttaaagc    4500 aagtaaaacc tctacaaatg tggtatggct gattatgatc gtcgaggatc cgttaaccga    4560
tatccgcgaa ttctcattag ggcttgtggg gagcgctctc gacctgcccc gggaggctcc    4620
agtcgctggg cttcccgtag tcggtgaggt cctgcgccga cacctggatg cagtacttgg    4680 cgtgggctt cgagttccgg agggtgaagg tcgtggcctc gatggggccg acttggcgga    4740
agtgggaggc gcctcggcgc cggtagcgga ggcggtactt gagcgagaag atgtccggga    4800
agggccagga ggccgggggg tgccagagca cctgcaggcg ctggcccgcc gtgcgcaggc    4860
gcacgccctc cggcgggtcc ggcttgatga tccgctccgc cacgaaggcc aggaggctgc    4920
tgctggcgcc gcccgggtgc accgccgtga cgttgagcat gtagggcacc gtggagaaca    4980
ggtgcacgtc ggggatggtg cagcgggagg cctgggggct ccgctgcagg cagggctggc    5040
tctgctgctg ggtggccacg ccgagccggt acgtggcgat gaaggacgtg gacctggtgg    5100
agttgggcgc ttgcagcggg gtccaggagc agtccacggc cacggggtag cgcgaggcgt    5160
ggcactgcac ccggggctgg ctcagggcca cgagcgccgt ctcggtatac ccggcgagc    5220 ggctggccca gagcgccagg ctcaggaaca ggagcttcga catttcttca caaacgtcga    5280
cagatccaaa cgctcctccg acgtccccag gcagaatggc ggttccctaa cgagcattg    5340 cttatataga cctcccatta ggcacgccta ccgcccattt acgtcaatgg aacgcccatt    5400
tgcgtcattg cccctcccca ttgacgtcaa tgggatgta cttggcagcc atcgcgggcc    5460
atttaccgcc attgacgtca atgggagtac tgccaatgta ccctggcgta cttccaatag    5520
taatgtactt gccaagttac tattaataga tattgatgta ctgccaagtg gccatttac    5580 cgtcattgac gtcaataggg ggcgtgagaa cggatatgaa tggcaatga ccatcctaa    5640 agaccatgag gccctttcgt ctcgcgcgtt tcggtgatga cggtgaaaac ctctgacaca    5700
tgcagctccc ggagacggtc acagcttgtc tgtaagcgga tgccgggagc agacaagccc    5760
gtcagggcgc gtcagcgggt gttggcgggt gtcggggctg gcttaactat gcggcatcag    5820
```

-continued

```
agcagattgt actgagagtg caccatatgc ggtgtgaaat accgcacaga tgccgtaagga    5880 gaaaataccg catcagattg gctattgg                                       5908

<210> SEQ ID NO 11
<211> LENGTH: 6025
<212> TYPE: DNA
<213> ORGANISM: Artificial Sequence
<220> FEATURE:
<223> OTHER INFORMATION: synthetic dual-promoter expression vector
      plasmid AG197 with human cytomegalovirus (CMV) promoter for murine
      IL-27 Epstein-Barr virus-induced gene 3 (EBI3) beta subunit
      expression and simian CMV promoter for murine IL-27 p28 alpha
      subunit expression

<400> SEQUENCE: 11
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660 ctcgtttagt gaaccgtcag atcgcctgga dacgccatcc acgctgtttt gacctccata     720
gaagacaccg ggaccgatcc agcctccgcg gcacgtgaag aaatgtcgaa gctcctgttc     780
ctgagcctgg cgctctgggc cagccgctcg ccggggtata ccgagacggc gctcgtggcc     840
ctgagccagc ccgggtgca gtgccacgcc tcgcgctacc ccgtggccgt ggactgctcc     900
tggaccccgc tgcaagcgcc caactccacc aggtccacgt ccttcatcgc cacgtaccgg     960
ctcggcgtgg ccacccagca gcagagccag ccctgcctgc agcggagccc ccaggcctcc    1020
cgctgcacca tccccgacgt gcacctgttc tccacggtgc cctacatgct caacgtcacg    1080
gcggtgcacc cgggcggcgc cagcagcagc ctcctggcct tcgtggcgga gcggatcatc    1140
aagccggacc cgccggaggg cgtgcgcctg cgcacgcgg ccagcgcct gcaggtgctc     1200 tggcaccccc cggcctcctg gcccttcccg gacatcttct cgctcaagta ccgcctccgc    1260
taccggcgcc gaggcgcctc ccacttccgc caagtcggcc catcgaggc cacgaccttc     1320 accctccgga actcgaagcc ccacgccaag tactgcatcc aggtgtcggc gcaggacctc    1380
accgactacg ggaagcccag cgactggagc ctccgggggc aggtcgagag cgctccccac    1440
aagccctaat gaggaattcg ctagcggcgc gccagatctg atatcggatc tgctgtgcct    1500
tctagttgcc agccatctgt tgtttgcccc tcccccgtgc cttccttgac cctggaaggt    1560
gccactccca ctgtcctttc ctaataaaat gaggaaattg catcgcattg tctgagtagg    1620
tgtcattcta ttctgggggg tggggtgggg caggacagca agggggagga ttgggaagac    1680
aatagcaggc atgctgggga tgcggtgggc tctatggta cccaggtgct gaagaattga     1740
cccggttcct cctgggccag aaagaagcag gcacatcccc ttctctgtga cacaccctgt    1800
ccacgcccct ggttcttagt tccagcccca ctcataggac actcataget caggagggct    1860
```

```
ccgccttcaa tcccacccgc taaagtactt ggagcggtct ctccctccct catcagccca    1920
ccaaaccaaa cctagcctcc aagagtggga agaaattaaa gcaagatagg ctattaagtg    1980
cagagggaga gaaaatgcct ccaacatgtg aggaagtaat gagagaaatc atagaatttc    2040
ttccgcttcc tcgctcactg actcgctgcg ctccgtcgtt cggctgcggc gagcggtatc    2100
agctcactca aaggcggtaa tacggttatc cacagaatca ggggataacg caggaaagaa    2160
catgtgagca aaaggccagc aaaaggccag gaaccgtaaa aaggccgcgt tgctggcgtt    2220
tttccatagg ctccgccccc ctgacgagca tcacaaaaat cgacgctcaa gtcagaggtg    2280
gcgaaacccg acaggactat aaagatacca ggcgtttccc cctggaagct ccctcgtgcg    2340
ctctcctgtt ccgaccctgc cgcttaccgg atacctgtcc gcctttctcc cttcgggaag    2400
cgtggcgctt tctcatagct cacgctgtag gtatctcagt tcggtgtagg tcgttcgctc    2460
caagctgggc tgtgtgcacg aaccccccgt tcagcccgac cgctgcgcct tatccggtaa    2520
ctatcgtctt gagtccaacc cggtaagaca cgacttatcg ccactggcag cagccactgg    2580
taacaggatt agcagagcga ggtatgtagg cggtgctaca gagttcttga agtggtggcc    2640
taactacggc tacactagaa gaacagtatt tggtatctgc gctctgctga gccagttac    2700 cttcggaaaa agagttggta gctcttgatc cggcaaacaa accaccgctg gtagcggtgg    2760
tttttttgtt tgcaagcagc agattacgcg cagaaaaaaa ggatctcaag aagatccttt    2820
gatcttttct acggggtctg acgctcagtg gaacgaaaac tcacgttaag ggattttggt    2880
catgagatta tcaaaaagga tcttcaccta gatccttta aattaaaaat gaagttttaa    2940
atcaatctaa agtatatatg agtaaacttg gtctgacagt taccaatgct taatcagtga    3000
ggcacctatc tcagcgatct gtctatttcg ttcatccata gttgcctgac tcggggggg    3060 ggggcgctga ggtctgcctc gtgaagaagg tgttgctgac tcataccagg cctgaatcgc    3120
cccatcatcc agccagaaag tgagggagcc acggttgatg agagctttgt tgtaggtgga    3180
ccagttggtg attttgaact tttgctttgc cacggaacgg tctgcgttgt cgggaagatg    3240
cgtgatctga tccttcaact cagcaaaagt tcgatttatt caacaaagcc gccgtcccgt    3300
caagtcagcg taatgctctg ccagtgttac aaccaattaa ccaattctga ttagaaaaac    3360
tcatcgagca tcaaatgaaa ctgcaattta ttcatatcag gattatcaat accatatttt    3420
tgaaaaagcc gtttctgtaa tgaaggagaa aactcaccga gcagttcca taggatggca    3480 agatcctggt atcggtctgc gattccgact cgtccaacat caatacaacc tattaatttc    3540
ccctcgtcaa aaataaggtt atcaagtgag aaatcaccat gagtgacgac tgaatccggt    3600
gagaatggca aaagcttatg catttctttc cagacttgtt caacaggcca gccattacgc    3660
tcgtcatcaa aatcactcgc atcaaccaaa ccgttattca ttcgtgattg cgcctgagcg    3720
agacgaaata cgcgatcgct gttaaaagga caattacaaa caggaatcga atgcaaccgg    3780
cgcaggaaca ctgccagcgc atcaacaata ttttcacctg aatcaggata ttcttctaat    3840
acctggaatg ctgttttccc ggggatcgca gtggtgagta accatgcatc atcaggagta    3900
cggataaaat gcttgatggt cggaagaggc ataaattccg tcagccagtt tagtctgacc    3960
atctcatctg taacatcatt ggcaacgcta cctttgccat gtttcagaaa caactctggc    4020
gcatcgggct tcccatacaa tcgatagatt gtcgcacctg attgcccgac attatcgcga    4080
gcccatttat acccatataa atcagcatcc atgttggaat ttaatcgcgg cctcgagcaa    4140
gacgtttccc gttgaatatg gctcataaca ccccttgtat tactgtttat gtaagcagac    4200
agttttattg ttcatgatga tatattttta tcttgtgcaa tgtaacatca gagattttga    4260
```

| | | | |
|---|---|---|---|
| gacacaacgt | ggatcatcca | gacatgataa | gatacattga tgagtttgga caaaccacaa | 4320 |
| ctagaatgca | gtgaaaaaaa | tgctttattt | gtgaaatttg tgatgctatt gctttatttg | 4380 |
| taaccattat | aagctgcaat | aaacaagtta | acaacaacaa ttgcattcat tttatgtttc | 4440 |
| aggttcaggg | ggaggtgtgg | gaggtttttt | aaagcaagta aaacctctac aaatgtggta | 4500 |
| tggctgatta | tgatcgtcga | ggatctgttt | aaactctaga tcattaggag tcccaggccg | 4560 |
| agcccgggcg | ccggggcagg | gacagcagga | gcaggtcccg caccgcccgg ctcaggacca | 4620 |
| gctccaggga | gtggaggagc | tggtaggtgt | agagcagctg gggccaggac acttgggagg | 4680 |
| acacctggtt | ggggccgccc | agggccccga | ggggcagctt cttttcctct tcttcctcct | 4740 |
| cttcctcttc | ctccttgtcc | tcctcctcct | tggagcactt gaagcccgcg gccaggactt | 4800 |
| ggaagcggag | gtgcctgtgc | aggtcccgga | ggtccagcct catggcccac agctgctccc | 4860 |
| tctcggagct | ggtccaggtc | ccctgggtcc | ccagcccgcc cagcatggcc gggaacggcc | 4920 |
| ggagcgtggt | ggcgaggaag | cagaggcgct | cggagtcgga gaggtggtgc caggcttgga | 4980 |
| acgtcaggga | gacgttgggg | aggtggtagc | ccaggggcag gaggtccagg ttcacgccgg | 5040 |
| gcaggcgcga | ctcggcgaag | ctgtggacgt | agccctggac ctcggagagc agcttccggg | 5100 |
| cgaggtacag | gctgacggtg | aactccctgc | gcagctcctg gaggctcagg ggatccgtgg | 5160 |
| ggaagcccca | gctccccgct | tggaccagga | ggaggggcag gagcaggagc gacaggcgcc | 5220 |
| acccgaggtc | cccggtgacc | tggcccattt | cttgtcgaca gatccaaacg ctcctccgac | 5280 |
| gtccccaggc | agaatggcgg | ttccctaaac | gagcattgct tatatagacc tcccattagg | 5340 |
| cacgcctacc | gcccatttac | gtcaatggaa | cgcccatttg cgtcattgcc cctcccatt | 5400 |
| gacgtcaatg | gggatgtact | tggcagccat | cgcgggccat ttaccgccat tgacgtcaat | 5460 |
| gggagtactg | ccaatgtacc | ctggcgtact | tccaatagta atgtacttgc caagttacta | 5520 |
| ttaatagata | ttgatgtact | gccaagtggg | ccatttaccg tcattgacgt caataggggg | 5580 |
| cgtgagaacg | gatatgaatg | gcaatgagc | catcccattg acgtcaatgg tgggtggtcc | 5640 |
| tattgacgtc | aatgggcatt | gagccaggcg | ggccatttac cgtaattgac gtcaatgggg | 5700 |
| gaggcgccat | atacgtcaat | aggaccgccc | atatgacgtc aataggtaag accatgaggc | 5760 |
| cctttcgtct | cgcgcgtttc | ggtgatgacg | gtgaaaacct ctgacacatg cagctcccgg | 5820 |
| agacggtcac | agcttgtctg | taagcggatg | ccggagcag acaagcccgt cagggcgcgt | 5880 |
| cagcgggtgt | tggcgggtgt | cggggctggc | ttaactatgc ggcatcagag cagattgtac | 5940 |
| tgagagtgca | ccatatgcgg | tgtgaaatac | cgcacagatg cgtaaggaga aaataccgca | 6000 |
| tcagattggc | tattggcatt | atgcc | | 6025 |

<210> SEQ ID NO 12
<211> LENGTH: 4711
<212> TYPE: DNA
<213> ORGANISM: Artificial Sequence
<220> FEATURE:
<223> OTHER INFORMATION: synthetic expression vector plasmid AG214 for human IL-27 Epstein-Barr virus-induced gene 3 (EBI3) beta subunit expression

<400> SEQUENCE: 12

| | | | |
|---|---|---|---|
| cctggccatt | gcatacgttg | tatccatatc | ataatatgta catttatatt ggctcatgtc | 60 |
| caacattacc | gccatgttga | cattgattat | tgactagtta ttaatagtaa tcaattacgg | 120 |
| ggtcattagt | tcatagccca | tatatggagt | tccgcgttac ataacttacg gtaaatggcc | 180 |
| cgcctggctg | accgcccaac | gacccccgcc | cattgacgtc aataatgacg tatgttccca | 240 |

```
tagtaacgcc aatagggact ttccattgac gtcaatgggt ggagtattta cggtaaactg    300
cccacttggc agtacatcaa gtgtatcata tgccaagtac gccccctatt gacgtcaatg    360
atggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg gcggtaggc gtgtacggtg ggaggtctat ataagcagag    660
ctcgtttagt gaaccgtcag atcgcctgga cgccatcc acgctgtttt gacctccata    720
gaagacaccg ggaccgatcc agcctccgcg ggaagaaatg acgccgcagc tgcttctggc    780
tctggtcctc tgggccagct gccctccgtg cagcggacgc aagggtcctc cagctgccct    840 gacctgccc agagtgcagt gcagagcctc gcgctacccc atcgctgtgg actgctcctg    900 gaccttcca cctgcaccca actccactc ccctgtctcc ttcatcgcca cgtaccggct    960
cggcatggcc gctagggtc acagctggcc ctgcctgcag cagacgccca catctacttc   1020
ctgcaccatc actgacgtgc agctgttctc catggctccc tacgtcctca acgtcacggc   1080
ggtgcacccg tggggctctt caagcagctt cgtccctttc atcactgagc acatcatcaa   1140
gccggaccca ccggagggag tgcgcctgtc tcctctcgcg gagcgccagc tgcaggtgca   1200
gtgggagccc ccaggttcct ggcccttccc ggagatcttc tcgctcaagt actggatcag   1260
atacaagcgc cagggcgccg ctagattcca cagagtcggc cccatcgagg ccacgtcttt   1320
catcctccga gcggtccgac ccagagcccg atactacgtg caggtggctg cgcaggacct   1380
caccgactac ggggagctta gcgactggag cctcccggct acagcaacta tgagtttggg   1440
aaagtaatga gaattcgcgg atatcggtta acggatccag atctgctgtg ccttctagtt   1500
gccagccatc tgttgtttgc ccctcccccg tgccttcctt gaccctggaa ggtgccactc   1560
ccactgtcct ttcctaataa aatgaggaaa ttgcatcgca ttgtctgagt aggtgtcatt   1620
ctattctggg gggtggggtg gggcaggaca gcaaggggga ggattgggaa gacaatagca   1680
ggcatgctgg ggatgcggtg ggctctatgg gtacccaggt gctgaagaat tgacccggtt   1740
cctcctgggc cagaaagaag caggcacatc cccttctctg tgacacaccc tgtccacgcc   1800
cctggttctt agttccagcc ccactcatag gacactcata gctcaggagg ctccgccttt   1860
caatcccacc cgctaaagta cttggagcgg tctctccctc cctcatcagc ccaccaaacc   1920
aaacctagcc tccaagagtg ggaagaaatt aaagcaagat aggctattaa gtgcagaggg   1980
agagaaaatg cctccaacat gtgaggaagt aatgagagaa atcatagaat tcttccgct   2040 tcctcgctca ctgactcgct gcgctcggtc gttcggctgc ggcgagcggt atcagctcac   2100
tcaaaggcgg taatacggtt atccacagaa tcagggggata acgcaggaaa gaacatgtga   2160
gcaaaaggcc agcaaaaggc caggaaccgt aaaaaggccg cgttgctggc gttttttccat   2220 aggctccgcc cccctgacga gcatcacaaa aatcgacgct caagtcagag gtggcgaaac   2280
ccgacaggac tataaagata ccaggcgttt ccccctggaa gctccctcgt gcgctctcct   2340
gttccgaccc tgccgcttac cggatacctg tccgcctttc tcccttcggg aagcgtggcg   2400
ctttctcata gctcacgctg taggtatctc agttcggtgt aggtcgttcg ctccaagctg   2460
ggctgtgtgc acgaaccccc cgttcagccc gaccgctgcg ccttatccgg taactatcgt   2520
cttgagtcca acccggtaag acacgactta tcgccactgg cagcagccac tggtaacagg   2580
attagcagag cgaggtatgt aggcggtgct acagagttct tgaagtggtg gcctaactac   2640
```

```
ggctacacta gaaggacagt atttggtatc tgcgctctgc tgaagccagt taccttcgga    2700
aaaagagttg gtagctcttg atccggcaaa caaaccaccg ctggtagcgg tggttttttt    2760
gtttgcaagc agcagattac gcgcagaaaa aaaggatctc aagaagatcc tttgatcttt    2820
tctacggggt ctgacgctca gtggaacgaa aactcacgtt aagggatttt ggtcatgaga    2880
ttatcaaaaa ggatcttcac ctagatcctt ttaaattaaa aatgaagttt taaatcaatc    2940
taaagtatat atgagtaaac ttggtctgac agttaccaat gcttaatcag tgaggcacct    3000
atctcagcga tctgtctatt tcgttcatcc atagttgcct gactcggggg gggggggcgc    3060
tgaggtctgc ctcgtgaaga aggtgttgct gactcatacc aggcctgaat cgccccatca    3120
tccagccaga aagtgaggga gccacggttg atgagagctt tgttgtaggt ggaccagttg    3180
gtgattttga acttttgctt tgccacgaaa cggtctgcgt tgtcgggaag atgcgtgatc    3240
tgatccttca actcagcaaa agttcgattt attcaacaaa gccgccgtcc cgtcaagtca    3300
gcgtaatgct ctgccagtgt tacaaccaat taaccaattc tgattagaaa aactcatcga    3360
gcatcaaatg aaactgcaat ttattcatat caggattatc aataccatat ttttgaaaaa    3420
gccgtttctg taatgaagga gaaaactcac cgaggcagtt ccataggatg caagatcct    3480 ggtatcggtc tgcgattccg actcgtccaa catcaataca acctattaat ttcccctcgt    3540
caaaaataag gttatcaagt gagaaatcac catgagtgac gactgaatcc ggtgagaatg    3600
gcaaaagctt atgcatttct ttccagactt gttcaacagg ccagccatta cgctcgtcat    3660
caaaatcact cgcatcaacc aaaccgttat tcattcgtga ttgcgcctga gcgagacgaa    3720
atacgcgatc gctgttaaaa ggacaattac aaacaggaat cgaatgcaac cggcgcagga    3780
acactgccag cgcatcaaca atattttcac ctgaatcagg atattcttct aatacctgga    3840
atgctgtttt cccggggatc gcagtggtga gtaaccatgc atcatcagga gtacggataa    3900
aatgcttgat ggtcggaaga ggcataaatt ccgtcagcca gtttagtctg accatctcat    3960
ctgtaacatc attggcaacg ctacctttgc catgtttcag aaacaactct ggcgcatcgg    4020
gcttcccata caatcgatag attgtcgcac ctgattgccc gacattatcg cgagcccatt    4080
tatacccata taaatcagca tccatgttgg aatttaatcg cggcctcgag caagacgttt    4140
cccgttgaat atggctcata caccccttg tattactgtt tatgtaagca gacagtttta    4200
ttgttcatga tgatatattt ttatcttgtg caatgtaaca tcagagattt tgagacacaa    4260
cgtggctttc cccccccccc cattattgaa gcatttatca gggttattgt ctcatgagcg    4320
gatacatatt tgaatgtatt tagaaaaata acaaataggg gttccgcgc acatttcccc    4380 gaaaagtgcc acctgacgtc taagaaacca ttattatcat gacattaacc tataaaaata    4440
ggcgtatcac gaggcccttt cgtctcgcgc gtttcggtga tgacggtgaa aacctctgac    4500
acatgcagct cccggagacg gtcacagctt gtctgtaagc ggatgccggg agcagacaag    4560
cccgtcaggg cgcgtcagcg ggtgttggcg ggtgtcgggg ctggcttaac tatgcggcat    4620
cagagcagat tgtactgaga gtgcaccata tgcggtgtga ataccgcac agatgcgtaa    4680 ggagaaaata ccgcatcaga ttggctattg                                     4711
```

<210> SEQ ID NO 13
<211> LENGTH: 4742
<212> TYPE: DNA
<213> ORGANISM: Artificial Sequence
<220> FEATURE:
<223> OTHER INFORMATION: synthetic expression vector plasmid AG215 for
      human IL-27 p28 alpha subunit expression

<400> SEQUENCE: 13

```
cctggccatt gcatacgttg tatccatatc ataatatgta catttatatt ggctcatgtc    60
caacattacc gccatgttga cattgattat tgactagtta ttaatagtaa tcaattacgg   120
ggtcattagt tcatagccca tatatggagt tccgcgttac ataacttacg gtaaatggcc   180
cgcctggctg accgcccaac gacccccgcc cattgacgtc aataatgacg tatgttccca   240
tagtaacgcc aatagggact ttccattgac gtcaatgggt ggagtattta cggtaaactg   300
cccacttggc agtacatcaa gtgtatcata tgccaagtac gccccctatt gacgtcaatg   360
atggtaaatg gcccgcctgg cattatgccc agtacatgac cttatgggac tttcctactt   420
ggcagtacat ctacgtatta gtcatcgcta ttaccatggt gatgcggttt tggcagtaca   480
tcaatgggcg tggatagcgg tttgactcac ggggatttcc aagtctccac cccattgacg   540
tcaatgggag tttgttttgg caccaaaatc aacgggactt tccaaaatgt cgtaacaact   600
ccgccccatt gacgcaaatg ggcggtaggc gtgtacggtg gaggtctat  ataagcagag   660
ctcgtttagt gaaccgtcag atcgcctgga dacgccatcc acgctgtttt gacctccata   720
gaagacaccg gaccgatcc  agcctccgcg ggcgcgcgtc gacaagaaat gggccagacg   780
gcggggacc  tcgggtggcg cctgtcgctt ctgctactgc ccctacttct ggtccaagcg   840
ggagtctggg gcttcccacg tccacccggc agaccgcagc tgagcctcca ggagcttcgc   900
agggagttca ccgtcagcct gcacctcgcc cggaagctgt gtccgaagt  cagaggccag   960
gcgcaccggt tcgccgagtc gcaccttcca ggcgtgaacc tgtacctctt gccccttggc  1020
gagcagctcc ccgacgtctc cctgacgttc aagcctggc  gacggctctc cgacccggag  1080
cgcctctgct tcatctcgac cacgctccag ccgttccacg ccctccttgg cgggttgggg  1140
acccagggga ggtggaccaa catggagagg atgcagctgt gggccatgag gcttgacctc  1200
cgggacctgc agaggcacct ccgcttccaa gtccttgccg ctggcttcaa cctccctgag  1260
gaggaggaag aagaggaaga agaggaagag gaggaacgga aggggctgct cccaggtgcc  1320
ctgggctcgg cgctgcaggg accggcacag gtgtcttggc cccagctgct ctcgacctac  1380
cggctccttc actccctgga gctggtcctg agccgggcgg tgcgggagct gcttctgttg  1440
tccaaagcgg gccactcggt ctggccgctt ggattcccca ccctctcgcc ccagccgtaa  1500
tgaggatcca gatctgctgt gccttctagt tgccagccat ctgttgtttg ccctccccc   1560
gtgccttcct tgaccctgga aggtgccact cccactgtcc tttcctaata aaatgaggaa  1620
attgcatcgc attgtctgag taggtgtcat tctattctgg ggggtggggt ggggcaggac  1680
agcaaggggg aggattggga agacaatagc aggcatgctg gggatgcggt gggctctatg  1740
ggtacccagg tgctgaagaa ttgacccggt tcctcctggg ccagaaagaa gcaggcacat  1800
ccccttctct gtgacacacc ctgtccacgc ccctggttct tagttccagc cccactcata  1860
ggacactcat agctcaggag ggctccgcct tcaatcccac ccgctaaagt acttggagcg  1920
gtctctccct ccctcatcag cccaccaaac caaacctagc ctccaagagt gggaagaaat  1980
taaagcaaga taggctatta agtgcagagg gagagaaaat gcctccaaca tgtgaggaag  2040
taatgagaga aatcatagaa tttcttccgc ttcctcgctc actgactcgc tgcgctcggt  2100
cgttcggctg cggcgagcgg tatcagctca ctcaaaggcg gtaatacggt tatccacaga  2160
atcagggat  aacgcaggaa agaacatgtg agcaaaaggc cagcaaaagg ccaggaaccg  2220
taaaaaggcc gcgttgctgg cgttttccca taggctccgc cccctgacg  agcatcacaa  2280
aaatcgacgc tcaagtcaga ggtggcgaaa cccgacagga ctataaagat accaggcgtt  2340
tccccctgga agctccctcg tgcgctctcc tgttccgacc ctgccgctta ccggatacct  2400
```

```
gtccgccttt ctcccttcgg gaagcgtggc gctttctcat agctcacgct gtaggtatct    2460
cagttcggtg taggtcgttc gctccaagct gggctgtgtg cacgaacccc ccgttcagcc    2520
cgaccgctgc gccttatccg gtaactatcg tcttgagtcc aacccggtaa gacacgactt    2580
atcgccactg gcagcagcca ctggtaacag gattagcaga gcgaggtatg taggcggtgc    2640
tacagagttc ttgaagtggt ggcctaacta cggctacact agaagaacag tatttggtat    2700
ctgcgctctg ctgaagccag ttaccttcgg aaaaagagtt ggtagctctt gatccggcaa    2760
acaaaccacc gctggtagcg gtggtttttt tgtttgcaag cagcagatta cgcgcagaaa    2820
aaaaggatct caagaagatc ctttgatctt ttctacgggg tctgacgctc agtggaacga    2880
aaactcacgt taagggattt tggtcatgag attatcaaaa aggatcttca cctagatcct    2940
tttaaattaa aaatgaagtt ttaaatcaat ctaaagtata tatgagtaaa cttggtctga    3000
cagttaccaa tgcttaatca gtgaggcacc tatctcagcg atctgtctat ttcgttcatc    3060
catagttgcc tgactcgggg ggggggggcg ctgaggtctg cctcgtgaag aaggtgttgc    3120
tgactcatac caggcctgaa tcgccccatc atccagccag aaagtgaggg agccacggtt    3180
gatgagagct ttgttgtagg tggaccagtt ggtgattttg aacttttgct ttgccacgga    3240
acggtctgcg ttgtcgggaa gatgcgtgat ctgatccttc aactcagcaa aagttcgatt    3300
tattcaacaa agccgccgtc ccgtcaagtc agcgtaatgc tctgccagtg ttacaaccaa    3360
ttaaccaatt ctgattagaa aaactcatcg agcatcaaat gaaactgcaa tttattcata    3420
tcaggattat caataccata ttttgaaaa agccgtttct gtaatgaagg agaaaactca    3480
ccgaggcagt tccataggat ggcaagatcc tggtatcggt ctgcgattcc gactcgtcca    3540
acatcaatac aacctattaa tttcccctcg tcaaaaataa ggttatcaag tgagaaatca    3600
ccatgagtga cgactgaatc cggtgagaat ggcaaaagct tatgcatttc tttccagact    3660
tgttcaacag gccagccatt acgctcgtca tcaaaatcac tcgcatcaac caaaccgtta    3720
ttcattcgtg attgcgcctg agcgagacga atacgcgat cgctgttaaa aggacaatta    3780
caaacaggaa tcgaatgcaa ccggcgcagg aacactgcca gcgcatcaac aatatttca    3840
cctgaatcag gatattcttc taatacctgg aatgctgttt tcccggggat cgcagtggtg    3900
agtaaccatg catcatcagg agtacggata aaatgcttga tggtcggaag aggcataaat    3960
tccgtcagcc agtttagtct gaccatctca tctgtaacat cattggcaac gctacctttg    4020
ccatgtttca gaaacaactc tggcgcatcg ggcttcccat acaatcgata gattgtcgca    4080
cctgattgcc cgacattatc gcgagcccat ttatacccat ataaatcagc atccatgttg    4140
gaatttaatc gcggcctcga gcaagacgtt cccgttgaa tatggctcat aacacccctt    4200
gtattactgt ttatgtaagc agacagtttt attgttcatg atgatatatt tttatcttgt    4260
gcaatgtaac atcagagatt ttgagacaca acgtggcttt ccccccccc ccattattga    4320
agcatttatc agggttattg tctcatgagc ggatacatat ttgaatgtat ttagaaaaat    4380
aaacaaatag ggttccgcg cacatttccc cgaaaagtgc cacctgacgt ctaagaaacc    4440
attattatca tgacattaac ctataaaaat aggcgtatca cgaggccctt tcgtctcgcg    4500
cgtttcggtg atgacggtga aaacctctga cacatgcagc tcccggagac ggtcacagct    4560
tgtctgtaag cggatgccgg gagcagacaa gcccgtcagg gcgcgtcagc gggtgttggc    4620
gggtgtcggg gctggcttaa ctatgcggca tcagagcaga ttgtactgag agtgcaccat    4680
atgcggtgtg aaataccgca cagatgcgta aggagaaaat accgcatcag attggctatt    4740
gg                                                                   4742
```

```
<210> SEQ ID NO 14
<211> LENGTH: 6030
<212> TYPE: DNA
<213> ORGANISM: Artificial Sequence
<220> FEATURE:
<223> OTHER INFORMATION: synthetic dual-promoter expression vector
      plasmid AG216 with human cytomegalovirus (CMV) promoter for human
      IL-27 p28 alpha subunit expression and simian CMV promoter for
      human IL-27 Epstein-Barr virus-induced gene 3 (EBI3) beta subunit
      expression

<400> SEQUENCE: 14
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg gcggtaggc gtgtacggtg gaggtctat ataagcagag      660 ctcgtttagt gaaccgtcag atcgcctgga gacgccatcc acgctgtttt gacctccata     720
gaagacaccg ggaccgatcc agcctccgcg gcgtcgacaa gaaatgggcc agacggcggg     780
ggacctcggg tggcgcctgt cgcttctgct actgccccta cttctggtcc aagcgggagt     840
ctggggcttc ccacgtccac ccggcagacc gcagctgagc ctccaggagc ttcgcaggga     900
gttcaccgtc agcctgcacc tcgcccggaa gctgttgtcc gaagtcagag gccaggcgca     960
ccggttcgcc gagtcgcacc ttccaggcgt gaacctgtac ctcttgcccc ttggcgagca    1020 gctcccccgac gtctccctga cgttccaagc ctggcgacgg ctctccgacc cggagcgcct    1080
ctgcttcatc tcgaccacgc tccagccgtt ccacgccctc cttggcgggt tggggaccca    1140
ggggaggtgg accaacatgg agaggatgca gctgtgggcc atgaggcttg acctccggga    1200
cctgcagagg cacctccgct tccaagtcct tgccgctggc ttcaacctcc ctgaggagga    1260
ggaagaagag gaagaagagg aagaggagga acggaagggg ctgctcccag gtgccctggg    1320
ctcggcgctg caggaccgg cacaggtgtc ttggcccag ctgctctcga cctaccggct     1380
ccttcactcc ctggagctgg tcctgagccg ggcggtgcgg gagctgcttc tgttgtccaa    1440
agcgggccac tcggtctggc cgcttggatt cccccaccctc tcgccccagc cgtaatgagg    1500
atctgatatc ggatctgctg tgccttctag ttgccagcca tctgttgttt gcccctcccc    1560
cgtgccttcc ttgaccctgg aaggtgccac tcccactgtc cttcctaat aaaatgagga    1620 aattgcatcg cattgtctga gtaggtgtca ttctattctg gggggtgggg tgggcagga     1680 cagcaagggg gaggattggg aagacaatag caggcatgct ggggatgcgg tgggctctat    1740
gggtacccag gtgctgaaga attgaccgg ttcctcctgg ccagaaaga agcaggcaca     1800 tccccttctc tgtgacacac cctgtccacg ccctggttc ttagttccag ccccactcat    1860
aggacactca tagctcagga gggctccgcc ttcaatccca cccgctaaag tacttggagc    1920
ggtctctccc tccctcatca gcccaccaaa ccaaacctag cctccaagag tgggaagaaa    1980
```

```
ttaaagcaag ataggctatt aagtgcagag ggagagaaaa tgcctccaac atgtgaggaa    2040
gtaatgagag aaatcataga atttcttccg cttcctcgct cactgactcg ctgcgctcgg    2100
tcgttcggct gcggcgagcg gtatcagctc actcaaaggc ggtaatacgg ttatccacag    2160
aatcagggga taacgcagga agaacatgt gagcaaaagg ccagcaaaag gccaggaacc     2220
gtaaaaaggc cgcgttgctg gcgttttcc ataggctccg ccccctgac gagcatcaca      2280 aaaatcgacg ctcaagtcag aggtggcgaa acccgacagg actataaaga taccaggcgt    2340 ttcccctgg aagctccctc gtgcgctctc ctgttccgac cctgccgctt accggatacc     2400
tgtccgcctt tctcccttcg ggaagcgtgg cgctttctca tagctcacgc tgtaggtatc    2460
tcagttcggt gtaggtcgtt cgctccaagc tgggctgtgt gcacgaaccc cccgttcagc    2520
ccgaccgctg cgccttatcc ggtaactatc gtcttgagtc caacccggta agacacgact    2580
tatcgccact ggcagcagcc actggtaaca ggattagcag agcgaggtat gtaggcggtg    2640
ctacagagtt cttgaagtgg tggcctaact acggctacac tagaagaaca gtatttggta    2700
tctgcgctct gctgaagcca gttaccttcg gaaaagagt tggtagctct tgatccggca     2760
aacaaaccac cgctggtagc ggtggttttt tgtttgcaa gcagcagatt acgcgcagaa     2820
aaaaaggatc tcaagaagat cctttgatct tttctacggg gtctgacgct cagtggaacg    2880
aaaactcacg ttaagggatt ttggtcatga gattatcaaa aaggatcttc acctagatcc    2940 tttttaaatta aaaatgaagt tttaaatcaa tctaaagtat atatgagtaa acttggtctg   3000
acagttacca atgcttaatc agtgaggcac ctatctcagc gatctgtcta tttcgttcat    3060
ccatagttgc ctgactcggg ggggggggc gctgaggtct gcctcgtgaa gaaggtgttg     3120
ctgactcata ccaggcctga atcgcccat catccagcca gaaagtgagg gagccacggt     3180
tgatgagagc tttgttgtag gtggaccagt tggtgatttt gaacttttgc tttgccacgg    3240
aacggtctgc gttgtcggga agatgcgtga tctgatcctt caactcagca aaagttcgat    3300
ttattcaaca agccgccgt cccgtcaagt cagcgtaatg ctctgccagt gttacaacca     3360
attaaccaat tctgattaga aaaactcatc gagcatcaaa tgaaactgca atttattcat    3420
atcaggatta tcaataccat attttgaaa aagccgtttc tgtaatgaag gagaaaactc     3480
accgaggcag ttccatagga tggcaagatc ctggtatcgg tctgcgattc cgactcgtcc    3540
aacatcaata caacctatta atttccctc gtcaaaata aggttatcaa gtgagaaatc     3600
accatgagtg acgactgaat ccggtgagaa tggcaaaagc ttatgcattt ctttccagac    3660
ttgttcaaca ggccagccat tacgctcgtc atcaaaatca ctcgcatcaa ccaaaccgtt    3720
attcattcgt gattgcgcct gagcgagacg aaatacgcga tcgctgttaa aaggacaatt    3780
acaaacagga atcgaatgca accggcgcag gaacactgcc agcgcatcaa caatatttttc   3840 acctgaatca ggatattctt ctaatacctg gaatgctgtt ttcccgggga tcgcagtggt    3900
gagtaaccat gcatcatcag gagtacggat aaaatgcttg atggtcggaa gaggcataaa   3960
ttccgtcagc cagtttagtc tgaccatctc atctgtaaca tcattggcaa cgctacctt    4020 gccatgtttc agaaacaact ctggcgcatc gggcttccca caatcgat agattgtcgc      4080 acctgattgc ccgacattat cgcgagccca tttatcccca tataatcag catccatgtt     4140 ggaatttaat cgcggcctcg agcaagacgt ttcccgttga atatggctca taacacccct    4200
tgtattactg tttatgtaag cagacagttt tattgttcat gatgatatat ttttatcttg    4260
tgcaatgtaa catcagagat tttgagacac aacgtggatc atccagacat gataagatac    4320
attgatgagt ttggacaaac cacaactaga atgcagtgaa aaaaatgctt tatttgtgaa    4380
```

| | |
|---|---|
| atttgtgatg ctattgcttt atttgtaacc attataagct gcaataaaca agttaacaac | 4440 |
| aacaattgca ttcattttat gtttcaggtt caggggagg tgtgggaggt tttttaaagc | 4500 |
| aagtaaaacc tctacaaatg tggtatggct gattatgatc gtcgaggatc cctcattact | 4560 |
| ttcccaaact catagttgct gtagccggga ggctccagtc gctaagctcc ccgtagtcgg | 4620 |
| tgaggtcctg cgcagccacc tgcacgtagt atcgggctct gggtcggacc gctcggagga | 4680 |
| tgaaagacgt ggcctcgatg gggccgactc tgtggaatct agcggcgccc tggcgcttgt | 4740 |
| atctgatcca gtacttgagc gagaagatct ccgggaaggg ccaggaacct ggggctccc | 4800 |
| actgcacctg cagctggcgc tccgcgagag gagacaggcg cactccctcc ggtgggtccg | 4860 |
| gcttgatgat gtgctcagtg atgaaaggga cgaagctgct tgaagagccc cacgggtgca | 4920 |
| ccgccgtgac gttgaggacg tagggagcca tggagaacag ctgcacgtca gtgatggtgc | 4980 |
| aggaagtaga tgtgggcgtc tgctgcaggc agggccagct gtgacccta gcggccatgc | 5040 |
| cgagccggta cgtggcgatg aaggagacag gggaggtgga gttgggtgca ggtggaaggg | 5100 |
| tccaggagca gtccacagcg atggggtagc gcgaggctct gcactgcact ctgggcaggg | 5160 |
| tcagggcagc tggaggaccc ttgcgtccgc tgcacggagg gcagctggcc cagaggacca | 5220 |
| gagccagaag cagctgcggc gtcatttctt gtttaaacgt cgacagatcc aaacgctcct | 5280 |
| ccgacgtccc caggcagaat ggcggttccc taaacgagca ttgcttatat agacctccca | 5340 |
| ttaggcacgc ctaccgccca tttacgtcaa tggaacgccc atttgcgtca ttgccctcc | 5400 |
| ccattgacgt caatggggat gtacttggca gccatcgcgg gccatttacc gccattgacg | 5460 |
| tcaatgggag tactgccaat gtaccctggc gtacttccaa tagtaatgta cttgccaagt | 5520 |
| tactattaat agatattgat gtactgccaa gtgggccatt taccgtcatt gacgtcaata | 5580 |
| ggggggcgtga aacggatat gaatgggcaa tgagccatcc cattgacgtc aatggtgggt | 5640 |
| ggtcctattg acgtcaatgg gcattgagcc aggcgggcca tttaccgtaa ttgacgtcaa | 5700 |
| tgggggaggc gccatatacg tcaataggac cgcccatatg acgtcaatag gtaagaccat | 5760 |
| gaggcccttt cgtctcgcgc gtttcggtga tgacggtgaa aacctctgac acatgcagct | 5820 |
| cccggagacg gtcacagctt gtctgtaagc ggatgccggg agcagacaag cccgtcaggg | 5880 |
| cgcgtcagcg ggtgttggcg ggtgtcgggg ctggcttaac tatgcggcat cagagcagat | 5940 |
| tgtactgaga gtgcaccata tgcggtgtga ataccgcac agatgcgtaa ggagaaaata | 6000 |
| ccgcatcaga ttggctattg gcattatgcc | 6030 |

<210> SEQ ID NO 15
<211> LENGTH: 6060
<212> TYPE: DNA
<213> ORGANISM: Artificial Sequence
<220> FEATURE:
<223> OTHER INFORMATION: synthetic dual-promoter expression vector
plasmid AG217 with human cytomegalovirus (CMV) promoter for human
IL-27 Epstein-Barr virus-induced gene 3 (EBI3) beta subunit
expression and simian CMV promoter for human IL-27 p28 alpha
subunit expression

<400> SEQUENCE: 15

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |

-continued

| | |
|---|---|
| cccacttggc agtacatcaa gtgtatcata tgccaagtac gcccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg ggaggtctat ataagcagag | 660 |
| ctcgtttagt gaaccgtcag atcgcctgga cgccatcc acgctgtttt gacctccata | 720 |
| gaagacaccg ggaccgatcc agcctccgcg ggcgcgcgtc gaaagaaatg acgccgcagc | 780 |
| tgcttctggc tctggtcctc tgggccagct gccctccgtg cagcggacgc aagggtcctc | 840 |
| cagctgccct gaccctgccc agagtgcagt gcagagcctc gcgctacccc atcgctgtgg | 900 |
| actgctcctg gaccctttcca cctgcaccca actccacctc ccctgtctcc ttcatcgcca | 960 |
| cgtaccggct cggcatggcc gctagggtc acagctggcc ctgcctgcag cagacgccca | 1020 |
| catctacttc ctgcaccatc actgacgtgc agctgttctc catggctccc tacgtcctca | 1080 |
| acgtcacggg ggtgcacccg tggggctctt caagcagctt cgtccctttc atcactgagc | 1140 |
| acatcatcaa gccggaccca ccggagggag tgcgcctgtc tcctctcgcg gagcgccagc | 1200 |
| tgcaggtgca gtgggagccc ccaggttcct ggccctttccc ggagatcttc tcgctcaagt | 1260 |
| actggatcag atacaagcgc cagggcgccg ctagattcca cagagtcggc cccatcgagg | 1320 |
| ccacgtcttt catcctccga gcggtccgac ccagagcccg atactacgtg caggtggctg | 1380 |
| cgcaggacct caccgactac ggggagctta gcgactggag cctcccggct acagcaacta | 1440 |
| tgagtttggg aaagtaatga ggaattcgct agcggcgcgc cagatctgat atcggatctg | 1500 |
| ctgtgccttc tagttgccag ccatctgttg tttgcccctc ccccgtgcct tccttgaccc | 1560 |
| tggaaggtgc cactcccact gtccctttcct aataaaatga ggaaattgca tcgcattgtc | 1620 |
| tgagtaggtg tcattctatt ctggggggtg gggtggggca ggacagcaag ggggaggatt | 1680 |
| gggaagacaa tagcaggcat gctggggatg cggtgggctc tatgggtacc caggtgctga | 1740 |
| agaattgacc cggttcctcc tgggccagaa agaagcaggc acatcccctt ctctgtgaca | 1800 |
| caccctgtcc acgccctggg ttcttagttc cagccccact cataggacac tcatagctca | 1860 |
| ggagggctcc gccttcaatc ccaccgcta aagtacttgg agcggtctct ccctccctca | 1920 |
| tcagcccacc aaaccaaacc tagcctccaa gagtgggaag aaattaaagc aagataggct | 1980 |
| attaagtgca gagggagaga aaatgcctcc aacatgtgag gaagtaatga gagaaatcat | 2040 |
| agaatttctt ccgcttcctc gctcactgac tcgctgcgct cggtcgttcg gctgcggcga | 2100 |
| gcggtatcag ctcactcaaa ggcggtaata cggttatcca cagaatcagg gataacgca | 2160 |
| ggaaagaaca tgtgagcaaa aggccagcaa aaggccagga accgtaaaaa ggccgcgttg | 2220 |
| ctggcgtttt tccataggct ccgcccccct gacgagcatc acaaaaatcg acgctcaagt | 2280 |
| cagaggtggc gaaacccgac aggactataa agataccagg cgtttccccc tggaagctcc | 2340 |
| ctcgtgcgct ctcctgttcc gaccctgccg cttaccggat acctgtccgc ctttctccct | 2400 |
| tcgggaagcg tggcgctttc tcatagctca cgctgtaggt atctcagttc ggtgtaggtc | 2460 |
| gttcgctcca agctgggctg tgtgcacgaa ccccccgttc agcccgaccg ctgcgcctta | 2520 |
| tccggtaact atcgtcttga gtccaacccg gtaagacacg acttatcgcc actggcagca | 2580 |
| gccactggta acaggattag cagagcgagg tatgtaggcg gtgctacaga gttcttgaag | 2640 |
| tggtggccta actacggcta cactagaaga acagtatttg gtatctgcgc tctgctgaag | 2700 |

```
ccagttacct tcggaaaaag agttggtagc tcttgatccg gcaaacaaac caccgctggt   2760
agcggtggtt ttttgtttg caagcagcag attacgcgca gaaaaaaagg atctcaagaa    2820
gatcctttga tcttttctac ggggtctgac gctcagtgga acgaaaactc acgttaaggg   2880
attttggtca tgagattatc aaaaaggatc ttcacctaga tccttttaaa ttaaaaatga   2940
agttttaaat caatctaaag tatatatgag taaacttggt ctgacagtta ccaatgctta   3000
atcagtgagg cacctatctc agcgatctgt ctatttcgtt catccatagt tgcctgactc   3060
gggggggggg ggcgctgagg tctgcctcgt gaagaaggtg ttgctgactc ataccaggcc   3120
tgaatcgccc catcatccag ccagaaagtg agggagccac ggttgatgag agctttgttg   3180
taggtggacc agttggtgat tttgaacttt tgctttgcca cggaacggtc tgcgttgtcg   3240
ggaagatgcg tgatctgatc cttcaactca gcaaaagttc gatttattca acaaagccgc   3300
cgtcccgtca agtcagcgta atgctctgcc agtgttacaa ccaattaacc aattctgatt   3360
agaaaaactc atcgagcatc aaatgaaact gcaatttatt catatcagga ttatcaatac   3420 catattttg aaaaagccgt ttctgtaatg aaggagaaaa ctcaccgagg cagttccata   3480
ggatggcaag atcctggtat cggtctgcga ttccgactcg tccaacatca atacaaccta   3540
ttaatttccc ctcgtcaaaa ataaggttat caagtgagaa atcaccatga gtgacgactg   3600
aatccggtga gaatggcaaa agcttatgca tttctttcca gacttgttca acaggccagc   3660
cattacgctc gtcatcaaaa tcactcgcat caaccaaacc gttattcatt cgtgattgcg   3720
cctgagcgag acgaaatacg cgatcgctgt taaaaggaca attacaaaca ggaatcgaat   3780
gcaaccggcg caggaacact gccagcgcat caacaatatt ttcacctgaa tcaggatatt   3840
cttctaatac ctggaatgct gttttcccgg ggatcgcagt ggtgagtaac catgcatcat   3900
caggagtacg gataaaatgc ttgatggtcg gaagaggcat aaattccgtc agccagttta   3960
gtctgaccat ctcatctgta acatcattgg caacgctacc tttgccatgt ttcagaaaca   4020
actctggcgc atcgggcttc ccatacaatc gatagattgt cgcacctgat tgcccgacat   4080
tatcgcgagc ccatttatac ccatataaat cagcatccat gttggaattt aatcgcggcc   4140
tcgagcaaga cgtttcccgt tgaatatggc tcataacacc ccttgtatta ctgtttatgt   4200
aagcagacag ttttattgtt catgatgata tatttttatc ttgtgcaatg taacatcaga   4260
gattttgaga cacaacgtgg atcatccaga catgataaga tacattgatg agtttggaca   4320
aaccacaact agaatgcagt gaaaaaaatg ctttatttgt gaaatttgtg atgctattgc   4380
tttatttgta accattataa gctgcaataa acaagttaac aacaacaatt gcattcattt   4440
tatgtttcag gttcagggg aggtgtggga ggttttttaa agcaagtaaa acctctacaa   4500
atgtggtatg gctgattatg atcgtcgagg atccggcgcc gtttaaactc attacggctg   4560
gggcgagagg gtggggaatc caagcggcca gaccgagtgg cccgctttgg acaacagaag   4620
cagctcccgc accgcccggc tcaggaccag ctccaggggag tgaaggagcc ggtaggtcga   4680
gagcagctgg ggccaagaca cctgtgccgg tccctgcagc gccgagccca gggcacctgg   4740
gagcagcccc ttccgttcct cctcttcctc ttcttcctct cttcctcct cctcaggag    4800 gttgaagcca gcggcaagga cttggaagcg gaggtgcctc tgcaggtccc ggaggtcaag   4860
cctcatggcc cacagctgca tcctctccat gttggtccac ctcccctggg tccccaaccc   4920
gccaaggagg gcgtggaacg gctggagcgt ggtcgagatg aagcagaggc gctccgggtc   4980
ggagagccgt cgccaggctt ggaacgtcag ggagacgtcg gggagctgct cgccaagggg   5040
caagaggtac aggttcacgc ctggaaggtg cgactcggcg aaccggtgcg cctggcctct   5100
```

```
gacttcggac aacagcttcc gggcgaggtg caggctgacg gtgaactccc tgcgaagctc    5160
ctggaggctc agctgcggtc tgccgggtgg acgtgggaag ccccagactc ccgcttggac    5220
cagaagtagg ggcagtagca gaagcgacag gcgccacccg aggtcccccg ccgtctggcc    5280
catttcttgt cgacagatcc aaacgctcct ccgacgtccc caggcagaat ggcggttccc    5340
taaacgagca tttgcttatat agacctccca ttaggcacgc ctaccgccca tttacgtcaa    5400
tggaacgccc atttgcgtca ttgcccctcc ccattgacgt caatgggat gtacttggca    5460 gccatcgcgg gccatttacc gccattgacg tcaatgggag tactgccaat gtaccctggc    5520
gtacttccaa tagtaatgta cttgccaagt tactattaat agatattgat gtactgccaa    5580
gtgggccatt taccgtcatt gacgtcaata ggggcgtga aacggatat gaatgggcaa    5640 tgagccatcc cattgacgtc aatggtgggt ggtcctattg acgtcaatgg gcattgagcc    5700
aggcgggcca tttaccgtaa ttgacgtcaa tgggggaggc gccatatacg tcaataggac    5760
cgcccatatg acgtcaatag gtaagaccat gaggcccttt cgtctcgcgc gtttcggtga    5820
tgacggtgaa aacctctgac acatgcagct cccggagacg tcacagctt gtctgtaagc    5880 ggatgccggg agcagacaag cccgtcaggg cgcgtcagcg ggtgttggcg ggtgtcgggg    5940
ctggcttaac tatgcggcat cagagcagat tgtactgaga gtgcaccata tgcggtgtga    6000
aataccgcac agatgcgtaa ggagaaaata ccgcatcaga ttggctattg cattatgcc    6060
```

```
<210> SEQ ID NO 16
<211> LENGTH: 570
<212> TYPE: DNA
<213> ORGANISM: Homo sapiens
<220> FEATURE:
<223> OTHER INFORMATION: human wildtype IL-23 p19 alpha subunit

<400> SEQUENCE: 16
```

```
atgctgggga gcagagctgt aatgctgctg ttgctgctgc cctggacagc tcagggcaga      60
gctgtgcctg ggggcagcag ccctgcctgg actcagtgcc agcagctttc acagaagctc     120
tgcacactgg cctggagtgc acatccacta gtgggacaca tggatctaag agaagaggga     180
gatgaagaga ctacaaatga tgttccccat atccagtgtg gagatggctg tgaccccaa     240 ggactcaggg acaacagtca gttctgcttg caaaggatcc accagggtct gattttttat     300
gagaagctgc taggatcgga tattttcaca ggggagcctt ctctgctccc tgatagccct     360
gtgggccagc ttcatgcctc cctactgggc ctcagccaac tcctgcagcc tgagggtcac     420
cactgggaga ctcagcagat tccaagcctc agtcccagcc agccatggca gcgtctcctt     480
ctccgcttca aaatccttcg cagcctccag gcctttgtgg ctgtagccgc ccgggtcttt     540
gcccatggag cagcaaccct gagtccctaa                                      570
```

```
<210> SEQ ID NO 17
<211> LENGTH: 189
<212> TYPE: PRT
<213> ORGANISM: Homo sapiens
<220> FEATURE:
<223> OTHER INFORMATION: human wildtype IL-23 p19 alpha subunit

<400> SEQUENCE: 17
```

Met Leu Gly Ser Arg Ala Val Met Leu Leu Leu Leu Pro Trp Thr
 1               5                  10                  15

Ala Gln Gly Arg Ala Val Pro Gly Gly Ser Ser Pro Ala Trp Thr Gln
            20                  25                  30

Cys Gln Gln Leu Ser Gln Lys Leu Cys Thr Leu Ala Trp Ser Ala His

```
            35                  40                  45
Pro Leu Val Gly His Met Asp Leu Arg Glu Glu Gly Asp Glu Glu Thr
 50                  55                  60

Thr Asn Asp Val Pro His Ile Gln Cys Gly Asp Gly Cys Asp Pro Gln
 65                  70                  75                  80

Gly Leu Arg Asp Asn Ser Gln Phe Cys Leu Gln Arg Ile His Gln Gly
                 85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 18
<211> LENGTH: 705
<212> TYPE: DNA
<213> ORGANISM: Mus musculus
<220> FEATURE:
<223> OTHER INFORMATION: murine wildtype IL-27 p28 alpha subunit

<400> SEQUENCE: 18
atgggccagg tgacaggaga ccttggctgg cggctcagcc tgttgctgct acccttgctt      60
ctggtacaag ctggttcctg ggggttccca acagaccccc tgagccttca agagctgcgc     120
agggaattca cagtcagcct gtaccttgcc aggaagctgc tctctgaggt tcagggctat     180
gtccacagct ttgctgaatc tcgattgcca ggagtgaacc tggacctcct gcccctggga     240
taccatcttc ccaatgtttc cctgactttc caggcatggc atcacctctc tgactctgag     300
agactctgct tcctcgctac cacacttcgg cccttccctg ccatgctggg agggctgggg     360
acccagggga cctggaccag ctcagagagg gagcagctgt gggccatgag ctggatctc     420 cgggacctgc acaggcacct ccgctttcag gtgctggctg caggattcaa atgttcaaag     480
gaggaggagg acaaggagga agaggaagag gaggaagaag aagaaaagaa gctgccccta     540
ggggctctgg gtggccccaa tcaggtgtca tcccaagtgt cctggcccca gctgctctat     600
acctaccagc tccttcactc cctggagctt gtcctgtctc gggctgttcg ggacctgctg     660
ctgctgtccc tgcccaggcg cccaggctca gcctgggatt cctaa                    705

<210> SEQ ID NO 19
<211> LENGTH: 234
<212> TYPE: PRT
<213> ORGANISM: Mus musculus
<220> FEATURE:
<223> OTHER INFORMATION: murine wildtype IL-27 p28 alpha subunit

<400> SEQUENCE: 19

Met Gly Gln Val Thr Gly Asp Leu Gly Trp Arg Leu Ser Leu Leu Leu
 1               5                  10                  15

Leu Pro Leu Leu Leu Val Gln Ala Gly Ser Trp Gly Phe Pro Thr Asp
            20                  25                  30

Pro Leu Ser Leu Gln Glu Leu Arg Arg Glu Phe Thr Val Ser Leu Tyr
```

```
                 35                  40                  45
Leu Ala Arg Lys Leu Leu Ser Glu Val Gln Gly Tyr Val His Ser Phe
 50                  55                  60
Ala Glu Ser Arg Leu Pro Gly Val Asn Leu Asp Leu Leu Pro Leu Gly
 65                  70                  75                  80
Tyr His Leu Pro Asn Val Ser Leu Thr Phe Gln Ala Trp His His Leu
                 85                  90                  95
Ser Asp Ser Glu Arg Leu Cys Phe Leu Ala Thr Thr Leu Arg Pro Phe
                100                 105                 110
Pro Ala Met Leu Gly Gly Leu Gly Thr Gln Gly Thr Trp Thr Ser Ser
                115                 120                 125
Glu Arg Glu Gln Leu Trp Ala Met Arg Leu Asp Leu Arg Asp Leu His
130                 135                 140
Arg His Leu Arg Phe Gln Val Leu Ala Ala Gly Phe Lys Cys Ser Lys
145                 150                 155                 160
Glu Glu Glu Asp Lys Glu Glu Glu Glu Glu Glu Glu Glu Glu Glu Lys
                165                 170                 175
Lys Leu Pro Leu Gly Ala Leu Gly Gly Pro Asn Gln Val Ser Ser Gln
                180                 185                 190
Val Ser Trp Pro Gln Leu Leu Tyr Thr Tyr Gln Leu Leu His Ser Leu
                195                 200                 205
Glu Leu Val Leu Ser Arg Ala Val Arg Asp Leu Leu Leu Ser Leu
                210                 215                 220
Pro Arg Arg Pro Gly Ser Ala Trp Asp Ser
225                 230

<210> SEQ ID NO 20
<211> LENGTH: 684
<212> TYPE: DNA
<213> ORGANISM: Mus musculus
<220> FEATURE:
<223> OTHER INFORMATION: murine wildtype IL-27 Epstein-Barr
      virus-induced gene 3 (EBI3) beta subunit

<400> SEQUENCE: 20
atgtccaagc tgctcttcct gtcacttgcc ctctgggcca gccgctcccc tggttacact      60
gaaacagctc tcgtggctct aagccagccc agagtgcaat gccatgcttc tcggtatccc     120
gtggccgtgg actgctcctg gactcctctc caggctccca actccaccag atccacgtcc     180
ttcattgcca cttacaggct cggtgtggcc acccagcagc agagccagcc ctgcctacaa     240
cggagccccc aggcctcccg atgcaccatc cccgacgtgc acctgttctc cacggtgccc     300
tacatgctaa atgtcactgc agtgcaccca ggcggcgcca gcagcagcct cctagccttt     360
gtggctgagc gaatcatcaa gccggaccct ccggaaggcg tgcgcctgcg cacagcggga     420
cagcgcctgc aggtgctctg gcatcccct gcttcctggc ctttcccgga catcttctct     480
ctcaagtacc gactccgcta ccggcgccga ggagcctctc acttccgcca ggtgggaccc     540
attgaagcca cgactttcac cctcaggaac tcgaaacccc atgccaagta ttgcatccag     600
gtgtcagctc aggacctcac agattatggg aaaccaagtg actggagcct ccctgggcaa     660
gtagaaagtg caccccataa gccc                                            684

<210> SEQ ID NO 21
<211> LENGTH: 228
<212> TYPE: PRT
<213> ORGANISM: Mus musculus
<220> FEATURE:
<223> OTHER INFORMATION: murine wildtype IL-27 Epstein-Barr
``` virus-induced gene 3 (EBI3) beta subunit

<400> SEQUENCE: 21

Met Ser Lys Leu Leu Phe Leu Ser Leu Ala Leu Trp Ala Ser Arg Ser
1               5                   10                  15

Pro Gly Tyr Thr Glu Thr Ala Leu Val Ala Leu Ser Gln Pro Arg Val
            20                  25                  30

Gln Cys His Ala Ser Arg Tyr Pro Val Ala Val Asp Cys Ser Trp Thr
        35                  40                  45

Pro Leu Gln Ala Pro Asn Ser Thr Arg Ser Thr Ser Phe Ile Ala Thr
    50                  55                  60

Tyr Arg Leu Gly Val Ala Thr Gln Gln Ser Gln Pro Cys Leu Gln
65                  70                  75                  80

Arg Ser Pro Gln Ala Ser Arg Cys Thr Ile Pro Asp Val His Leu Phe
                85                  90                  95

Ser Thr Val Pro Tyr Met Leu Asn Val Thr Ala Val His Pro Gly Gly
            100                 105                 110

Ala Ser Ser Ser Leu Leu Ala Phe Val Ala Glu Arg Ile Ile Lys Pro
            115                 120                 125

Asp Pro Pro Glu Gly Val Arg Leu Arg Thr Ala Gly Gln Arg Leu Gln
    130                 135                 140

Val Leu Trp His Pro Pro Ala Ser Trp Pro Phe Pro Asp Ile Phe Ser
145                 150                 155                 160

Leu Lys Tyr Arg Leu Arg Tyr Arg Arg Gly Ala Ser His Phe Arg
                165                 170                 175

Gln Val Gly Pro Ile Glu Ala Thr Thr Phe Thr Leu Arg Asn Ser Lys
            180                 185                 190

Pro His Ala Lys Tyr Cys Ile Gln Val Ser Ala Gln Asp Leu Thr Asp
            195                 200                 205

Tyr Gly Lys Pro Ser Asp Trp Ser Leu Pro Gly Gln Val Glu Ser Ala
    210                 215                 220

Pro His Lys Pro
225

<210> SEQ ID NO 22
<211> LENGTH: 687
<212> TYPE: DNA
<213> ORGANISM: Homo sapiens
<220> FEATURE:
<223> OTHER INFORMATION: human wildtype IL-27 Epstein-Barr virus-induced
      gene 3 (EBI3) beta subunit

<400> SEQUENCE: 22 atgacccgc agcttctcct ggcccttgtc ctctgggcca gctgcccgcc ctgcagtgga        60
aggaaagggc ccccagcagc tctgacactg ccccgggtgc aatgccgagc ctctcggtac       120
ccgatcgccg tggattgctc ctggaccctg ccgcctgctc caaactccac cagccccgtg       180
tccttcattg ccacgtacag gctcggcatg gctgcccggg ccacagctg ccctgcctg        240 cagcagacgc caacgtccac cagctgcacc atcacggatg tccagctgtt ctccatggct       300
ccctacgtgc tcaatgtcac cgccgtccac cctgggggct ccagcagcag cttcgtgcct       360
ttcataacag agcacatcat caagcccgac cctccagaag gcgtgcgcct aagcccctc       420 gctgagcgcc agctacaggt gcagtgggag cctcccgggt cctggccctt cccagagatc       480
ttctcactga agtactggat ccgttacaag cgtcagggag ctgcgcgctt ccaccgggtg       540
gggcccattg aagccacgtc cttcatcctc agggctgtgc ggccccgagc caggtactac       600

```
gtccaagtgg cggctcagga cctcacagac tacggggaac tgagtgactg gagtctcccc      660
gccactgcca caatgagcct gggcaag                                          687
```

<210> SEQ ID NO 23
<211> LENGTH: 229
<212> TYPE: PRT
<213> ORGANISM: Homo sapiens
<220> FEATURE:
<223> OTHER INFORMATION: human wildtype IL-27 Epstein-Barr virus-induced
      gene 3 (EBI3) beta subunit

<400> SEQUENCE: 23

```
Met Thr Pro Gln Leu Leu Leu Ala Leu Val Leu Trp Ala Ser Cys Pro
 1               5                  10                  15

Pro Cys Ser Gly Arg Lys Gly Pro Pro Ala Ala Leu Thr Leu Pro Arg
            20                  25                  30

Val Gln Cys Arg Ala Ser Arg Tyr Pro Ile Ala Val Asp Cys Ser Trp
        35                  40                  45

Thr Leu Pro Pro Ala Pro Asn Ser Thr Ser Pro Val Ser Phe Ile Ala
    50                  55                  60

Thr Tyr Arg Leu Gly Met Ala Ala Arg Gly His Ser Trp Pro Cys Leu
65                  70                  75                  80

Gln Gln Thr Pro Thr Ser Thr Ser Cys Thr Ile Thr Asp Val Gln Leu
                85                  90                  95

Phe Ser Met Ala Pro Tyr Val Leu Asn Val Thr Ala Val His Pro Trp
            100                 105                 110

Gly Ser Ser Ser Ser Phe Val Pro Phe Ile Thr Glu His Ile Ile Lys
        115                 120                 125

Pro Asp Pro Pro Glu Gly Val Arg Leu Ser Pro Leu Ala Glu Arg Gln
    130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
            180                 185                 190

Val Arg Pro Arg Ala Arg Tyr Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225
```

<210> SEQ ID NO 24
<211> LENGTH: 732
<212> TYPE: DNA
<213> ORGANISM: Homo sapiens
<220> FEATURE:
<223> OTHER INFORMATION: human wildtype IL-27 p28 alpha subunit

<400> SEQUENCE: 24

```
atgggccaga cggcaggcga ccttggctgg cggctcagcc tgttgctgct tcccttgctc      60
ctggttcaag ctggtgtctg gggattccca aggcccccag ggaggcccca gctgagcctg     120
caggagctgc ggagggagtt cacagtcagc ctgcatctcg ccaggaagct gctctccgag     180
gttcggggcc aggcccaccg ctttgcggaa tctcacctgc aggagtgaa cctgtacctc      240 ctgccctgg gagagcagct ccctgatgtt tccctgacct ccaggcctg gcgccgcctc      300
```

-continued

```
tctgacccgg agcgtctctg cttcatctcc accacgcttc agcccttcca tgccctgctg    360
ggagggctgg ggacccaggg ccgctggacc aacatggaga ggatgcagct gtgggccatg    420
aggctggacc tccgcgatct gcagcggcac ctccgcttcc aggtgctggc tgcaggattc    480
aacctcccgg aggaggagga ggaggaagag gaggaggagg aggaggagag gaaggggctg    540
ctcccagggg cactgggcag cgccttacag ggcccggccc aggtgtcctg ccccagctc     600 ctctccacct accgcctgct gcactccttg gagctcgtct tatctcgggc cgtgcgggag    660
ttgctgctgc tgtccaaggc tgggcactca gtctggccct ggggttccc aacattgagc    720 ccccagccct ga                                                       732
```

<210> SEQ ID NO 25
<211> LENGTH: 243
<212> TYPE: PRT
<213> ORGANISM: Homo sapiens
<220> FEATURE:
<223> OTHER INFORMATION: human wildtype IL-27 p28 alpha subunit

<400> SEQUENCE: 25

```
Met Gly Gln Thr Ala Gly Asp Leu Gly Trp Arg Leu Ser Leu Leu Leu
  1               5                  10                  15

Leu Pro Leu Leu Leu Val Gln Ala Gly Val Trp Gly Phe Pro Arg Pro
             20                  25                  30

Pro Gly Arg Pro Gln Leu Ser Leu Gln Glu Leu Arg Arg Glu Phe Thr
         35                  40                  45

Val Ser Leu His Leu Ala Arg Lys Leu Leu Ser Glu Val Arg Gly Gln
     50                  55                  60

Ala His Arg Phe Ala Glu Ser His Leu Pro Gly Val Asn Leu Tyr Leu
 65                  70                  75                  80

Leu Pro Leu Gly Glu Gln Leu Pro Asp Val Ser Leu Thr Phe Gln Ala
                 85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro
```

<210> SEQ ID NO 26
<211> LENGTH: 573
<212> TYPE: DNA
<213> ORGANISM: Artificial Sequence
<220> FEATURE:
<223> OTHER INFORMATION: synthetic human IL-23 p19 alpha subunit improved RNA with minimized inhibitory/instability sequences

<400> SEQUENCE: 26

```
atgctgggga gccgcgcggt catgctgctc ttgctgctcc cctggacggc ccagggccgg      60
gcggtgcccg ggggctcgag cccggcctgg acgcagtgcc agcagctcag ccagaagctc     120
tgcaccctgg cctggtcggc ccaccgctc gtgggccaca tggacctccg ggaggagggc      180
gacgaggaga cgaccaacga cgtccccac atccagtgcg cgacggctg cgaccccag       240
ggcctccggg acaactcgca gttctgcctg cagcgcatcc accagggcct gatcttctac     300
gagaagctgc tcggctcgga catcttcacg ggggagccgt cgctgctccc ggacagcccg     360
gtgggccagc tccacgcctc cctcctgggc ctctcgcaac ttctgcaacc ggagggccac     420
cactgggaga cgcagcagat cccgagcctc tcgcccagcc agccgtggca gcggctcctg     480
ctcagattca agatcttgcg ctccctccaa gccttcgtgg cggtcgccgc ccgggtcttc     540
gcccacggcg cggccaccct gagcccctga taa                                  573
```

<210> SEQ ID NO 27
<211> LENGTH: 708
<212> TYPE: DNA
<213> ORGANISM: Artificial Sequence
<220> FEATURE:
<223> OTHER INFORMATION: synthetic murine IL-27 p28 alpha subunit
    improved RNA with minimized inhibitory/instability sequences

<400> SEQUENCE: 27

```
atgggccagg tcaccgggga cctcgggtgg cgcctgtcgc tcctgctcct gcccctcctc      60
ctggtccaag cggggagctg gggcttcccc acggatcccc tgagcctcca ggagctgcgc     120
agggagttca ccgtcagcct gtacctgccc cggaagctgc tctccgaggt ccagggctac     180
gtccacagct cgccgagtc gcgcctgccc ggcgtgaacc tggacctcct gccctgggc      240
taccacctcc ccaacgtctc cctgacgttc aagcctggc accacctctc cgactccgag     300
cgcctctgct cctcgccac cacgctccgg ccgttcccgg ccatgctggg cgggctgggg     360
acccagggga cctggaccag ctccgagagg gagcagctgt gggccatgag gctggacctc     420
cgggacctgc acaggcacct ccgcttccaa gtcctggccg cgggcttcaa gtgctccaag     480
gaggaggagg acaaggagga agaggaagag gaggaagaag aggaaaagaa gctgcccctc     540
gggcgcctgg gcggccccaa ccaggtgtcc tcccaagtgt cctgccccca gctgctctac     600
acctaccagc cctccactc cctggagctg gtcctgagcc gggcggtgcg ggacctgctc     660
ctgctgtccc tgccccggcg cccggctcg gcctgggact cctaatga                   708
```

<210> SEQ ID NO 28
<211> LENGTH: 690
<212> TYPE: DNA
<213> ORGANISM: Artificial Sequence
<220> FEATURE:
<223> OTHER INFORMATION: synthetic murine IL-27 Epstein-Barr
    virus-induced gene 3 (EBI3) beta subunit improved RNA with
    minimized inhibitory/instability sequences

<400> SEQUENCE: 28

```
atgtcgaagc tcctgttcct gagcctggcg ctctgggcca gccgctcgcc ggggtatacc      60
gagacggcgc tcgtggccct gagccagccc cgggtgcagt gccacgcctc gcgctacccc     120
gtggccgtgg actgctcctg gacccgctg caagcgccca actccaccag gtccacgtcc      180
ttcatcgcca cgtaccggct cggcgtggcc acccagcagc agagccagcc ctgcctgcag     240
cggagccccc aggcctcccg ctgcaccatc cccgacgtgc acctgttctc cacggtgccc     300
```

```
tacatgctca acgtcacggc ggtgcacccg ggcggcgcca gcagcagcct cctggccttc    360
gtggcggagc ggatcatcaa gccggacccg ccggagggcg tgcgcctgcg cacggcgggc    420
cagcgcctgc aggtgctctg gcaccccccg gcctcctggc ccttcccgga catcttctcg    480
ctcaagtacc gcctccgcta ccggcgccga ggcgcctccc acttccgcca agtcggcccc    540
atcgaggcca cgaccttcac cctccggaac tcgaagcccc acgccaagta ctgcatccag    600
gtgtcggcgc aggacctcac cgactacggg aagcccagcg actggagcct cccggggcag    660
gtcgagagcg ctccccacaa gccctaatga                                     690
```

<210> SEQ ID NO 29
<211> LENGTH: 735
<212> TYPE: DNA
<213> ORGANISM: Artificial Sequence
<220> FEATURE:
<223> OTHER INFORMATION: synthetic human IL-27 p28 alpha subunit
      improved RNA with minimized inhibitory/instability sequences

<400> SEQUENCE: 29

```
atgggccaga cggcggggga cctcgggtgg cgcctgtcgc ttctgctact gcccctactt    60
ctggtccaag cgggagtctg gggcttccca cgtccacccg gcagaccgca gctgagcctc    120
caggagcttc gcagggagtt caccgtcagc ctgcacctcg cccggaagct gttgtccgaa    180
gtcagaggcc aggcgcaccg gttcgccgag tcgcaccttc aggcgtgaa cctgtacctc    240 ttgccccttg cgagcagct ccccgacgtc tccctgacgt tccaagcctg cgacgggctc    300
tccgacccgg agcgcctctg cttcatctcg accacgctcc agccgttcca cgccctcctt    360
ggcgggttgg ggacccaggg gaggtggacc aacatggaga ggatgcagct gtgggccatg    420
aggcttgacc tccgggacct gcagaggcac ctccgcttcc aagtccttgc cgctggcttc    480
aacctccctg aggaggagga agaagaggaa gaagaggaag aggaggaacg gaaggggctg    540
ctcccaggtg ccctgggctc ggcgctgcag ggaccggcac aggtgtcttg gccccagctg    600
ctctcgacct accggctcct tcactccctg gagctggtcc tgagccgggc ggtgcgggag    660
ctgcttctgt tgtccaaagc gggccactcg gtctggccgc ttggattccc caccctctcg    720
ccccagccgt aatga                                                     735
```

<210> SEQ ID NO 30
<211> LENGTH: 693
<212> TYPE: DNA
<213> ORGANISM: Artificial Sequence
<220> FEATURE:
<223> OTHER INFORMATION: synthetic human IL-27 Epstein-Barr
      virus-induced gene 3 (EBI3) beta subunit improved RNA with
      minimized inhibitory/instability sequences

<400> SEQUENCE: 30

```
atgacgccgc agctgcttct ggctctggtc tctgggccca gctgccctcc gtgcagcgga    60
cgcaagggtc ctccagctgc cctgaccctg cccagagtgc agtgcagagc ctcgcgctac    120
cccatcgctg tggactgctc ctggaccctt ccacctgcac ccaactccac ctcccctgtc    180
tccttcatcg ccacgtaccg gctcggcatg gccgctaggg gtcacagctg gccctgcctg    240
cagcagacgc ccacatctac ttcctgcacc atcactgacg tgcagctgtt ctccatggct    300
ccctacgtcc tcaacgtcac ggcggtgcac ccgtggggct cttcaagcag cttcgtccct    360
ttcatcactg agcacatcat caagccggac ccaccggagg gagtgcgcct gtctcctctc    420
gcggagcgcc agctgcaggt gcagtgggag cccccaggtt cctggcccct tccggagatc    480
```

| | | |
|---|---|---|
| ttctcgctca agtactggat cagatacaag cgccagggcg ccgctagatt ccacagagtc | 540 | |
| ggccccatcg aggccacgtc tttcatcctc cgagcggtcc gacccagagc ccgatactac | 600 | |
| gtgcaggtgg ctgcgcagga cctcaccgac tacggggagc ttagcgactg gagcctcccg | 660 | |
| gctacagcaa ctatgagttt gggaaagtaa tga | 693 | |

<210> SEQ ID NO 31
<211> LENGTH: 4024
<212> TYPE: DNA
<213> ORGANISM: Artificial Sequence
<220> FEATURE:
<223> OTHER INFORMATION: synthetic single expression cassette vector
      CMVkan vector backbone

<400> SEQUENCE: 31

| | |
|---|---|
| cctggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| atggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg ggcggtaggc gtgtacggtg gaggtctat ataagcagag | 660 |
| ctcgtttagt gaaccgtcag atcgcctgga cgccatcc acgctgtttt gacctccata | 720 |
| gaagacaccg gaccgatcc agcctccgcg ggcgcgcgtc gacgctagcg gcgcgccgcg | 780 |
| gccgccaatt gagatctgct gtgccttcta gttgccagcc atctgttgtt tgcccctccc | 840 |
| ccgtgccttc cttgaccctg gaaggtgcca ctcccactgt cctttcctaa taaaatgagg | 900 |
| aaattgcatc gcattgtctg agtaggtgtc attctattct ggggggtggg gtggggcagg | 960 |
| acagcaaggg ggaggattgg gaagacaata gcaggcatgc tggggatgcg gtgggctcta | 1020 |
| tgggtaccca ggtgctgaag aattgacccg gttcctcctg ggccagaaag aagcaggcac | 1080 |
| atccccttct ctgtgacaca ccctgtccac gcccctggtt cttagttcca gccccactca | 1140 |
| taggacactc atagctcagg agggctccgc cttcaatccc acccgctaaa gtacttggag | 1200 |
| cggtctctcc ctccctcatc agcccaccaa accaaaccta gcctccaaga gtgggaagaa | 1260 |
| attaaagcaa gataggctat taagtgcaga gggagagaaa atgcctccaa catgtgagga | 1320 |
| agtaatgaga gaaatcatag aatttcttcc gcttcctcgc tcactgactc gctgcgctcg | 1380 |
| gtcgttcggc tgcggcgagc ggtatcagct cactcaaagg cggtaatacg gttatccaca | 1440 |
| gaatcagggg ataacgcagg aaagaacatg tgagcaaaag gccagcaaaa ggccaggaac | 1500 |
| cgtaaaaagg ccgcgttgct ggcgtttttc cataggctcc gcccccctga cgagcatcac | 1560 |
| aaaaatcgac gctcaagtca gaggtggcga aacccgacag gactataaag ataccaggcg | 1620 |
| tttccccctg gaagctccct cgtgcgctct cctgttccga cctgccgct taccggatac | 1680 |
| ctgtccgcct ttctcccttc gggaagcgtg gcgctttctc atagctcacg ctgtaggtat | 1740 |
| ctcagttcgg tgtaggtcgt tcgctccaag ctgggctgtg tgcacgaacc cccgttcag | 1800 |
| cccgaccgct gcgccttatc cggtaactat cgtcttgagt ccaacccggt aagacacgac | 1860 |

```
ttatcgccac tggcagcagc cactggtaac aggattagca gagcgaggta tgtaggcggt    1920
gctacagagt tcttgaagtg gtggcctaac tacggctaca ctagaagaac agtatttggt    1980
atctgcgctc tgctgaagcc agttaccttc ggaaaaagag ttggtagctc ttgatccggc    2040
aaacaaacca ccgctggtag cggtggtttt tttgtttgca agcagcagat tacgcgcaga    2100 aaaaaggat ctcaagaaga tcctttgatc ttttctacgg ggtctgacgc tcagtggaac     2160
gaaaactcac gttaagggat tttggtcatg agattatcaa aaaggatctt cacctagatc    2220
cttttaaatt aaaaatgaag ttttaaatca atctaaagta tatatgagta aacttggtct    2280
gacagttacc aatgcttaat cagtgaggca cctatctcag cgatctgtct atttcgttca    2340
tccatagttg cctgactcgg ggggggggg cgctgaggtc tgcctcgtga agaaggtgtt     2400
gctgactcat accaggcctg aatcgcccca tcatccagcc agaaagtgag ggagccacgg    2460
ttgatgagag ctttgttgta ggtggaccag ttggtgattt tgaacttttg ctttgccacg    2520
gaacggtctg cgttgtcggg aagatgcgtg atctgatcct tcaactcagc aaaagttcga    2580
tttattcaac aaagccgccg tcccgtcaag tcagcgtaat gctctgccag tgttacaacc    2640
aattaaccaa ttctgattag aaaaactcat cgagcatcaa atgaaactgc aatttattca    2700
tatcaggatt atcaatacca tatttttgaa aaagccgttt ctgtaatgaa ggagaaaact    2760
caccgaggca gttccatagg atggcaagat cctggtatcg gtctgcgatt ccgactcgtc    2820
caacatcaat acaacctatt aatttcccct cgtcaaaaat aaggttatca agtgagaaat    2880
caccatgagt gacgactgaa tccggtgaga atggcaaaag cttatgcatt tctttccaga    2940
cttgttcaac aggccagcca ttacgctcgt catcaaaatc actcgcatca accaaaccgt    3000
tattcattcg tgattgcgcc tgagcgagac gaaatacgcg atcgctgtta aaaggacaat    3060
tacaaacagg aatcgaatgc aaccggcgca ggaacactgc cagcgcatca acaatatttt    3120
cacctgaatc aggatattct tctaatacct ggaatgctgt tttcccgggg atcgcagtgg    3180
tgagtaacca tgcatcatca ggagtacgga taaaatgctt gatggtcgga agaggcataa    3240
attccgtcag ccagtttagt ctgaccatct catctgtaac atcattggca acgctacctt    3300
tgccatgttt cagaaacaac tctggcgcat cgggcttccc atacaatcga tagattgtcg    3360
cacctgattg cccgacatta tcgcgagccc atttataccc atataaatca gcatccatgt    3420
tggaatttaa tcgcggcctc gagcaagacg tttcccgttg aatatggctc ataacacccc    3480
ttgtattact gtttatgtaa gcagacagtt ttattgttca tgatgatata ttttatctt     3540 gtgcaatgta acatcagaga ttttgagaca caacgtggct ttcccccccc ccccattatt    3600
gaagcattta tcagggttat tgtctcatga gcggatacat atttgaatgt atttagaaaa    3660
ataaacaaat aggggttccg cgcacatttc cccgaaaagt gccacctgac gtctaagaaa    3720
ccattattat catgacatta acctataaaa ataggcgtat cacgaggccc tttcgtctcg    3780
cgcgtttcgg tgatgacggt gaaaacctct gacacatgca gctcccggag acggtcacag    3840
cttgtctgta agcggatgcc gggagcagac aagcccgtca gggcgcgtca gcgggtgttg    3900
gcgggtgtcg ggctggctt aactatgcgg catcagagca gattgtactg agagtgcacc     3960
atatgcggtg tgaaataccg cacagatgcg taaggagaaa ataccgcatc agattggcta    4020
ttgg                                                                 4024

<210> SEQ ID NO 32
<211> LENGTH: 4622
<212> TYPE: DNA
<213> ORGANISM: Artificial Sequence
```

```
<220> FEATURE:
<223> OTHER INFORMATION: synthetic dual promoter expression vector DP
      vector backbone
<400> SEQUENCE: 32
cctggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gaccccccgcc cattgacgtc aataatgacg tatgttccca    240
tagtaacgcc aatagggact ttccattgac gtcaatgggt ggagtattta cggtaaactg     300
cccacttggc agtacatcaa gtgtatcata tgccaagtac gccccctatt gacgtcaatg     360
atggtaaatg gcccgcctgg cattatgccc agtacatgac cttatgggac tttcctactt     420
ggcagtacat ctacgtatta gtcatcgcta ttaccatggt gatgcggttt tggcagtaca    480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg ggaggtctat ataagcagag     660
ctcgtttagt gaaccgtcag atcgcctgga cgccatcc acgctgtttt gacctccata      720
gaagacaccg gaccgatcc agcctccgcg ggcgcgcgtc gaggaattcg ctagcggcgc      780
gccagatctg atatcggatc tgctgtgcct tctagttgcc agccatctgt tgtttgcccc     840
tcccccgtgc cttccttgac cctggaaggt gccactccca ctgtcctttc ctaataaaat     900
gaggaaattg catcgcattg tctgagtagg tgtcattcta ttctgggggg tggggtgggg     960
caggacagca agggggagga ttgggaagac aatagcaggc atgctgggga tgcggtgggc    1020
tctatgggta cccaggtgct gaagaattga cccggttcct cctgggccag aaagaagcag    1080
gcacatcccc ttctctgtga cacaccctgt ccacgcccct ggttcttagt tccagcccca    1140
ctcataggac actcatagct caggagggct ccgccttcaa tcccacccgc taaagtactt    1200
ggagcggtct ctccctccct catcagccca ccaaaccaaa cctagcctcc aagagtggga    1260
agaaattaaa gcaagatagg ctattaagtg cagagggaga gaaatgcct ccaacatgtg     1320 aggaagtaat gagagaaatc atagaatttc ttccgcttcc tcgctcactg actcgctgcg    1380
ctcggtcgtt cggctgcggc gagcggtatc agctcactca aaggcggtaa tacgttatc     1440 cacagaatca ggggataacg caggaaagaa catgtgagca aaaggccagc aaaaggccag    1500
gaaccgtaaa aaggccgcgt tgctggcgtt tttccatagg ctccgccccc ctgacgagca    1560
tcacaaaaat cgacgctcaa gtcagaggtg gcgaaacccg acaggactat aaagatacca    1620 ggcgttccc cctggaagct ccctcgtgcg ctctcctgtt ccgaccctgc cgcttaccgg     1680
atacctgtcc gcctttctcc cttcgggaag cgtggcgctt tctcatagct cacgctgtag    1740
gtatctcagt tcggtgtagg tcgttcgctc caagctgggc tgtgtgcacg aaccccccgt    1800
tcagcccgac cgctgcgcct tatccggtaa ctatcgtctt gagtccaacc cggtaagaca    1860
cgacttatcg ccactggcag cagccactgg taacaggatt agcagagcga ggtatgtagg    1920
cggtgctaca gagttcttga agtggtgcc taactacggc tacactagaa gaacagtatt     1980
tggtatctgc gctctgctga agccagttac cttcggaaaa agagttggta gctcttgatc    2040
cggcaaacaa accaccgctg gtagcggtgg tttttttgtt tgcaagcagc agattacgcg    2100
cagaaaaaaa ggatctcaag aagatccttt gatcttttct acgggtctg acgctcagtg     2160 gaacgaaaac tcacgttaag ggattttggt catgagatta tcaaaaagga tcttcaccta    2220
gatcctttta aattaaaaat gaagttttaa atcaatctaa agtatatatg agtaaacttg    2280
```

```
gtctgacagt taccaatgct taatcagtga ggcacctatc tcagcgatct gtctatttcg   2340
ttcatccata gttgcctgac tcggggggggg ggggcgctga ggtctgcctc gtgaagaagg   2400
tgttgctgac tcataccagg cctgaatcgc cccatcatcc agccagaaag tgagggagcc   2460
acggttgatg agagctttgt tgtaggtgga ccagttggtg attttgaact tttgctttgc   2520
cacggaacgg tctgcgttgt cgggaagatg cgtgatctga tccttcaact cagcaaaagt   2580
tcgatttatt caacaaagcc gccgtcccgt caagtcagcg taatgctctg ccagtgttac   2640
aaccaattaa ccaattctga ttagaaaaac tcatcgagca tcaaatgaaa ctgcaattta   2700
ttcatatcag gattatcaat accatatttt tgaaaaagcc gtttctgtaa tgaaggagaa   2760
aactcaccga ggcagttcca taggatggca agatcctggt atcggtctgc gattccgact   2820
cgtccaacat caatacaacc tattaatttc ccctcgtcaa aaataaggtt atcaagtgag   2880
aaatcaccat gagtgacgac tgaatccggt gagaatggca aaagcttatg catttctttc   2940
cagacttgtt caacaggcca gccattacgc tcgtcatcaa aatcactcgc atcaaccaaa   3000
ccgttattca ttcgtgattg cgcctgagcg agacgaaata cgcgatcgct gttaaaagga   3060
caattacaaa caggaatcga atgcaaccgg cgcaggaaca ctgccagcgc atcaacaata   3120
ttttcacctg aatcaggata ttcttctaat acctggaatg ctgttttccc ggggatcgca   3180
gtggtgagta accatgcatc atcaggagta cggataaaat gcttgatggt cggaagaggc   3240
ataaattccg tcagccagtt tagtctgacc atctcatctg taacatcatt ggcaacgcta   3300
cctttgccat gtttcagaaa caactctggc gcatcgggct tcccatacaa tcgatagatt   3360
gtcgcacctg attgcccgac attatcgcga gcccatttat acccatataa atcagcatcc   3420
atgttggaat ttaatcgcgg cctcgagcaa gacgtttccc gttgaatatg gctcataaca   3480
ccccttgtat tactgtttat gtaagcagac agttttattg ttcatgatga tatattttta   3540
tcttgtgcaa tgtaacatca gagattttga gacacaacgt ggatcatcca gacatgataa   3600
gatacattga tgagtttgga caaaccacaa ctagaatgca gtgaaaaaaa tgctttattt   3660
gtgaaatttg tgatgctatt gctttatttg taaccattat aagctgcaat aaacaagtta   3720
acaacaacaa ttgcattcat tttatgtttc aggttcaggg ggaggtgtgg gaggtttttt   3780
aaagcaagta aaacctctac aaatgtggta tggctgatta tgatcgtcga ggatccggcg   3840
ccgtttaaac gtcgacagat ccaaacgctc ctccgacgtc cccaggcaga atggcggttc   3900
cctaaacgag cattgcttat atagacctcc cattaggcac gcctaccgcc catttacgtc   3960
aatggaacgc ccatttgcgt cattgcccct ccccattgac gtcaatgggg atgtacttgg   4020
cagccatcgc gggccatttta ccgccattga cgtcaatggg agtactgcca atgtaccctg   4080
gcgtacttcc aatagtaatg tacttgccaa gttactatta atagatattg atgtactgcc   4140
aagtgggcca tttaccgtca ttgacgtcaa taggggggcgt gagaacggat atgaatgggc   4200
aatgagccat cccattgacg tcaatggtgg gtggtcctat tgacgtcaat gggcattgag   4260
ccaggcgggc catttaccgt aattgacgtc aatggggagg cgccatata cgtcaatagg   4320 accgcccata tgacgtcaat aggtaagacc atgaggcccc ttcgtctcgc gcgtttcggt   4380
gatgacggtg aaaacctctg acacatgcag ctcccggaga cggtcacagc ttgtctgtaa   4440
gcggatgccg ggagcagaca agcccgtcag gcgcgtcag cgggtgttgg cgggtgtcgg   4500
ggctggctta actatgcggc atcagagcag attgtactga gagtgcacca tatgcggtgt   4560
gaaataccgc acagatgcgt aaggagaaaa taccgcatca gattggctat tggcattatg   4620
cc                                                                  4622
```

<210> SEQ ID NO 33
<211> LENGTH: 987
<212> TYPE: DNA
<213> ORGANISM: Artificial Sequence
<220> FEATURE:
<223> OTHER INFORMATION: synthetic human IL-12 p40 beta subunit improved
RNA with minimized inhibitory/instability
sequences

<400> SEQUENCE: 33

```
atgtgccacc agcagctggt catcagctgg ttcagcctcg ttttcctcgc ctcgccgctg      60
gtcgccatat gggagctcaa gaaggacgta tacgtggtgg agctggactg gtaccccgac     120
gcgccgggcg agatggtcgt cctgacgtgc gacacgccgg aggaggacgg catcacgtgg     180
acgctggacc agtccagcga ggtcctcggc tccggcaaga cgctgacgat ccaggtcaag     240
gagttcggcg acgcgggcca gtacacgtgc cacaagggcg gcgaggtcct gagccactcc     300
ctcctcctgc tacacaagaa ggaggacggg atctggagca cggacatcct caaggaccag     360
aaggagccga gaacaagac cttcctgcgc tgcgaggcga agaattactc gggccggttc     420
acgtgctggt ggctcaccac gatcagcacg gacctgacgt tctcggtcaa gtcgtcgcgg     480
ggctcgtcgg acccccaggg ggtgacctgc ggcgcggcga cgctgtcggc ggagcgggtg     540
cggggcgaca caaggagta cgagtactcg gtcgagtgcc aggaggactc ggcgtgcccg     600
gcggcggagg agtcgctgcc gatcgaggtg atggtcgacg cggtccacaa gctgaagtac     660
gagaactaca cgtcgtcgtt cttcatccgg gacatcatca gccggacccc gccgaagaac     720
ctgcagctga agccgctgaa gaactcgcgg caggtcgagg tctcgtggga gtacccggac     780
acgtggtcga cgccgcactc gtacttctcg ctgacgttct gcgtccaagt gcagggcaag     840
tcgaagcggg agaagaagga ccgggtgttc accgacaaga cgagcgcgac ggtgatctgc     900
cggaagaacg cgtcgatctc ggtgcgggcg caggaccggt actactcgtc gtcgtggtcg     960
gagtgggcgt cggtgccgtg cagctag                                         987
```

<210> SEQ ID NO 34
<211> LENGTH: 660
<212> TYPE: DNA
<213> ORGANISM: Artificial Sequence
<220> FEATURE:
<223> OTHER INFORMATION: synthetic human IL-12 p35 alpha subunit
improved RNA with minimized inhibitory/instability sequences

<400> SEQUENCE: 34

```
atgtgcccgg cgcgctccct gctgctcgtg gcgacgctgg tcctgctcga ccacctgagc      60
ctggcgcgga acctgccggt ggcgacgccg gacccgggga tgttcccgtg cctgcaccac     120
agccagaacc tgctgcgggc ggtgtcgaac atgctgcaga aggcgcggca gacgctggag     180
ttctacccgt gcacgagcga ggagatcgac cacgaggaca tcacgaagga caagaccagc     240
acggtggagg cgtgcctgcc gctggagctg acgaagaacg agtcgtgcct gaactcgagg     300
gagacgtcgt tcatcacgaa cgggtcgtgc ctggcgtcgc ggaagacgtc gttcatgatg     360
gcgctgtgcc tgtcgtcgat ctacgaggac ctgaagatgt accaggtgga gttcaagacg     420
atgaacgcga agctgctgat ggaccccgaa gcggcagatc tcctcgacca gaacatgctg     480
gcggtgatcg acgagctcat gcaggcgctc aacttcaaca gcgagacggt gccgcagaag     540
tcgtcgctcg aggagccgga cttctacaag acgaagatca agctctgcat cctgctgcac     600
gctttccgga tccgggcggt gacgatcgac cgggtgatgt cgtacctgaa cgcttcgtaa     660
```

EXPRESSION OF IL-12 FAMILY HETERODIMERS

CROSS-REFERENCE TO RELATED APPLICATIONS

This application is a U.S. National Stage Application of PCT International Application No. PCT/US2009/043481, filed May 11, 2009, which claims the benefit of U.S. Provisional Application Ser. No. 61/052,239, filed on May 11, 2008, and U.S. Provisional Application No. 61/052,916, filed on May 13, 2008, the entire disclosures of which are hereby incorporated herein by reference.

FIELD OF THE INVENTION

The present invention provides methods for improved expression of IL-12 family cytokine heterodimeric proteins. The levels and efficiency of expression of heterodimeric proteins is improved by adjusting the relative ratios of transcription and translation of the polypeptides of a IL-12 family cytokine heterodimeric pair of polypeptides, e.g., alpha and beta subunits, e.g., in comparison to expression of the subunits at equimolar ratios.

BACKGROUND OF THE INVENTION

Many proteins are multimeric, composed of multiple and different subunits. Expression of the respective subunits provides a critical step in the production of a functional protein. To obtain maximal production of such proteins it is important to also optimize expression levels of individual subunits. The present invention is based, in part, on the discovery that production levels and secretion of several multimeric cytokines depends not only on the absolute levels of expression, but also on the relative levels of expression of individual subunits. Optimized ratios of the subunits resulted in greatly increased extracellular levels of the heterodimeric proteins. We have identified the optimal ratios of subunits for several heterodimeric cytokines, including IL-12 family cytokines, e.g., IL-12 chains p35 and p40, IL-23 chains p19 and p40, IL-27 chains p28 and EBI3. The use of optimized expression strategies leads to improvement of cytokine expression. This strategy is of general application for the expression of any multimeric protein.

BRIEF SUMMARY OF THE INVENTION

The present invention provides methods for improving the expression of IL-12 family cytokine heterodimers by determining the relative ratio of expression of the alpha and beta subunits comprising the heterodimers that produces increased levels of expression, e.g., highest or desired levels of extracellular expression and stability of heterodimer.

Accordingly, in a first aspect, the invention provides methods of improving the level and stability of expression of an IL-12 family cytokine, wherein the IL-12 family cytokine comprises an alpha subunit and a beta subunit. In some embodiments, the methods comprise:
a) determining the ratio of the alpha subunit and the beta subunit that produces an increased level of expression of heterodimer; and
b) expressing the alpha subunit and the beta subunit from a cell at the determined ratio. The level of expression can be in comparison to expressing the alpha subunit and the beta subunit at a 1:1 ratio. Increased levels of expression of a IL-12 family cytokine are achieved when the alpha and beta subunits are expressed at a ratio other than 1:1, i.e., not at a 1:1 ratio.

In some embodiments, the IL-12 family cytokine is IL-12, and the alpha subunit (p35) and the beta subunit (p40) are expressed at a relative ratio in the range of about 1:3 to about 1:15, for example, about 1:8 to about 1:10, or at a ratio of about 1:5, 1:8, 1:10, 1:12, or 1:15.

In some embodiments, the IL-12 family cytokine is IL-23, and the alpha subunit (p19) and the beta subunit (p40) are expressed at a relative ratio in the range of about 1:3 to about 1:15, for example, about 1:8 to about 1:10, or at a ratio of about 1:5, 1:8, 1:10, 1:12, or 1:15.

In some embodiments, the IL-12 family cytokine is IL-27, and the alpha subunit (p28) and the beta subunit (EBI3) are expressed at a relative ratio in the range of about 3:1 to about 15:1, for example, about 8:1 to about 10:1, or at a ratio of about 5:1, 8:1, 10:1, 12:1, or 15:1.

In some embodiments, the highest level of extracellular expression of heterodimer is determined. In some embodiments, the expression of heterodimer is increased 3-fold, 4-fold, 5-fold, 10-fold, 15-fold, 20-fold, 30-fold, or more, as measured in vitro or in vivo, in comparison to heterodimers expressed at a relative molar ratio of 1:1.

In some embodiments, the alpha subunit and the beta subunit are expressed at the determined ratio by cotransfecting the cell with a first nucleic acid encoding the alpha subunit and a second nucleic acid encoding the beta subunit at the determined ratio for expression.

In some embodiments, the alpha subunit and the beta subunit are expressed at the determined ratio by transfecting the cell with a single plasmid comprising a first nucleic acid encoding the alpha subunit under the control of a first promoter and a second nucleic acid encoding the beta subunit under the control of a second promoter, wherein the first promoter and the second promoter are of different relative expression strengths to allow expression of the alpha subunit and the beta subunits at a determined ratio of expression. In some embodiments, the first promoter is relatively weaker in promoting expression and the second promoter is relatively stronger in promoter expression. In some embodiments, the first promoter is a simian CMV promoter and the second promoter is a human CMV promoter.

In some embodiments, the alpha subunit and the beta subunit are expressed at the determined ratio by transfecting the cell with a bicistronic nucleic acid encoding the alpha subunit and the beta subunit, wherein the nucleic acid encoding the alpha subunit and the nucleic acid encoding the beta subunit are separated by an internal ribosomal entry site.

In a related aspect, the invention provides methods of promoting the stability and secretion of an IL-12 heterodimer comprised of a p35 subunit and a p40 subunit, comprising expressing the p35 subunit and the p40 subunit in a cell at a ratio in the range of about 1:3 to about 1:15.

In some embodiments, the p35 subunit shares at least 95%, 96%, 97%, 98% or 99% nucleic acid sequence identity with SEQ ID NO:34 and the p40 subunit shares at least 95%, 96%, 97%, 98% or 99% nucleic acid sequence identity with SEQ ID NO:33. In some embodiments, the p35 subunit is SEQ ID NO:34 and the p40 subunit is SEQ ID NO:33.

In some embodiments, the p35 subunit and the p40 subunit are expressed at the ratio in the range of about 1:3 to about 1:15 by cotransfecting the cell with a first nucleic acid encoding the p35 subunit and a second nucleic acid encoding the p40 subunit at the ratio in the range of about 1:3 to about 1:15.

In some embodiments, the p35 subunit and the p40 subunit are expressed at the ratio in the range of about 1:3 to about 1:15 by transfecting the cell with a single plasmid comprising a first nucleic acid encoding the p35 subunit under the control of a first promoter and a second nucleic acid encoding the p40 subunit under the control of a second promoter, wherein the first promoter and the second promoter are of relative expression strengths to allow expression of the p35 subunit and the p40 subunits at the ratio in the range of about 1:3 to about 1:15. In some embodiments for expression of IL-12, the first promoter is a simian CMV promoter and the second promoter is a human CMV promoter.

In some embodiments, the p35 subunit and the p40 subunit are expressed at the ratio in the range of about 1:3 to about 1:15 by transfecting the cell with a bicistronic nucleic acid encoding the p35 subunit and the p40 subunit, wherein the nucleic acid encoding the p35 subunit and the nucleic acid encoding the p40 subunit are separated by an internal ribosomal entry site.

In another aspect, the invention provides methods of promoting the stability and secretion of an IL-23 heterodimer comprised of a p19 subunit and a p40 subunit, comprising expressing the p19 subunit and the p40 subunit in a cell at a ratio in the range of about 1:3 to about 1:15.

In some embodiments, the p19 subunit shares at least 95%, 96%, 97%, 98% or 99% nucleic acid sequence identity with SEQ ID NO:26 and the p4-0 subunit shares at least 95%, 96%, 97%, 98% or 99% nucleic acid sequence identity with SEQ ID NO:33. In some embodiments, the p19 subunit is SEQ ID NO:26 and the p40 subunit is SEQ ID NO:33.

In some embodiments, the p19 subunit and the p40 subunit are expressed at the ratio in the range of about 1:3 to about 1:15 by cotransfecting the cell with a first nucleic acid encoding the p19 subunit and a second nucleic acid encoding the p40 subunit at the ratio in the range of about 1:3 to about 1:15.

In some embodiments, the p19 subunit and the p40 subunit are expressed at the ratio in the range of about 1:3 to about 1:15 by transfecting the cell with a single plasmid comprising a first nucleic acid encoding the p19 subunit under the control of a first promoter and a second nucleic acid encoding the p40 subunit under the control of a second promoter, wherein the first promoter and the second promoter are of relative expression strengths to allow expression of the p19 subunit and the p40 subunits at the ratio in the range of about 1:3 to about 1:15. In some embodiments for expression of IL-23, the first promoter is a simian CMV promoter and the second promoter is a human CMV promoter.

In some embodiments, the p19 subunit and the p40 subunit are expressed at the ratio in the range of about 1:3 to about 1:15 by transfecting the cell with a bicistronic nucleic acid encoding the p19 subunit and the p40 subunit, wherein the nucleic acid encoding the p19 subunit and the nucleic acid encoding the p40 subunit are separated by an internal ribosomal entry site.

In a further aspect, the invention provides methods of promoting the stability and secretion of an IL-27 heterodimer comprised of a p28 subunit and an EBI3 subunit, comprising expressing the p28 subunit and the EBI3 subunit in a cell at a ratio in the range of about 3:1 to about 15:1.

In some embodiments, the p28 subunit shares at least 95%, 96%, 97%, 98% or 99% nucleic acid sequence identity with SEQ ID NO:29 and the EBI3 subunit shares at least 95%, 96%, 97%, 98% or 99% nucleic acid sequence identity with SEQ ID NO:30. In some embodiments, the p28 subunit is SEQ ID NO:29 and the EBI3 subunit is SEQ ID NO:30.

In some embodiments, the p28 subunit shares at least 95%, 96%, 97%, 98% or 99% nucleic acid sequence identity with SEQ ID NO:27 and the EBI3 subunit shares at least 95%, 96%, 97%, 98% or 99% nucleic acid sequence identity with SEQ ID NO:28. In some embodiments, the p28 subunit is SEQ ID NO:27 and the EBI3 subunit is SEQ ID NO:28.

In some embodiments, the p28 subunit and the EBI3 subunit are expressed at the ratio in the range of about 3:1 to about 15:1 by cotransfecting the cell with a first nucleic acid encoding the p28 subunit and a second nucleic acid encoding the EBI3 subunit at the ratio in the range of about 3:1 to about 15:1.

In some embodiments, the p28 subunit and the EBI3 subunit are expressed at the ratio in the range of about 3:1 to about 15:1 by transfecting the cell with a single plasmid comprising a first nucleic acid encoding the p28 subunit under the control of a first promoter and a second nucleic acid encoding the EBI3 subunit under the control of a second promoter, wherein the first promoter and the second promoter are of relative expression strengths to allow expression of the p28 subunit and the EBI3 subunits at the ratio in the range of about 3:1 to about 15:1. In some embodiments for expression of IL-27, the first promoter is a human CMV promoter and the second promoter is a simian CMV promoter.

In some embodiments, the p28 subunit and the EBI3 subunit are expressed at the ratio in the range of about 3:1 to about 15:1 by transfecting the cell with a bicistronic nucleic acid encoding the p28 subunit and the EBI3 subunit, wherein the nucleic acid encoding the p28 subunit and the nucleic acid encoding the EBI3 subunit are separated by an internal ribosomal entry site.

In a related aspect, the invention provides dual expression vectors for expressing a first subunit and a second subunit of a heterodimeric protein, comprising a first expression cassette for expressing the first subunit under the control of a relatively stronger promoter and a second expression cassette for expressing the second subunit under the control of a relatively weaker promoter.

With respect to the embodiments of the dual expression vectors some embodiments, the first subunit and the second subunit are expressed at a relative ratio in the range of about 3:1 to about 15:1.

In some embodiments, the relatively stronger promoter is a human CMV promoter and the relatively weaker promoter is a simian CMV promoter.

In some embodiments, the heterodimeric protein is an IL-12 family cytokine. In some embodiments, the IL-12 family cytokine is IL-12, and the first subunit is IL-12 p40 and the second subunit is IL-12 p35. In some embodiments, the dual expression vector comprises a first expression cassette that expresses IL-12 p40 under the control of a human CMV promoter and a second expression cassette that expresses IL-12 p35 under the control of the simian CMV promoter. In some embodiments, the p35 subunit shares at least 95%, 96%, 97%, 98% or 99% nucleic acid sequence identity with SEQ ID NO:34 and the p40 subunit shares at least 95%, 96%, 97%, 98% or 99% nucleic acid sequence identity with SEQ ID NO:33. In some embodiments, the p35 subunit is SEQ ID NO:34 and the p40 subunit is SEQ ID NO:33.

In some embodiments, the IL-12 family cytokine is IL-23, and the first subunit is IL-23 p40 and the second subunit is IL-23 p19. In some embodiments, the dual expression vector comprises a first expression cassette that expresses IL-23 p40 (i.e., IL-12 p40) under the control of a human CMV promoter and a second expression cassette that expresses IL-23 p19 under the control of the simian CMV promoter. In some embodiments, the p19 subunit shares at least 95%, 96%, 97%, 98% or 99% nucleic acid sequence identity with SEQ ID NO:26 and the p40 subunit shares at least 95%, 96%, 97%, 98% or 99% nucleic acid sequence identity with SEQ ID NO:33. In some embodiments, the p19 subunit is SEQ ID NO:26 and the p40 subunit is SEQ ID NO:33.

In some embodiments, the IL-12 family cytokine is IL-27, and the first subunit is IL-27 p28 and the second subunit is EBI3. In some embodiments, the dual expression vector comprises a first expression cassette that expresses IL-27 p28 under the control of a human CMV promoter and a second expression cassette that expresses IL-27 EBI3 under the control of the simian CMV promoter. In some embodiments, the p28 subunit shares at least 95%, 96%, 97%, 98% or 99% nucleic acid sequence identity with SEQ ID NO:29 and the EBI3 subunit shares at least 95%, 96%, 97%, 98% or 99% nucleic acid sequence identity with SEQ ID NO:30. In some embodiments, the p28 subunit is SEQ ID NO:29 and the EBI3 subunit is SEQ ID NO:30. In some embodiments, the p28 subunit shares at least 95%, 96%, 97%, 98% or 99% nucleic acid sequence identity with SEQ ID NO:27 and the EBI3 subunit shares at least 95%, 96%, 97%, 98% or 99% nucleic acid sequence identity with SEQ ID NO:28. In some embodiments, the p28 subunit is SEQ ID NO:27 and the EBI3 subunit is SEQ ID NO:28.

In some embodiments, the dual expression vector comprises a nucleic acid sequence of SEQ ID NO:1 (plasmid AG181). In some embodiments, the dual expression vector comprises a nucleic acid sequence of SEQ ID NO:3 (plasmid AG157). In some embodiments, the dual expression vector comprises a nucleic acid sequence of SEQ ID NO:7 (plasmid AG184). In some embodiments, the dual expression vector comprises a nucleic acid sequence of SEQ ID NO:10 (plasmid AG205). In some embodiments, the dual expression vector comprises a nucleic acid sequence of SEQ ID NO:14 (plasmid AG216). In some embodiments, the dual expression vector comprises a nucleic acid sequence of SEQ ID NO:32.

In a related aspect, the invention provides a nucleic acid sequence pair encoding an improved human interleukin-23 (IL-23) protein heterodimer comprised of a p19 subunit and a p40 subunit, wherein the nucleic acid sequence encoding the p19 subunit shares at least 95%, 96%, 97%, 98% or 99% nucleic acid sequence identity to SEQ ID NO:26 and the nucleic acid sequence encoding the p40 subunit shares at least 95%, 96%, 97%, 98% or 99% nucleic acid sequence identity to SEQ ID NO:33. In some embodiments, the nucleic acid sequence encoding the p19 subunit is SEQ ID NO:26 and the nucleic acid sequence encoding the p40 subunit is SEQ ID NO:33.

In another aspect, the invention provides a nucleic acid sequence pair encoding an improved human interleukin-27 (IL 27) protein heterodimer comprised of a p28 subunit and an EBI3 subunit, wherein the nucleic acid sequence encoding the p28 subunit shares at least 95%, 96%, 97%, 98% or 99% nucleic acid sequence identity to SEQ ID NO:29 and the nucleic acid sequence encoding the EBI3 subunit shares at least 95%, 96%, 97%, 98% or 99% nucleic acid sequence identity to SEQ ID NO:30. In some embodiments, the nucleic acid sequence encoding the p28 subunit is SEQ ID NO:29 and the nucleic acid sequence encoding the EBI3 subunit is SEQ ID NO:30.

In a related aspect, the invention provides a nucleic acid sequence pair encoding an improved murine interleukin-27 (IL 27) protein heterodimer comprised of a p28 subunit and an EBI3 subunit, wherein the nucleic acid sequence encoding the p28 subunit shares at least 95%, 96%, 97%, 98% or 99% nucleic acid sequence identity to SEQ ID NO:27 and the nucleic acid sequence encoding the EBI3 subunit shares at least 95%, 96%, 97%, 98% or 99% nucleic acid sequence identity to SEQ ID NO:28. In some embodiments, the nucleic acid sequence encoding the p28 subunit is SEQ ID NO:27 and the nucleic acid sequence encoding the EBI3 subunit is SEQ ID NO:28.

The invention further provides host cells, e.g., mammalian host cells, comprising the vectors and nucleic acids of the invention. The invention further provides expression cassettes and expression vectors comprising the improved IL-12 family nucleic acid pairs. The invention also provides compositions comprising the vectors and nucleic acids of the invention in a pharmaceutically acceptable carrier or excipient, e.g., for use as an adjuvant.

DEFINITIONS

A "IL-12 family cytokine" refers to a heterodimeric ligands comprised of an α subunit with helical structure (e.g., IL-12p35, IL-23p19, IL-27p28) and a β subunit (e.g., IL-12p40, IL-23p40 (which is identical to IL-12p40), EBI3). Exemplary members include IL-12, IL-23 and IL-27. Biologically active IL-12 is comprised of p35 and p40 subunits that together form the IL-12p70 heterodimer, which binds specifically to the IL-12Rβ1/IL-12Rβ2 receptor. IL-23 is comprised of the IL-12 p40 subunit paired with a p19 subunit protein. The IL-23 heterodimer binds to IL-12Rβ1 paired not with the IL-12Rβ2 subunit, but with the unique IL-23R. IL-27 is a heterodimeric cytokine containing the Epstein-Barr virus-induced gene 3 (EBI3) subunit (related to the IL-12 p40 subunit) paired with a p28 subunit with homology to the IL-12 p35 subunit. IL-27 binds to a receptor comprised of the IL-27Rα subunit and the gp130 subunit. IL-12 family cytokines are predominantly produced by activated monocytes, macrophages, and dendritic cells. The respective receptors are broadly expressed in many lymphocyte subsets and show some variation in expression levels on naïve-versus memory-phenotype CD4+ T cells. IL-12 family cytokine receptors are expressed on macrophages, dendritic cells, NK cells, and activated T cells. Functionally, IL-12 family cytokines regulate diverse functions of several lymphocyte subsets. They play a role in NK cell activation, as co-factors for T cell receptor (TCR)-induced T cell proliferation, as promoters of T cell cytokine production, and as regulators of B cell antibody production. IL-12 family cytokines are reviewed, for example, in Trinchieri, et al., *Immunity* (2003) 19:641-644; Brombacher, et al, *Trends in Immunol* (2003) 24(4):207-212; Holscher, et al., *Med Microbial Immunol* (2004) 193:1-17; Goriely, et al., *Nature Rev Immunol* (2008) 8(1):81-6; Kastelein, et al., *Annu Rev Immunol* (2007) 25:221-42; Beadling and Slifka, *Arch Immunol Ther Exp* (2006) 54(1):15-24; and Goriely and Goldman, *Am J Transplant* (2007) 7(2):278-84.

The terms "IL-12 protein heterodimer" or "IL-12 heterodimer" or "IL-12p70" refer to an IL-12 cytokine protein composed of its two monomeric polypeptide subunits, an IL-12p35 chain and an IL-12p40 chain. See, for example, Airoldi, et al., *Haematologica* (2002) 87:434-42.

The term "native mammalian IL-12" refers to any naturally occurring interleukin-12 nucleic acid and amino acid sequences of the IL-12 monomeric sequences, IL-12p35 and IL-12p40 from a mammalian species. Those of skill in the art will appreciate that interleukin-12 sequences are publicly available in gene databases, for example, GenBank through the National Center for Biotechnological Information on the worldwideweb at ncbi.nlm.nih.gov/entrez/query.fcgi?db=Nucleotide and ncbi.nlm.nih.gov/entrez/query.fcgi?db=Protein. Exemplified native mammalian IL-12 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-12 nucleic acid sequences include NM_002187 (human p40), NM_000882 (human p35), AY234218 (baboon p40), AY234219 (baboon p35); U19841 (rhesus monkey p40), U19842 (rhesus monkey p35); NM_022611 (rat p40), NM_053390 (rat p35), and NM_008352 (mouse p40), NM_008351 (mouse p35). Accession numbers for exemplified native mammalian IL-12 amino acid sequences include NP_002178 (human p40), NP_000873 (human p35), AAK84425 or AAD56385 (human p35); AAA86707 (rhesus monkey p35); P48095 (rhesus monkey p40); NP_072133 (rat p40), AAD51364 (rat p35), and NP_032378 (mouse p35), NP_032377 (mouse p40).

The term "interleukin-12" or "IL-12" refers to a polypeptide that has at least 90%, 91%, 92%, 93%, 94%, 95%, 96%, 97%, 98% or 99% sequence identity to a native mammalian IL-12 amino acid sequence (e.g., as described above and herein), or a nucleotide encoding such a polypeptide, is biologically active, meaning the mutated protein ("mutein") has functionality similar (75% or greater) to that of a native IL-12 protein in at least one functional assay. Exemplified functional assays of an IL-12 polypeptide include inducing the production of interferon-gamma (IFN-γ), for example, by T cells or natural killer (NK) cells, and promoting the differentiation of T helper-1 (Th1) cells. A T helper cell differentiated into a Th1 cell can be identified by secretion of IFN-γ. IFN-γ secreted by IL-12 stimulated T cells or NK cells can be conveniently detected, for example, in serum or cell culture supernatant using ELISA. ELISA methods and techniques are well known in the art, and kits for detecting IFN-γ are commercially available (e.g., R&D Systems, Minneapolis, Minn.; Peprotech, Rocky Hill, N.J.; and Biosource Intl., Camarillo, Calif.) See also, Coligan, et al., Current Methods in Immunology, 1991-2006, John Wiley & Sons; Harlow and Lane, *Using Antibodies: A Laboratory Manual*, 1998, Cold Spring Harbor Laboratory Press; and *The ELISA Guidebook*, Crowther, ed., 2000, Humana Press.

The terms "IL-23 protein heterodimer" or "IL-23 heterodimer" or "IL-23" refer to an IL-23 cytokine protein composed of its two monomeric polypeptide subunits, an IL-23p19 chain and an IL-23p40 chain (the same as an IL-12p40 chain). See, e.g., Kastelein, et al., *Annu Rev Immunol* (2007) 25:221-42; and Hunter, et al, *Nature Rev Immunol* (2005) 5:521-531.

The term "native mammalian IL-23" refers to any naturally occurring interleukin-23 nucleic acid and amino acid sequences of the IL-23 monomeric sequences, IL-23p19 and an IL-23p40 from a mammalian species (identical to the IL-12p40 described herein). Those of skill in the art will appreciate that interleukin-23 sequences are publicly available in gene databases, for example, GenBank. Exemplified native mammalian IL-23 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-23 p19 nucleic acid sequences include NM_016584 (human); AY359083 (human); AF301620 (human); XM 522436 (Pan troglodytes); and XM_001115026 (*Macaca mulatta*). Accession numbers for exemplified native mammalian IL-23 p19 amino acid sequences include NP_057668 (human); AAG37232 (human); AAH66267 (human); AAH66269 (human); XP_001115026 (*Macaca mulatta*); NP_001075991 (*Equus caballus*); ABB01676 (*Felts catus*); NP 569094 (*Rattus norvegicus*); ACC77208 (*Bos taurus*); and NP_112542 (*Mus musculus*). Additional sequences are described herein.

The term "interleukin-23" or "IL-23" refers to a polypeptide that has at least 90%, 91%, 92%, 93%, 94%, 95%, 96%, 97%, 98% or 99% sequence identity to a native mammalian IL-23 amino acid sequence (e.g., as described above and herein), or a nucleotide encoding such a polypeptide, is biologically active, meaning the mutated protein ("mutein") has functionality similar (75% or greater) to that of a native IL-23 protein in at least one functional assay. Both IL-23 and IL-12 can activate the transcription activator STAT4, and stimulate the production of interferon-gamma (IFNγ). In contrast to IL-12, which acts mainly on naive CD4(+) T cells, IL-23 preferentially acts on memory CD4(+) T cells. IL-23 promotes IL-17 production by several T-cell types including the T helper 17 (Th17)-cell subset. IL-17 is a potent pro-inflammatory cytokine that induces tissue damage at least in part through neutrophil recruitment. Exemplified functional assays of an IL-23 polypeptide include inducing the production of interferon-gamma (IFN-γ), for example, by T cells or natural killer (NK) cells, and promoting the differentiation of Th17 cells. See, e.g., Kastelein, et al., *Annu Rev Immunol* (2007) 25:221-42; Goriely, et al., *Nature Rev Immunol* (2008) 8(1):81-6; and Goriely and Goldman, *Am J Transplant* (2007) 7(2):278-84. IFN-γ secreted by IL-23 stimulated T cells or NK cells can be conveniently detected, for example, in serum or cell culture supernatant using ELISA, as described above.

The terms "IL-27 protein heterodimer" or "IL-27 heterodimer" or "IL-27" refer to an IL-27 cytokine protein composed of its two monomeric polypeptide subunits, an IL-27p28 chain and a Epstein-Barr virus-induced gene 3 (EBI3) subunit. The IL-27p28 subunit shares structural homology with the IL-12p35 subunit; the EBI3 subunit shares structural homology with the IL-12p40 subunit. See, e.g., Kastelein, et al., *Annu Rev Immunol* (2007) 25:221-42; and Hunter, et al, *Nature Rev Immunol* (2005) 5:521-531.

The term "native mammalian IL-27" refers to any naturally occurring interleukin-27 nucleic acid and amino acid sequences of the IL-27 monomeric sequences, IL-27p28 and an Epstein-Barr virus-induced gene 3 (EBI3) subunit from a mammalian species. Those of skill in the art will appreciate that interleukin-27 sequences are publicly available in gene databases, for example, GenBank. Exemplified native mammalian IL-23 nucleic acid or amino acid sequences can be from, for example, human, primate, canine, feline, porcine, equine, bovine, ovine, rodentia, murine, rat, hamster, guinea pig, etc. Accession numbers for exemplified native mammalian IL-27 p28 nucleic acid sequences include NM_145659 (human); BC062422 (human); AY099296 (human); EF064720 (human); XM_01169965 (Pan troglodytes); XM_001138224 (*Pan troglodytes*); XM_001097165 (*Macaca mulatta*); BC_119402 (*Mus musculus*); NM_145636 (*Mus musculus*); and XM_344962 (*Rattus norvegicus*). Accession numbers for exemplified native mammalian IL-27 p28 amino acid sequences include NP_663634 (human); AAH62422 (human); AAM34498 (human); XP_001496678 (*Equus caballus*); XP_001138224 (*Pan troglodytes*); XP_849828 (*Canis familiaris*); NP 663611 (*Mus musculus*); EDL17402 (*Mus museumus*) and XP_344963 (*Rattus norvegicus*). Accession numbers for exemplified native mammalian EBI3 nucleic acid sequences include NM_005755 (human); BC015364 (human); BC046112 (human); L08187 (human); EF064740 (human). Accession numbers for exemplified native mammalian EBI3 amino acid sequences include NP_005746 (human); ABK41923; EAW69244 (human); AAA93193 (human); XP_001138182 (*Pan troglodytes*); NP_001093835 (*Bos laurus*); XP_542161 (*Canis familiaris*); XP_001118027

(*Macaca mulatta*); NP_056581 (*Mus musculus*); and NP_001102891 (*Rattus norvegicus*). Additional sequences are described herein.

The term "interleukin-27" or "IL-27" refers to a polypeptide that has at least 90%, 91%, 92%, 93%, 94%, 95%, 96%, 97%, 98% or 99% sequence identity to a native mammalian IL-27 amino acid sequence (e.g., as described above and herein), or a nucleotide encoding such a polypeptide, is biologically active, meaning the mutated protein ("mutein") has functionality similar (75% or greater) to that of a native IL-27 protein in at least one functional assay. IL-27 shares homology with IL-12p70 and IL-23 and signals through a receptor that shares the gp130 chain with the IL-6 receptor. IL-27 promotes Th1-cell differentiation, an effect that is most prominent in the absence of IL-12. However, IL-27 also has a major regulatory role by limiting Th17-cell differentiation. IL-27 also has a profound suppressive effect on the CD4+ T cell production of IL-2. IL-27 activates STAT1 and thereby upregulates suppressor of cytokine signaling 3 (SOCS3). See, e.g., Kastelein, et al., *Annu Rev Immunol* (2007) 25:221-42; Goriely, et al., *Nature Rev Immunol* (2008) 8(1):81-6; and Goriely and Goldman, *Am J Transplant* (2007) 7(2):278-84.

The term "nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Degenerate codon substitutions can be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Degenerate codon substitutions for naturally occurring amino acids are in Table 1.

TABLE 1

| 1<sup>st</sup> position | 2<sup>nd</sup> position | | | | 3<sup>rd</sup> position |
|---|---|---|---|---|---|
| (5' end) | U(T) | C | A | G | (3' end) |
| U(T) | Phe | Ser | Tyr | Cys | U(T) |
|  | Phe | Ser | Tyr | Cys | C |
|  | Leu | Ser | STOP | STOP | A |
|  | Leu | Ser | STOP | Trp | G |
| C | Leu | Pro | His | Arg | U(T) |
|  | Leu | Pro | His | Arg | C |
|  | Leu | Pro | Gln | Arg | A |
|  | Leu | Pro | Gln | Arg | G |
| A | Ile | Thr | Asn | Ser | U(T) |
|  | Ile | Thr | Asn | Ser | C |
|  | Ile | Thr | Lys | Arg | A |
|  | Met | Thr | Lys | Arg | G |

TABLE 1-continued

| 1<sup>st</sup> position | 2<sup>nd</sup> position | | | | 3<sup>rd</sup> position |
|---|---|---|---|---|---|
| (5' end) | U(T) | C | A | G | (3' end) |
| G | Val | Ala | Asp | Gly | U(T) |
|  | Val | Ala | Asp | Gly | C |
|  | Val | Ala | Glu | Gly | A |
|  | Val | Ala | Glu | Gly | G |

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region to a reference sequence (e.g., any one of the Accession Numbers or SEQ ID NOs disclosed herein) when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or can be applied to, the compliment of a test sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of am amino acid or nucleic acid sequences.

For sequence comparison, typically one sequence acts as a reference sequence, to which test sequences are compared (here, an entire "native mammalian" IL-12 p35 or IL-12 p40 amino acid or nucleic acid sequence). When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithm that is suitable for determining percent sequence identity and sequence similarity are the BLAST algorithms, which are described in Altschul et al., *Nuc. Acids Res.* 25:3389-3402 (1977) and Altschul et al., *J. Mol. Biol.* 215:403-410 (1990), respectively. BLAST software is publicly available through the National Center for Biotechnology Information on the worldwide web at ncbi.nlm.nih.gov/. Both default parameters or other non-default parameters can be used. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

"Conservatively modified variants" as used herein applies to amino acid sequences. One of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

The term "GC content" refers to the percentage of a nucleic acid sequence comprised of deoxyguanosine (G) and/or deoxycytidine (C) deoxyribonucleosides, or guanosine (G) and/or cytidine (C) ribonucleoside residues.

The terms "mammal" or "mammalian" refer to any animal within the taxonomic classification mammalia. A mammal can refer to a human or a non-human primate. A mammal can refer to a domestic animal, including for example, canine, feline, rodentia, including lagomorpha, murine, rattus, Cricetinae (hamsters), etc. A mammal can refer to an agricultural animal, including for example, bovine, ovine, porcine, equine, etc.

BRIEF DESCRIPTION OF THE DRAWINGS

FIG. 2 provides a schematic of exemplary dual expression vectors for use in the present invention. The dual expression plasmids contain the human CMV promoter (stronger) and the bovine poly A signal, and the simian CMV promoter (weaker) and the SV40 polyA signal; the plasmid backbone contains the kanamycin resistance gene. In the plasmid AG181, the IL-12 p40 subunit is expressed from the stronger human CMV promoter and p35 is expressed from the weaker simian CMV promoter. In the plasmid AG183, the IL-12 p35 subunit is expressed from the stronger human CMV promoter and the IL-12 p40 subunit is expressed from the weaker simian CMV promoter.

FIG. 6 illustrates rhesus macaque IL-12 dual expression plasmids. In plasmid AG157, the rhesus macaque IL-12 p4-0 subunit is expressed from the stronger human CMV promoter and p35 is expressed from the weaker simian CMV promoter. In plasmid AG159, the IL-12 p35 subunit is expressed from the stronger human CMV promoter and IL-12 p40 is expressed from the weaker simian CMV promoter.

FIG. 10 illustrates that IL-23 consists of two subunits: p19 and p40 (IL-23 p40 is identical to IL-12 p40). Plasmid AG177 produces human p19 from an improved RNA nucleic acid sequence having minimized inhibitory/instability sequences (SEQ ID NO:26). The plasmid AG177 expresses human p19 under the control of the human CMV promoter and the BGH polyA signal. The improved RNA nucleic acid sequence encoding the human IL-12 p40 subunit is expressed under the control of the human CMV promoter in plasmid AG180.

FIG. 14 illustrates that IL-27 consists of the p28 and EBI3 subunits. Expression plasmids encoding improved RNA nucleic acid sequences (i.e., having minimized inhibitory/instability sequences) for murine IL-27 p28 (SEQ ID NO:27) and murine EBI3 (SEQ ID NO:28) were generated. The murine IL-27 p28 subunit is expressed under the control of the human CMV promoter in plasmid AG193. The murine IL-27 EBI3 subunit is expressed under the control of the human CMV promoter in plasmid AG194.

FIG. 16 illustrates dual promoter expression plasmids for murine IL-27. The p28 subunit is expressed from the stronger human CMV promoter and the EBI3 subunit is expressed from the weaker simian CMV promoter in AG205. The EBI3 subunit is expressed from the stronger human CMV promoter and the p28 subunit is expressed from the weaker simian CMV promoter in AG197.

FIG. 18 illustrates expression plasmids for the EBI3 and p28 subunits of the human IL-27. Improved RNA nucleic acid sequences of the human EBI3 (SEQ ID NO:30) and human p28 (SEQ ID NO:29) genes, having minimized instability/inhibitory sequences, were inserted between the human CMV promoter and the BGH polyA signal in plasmids AG214 and AG215, respectively.

FIG. 19 illustrates dual promoter expression plasmids for expression human IL-27 heterodimer. The human IL-27 p28 subunit is expressed from the stronger human CMV promoter and the EBI3 subunit is expressed from the weaker simian CMV promoter in AG216. The EBI3 subunit is expressed from the stronger human CMV promoter and the p28 subunit is expressed from the weaker simian CMV promoter in AG217.

DETAILED DESCRIPTION

1. Introduction

Figure 1:
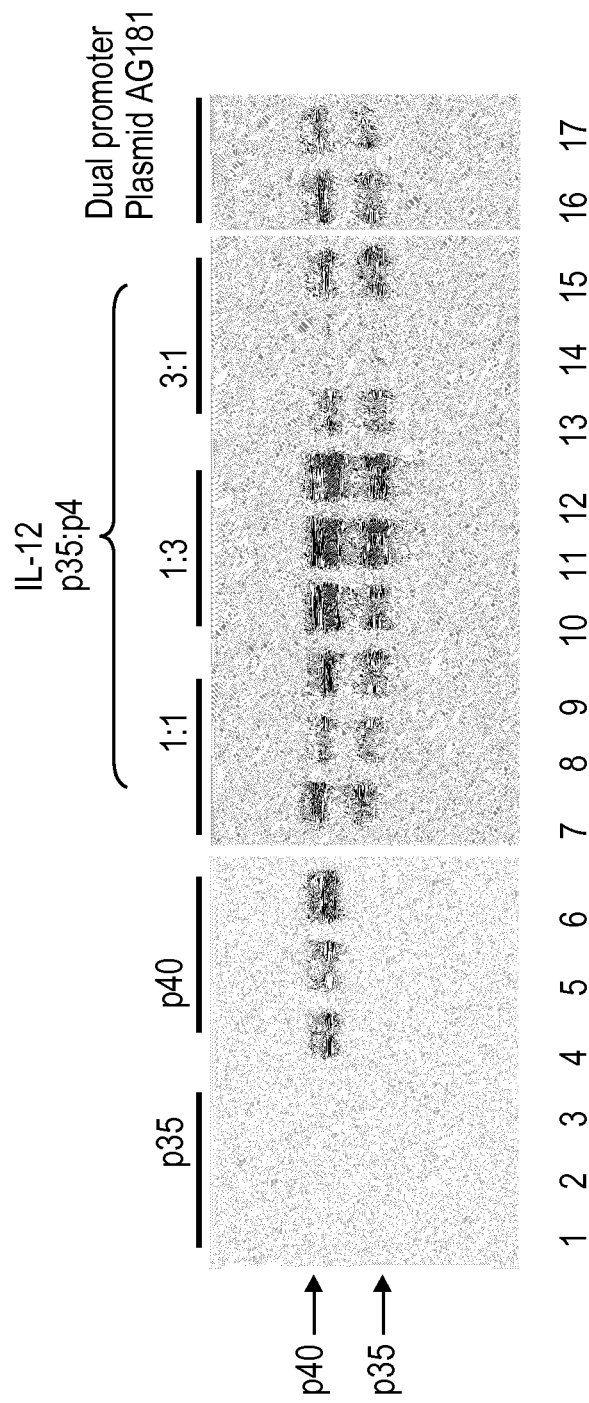
FIG. 1 demonstrates that the presence of excess of the IL-12 p40 subunit promotes stabilization and increased secretion of the IL-12 p35 subunit, resulting in increased production of human IL-12 heterodimer (p35+p40). Human 293 cells were transfected with 100 ng each of two plasmids expressing the individual subunits of human IL-12: p35 (lanes 1-3) and p40 (lanes 4-6), respectively. Three independent (identical) clones of each plasmid were purified and tested in the three lanes. Cotransfection of the p35+p40 subunits at a ratio of 1:1 (lanes 7-9), 1:3 (lanes 11-13) or 3:1 (lanes 13-15) were performed in triplicate. Transfection of IL-12 from the dual promoter plasmid AG181 (see, FIG. 2 below) was performed using two independent clones (lanes 16, 17). Supernatants were analyzed on Western immunoblots, and probed with an anti human IL-12 p70 antibody. In the presence of increased levels of the p40 subunit higher levels of the IL-12 heterodimer are produced and secreted. All coding sequence were improved, i.e., had inhibitory and/or instability sequences minimized, for expression.
Figure 3:
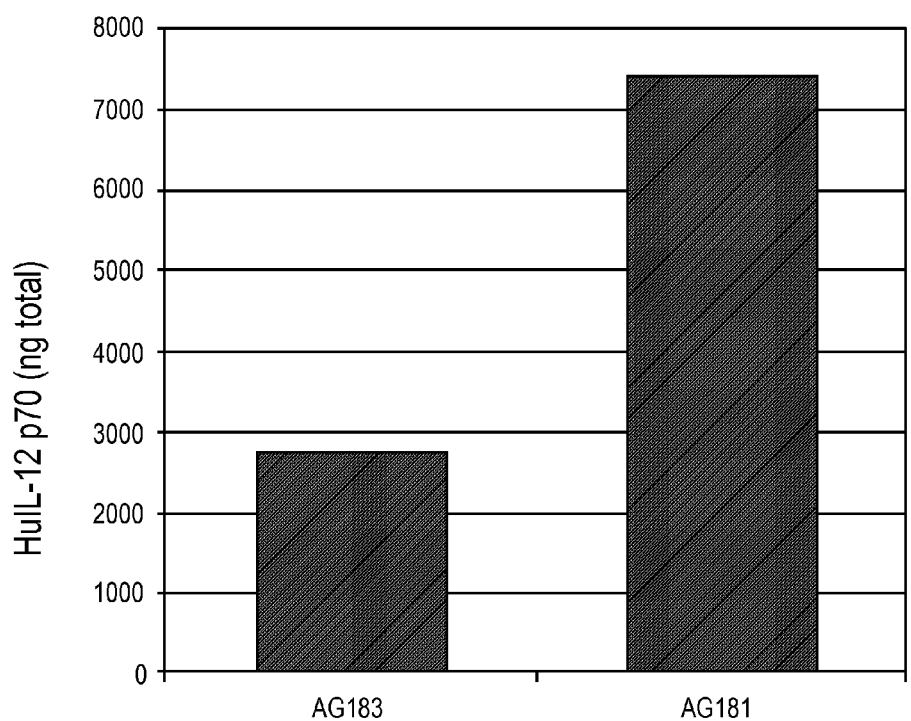
FIG. 3 illustrates expression of human IL-12 from dual expression plasmids AG181 and AG183 in transfected human 293 cells. Expressing the p40 subunit from the stronger human CMV promoter in plasmid AG181 produces about 3-fold higher levels of IL-12 (p70) in comparison to expressing the IL-12 p40 subunit from the weaker simian CMV promoter in plasmid AG183. Measurement of IL-12 was performed with a commercial ELISA (R&D or eBioscience) from the supernatant of the transfected cells.
Figure 4:
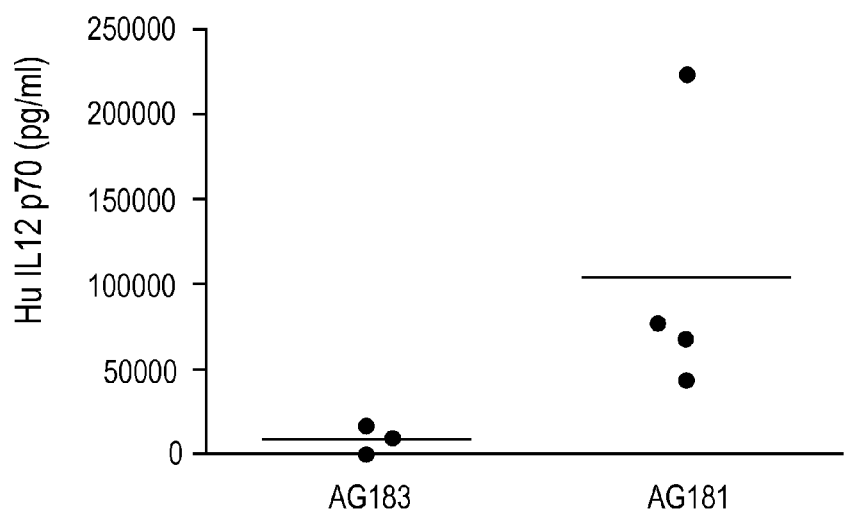
FIG. 4 illustrates expression of human IL-12 from the dual expression plasmids AG181 and AG183 upon DNA delivery in mice (hydrodynamic injection). 100 ng of plasmid DNA was injected in 1.6 ml of 0.9% NaCl solution over seven seconds in the tail vein of the mice. Expressing the p40 subunit from the stronger human CMV promoter in plasmid AG181 produces higher levels of IL-12 (p70) (103580 pg/ml+/−81554 average+/−SD) in comparison to expressing the IL-12 p4-0 subunit from the weaker simian CMV promoter in plasmid AG183 (9172 pg/ml+/−7935 average+/−SD). Measurement of IL-12 heterodimer was performed using a commercial ELISA (R&D) in the plasma of the injected mice at day 3 post injection.
Figure 5:
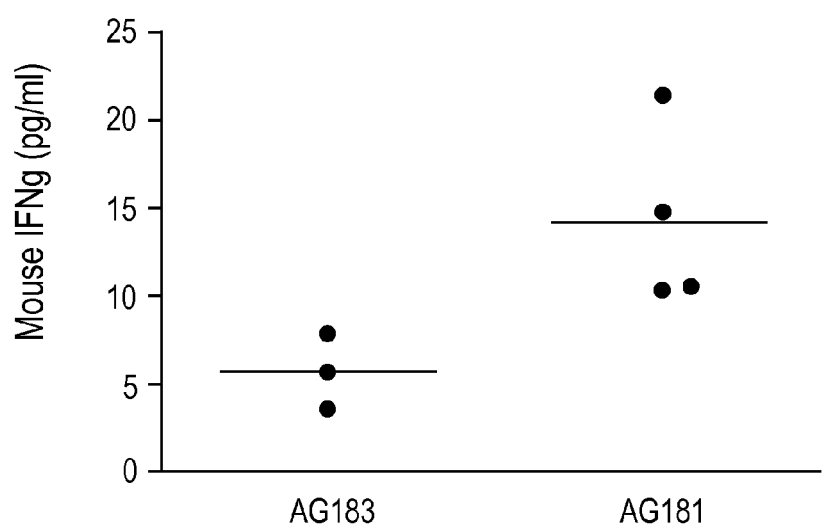
FIG. 5 illustrates that more efficient production of IL-12 promotes induction of higher levels of IFN-γ in the plasma of injected mice (hydrodynamic injection, as described in FIG. 4). At three days post-injection, the IFN-γ levels were measured in the plasma by ELISA (eBioscience). It should be noted that human IL-12 is minimally bioactive in mice, therefore the mouse IFN-γ levels produced were much lower that those produced after mouse IL-12 DNA injection.
Figure 7:
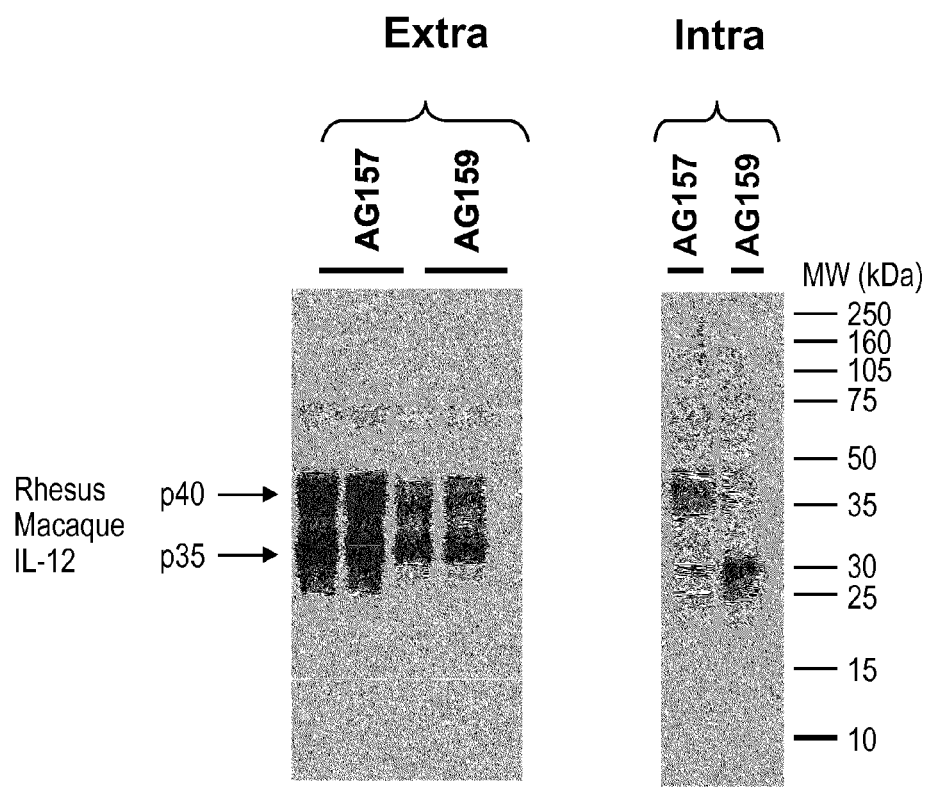
FIG. 7 illustrates expression of the rhesus macaque IL-12 from the dual expression plasmids in transfected human 293 cells. Supernatants and cell extracts were analyzed for the presence of IL-12 from transfected human 293 cells by Western immunoblot. AG157 expressing the IL-12 p40 subunit from the stronger human CMV promoter in plasmid AG157 produces more rhesus macaque IL-12 (p70) in comparison to expressing the IL-12 p40 subunit from the weaker simian CMV promoter in plasmid AG159. The presence of higher levels of p40 leads to more efficient export and stabilization of p35.
Figure 8:
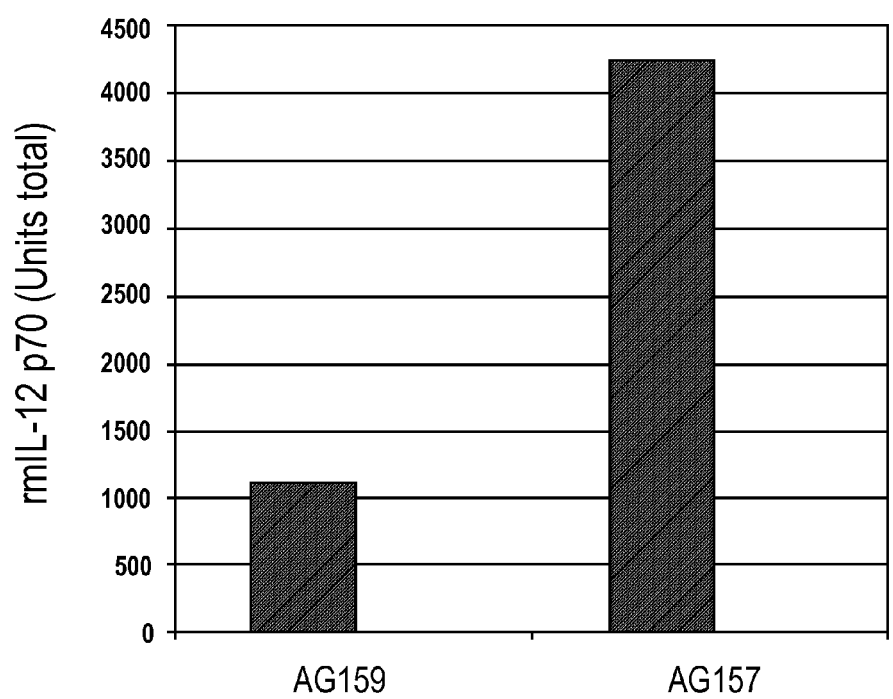
FIG. 8 illustrates quantification of the levels of rhesus macaque IL-12 expression (p70 heterodimer) upon transfection of human 293 cells using commercial ELISA. Expressing the p40 subunit from the stronger human CMV promoter in plasmid AG157 produces about 4-fold higher levels of IL-12 (p70) in comparison to expressing the IL-12 p40 subunit from the weaker simian CMV promoter in plasmid AG159 (analogous to the data presented for human IL-12 p70 heterodimer in FIG. 3).
Figure 9:
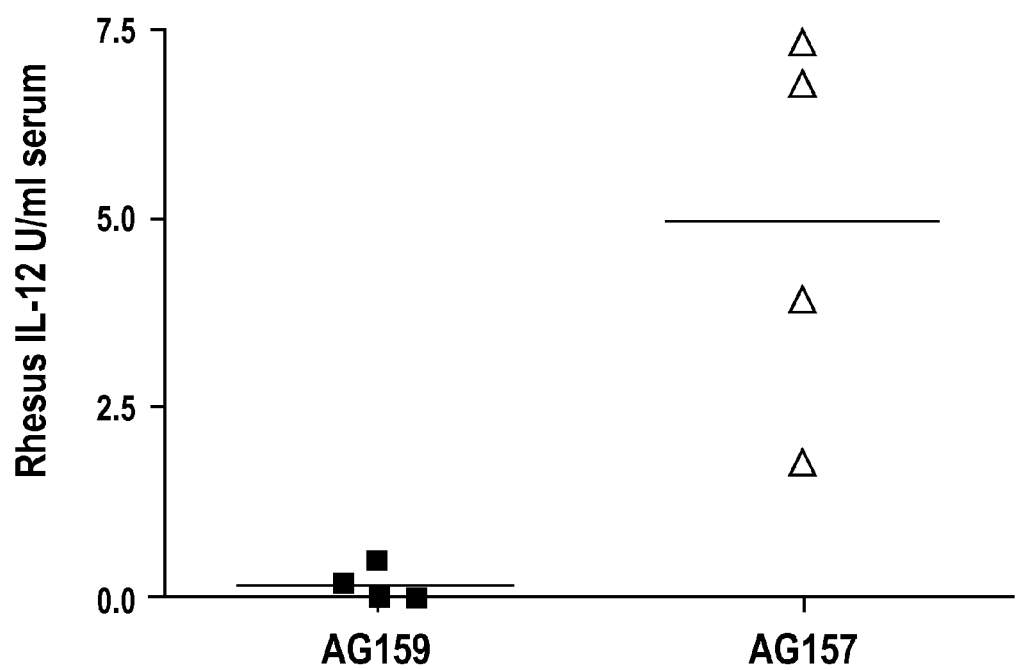
FIG. 9 illustrates expression of rhesus macaque IL-12 upon intramuscular injection of the dual expression plasmids in the macaques. 100 micrograms of either the AG157 or AG159 DNA were injected intramuscularly into the macaques. Serum levels of the rhesus macaque IL-12 (p70) were measured at day 4 by ELISA. AG157 produces about 30-fold higher levels of IL-12 p70 heterodimer in comparison to AG159.
Figure 11:
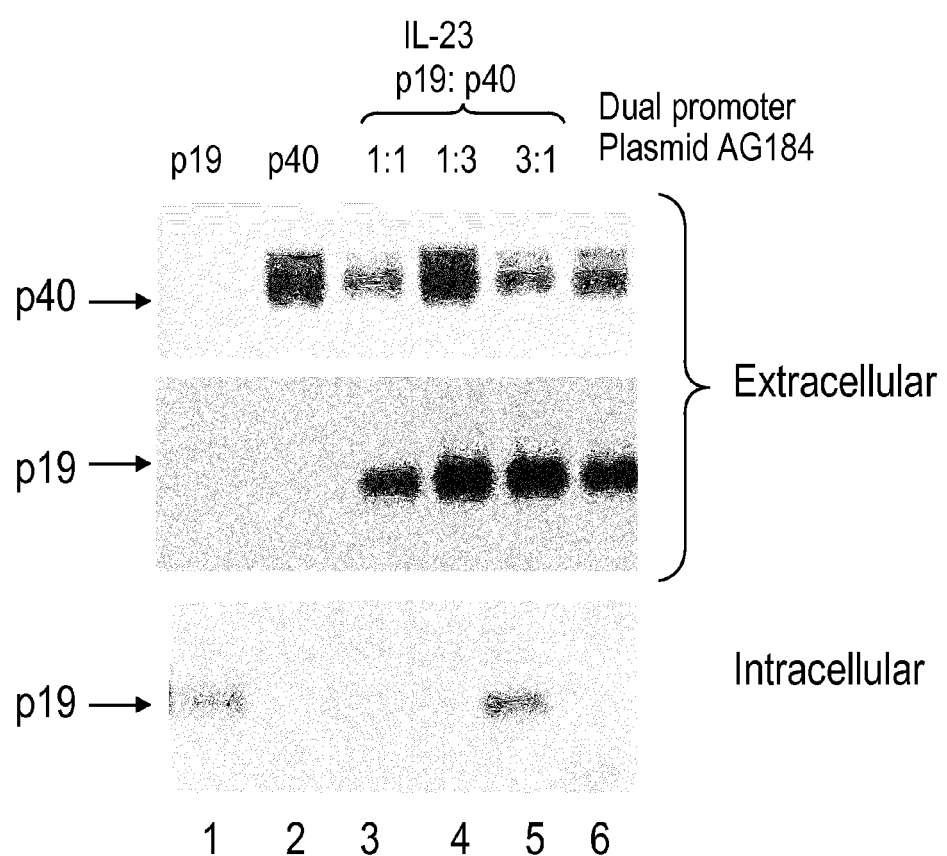
FIG. 11 illustrates more efficient human IL-23 heterodimer production in the presence of high levels of the IL-12 subunit p40. The plasmids expressing p19 (AG177) and p40 (AG180) were transfected into human 293 cells and one day later the cells were analyzed by Western immunoblot. Expression of the p19 (lane 1) and p40 (lane 2) subunits alone shows that the p19 subunit remains cell-associated when expressed alone. Co-transfection of p19 and p40 at different ratios, as indicated: p19:p40 at 1:1 (lane 3), 1:3 (lane 4) or 3:1 (lane 5) demonstrates that the presence of higher levels of p40 results in higher levels of IL-23 heterodimer production (lane 4). Lane 6 shows IL-23 heterodimer production from the dual promoter plasmid AG184 (see, FIG. 12, below).

The invention relates to increased expression levels of heterodimeric proteins, e.g., IL-12 family cytokines, and in general multimeric protein production by optimizing the relative expression ratios of the subunits in vitro and in vivo. Surprisingly, expressing the first and second subunits of a heterodimeric protein, e.g., an IL-12 family cytokine, at appropriate relative molar ratios results in increased expression levels, e.g., in the extracellular space, that are at least about 3-fold or 4-fold as measured in vitro (e.g., concentration in culture media) and at least about 20-fold or 30-fold as measured in vivo (e.g., concentration in serum) in comparison to expressing the first and second subunits at an equimolar ratio. Furthermore, achieving higher levels of extracellular expression of IL-12 family cytokines facilitates their efficacious concentrations when administered in vivo.

The invention finds use, for example, for the improved expression of heterodimeric and multimeric cytokines and other proteins of mammalian origin, e.g., murine, rhesus and human origin. Experimental testing is performed to identify which subunit is limiting and general methods are provided for increasing expression of heterodimeric polypeptides. Once determined, relative expression ratios of the subunits can be achieved using any known methods. For example, optimized expression can be achieved upon coordinate production of optimal ratios of the respective subunits. Alternatively, the two or more subunits can be expressed from a single plasmid containing two or more promoters that differ in their expression strength (e.g., the human CMV promoter is stronger than the simian CMV promoter). Alternatively, the two subunits can be produced by bicistronic mRNAs (for example, ones that have internal ribosome entry sites, IRES) in the appropriate order so that expression ratios are optimal. The use of these optimized expression strategies leads to improvement of cytokine expression and prevents negative effects due to the excess production of single chains. This strategy is of general application to express multimeric proteins.

2. Nucleic Acid Sequences

As described herein, the nucleic acid and amino acid sequences of IL-12 family cytokine alpha and beta subunits, e.g., IL-12, IL-23, and IL-27 alpha and beta subunits, are known in the art. The sequences of native or naturally occurring IL-12 family cytokine subunits can be used. Alternatively, the coding sequences of one or more of the alpha and beta subunits can be improved to minimize or eliminate inhibitory or instability sequences according to known methods, e.g., described for example, in U.S. Pat. Nos. 5,965,726; 5,972,596; 6,174,666; 6,291,664; 6,414,132; and 6,794,498 and in PCT Publication Nos. WO 07/084,364 and WO 07/084,342, the disclosures of each of which are hereby incorporated herein by reference in their entirety for all purposes.

The improved high expressing IL-12 family cytokine nucleic acid sequences of the invention are generally based on a native mammalian interleukin-12 family cytokine coding sequence as a template. Nucleic acids sequences encoding native interleukin-12 family cytokines can be readily found in publicly available databases including, e.g., nucleotide, protein and scientific databases available on the worldwide web through the National Center for Biotechnology Information at ncbi.nlm.nih.gov. Native IL-12 family cytokine nucleic acid sequences can be conveniently cloned from mammalian dendritic cells and macrophages following appropriate stimulation (See, e.g., Goriely, et al., *Nature Rev Immunol* (2008) 8(1):81-6; Kastelein, et al., *Annu Rev Immunol* (2007) 25:221-42; Beadling and Slifka, *Arch Immunol Ther Exp* (2006) 54(1):15-24; and Goriely and Goldman, *Am J Transplant* (2007) 7(2):278-84). Protocols for isolation and stimulation of desired immune cell populations are well known in the art. See, for example, *Current Protocols in Immunology*, Coligan, et al., eds., 1991-2008, John Wiley & Sons.

The sequences are modified according to methods that simultaneously rectify several factors affecting mRNA traffic, stability and expression. Codons are altered to change the overall mRNA AT(AU)-content, to minimize or remove all potential splice sites, and to alter any other inhibitory sequences and signals affecting the stability and processing of mRNA such as runs of A or T/U nucleotides, AATAAA, ATTTA and closely related variant sequences, known to negatively affect mRNA stability. The methods applied to IL-12 coding nucleic acid sequences in the present application have been described in U.S. Pat. Nos. 6,794,498; 6,414,132; 6,291,664; 5,972,596; and 5,965,726 the disclosures of each of which are hereby incorporated herein by reference in their entirety for all purposes.

Generally, the changes to the nucleotide bases or codons of a coding IL-12 family cytokine sequences do not alter the amino acid sequence of the translated monomers comprising an IL-12 family cytokine heterodimer from the native alpha and beta subunit polypeptides. The changes are based upon the degeneracy of the genetic code, utilizing an alternative codon for an identical amino acid, as summarized in Table 1, above. In certain embodiments, it will be desirable to alter one or more codons to encode a similar amino acid residue rather than an identical amino acid residue. Applicable conservative substitutions of coded amino acid residues are described above.

Oftentimes, in carrying out the present methods for increasing the stability of an IL-12 family cytokine coding sequence, a relatively more A/T-rich codon of a particular amino acid is replaced with a relatively more G/C rich codon encoding the same amino acid. For example, amino acids encoded by relatively more A/T-rich and relatively more G/C rich codons are shown in Table 2.

TABLE 2

| Amino Acid | relatively more A/T-rich codon(s) | relatively more G/C-rich codon(s) |
|---|---|---|
| Ala | GCA, GCT | GCC, GCG |
| Asn | AAT | AAC |
| Asp | GAT | GAC |
| Arg | CGA, CGT, AGA | CGC, CGG, AGG |
| Cys | TGT | TGC |
| Gln | CAA | CAG |
| Glu | GAA | GAG |
| Gly | GGA, GGT | GGC, GGG |
| His | CAT | CAC |
| Ile | ATA, ATT | ATC |
| Leu | TTA, CTA, CTT | TTG, CTC, CTG |
| Lys | AAA | AAG |
| Phe | TTT | TTC |
| Pro | CCA, CCT | CCC, CCG |
| Ser | TCA, TCT, AGT | TCC, TCG, AGC |
| Thr | ACA, ACT | ACC, ACG |
| Tyr | TAT | TAC |
| Val | GTA, GTT | GTC, GTG |

Depending on the number of changes introduced, the improved IL-12 family cytokine nucleic acid sequences of the present invention can be conveniently made as completely synthetic sequences. Techniques for constructing synthetic nucleic acid sequences encoding a protein or synthetic gene sequences are well known in the art. Synthetic gene sequences can be commercially purchased through any of a number of service companies, including DNA 2.0 (Menlo Park, Calif.), Geneart (Toronto, Ontario, Canada), CODA Genomics (Irvine, Calif.), and GenScript, Corporation (Piscataway, N.J.). Alternatively, codon changes can be introduced using techniques well known in the art. The modifications also can be carried out, for example, by site-specific in vitro mutagenesis or by PCR or by any other genetic engineering methods known in art which are suitable for specifically changing a nucleic acid sequence. In vitro mutagenesis protocols are described, for example, in *In Vitro Mutagenesis Protocols*, Braman, ed., 2002, Humana Press, and in Sankaranarayanan, *Protocols in Mutagenesis*, 2001, Elsevier Science Ltd.

High level expressing improved IL-12 family cytokine sequences can be constructed by altering select codons throughout a native IL-12 family cytokine nucleic acid sequence, or by altering codons at the 5'-end, the 3'-end, or within a middle subsequence. It is not necessary that every codon be altered, but that a sufficient number of codons are altered so that the expression (i.e., transcription and/or translation) of the improved IL-12 family cytokine nucleic acid sequence is at least about 10%, 20%, 30%, 40%, 50%, 60%, 70%, 80%, 90%, 1-fold, 2-fold, 3-fold, 4-fold, 5-fold, 6-fold, or more abundant in comparison to expression from a native IL-12 family cytokine nucleic acid sequence under the same conditions. Expression can be detected over time or at a designated endpoint, using techniques known to those in the art, for example, using gel electrophoresis or anti-IL-12 antibodies in solution phase or solid phase binding reactions (e.g., ELISA, immunohistochemistry). ELISA kits for detecting either the alpha and beta subunits of IL-12 family cytokine family polypeptides and heterodimers are commercially available from, for example, R & D Systems (Minneapolis, Minn.), Invitrogen-Biosource (Carlsbad, Calif.), eBioscience (San Diego, Calif.), Santa Cruz Biotech (Santa Cruz, Calif.) and PeproTech, (Rocky Hill, N.J.).

The GC-content of an improved IL-12 family cytokine nucleic acid sequence is usually increased in comparison to a native IL-12 family cytokine nucleic acid sequence when applying the present methods. For example, the GC-content of an improved IL-12 p35, IL-12 p40 (IL-23 p40), IL-23 p19, IL-27 p28 or IL-27 EBI3 nucleic acid sequence can be at least about 50%, 51%, 52%, 53%, 54%, 55%, 56%, 57%, 58%, 59%, 60%, 61%, 62%, 63%, 64%, 65%, 70%, or more.

Exemplary improved IL-12 heterodimer sequences (i.e., p35 and p40 subunits) are described, for example, in PCT Publication No. WO 2007/084364. In some embodiments, the improved nucleic acid sequence encoding a human IL-23 p19 with reduced inhibitory/instability sequences is SEQ ID NO:26. In some embodiments, the improved nucleic acid sequence encoding a murine IL-27 p28 with reduced inhibitory/instability sequences is SEQ ID NO:27. In some embodiments, the improved nucleic acid sequence encoding a murine IL-27 EBI3 with reduced inhibitory/instability sequences is SEQ ID NO:28. In some embodiments, the improved nucleic acid sequence encoding a human IL-27 p28 with reduced inhibitory/instability sequences is SEQ ID NO:29. In some embodiments, the improved nucleic acid sequence encoding a human IL-27 EBI3 with reduced inhibitory/instability sequences is SEQ ID NO:30.

Once a high level expressing improved IL-12 nucleic acid sequence has been constructed, it can be cloned into a cloning vector, for example a TA-cloning® vector (Invitrogen, Carlsbad, Calif.) before subjecting to further manipulations for insertion into one or more expression vectors. Manipulations of improved IL-12 nucleic acid sequences, including recombinant modifications and purification, can be carried out using procedures well known in the art. Such procedures have been published, for example, in Sambrook and Russell, *Molecular Cloning: A Laboratory Manual*, 2001, Cold Spring Harbor Laboratory Press and *Current Protocols in Molecular Biology*, Ausubel, et al., eds., 1987-2008, John Wiley & Sons.

3. Expression Vectors

The alpha and beta subunit chains of the IL-12 family cytokines can be recombinantly expressed from a single plasmid or expression vector or from multiple plasmids or expression vectors. The alpha and beta subunit chains can be expressed from a single expression cassette or separate, independent expression cassettes. The expression vectors of the invention typically have at least two independent expression cassettes, one that will express an alpha subunit and one that will express a beta subunit of the heterodimer. Within each expression cassette, sequences encoding one or both IL-12 family cytokine subunit chains will be operably linked to expression regulating sequences. "Operably linked" sequences include both expression control sequences that are contiguous with the nucleic acid of interest and expression control sequences that act in trans or at a distance to control the gene of interest. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., Kozak consensus sequence); sequences that enhance protein stability; and when desired, sequences that enhance protein secretion. The regulating sequences independently can be the same or different between the two expression cassettes. Usually, the regulating sequences will be different. When expressing the alpha and beta subunit chains from a single expression cassette, an internal ribosome entry site (IRES) is included.

The expression vector can optionally also have a third independent expression vector for expressing a selectable marker. Selectable markers are well known in the art, and can include, for example, proteins that confer resistance to an antibiotics, fluorescent proteins, antibody epitopes, etc. Exemplified markers that confer antibiotic resistance include sequences encoding β-lactamases (against β-lactamsincluding penicillin, ampicillin, carbenicillin), or sequences encoding resistance to tetracylines, aminoglycosides (e.g., kanamycin, neomycin), etc. Exemplified fluorescent proteins include green fluorescent protein, yellow fluorescent protein and red fluorescent protein.

The promoter(s) included in the expression cassette(s) should promote expression of one or both of the alpha and beta subunit chains in a mammalian cell. The promoter or promoters can be viral, oncoviral or native mammalian, constitutive or inducible, or can preferentially regulate transcription of one or both alpha and beta subunit chains in a particular tissue type or cell type (e.g., "tissue-specific").

A "constitutive" promoter is a promoter that is active under most environmental and developmental conditions. Exemplified constitutive promoters in mammalian cells include oncoviral promoters (e.g., simian cytomegalovirus (CMV), human CMV, simian virus 40 (SV40), rous sarcoma virus (RSV)), promoters for immunoglobulin elements (e.g., IgH), promoters for "housekeeping" genes (e.g., β-actin, dihydrofolate reductase).

As discussed below, the promoters controlling the expression of the alpha and beta subunits can be of relatively different (weaker or stronger) strengths to allow for expression of the alpha and beta subunits at the desired relative molar ratios. For example, the relatively stronger promoter can be a human CMV promoter and the relatively weaker promoter can be a simian CMV promoter. In another embodiment, the relatively stronger promoter can be a constitutive promoter and the relatively weaker promoter can be an inducible promoter.

In another embodiment, inducible promoters may be desired. An "inducible" promoter is a promoter that is active under environmental or developmental regulation. Inducible promoters are those which are regulated by exogenously supplied compounds, including without limitation, a zinc-inducible metallothionine (MT) promoter; an isopropyl thiogalactose (IPTG)-inducible promoter, a dexamethasone (Dex)-inducible mouse mammary tumor virus (MMTV) promoter; a tetracycline-repressible system (Gossen et al, *Proc. Natl. Acad. Sci. USA*, 89: 5547-5551 (1992)); the tetracycline-inducible system (Gossen et al., *Science*, 268: 1766-1769 (1995); see also Harvey et al., *Curr. Opin. Chem. Biol.*, 2: 512-518 (1998)); the RU486-inducible system (Wang et al., *Nat. Biotech.*, 15: 239-243 (1997) and Wang et al., *Gene Ther.*, 4: 432-441 (1997)); and the rapamycin-inducible system (Magari et al. *J. Clin. Invest.*, 100: 2865-2872 (1997)). Other types of inducible promoters which can be useful in this context are those which are regulated by a specific physiological state, e.g., temperature, acute phase, or in replicating cells only.

In another embodiment, the native promoter for a mammalian IL-12 family cytokine subunit can be used. The native promoter may be preferred when it is desired that expression of improved IL-12 family cytokine sequences should mimic the native expression. The native promoter can be used when expression of the improved IL-12 family cytokine must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic expression of a native IL-12 family cytokine polypeptide.

In another embodiment, the improved IL-12 family cytokine sequences can be operably linked to a tissue-specific promoter. For instance, if expression in lymphocytes or monocytes is desired, a promoter active in lymphocytes or monocytes, respectively, should be used. Examples of promoters that are tissue-specific are known for numerous tissues, including liver (albumin, Miyatake et al. *J. Virol.*, 71: 5124-32 (1997); hepatitis B virus core promoter, Sandig et al., *Gene Ther.*, 3: 1002-9 (1996); alpha-fetoprotein (AFP), Arbuthnot et al., *Hum. Gene Ther.* 7: 1503-14 (1996)), bone (osteocalcin, Stein et al., *Mol. Biol. Rep.*, 24: 185-96 (1997); bone sialoprotein, Chen et al., *J. Bone Miner. Res.*, 11: 654-64 (1996)), lymphocytes (CD2, Hansal et al., *J. Immunol.*, 161: 1063-8 (1998); immunoglobulin heavy chain; T cell receptor a chain), neuronal (neuron-specific enolase (NSE) promoter, Andersen et al. *Cell. Mol. Neurobiol.*, 13: 503-15 (1993); neurofilament light-chain gene, Piccioli et al., *Proc. Natl. Acad. Sci. USA*, 88: 5611-5 (1991); the neuron-specific vgf gene, Piccioli et al., *Neuron*, 15: 373-84 (1995)); among others.

Figure 12:
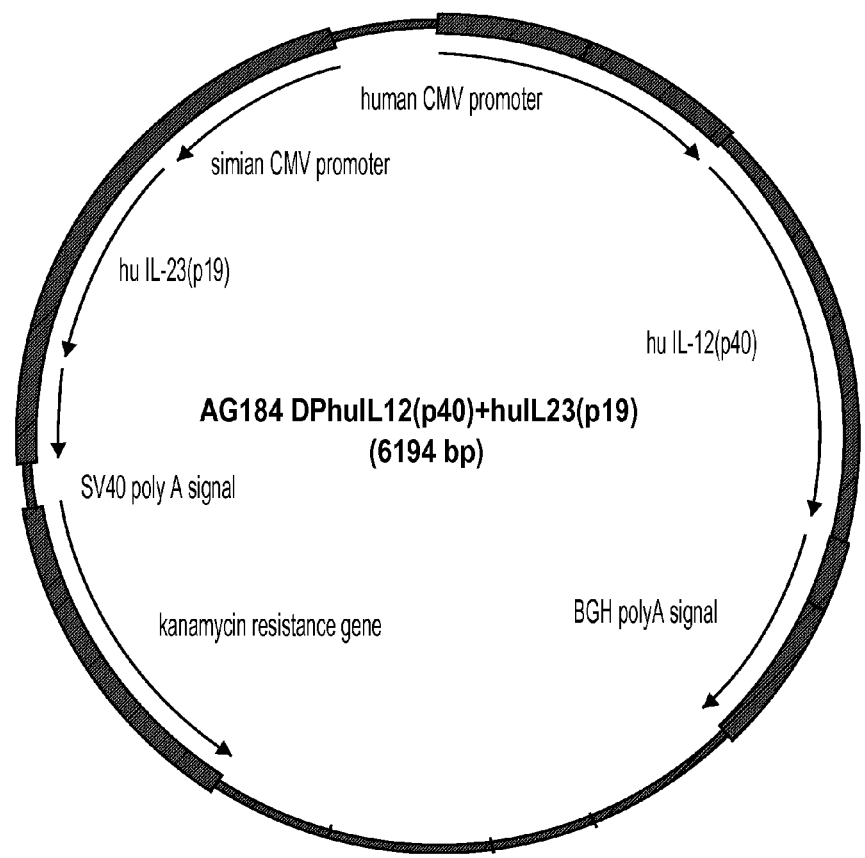
FIG. 12 illustrates a dual promoter expression plasmid AG184, for human IL-23. The p40 subunit is expressed from the stronger human CMV promoter and the p19 subunit is expressed from the weaker simian CMV promoter.
Figure 13:
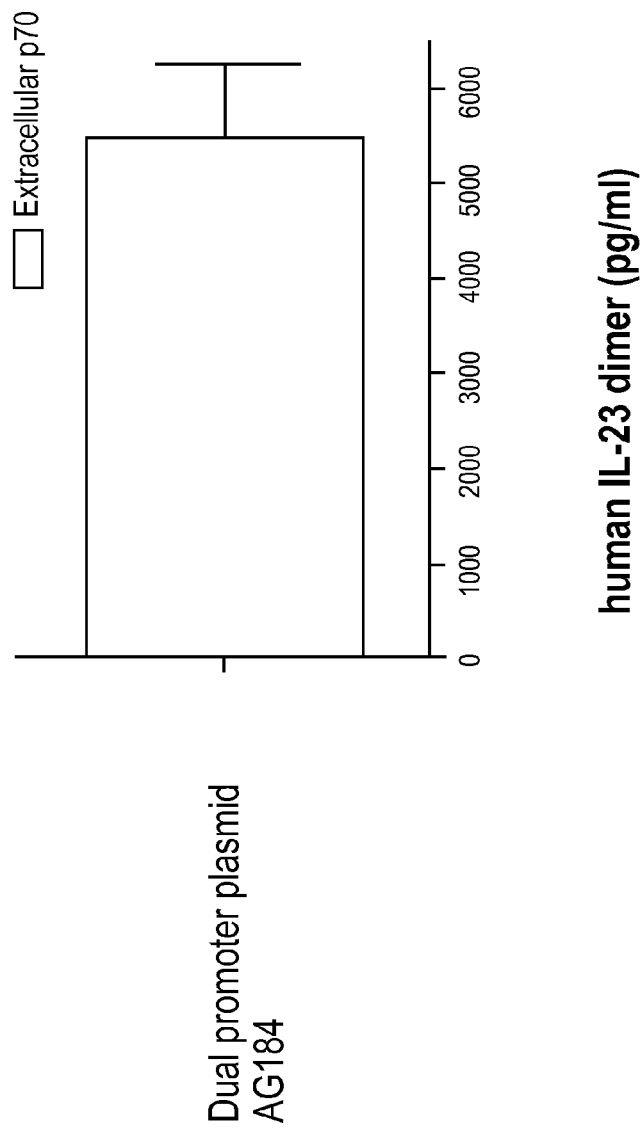
FIG. 13 illustrates quantification of human IL-23 heterodimer production from the dual promoter expression plasmid AG184. Human 293 cells were transfected with 100 ng of AG184 and IL-23 heterodimer was measured in the supernatant 2 days later by ELISA (eBioscience). Total supernatant volume was 4 ml per plate.
Figure 15:
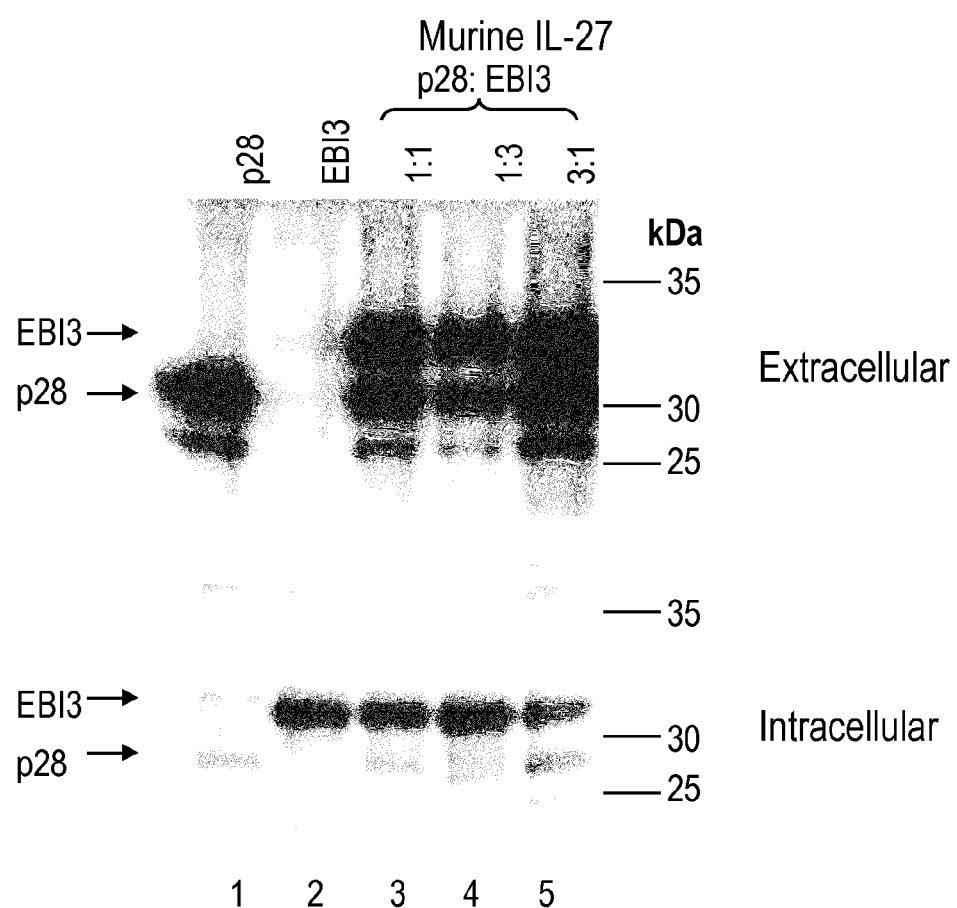
FIG. 15 illustrates expression of the murine IL-27 heterodimer from transfected human 293 cells. Expression of the p28 (lane 1) or EBI3 (lane 2) subunit alone shows that EBI3 remains cell-associated. Co-expression of the subunits (lanes 3-5) at a ratio of p28:EBI3 of 1:1 (lane 3), 1:3 (lane 4) or 3:1 (lane 5) shows that higher p28 levels result in higher IL-27 heterodimer production in the supernatant. Therefore, excess of p28 promotes stabilization and secretion of EBI3.
Figure 17:
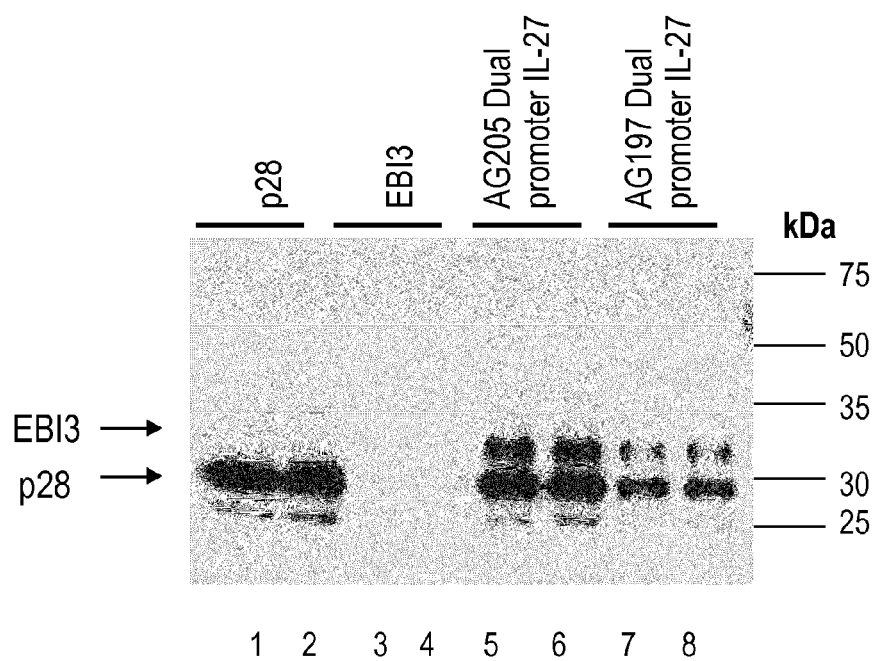
FIG. 17 illustrates more efficient murine IL-27 heterodimer production from the dual promoter expression plasmid. The plasmid expressing the p28 subunit form the human CMV promoter (AG205) (lanes 5, 6) produces higher levels of IL-27 compared to levels obtained from AG197 (lanes 7, 8). The presence of both subunits is essential for IL-27 production. Expression of p28 alone (lanes 1, 2) or EBI3 alone (lanes 3, 4) show that in the absence of cotransfected p28, the EBI3 subunit is not secreted.
Figure 20:
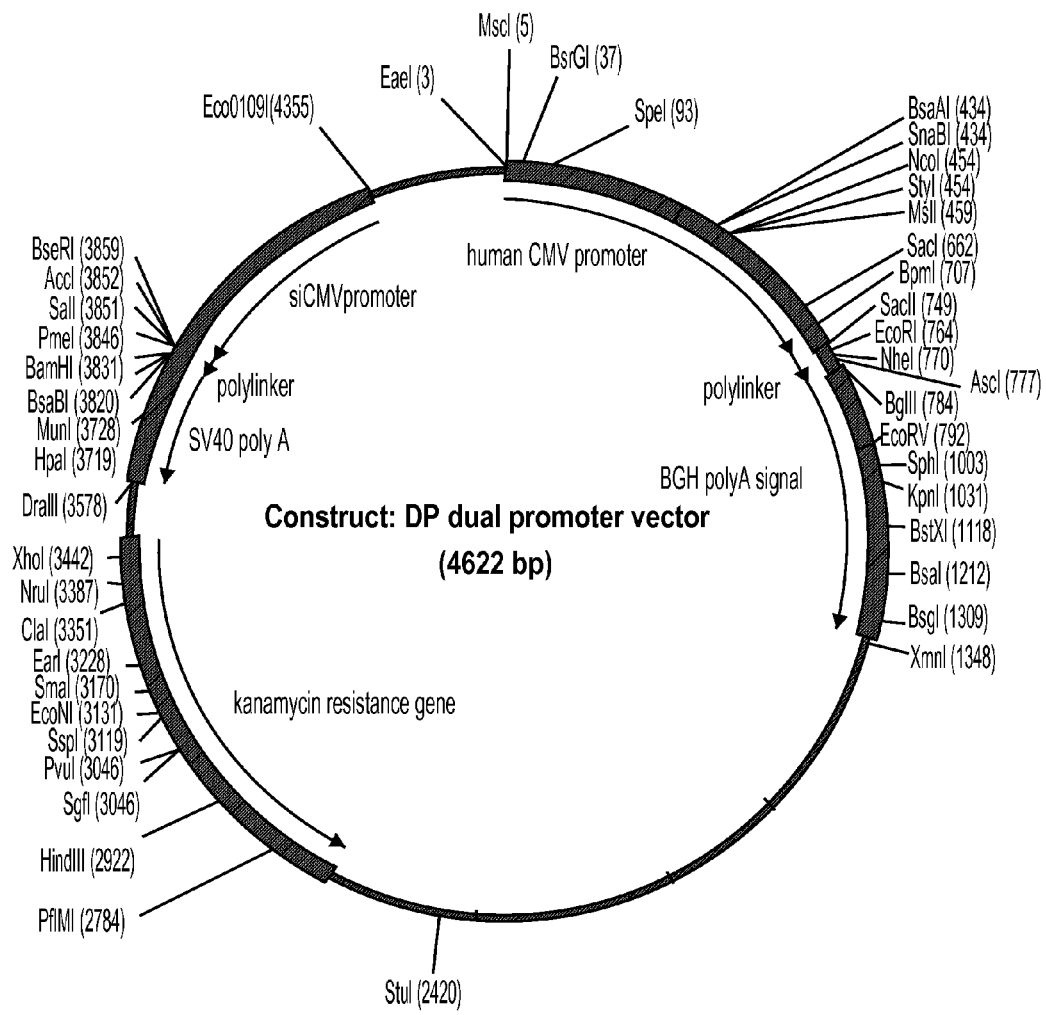
FIG. 20 illustrates schematics of vector backbones for single expression cassette vector CMVkan (SEQ ID NO:31) and dual expression promoter DP (SEQ ID NO:32), comprising a first expression cassette for expression a first subunit of a heterodimeric protein from the relatively stronger human CMV promoter and a second expression cassette for expression of a second subunit of a heterodimeric protein from the relatively weaker simian CMV promoter.
Figure 20:
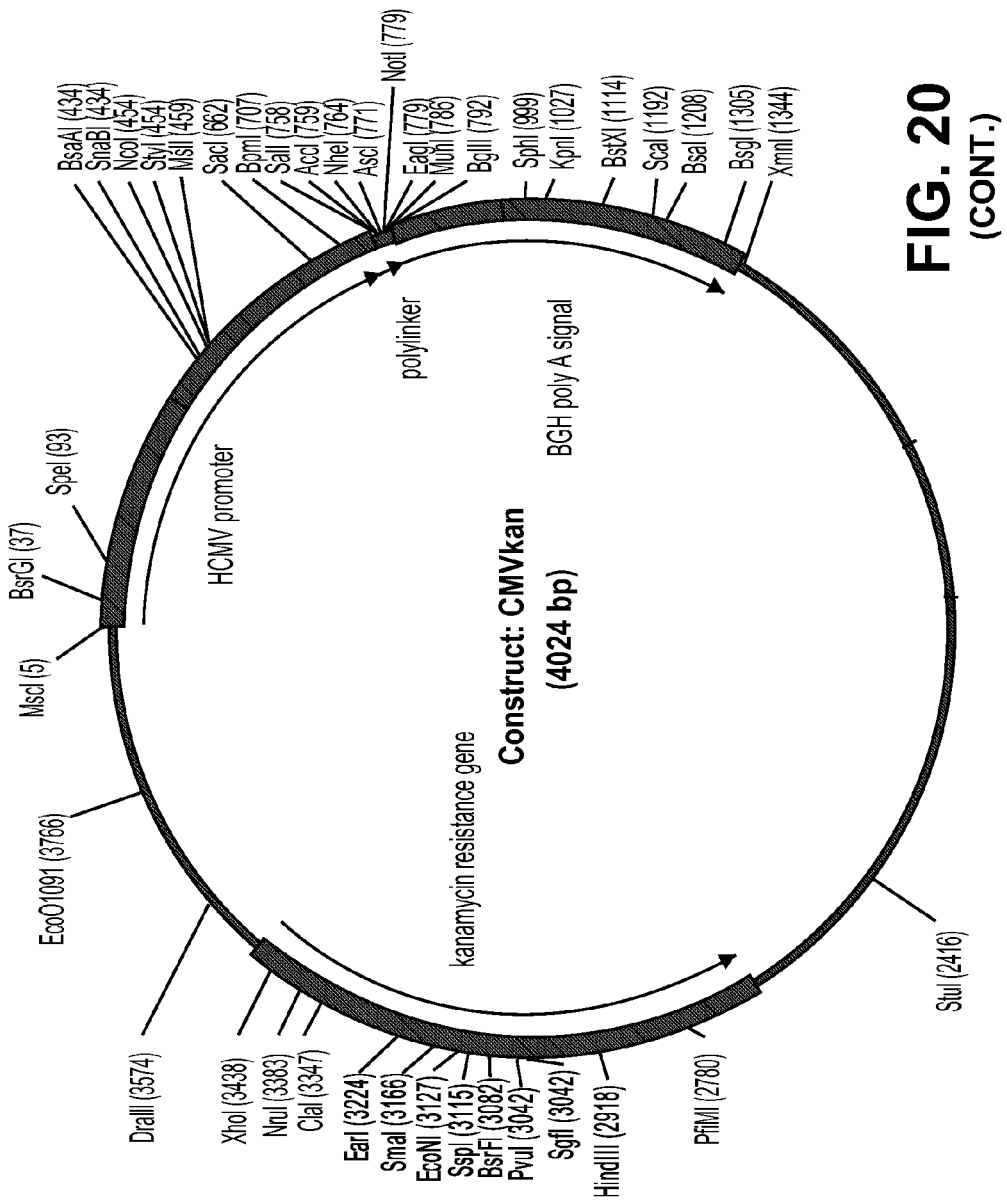

Dual-promoter expression vectors for the concurrent expression of two polypeptide chains in a mammalian cell are commercially available, for example, the pVITRO vector from InvivoGen (San Diego, Calif.). Exemplified dual-promoter expression vectors are shown in FIGS. 2, 6, 12, 16, 19 and 20 and as SEQ ID NOS:1, 3, 7, 10, 14 and 32.

As discussed below, the expression vectors can also be viral vectors.

4. Mammalian Host Cells

The expression vectors of the invention can be expressed in mammalian host cells. The host cells can be in vivo in a host or in vitro. For example, expression vectors containing high-level expressing IL-12 family cytokine nucleic acid sequences can be transfected into cultured mammalian host cells in vitro, or delivered to a mammalian host cell in a mammalian host in vivo.

Exemplary host cells that can be used to express improved IL-12 nucleic acid sequences include mammalian primary cells and established mammalian cell lines, including COS, CHO, HeLa, NIH3T3, HEK 293-T, RD and PC12 cells. Mammalian host cells for expression of IL-12 family cytokine subunits polypeptides are commercially available from, for example, the American Type Tissue Collection (ATCC), Manassas, Va. Protocols for in vitro culture of mammalian cells is also well known in the art. See, for example, *Handbook of Industrial Cell Culture: Mammalian, Microbial, and Plant Cells*, Vinci, et al., eds., 2003, Humana Press; and *Mammalian Cell Culture: Essential Techniques*, Doyle and Griffiths, eds., 1997, John Wiley & Sons.

Protocols for transfecting mammalian host cells in vitro and expressing recombinant nucleic acid sequences are well known in the art. See, for example, Sambrook and Russell, and Ausubel, et al, supra; *Gene Delivery to Mammalian Cells: Nonviral Gene Transfer Techniques*, Methods in Molecular Biology series, Heiser, ed., 2003, Humana Press; and Makrides, *Gene Transfer and Expression in Mammalian Cells*, New Comprehensive Biochemistry series, 2003, Elsevier Science. Mammalian host cells modified to express the improved IL-12 family cytokine nucleic acid sequences can be transiently or stably transfected with a recombinant vector. The improved IL-12 family cytokine sequences can remain epigenetic or become chromasomally integrated.

5. Vaccine Adjuvants

The high level expression improved IL-12 family cytokine nucleic acid sequences are suitable for use as an adjuvant co-delivered with a vaccine antigen. The use of IL-12 family cytokines as adjuvants in antimicrobial therapy, anticancer therapy and for stimulating mucosal immunity is known in the art. See, for example, Tomioka, *Curr Pharm Des* (2004) 10:3297; El-Aneed, *Eur J Pharmacol* (2004) 498:1; Stevceva and Ferrari, *Curr Pharm Des* (2005) 11:801; Toka, et al., *Immunol Rev* (2004) 199:100; Overwijk, et al., *J Immunol.* (2006) 176(9): 5213-5222; Matsui, et al. *Journal of Virology*, (2004) 78(17):9093-9104; Goldberg, et al., *J Immunol*, (2004) 173:1171-1178).

In a preferred embodiment, high level expressing improved IL-12 family cytokine nucleic acid sequences are co-administered with one or more vaccine antigens, with at least the improved IL-12 family cytokine nucleic acid sequences delivered as naked DNA. The antigen can be delivered as one or more polypeptide antigens or a nucleic acid encoding one or more antigens. Naked DNA vaccines are generally known in the art; see, Wolff, et al., *Science* (1990) 247:1465; Brower, *Nature Biotechnology* (1998) 16:1304-130; and Wolff, et al., *Adv Genet* (2005) 54:3. Methods for the use of nucleic acids as DNA vaccines are well known to one of ordinary skill in the art. See, *DNA Vaccines*, Ertl, ed., 2003, Kluwer Academic Pub and *DNA Vaccines: Methods and Protocols*, Lowrie and Whalen, eds., 1999, Humana Press. The methods include placing a nucleic acid encoding one or more antigens under the control of a promoter for expression in a patient. Co-administering high level expressing improved IL-12 family cytokine nucleic acid sequences further enhances the immune response against the one or more antigens. Without being bound by theory, following expression of the polypeptide encoded by the DNA vaccine, cytotoxic T-cells, helper T-cells and antibodies are induced which recognize and destroy or eliminate cells or pathogens expressing the antigen.

The invention contemplates compositions comprising improved IL-12 family cytokine nucleic acid sequences in a physiologically acceptable carrier. While any suitable carrier known to those of ordinary skill in the art may be employed in the pharmaceutical compositions of this invention, the type of carrier will vary depending on the mode of administration. For parenteral administration, including subcutaneous or intramuscular injection, the carrier preferably comprises water, saline, and optionally an alcohol, a fat, a polymer, a wax, one or more stabilizing amino acids or a buffer. General formulation technologies are known to those of skill in the art (see, for example, *Remington: The Science and Practice of Pharmacy* (20th edition), Gennaro, ed., 2000, Lippincott Williams & Wilkins; *Injectable Dispersed Systems: Formulation, Processing And Performance*, Burgess, ed., 2005, CRC Press; and *Pharmaceutical Formulation Development of Peptides and Proteins*, Frkjr et al., eds., 2000, Taylor & Francis).

Naked DNA can be delivered in solution (e.g., a phosphate-buffered saline solution) by injection, usually by an intra-arterial, intravenous, subcutaneous or intramuscular route. In general, the dose of a naked nucleic acid composition is from about 10 μg to 10 mg for a typical 70 kilogram patient. Subcutaneous or intramuscular doses for naked nucleic acid (typically DNA encoding a fusion protein) will range from 0.1 mg to 50 mg for a 70 kg patient in generally good health.

DNA vaccinations can be administered once or multiple times. In some embodiments, the improved IL-12 family cytokine nucleic acid sequences are administered more than once, for example, 2, 3, 4, 5, 6, 7, 8, 10, 15, 20 or more times as needed to induce the desired response (e.g., specific antigenic response). Multiple administrations can be administered, for example, bi-weekly, weekly, bi-monthly, monthly, or more or less often, as needed, for a time period sufficient to achieve the desired response.

In some embodiments, the improved IL-12 family cytokine nucleic acid compositions are administered by liposome-based methods, electroporation or biolistic particle acceleration. A delivery apparatus (e.g., a "gene gun") for delivering DNA into cells in vivo can be used. Such an apparatus is commercially available (e.g., BioRad, Hercules, Calif., Chiron Vaccines, Emeryville, Calif.). Naked DNA can also be introduced into cells by complexing the DNA to a cation, such as polylysine, which is coupled to a ligand for a cell-surface receptor (see, for example, Wu, G. and Wu, C. H. (1988) *J. Biol. Chem.* 263:14621; Wilson et al. (1992) *J. Biol. Chem.* 267:963-967; and U.S. Pat. Nos. 5,166,320; 6,846,809; 6,733,777; 6,720,001; 6,290,987). Liposome formulations for delivery of naked DNA to mammalian host cells are commercially available from, for example, Encapsula Nano-Sciences, Nashville, Tenn. An electroporation apparatus for use in delivery of naked DNA to mammalian host cells is commercially available from, for example, Inovio Biomedical Corporation, San Diego, Calif.

The improved IL-12 family cytokine nucleic acid vaccine compositions are administered to a mammalian host (i.e., individual, patient). The mammalian host usually is a human or a primate. In some embodiments, the mammalian host can be a domestic animal, for example, canine, feline, lagomorpha, rodentia, rattus, hamster, murine. In other embodiment, the mammalian host is an agricultural animal, for example, bovine, ovine, porcine, equine, etc.

6. Methods of Improving Expression of IL-12 Family Cytokines

The methods of the present invention provide for expressing an IL-12 family cytokine from an improved coding sequence in a mammalian cell by introducing a recombinant vector into the cell to express the high level improved alpha and beta nucleic acid sequences described herein. The transfected mammalian cell can be in vitro or in vivo in a mammalian host.

The alpha and beta subunits of the IL-12 family cytokines are co-expressed in a host cell to determine the relative ratio of expression of the alpha and beta subunits that achieves an increased, e.g., in some instances the highest, level and stability of extracellular expression. The host cell can be prokaryotic or eukaryotic. In some embodiments, the host cell for expression is a eukaryotic cell, e.g., a mammalian cell (as described above), an insect cell, a plant cell, etc. Test host cell populations are co-transfected with nucleic acids encoding the alpha and beta subunits of an IL-12 family cytokine at different relative ratios, e.g., relative ratios in the range of about 15:1 to about 1:15 (excluding equimolar ratios, i.e., a 1:1 ratio), for example, about 15:1, 12:1, 10:1, 8:1, 5:1, 4:1, 3:1, 2:1, 1:2, 1:3, 1:4, 1:5, 1:8, 1:10, 1:12, 1:15, etc. The desired ratio can be the ratio that produces the highest level of expression, or can be a ratio that produces less than the highest level of expression, depending on the context of use of the IL-12 family cytokine. The desired ratio or the highest ratio may be different depending on the context of expression of the IL-12 family cytokine, e.g., in vitro expression versus in vivo expression; in vivo expression in mice, primate or human.

The expression levels of the alpha and beta subunits, e.g., in the extracellular space, in cell culture media, in serum, are then quantified employing any method known in the art. For example, the relative ratios can be quantified by Western immunoblot or by ELISA. Antibodies against IL-12, IL-23 and IL-27 are commercially available, for example, from AbCam, Cambridge, Mass.; BioLegend, San Diego, Calif.; GenWay Biotech, San Diego, Calif.; Lifespan Biosciences, Seattle, Wash.; Novus Biologicals, Littleton, Colo.; R&D Systems, Minneapolis, Minn.; Peprotech, Rocky Hill, N.J.; and Biosource Intl., Camarillo, Calif. See also, Coligan, et al., *Current Methods in Immunology*, 1991-2006, John Wiley & Sons; Harlow and Lane, *Using Antibodies: A Laboratory Manual*, 1998, Cold Spring Harbor Laboratory Press; and *The ELISA Guidebook*, Crowther, ed., 2000, Humana Press.

Upon determination of the relative ratios of expression of the alpha and beta subunits that result in the desired (e.g., highest) levels and stability of expression of the IL-12 family cytokines, host cells are then transfected with one or more polynucleotides in a manner sufficient to express the alpha and beta subunits at the appropriate relative ratios. Expression of the alpha and beta subunits at a desired relative ratio can be achieved using any method known in the art.

For example, host cells can be co-transfected with a first polynucleotide encoding the alpha subunit and a second polynucleotide encoding the beta subunit, wherein the first and second polynucleotides are co-transfected at a relative molar ratio that corresponds to the desired relative ratio of expression of the alpha and beta subunits, e.g., at molar ratios in the range of about 15:1 to about 1:15 (excluding equimolar ratios, i.e., a 1:1 ratio), for example, about 15:1, 12:1, 10:1, 8:1, 5:1, 4:1, 3:1, 2:1, 1:2, 1:3, 1:4, 1:5, 1:8, 1:10, 1:12, 1:15, etc.

In another embodiment, the host cells can be transfected with a single polynucleotide having first and second expression cassettes, the first expression cassette comprising a first promoter that controls expression of a nucleic acid encoding the alpha subunit, and the second expression cassette comprising a second promoter that controls expression of a nucleic acid encoding the beta subunits. The strengths of the first and second promoters are selected such that the desired relative ratio of expression of the alpha and beta subunits, e.g., molar ratios in the range of about 15:1 to about 1:15, excluding equimolar (1:1 ratio) expression, for example, about 15:1, 12:1, 10:1, 8:1, 5:1, 4:1, 3:1, 2:1, 1:2, 1:3, 1:4, 1:5, 1:8, 1:10, 1:12, 1:15, etc., are achieved. For example, in a mammalian host cell, the human CMV promoter is stronger than the simian CMV promoter. Accordingly, the subunit to be expressed at relatively higher levels is placed under the control of the human CMV promoter, and the subunit to be expressed at relatively lower levels is placed under the control of the simian CMV promoter.

In a further embodiment, the host cells can be transfected with a bicistronic polynucleotide that comprises a single promoter and two ribosomal entry sites, a first ribosomal entry site proximal to the promoter and a second or internal ribosomal entry site that is distal from the promoter (i.e., separated by the coding sequence of an alpha or beta subunit). The coding sequence of the subunit to be expressed at relatively higher levels is located proximal to the promoter, or relatively 5' in the bicistronic polynucleotide. The coding sequence of the subunit to be expressed at relatively lower levels is located distal to the promoter, or relatively 3' in the bicistronic polynucleotide, e.g., 3' to the internal ribosomal entry site.

Introduction of Expression Vectors into Cells

As discussed herein, standard transfection methods are used to introduce the polynucleotides, expression cassettes and/or expression vectors encoding IL-12 family cytokine subunits into cells. The expression vectors can be plasmid expression vectors or other commonly used expression vectors including viral expression vectors. In some embodiments, naked mRNA coding sequences are delivered into the cells. See, e.g., Pascolo, *Handb Exp Pharmacol*. (2008) 183: 221-35; Weide, et al., *Immunol Lett*. (2008) 115(1):33-42; and Van Tendeloo, *Curr Opin Mol Ther*. (2007) 9(5):423-31. Gene transfer techniques include the use of calcium phosphate transfection, polybrene, protoplast fusion, electroporation, liposomes, microinjection, plasma vectors, viral vectors and any of the other well known methods for introducing heterologous nucleic acids into a host cell (see, e.g., Sambrook, supra). The vectors can be used for in vitro experiments or in vivo.

The cells are typically mammalian cells, e.g., human cells. Cells into which the vectors are introduced can be primary cells as well as cell lines. Exemplary cell types include circulating cells such as peripheral blood cells, monocytes, lymphocytes, and cells of these lineages, including $CD4^+$ T cells, and the like; muscle cells, epidermal cells, neuronal cell types, fibroblasts, hepatocytes, cardiac cells, mammary cells, prostate cells, pancreatic cells, lung cells, endocrine cells, splenocytes, and the like. Such cells may be normal or cancerous.

Non-Viral Delivery Methods

Methods of non-viral delivery of DNA or RNA polynucleotides encoding IL-12 family cytokine heterodimers include lipofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024. Delivery can be to cells either in vitro or in vivo. Delivery can be by injection (e.g., intramuscular), by inhalation or any other appropriate route that allows expression in a targeted host cell.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther*. 2:291-297 (1995); Behr et al., *Bioconjugate Chem*. 5:382-389 (1994); Remy et al., *Bioconjugate Chem*. 5:647-654 (1994); Gao et al., *Gene Therapy* 2:710-722 (1995); Ahmad et al., *Cancer Res*. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Viral Delivery Method

The use of RNA or DNA viral based systems for the delivery of vectors, e.g., comprising the nucleic acids encoding IL-12 family cytokine subunits, are known in the art. Conventional viral based systems include without limitation lentivirus, retroviral, adenoviral, adeno-associated, herpes simplex virus, and various other viral vectors for gene transfer. The polynucleotides encoding the alpha and beta subunits of the IL-12 family cytokine can be in the same viral vector or in different viral vectors.

In many applications, it is desirable a vector be delivered with a high degree of specificity to a cell type, e.g., for delivery in vivo. A viral vector can be modified to have specificity for a given cell type by expressing a ligand as a fusion protein with a viral coat protein on the viruses outer surface. The ligand is chosen to have affinity for a receptor known to be present on the cell type of interest. For example, Han et al., PNAS 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g. Fab or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Vectors can be delivered in vivo by administration to an individual patient, typically by systemic administration (e.g., intravenous, intraperitoneal, intramuscular, intranasally, inhalationally, subdermal, or intracranial infusion) or topical application, as described below. Alternatively, vectors can also be delivered to cells in vitro. Such methods include ex vivo methods, e.g., for introducing DNA into cells explanted from an individual patient.

Ex vivo cell transfection for diagnostics, research, or for gene therapy (e.g., via re-infusion of the transfected cells into the host organism) is well known to those of skill in the art. In some embodiments, cells are isolated from the subject organism (e.g., mammal, human), transfected with expression vectors comprising the nucleic acids encoding IL-12 family cytokine heterodimer and re-infused back into the subject organism (e.g., mammal, human). Various cell types suitable for ex vivo transfection are well known to those of skill in the art (see, e.g., Freshney et al., Culture of Animal Cells, A Manual of Basic Technique (5th ed. 2005), Wiley-Liss) and the references cited therein for a discussion of how to isolate and culture cells from patients, e.g., mammals, humans).

Vectors (e.g., lentiviruses, retroviruses, adenoviruses, liposomes, etc.) containing therapeutic nucleic acids can also be administered directly to an organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

The data obtained from cell culture assays and animal studies can be used to formulate a dosage range for use in humans. The dosage can vary within this range depending upon the dosage form employed and the route of administration.

When administering a viral vector, the amount of virus (number of virions) per dose will vary depending on results of different titrations used in clinical trials. The range can range, e.g., from only a few infectious units, to about $10^4$ to $10^{10}$ infectious units (i.e., virions) per dose. Protocols and means to determine safety and efficacy used for other attenuated vaccines can be adapted and used with the novel reagents provided by the invention; see, e.g., Belshe (1998) *N. Engl. J. Med*. 338:1405-1412; Gruber (1997) *Vaccine* 15:1379-1384; Tingle (1997) *Lancet* 349:1277-1281; Varis (1996) *J. Infect. Dis*. 174:S330-S334; Gruber (1996) *J. Infect. Dis*. 173:1313-1319.

The vaccine can be administered in conjunction with other treatment regimens, e.g., it can be coadministered or administered before or after any anti-viral pharmaceutical (see, e.g., Moyle (1998) *Drugs* 55:383-404) or a killed (completely inactivated) anti-HIV vaccine. The vaccine can be administered in any form of schedule regimen, e.g., in a single dose, or, using several doses (e.g., boosters) at dosages and time intervals to be determined by clinical trials.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., Remington: The Science and Practice of Pharmacy, University of the Sciences in Philadelphia, 21st edition, 2005, Lippincott, Williams and Wilkins).

EXAMPLES

The following examples are offered to illustrate, but not to limit the claimed invention.

Example 1

The strategy for introducing nucleotide changes into IL-12 family cytokine sequences is to simultaneously rectify several factors affecting mRNA traffic, stability and expression. Codons are altered to change the overall mRNA AT(AU)-content or to remove any other inhibitory signals within the RNA such as all potential splice sites (computer programs predicting potential splice sites can be found for example at web sites such as fruitfly.org/seq_tools/splice.html, or sun1.softberry.com/berry.phtml) and also to alter sequences such as runs of A or T/U nucleotides, AATAAA, ATTTA and closely related variant sequences, known to negatively affect mRNA. By substituting codons with a different codon encoding the identical amino acid, the chosen codon can be more GC-rich, or can have a different sequence that is sufficient to alter the RNA structure. This approach has been described in several patents, each of which is hereby incorporated herein by reference in their entirety: U.S. Pat. Nos. 5,965,726; 5,972,596; 6,174,666; 6,291,664; 6,414,132; 6,794,498, WO 07/084,364 and WO 07/084,342.

Standard lab techniques are used to generate, purify and sequence plasmid DNAs. One microgram (1 µg) of the plasmids containing the indicated IL-12 family cytokine coding sequence were transfected into human 293 or RD cells seeded into 60 mm plates the day before with $10^6$ cells using calcium coprecipitation technique (293 cells) and the SuperFect Reagent protocol (Qiagen) for RD4 cells. 2-3 days later, intracellular and extracellular and total IL-12 family protein was measured using commercial kits.

DNA Plasmids

The backbone vector used for the generation of all the constructs, pCMVkan, contains the human cytomegalovirus promoter, the bovine growth hormone polyadenylation site, and the kanamycin resistance gene (Rosati, et al., (2005) J. Virol. 79:8480-8492 and Schneider, et al., (1997) J. Virol. 71:4892-4903). The IL-12, IL-23 and IL-27 cytokines were RNA/codon-optimized by introducing multiple silent point mutations that result in more stable mRNA. For the in vivo studies, highly purified, endotoxin-free DNA plasmid preparations were produced using Qiagen EndoFree Giga kit (Hilden, Germany)

In Vitro Transient Transfection and Protein Expression

Human 293 cells were transfected by the calcium phosphate coprecipitation technique using 0.1 µg of each plasmid, and cells were harvested after 24 or 48 h. Co-transfection of 0.05 µg of the GFP expression vector pFRED143 (Stauber, et al., (1995) Virology 213, 439-449) served as internal control. GFP variation in the different samples was less than 50%.

Levels of expressed IL-12, IL-23 or IL-27 were measured by ELISA or by Western immunoblot. Human IL-12 was measured using as primary antibody polyclonal Goat Anti Human IL-12 p70 Neutralizing Ab (R&D Systems; AF219; 1:5000); and as secondary antibody Donkey Anti Goat IgG-HRP (R&D Systems; HAF109; 1:1000). Human IL-23 was measured using as primary antibodies a mixture of Polyclonal Goat Anti Human IL-12 p28 Neutralizing Ab (1:3000) and mouse anti-human p19 antibody (capture Ab from eBioscience HuIL23 ELISA KIT; 1:1250); and as secondary antibodies a mixture of Donkey Anti Goat IgG-HRP (R&D Systems; HAF 109; 1:1000) and Anti-Mouse IgG-HRP (GE Healthcare; NA934V; 1:5000). Murine IL-27 was measured using as primary antibodies a mixture of Polyclonal Goat Anti Mouse IL-27 p28 Neutralizing Ab (R&D Systems; AF1834; 1:1000) and Rabbit anti-mouse EBI3 (M-75) antibody (Santa Cruz Biotechnology, Inc.; sc-32869; 1:1000); and as secondary antibodies a mixture of Donkey Anti Goat IgG-HRP (R&D Systems; HAF109; 1:1000) and Donkey Anti-Rabbit IgG-HRP (GE Healthcare; NA934V; 1:5000). Protein bands were visualized on immunoblots by enhanced chemiluminescence (GE Healthcare).

In Vivo Hydrodynamic DNA Delivery

Six-week-old female BALB/c mice were obtained from Charles River Laboratories, Inc. (Frederick, Md.). Hydrodynamic injection of the plasmid DNA (Liu, et al., (1999) Gene Ther. 6, 1258-1266) encoding IL-12, IL-23 or IL-27 was performed essentially as described in Ortaldo, et al., (2005) J. Immunol. 175, 693-699. Briefly, the plasmid(s) in 1.6 ml of sterile 0.9% NaCl were injected into mice through the tail vein within 7 s using a 27.5-gauge needle. Mice were bled at day 1 and day 3 after injection, and the serum levels of IL-12, IL-23 or IL-27 were measured by immunoassay. Three days after injection, mice were sacrificed, and liver, lungs, spleen, and mesenteric lymph nodes were collected and analyzed.

Spleen, Lung, and Liver Cell Analysis

To make single cell suspensions, spleens were gently squeezed through a 100-µm Cell Strainer (Thomas) and washed in RPMI 1640 medium (Invitrogen) to remove any remaining organ stroma. The cells were resuspended in RPMI 1640 medium containing 10% fetal calf serum and counted using acridine orange (Molecular Probes)/ethidium bromide (Fisher) dye. Lung and liver were minced and incubated with 200 units/ml of collagenase (Sigma) and 30 units/ml of DNase (Roche Applied Science) for 1 h at 37° C., and single cells were then collected and resuspended in complete RPMI 1640 medium with 10% fetal calf serum.

Example 2

Comparison of Human IL-12 Expression and Secretion Using Different Ratios of Improved DNA Expression Vectors Human 293 cells were transfected as described with a mix of 2 different expression vectors for IL-12 subunits p35 and p40. The amount of p35 was kept the same (100 ng) and increasing amounts of p40 plasmid were provided to the specified ratios below. Supernatants of transfected cells were assayed for human IL-12 p70 expression using a commercial ELISA (eBioscience). The results (average of two plates of cells per point) indicate that ratios of up to 1:10 result in increased expression of IL-12. See, Table 3.

TABLE 3

| human IL-12 subunits: p35:p40 ratio | vectors | P70 ng/ml in cell supernatant |
|---|---|---|
| 1:3 | AG182 + AG180 (1:3) | 5243.8 |
| 1:5 | AG182 + AG180 (1:5) | 4236.9 |
| 1:8 | AG182 + AG180 (1:8) | 18175.5 |
| 1:10 | AG182 + AG180 (1:10) | 35485.0 |
| 1:20 | AG182 + AG180 (1:20) | 2984.2 |
| no p35, negative control | AG177 + AG180 (1:1) | 0.6 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications and sequence accession numbers cited herein are hereby incorporated by reference in their entirety for all purposes.

```
INFORMAL SEQUENCE LISTING
                                                      SEQ ID NO: 1
- AG181
flanking sequences in lower case; coding sequences underlined
human IL-12 heterodimer expressed; p40 from human CMV promoter
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGcgcgcgtcgaggaatttcgagaagaaATGTGCCACCAGCAGCTGGTCATCAGCT

GGTTCAGCCTCGTTTTCCTCGCCTCGCCGCTGGTCGCCATATGGGAGCTCAAGAAGGACGTA

TACGTGGTGGAGCTGGACTGGTACCCCGACGCGCCGGGCGAGATGGTCGTCCTGACGTGCGA

CACGCCGGAGGAGGACGGCATCACGTGGACGCTGGACCAGTCCAGCGAGGTCCTCGGCTCCG

GCAAGACGCTGACGATCCAGGTCAAGGAGTTCGGCGACGCGGGCCAGTACACGTGCCACAAG

GGCGGCGAGGTCCTGAGCCACTCCCTCCTCCTGCTACACAAGAAGGAGGACGGGATCTGGAG

CACGGACATCCTCAAGGACCAGAAGGAGCCGAAGAACAAGACCTTCCTGCGCTGCGAGGCGA

AGAATTACTCGGGCCGGTTCACGTGCTGGTGGCTCACCACGATCAGCACGGACCTGACGTTC

TCGGTCAAGTCGTCGCGGGGCTCGTCGGACCCCCAGGGGGTGACCTGCGGCGCGGCGACGCT

GTCGGCGGAGCGGGTGCGGGGCGACAACAAGGAGTACGAGTACTCGGTCGAGTGCCAGGAGG

ACTCGGCGTGCCCGGCGGCGGAGGAGTCGCTGCCGATCGAGGTGATGGTCGACGCGGTCCAC

AAGCTGAAGTACGAGAACTACACGTCGTCGTTCTTCATCCGGGACATCATCAAGCCGGACCC

GCCGAAGAACCTGCAGCTGAAGCCGCTGAAGAACTCGCGGCAGGTCGAGGTCTCGTGGGAGT

ACCCGGACACGTGGTCGACGCCGCACTCGTACTTCTCGCTGACGTTCTGCGTCCAAGTGCAG

GGCAAGTCGAAGCGGGAGAAGAAGGACCGGGTGTTCACCGACAAGACGAGCGCGACGGTGAT

CTGCCGGAAGAACGCGTCGATCTCGGTGCGGGCGCAGGACCGGTACTACTCGTCGTCGTGGT

CGGAGTGGGCGTCGGTGCCGTGCAGCTAGacctagggcgcgccagatctgatatcggatct gCTGTGCCTTCTAGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCATCGCATTGTCTGA

GTAGGTGTCATTCTATTCTGGGGGGTGGGGTGGGCAGGACAGCAAGGGGGAGGATTGGGAA

GACAATAGCAGGCATGCTGGGGATGCGGTGGGCTCTATGGGTACCCAGGTGCTGAAGAATTG

ACCCGGTTCCTCCTGGGCCAGAAAGAAGCAGGCACATCCCCTTCTCTGTGACACACCCTGTC

CACGCCCCTGGTTCTTAGTTCCAGCCCCACTCATAGGACACTCATAGCTCAGGAGGGCTCCG
```

-continued

```
CCTTCAATCCCACCCGCTAAAGTACTTGGAGCGGTCTCTCCCTCCCTCATCAGCCCACCAAA

CCAAACCTAGCCTCCAAGAGTGGGAAGAAATTAAAGCAAGATAGGCTATTAAGTGCAGAGGG

AGAGAAAATGCCTCCAACATGTGAGGAAGTAATGAGAGAAATCATAGAATTTCTTCCGCTTC

CTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAGGCTCCG

CCCCCCTGACGAGCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCACGAAC

CCCCCGTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGAACAGTAT

TTGGTATCTGCGCTCTGCTGAAGCCAGTTACCTTCGGAAAAAGAGTTGGTAGCTCTTGATCC

GGCAAACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGATCCTT

TTAAATTAAAAATGAAGTTTTAAATCAATCTAAAGTATATATGAGTAAACTTGGTCTGACAG

TTACCAATGCTTAATCAGTGAGGCACCTATCTCAGCGATCTGTCTATTTCGTTCATCCATAG

TTGCCTGACTCGGGGGGGGGGGCGCTGAGGTCTGCCTCGTGAAGAAGGTGTTGCTGACTCA

TACCAGGCCTGAATCGCCCCATCATCCAGCCAGAAAGTGAGGGAGCCACGGTTGATGAGAGC

TTTGTTGTAGGTGGACCAGTTGGTGATTTTGAACTTTTGCTTTGCCACGGAACGGTCTGCGT

TGTCGGGAAGATGCGTGATCTGATCCTTCAACTCAGCAAAAGTTCGATTTATTCAACAAAGC

CGCCGTCCCGTCAAGTCAGCGTAATGCTCTGCCAGTGTTACAACCAATTAACCAATTCTGAT

TAGAAAAACTCATCGAGCATCAAATGAAACTGCAATTTATTCATATCAGGATTATCAATACC

ATATTTTTGAAAAAGCCGTTTCTGTAATGAAGGAGAAAACTCACCGAGGCAGTTCCATAGGA

TGGCAAGATCCTGGTATCGGTCTGCGATTCCGACTCGTCCAACATCAATACAACCTATTAAT

TTCCCCTCGTCAAAAATAAGGTTATCAAGTGAGAAATCACCATGAGTGACGACTGAATCCGG

TGAGAATGGCAAAAGCTTATGCATTTCTTTCCAGACTTGTTCAACAGGCCAGCCATTACGCT

CGTCATCAAAATCACTCGCATCAACCAAACCGTTATTCATTCGTGATTGCGCCTGAGCGAGA

CGAAATACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATACCTGGA

ATGCTGTTTTCCCGGGGATCGCAGTGGTGAGTAACCATGCATCATCAGGAGTACGGATAAAA

TGCTTGATGGTCGGAAGAGGCATAAATTCCGTCAGCCAGTTTAGTCTGACCATCTCATCTGT

AACATCATTGGCAACGCTACCTTTGCCATGTTTCAGAAACAACTCTGGCGCATCGGGCTTCC

CATACAATCGATAGATTGTCGCACCTGATTGCCCGACATTATCGCGAGCCCATTTATACCCA

TATAAATCAGCATCCATGTTGGAATTTAATCGCGGCCTCGAGCAAGACGTTTCCCGTTGAAT

ATGGCTCATAACACCCCTTGTATTACTGTTTATGTAAGCAGACAGTTTTATTGTTCATGATG

ATATATTTTTATCTTGTGCAATGTAACATCAGAGATTTTGAGACACAACGTGGATCATCCAG

ACATGATAAGATACATTGATGAGTTTGGACAAACCACAACTAGAATGCAGTGAAAAAAATGC
```

-continued

```
TTTATTTGTGAAATTTGTGATGCTATTGCTTTATTTGTAACCATTATAAGCTGCAATAAACA

AGTTAACAACAACAATTGCATTCATTTTATGTTTCAGGTTCAGGGGGAGGTGTGGGAGGTTT

TTTAAAGCAAGTAAAACCTCTACAAATGTGGTATGGCTGATTATGATCgtcgaggatccggc gccggtttcgcgtcgatatcTTACGAAGCGTTCAGGTACGACATCACCCGGTCGATCGTCAC

CGCCCGGATCCGGAAAGCGTGCAGCAGGATGCAGAGCTTGATCTTCGTCTTGTAGAAGTCCG

GCTCCTCGAGCGACGACTTCTGCGGCACCGTCTCGCTGTTGAAGTTGAGCGCCTGCATGAGC

TCGTCGATCACCGCCAGCATGTTCTGGTCGAGGAAGATCTGCCGCTTCGGGTCCATCAGCAG

CTTCGCGTTCATCGTCTTGAACTCCACCTGGTACATCTTCAGGTCCTCGTAGATCGACGACA

GGCACAGCGCCATCATGAACGACGTCTTCCGCGACGCCAGGCACGACCCGTTCGTGATGAAC

GACGTCTCCCTCGAGTTCAGGCACGACTCGTTCTTCGTCAGCTCCAGCGGCAGGCACGCCTC

CACCGTGCTGGTCTTGTCCTTCGTGATGTCCTCGTGGTCGATCTCCTCGCTCGTGCACGGGT

AGAACTCCAGCGTCTGCCGCGCCTTCTGCAGCATGTTCGACACCGCCCGCAGCAGGTTCTGG

CTGTGGTGCAGGCACGGGAACATCCCCGGGTCCGGCGTCGCCACCGGCAGGTTCCGCGCCAG

GCTCAGGTGGTCGAGCAGGACCAGCGTCGCCACGAGCAGCAGGGAGCGCGCCGGGCACATtt ctttctagaaacgtcgacagatccAAACGCTCCTCCGACGTCCCCAGGCAGAATGGCGGTTC

CCTAAACGAGCATTGCTTATATAGACCTCCCATTAGGCACGCCTACCGCCCATTTACGTCAA

TGGAACGCCCATTTGCGTCATTGCCCCTCCCCATTGACGTCAATGGGGATGTACTTGGCAGC

CATCGCGGGCCATTTACCGCCATTGACGTCAATGGGAGTACTGCCAATGTACCCTGGCGTAC

TTCCAATAGTAATGTACTTGCCAAGTTACTATTAATAGATATTGATGTACTGCCAAGTGGGC

CATTTACCGTCATTGACGTCAATAGGGGGCGTGAGAACGGATATGAATGGGCAATGAGCCAT

CCCATTGACGTCAATGGTGGGTGGTCCTATTGACGTCAATGGGCATTGAGCCAGGCGGGCCA

TTTACCGTAATTGACGTCAATGGGGGAGGCGCCATATACGTCAATAGGACCGCCCATATGAC

GTCAATAGGTAAGACCATGAGGCCCTTTCGTCTCGCGCGTTTCGGTGATGACGGTGAAAACC

TCTGACACATGCAGCTCCCGGAGACGGTCACAGCTTGTCTGTAAGCGGATGCCGGGAGCAGA

CAAGCCCGTCAGGGCGCGTCAGCGGGTGTTGGCGGGTGTCGGGGCTGGCTTAACTATGCGGC

ATCAGAGCAGATTGTACTGAGAGTGCACCATATGCGGTGTGAAATACCGCACAGATGCGTAA

GGAGAAAATACCGCATCAGATTGGCTATTGG
```

SEQ ID NO: 2
- AG183
flanking sequences in lower case; coding sequences underlined
human IL-12 heterodimer expressed; p40 from simian CMV
promoter

```
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT
```

-continued

```
CGCCTGGAGACGCCATCCACGCTGTTTTGACCTCCATAGAAGACACCGGGACCGATCCAGCC
TCCGCGGGcgcgcgtcgaggaattcgctagaaagaaATGTGCCCGGCGCGCTCCCTGCTGCT
CGTGGCGACGCTGGTCCTGCTCGACCACCTGAGCCTGGCGCGGAACCTGCCGGTGGCGACGC
CGGACCCGGGGATGTTCCCGTGCCTGCACCACAGCCAGAACCTGCTGCGGGCGGTGTCGAAC
ATGCTGCAGAAGGCGCGGCAGACGCTGGAGTTCTACCCGTGCACGAGCGAGGAGATCGACCA
CGAGGACATCACGAAGGACAAGACCAGCACGGTGGAGGCGTGCCTGCCGCTGGAGCTGACGA
AGAACGAGTCGTGCCTGAACTCGAGGGAGACGTCGTTCATCACGAACGGGTCGTGCCTGGCG
TCGCGGAAGACGTCGTTCATGATGGCGCTGTGCCTGTCGTCGATCTACGAGGACCTGAAGAT
GTACCAGGTGGAGTTCAAGACGATGAACGCGAAGCTGCTGATGGACCCGAAGCGGCAGATCT
TCCTCGACCAGAACATGCTGGCGGTGATCGACGAGCTCATGCAGGCGCTCAACTTCAACAGC
GAGACGGTGCCGCAGAAGTCGTCGCTCGAGGAGCCGGACTTCTACAAGACGAAGATCAAGCT
CTGCATCCTGCTGCACGCTTTCCGGATCCGGGCGGTGACGATCGACCGGGTGATGTCGTACC
TGAACGCTTCGTAAgatatcgacgcgccagatctgatatcggatctGCTGTGCCTTCTAGTT
GCCAGCCATCTGTTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGGCATG
CTGGGGATGCGGTGGGCTCTATGGGTACCCAGGTGCTGAAGAATTGACCCGGTTCCTCCTGG
GCCAGAAAGAAGCAGGCACATCCCCTTCTCTGTGACACACCCTGTCCACGCCCTGGTTCTT
AGTTCCAGCCCCACTCATAGGACACTCATAGCTCAGGAGGGCTCCGCCTTCAATCCCACCCG
CTAAAGTACTTGGAGCGGTCTCTCCCTCCCTCATCAGCCCACCAAACCAAACCTAGCCTCCA
AGAGTGGGAAGAAATTAAAGCAAGATAGGCTATTAAGTGCAGAGGGAGAGAAAATGCCTCCA
ACATGTGAGGAAGTAATGAGAGAAATCATAGAATTTCTTCCGCTTCCTCGCTCACTGACTCG
CTGCGCTCGGTCGTTCGGCTGCGGCGAGCGGTATCAGCTCACTCAAAGGCGGTAATACGGTT
ATCCACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGCTTTCTCAATGCTCACGCTGTAGGTATCTC
AGTTCGGTGTAGGTCGTTCGCTCCAAGCTGGGCTGTGTGCACGAACCCCCCGTTCAGCCCGA
CCGCTGCGCCTTATCCGGTAACTATCGTCTTGAGTCCAACCCGGTAAGACACGACTTATCGC
CACTGGCAGCAGCCACTGGTAACAGGATTAGCAGAGCGAGGTATGTAGGCGGTGCTACAGAG
TTCTTGAAGTGGTGGCCTAACTACGGCTACACTAGAAGAACAGTATTTGGTATCTGCGCTCT
GCTGAAGCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGATCTCAA
GAAGATCCTTTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATTAAAAATGAA
GTTTTAAATCAATCTAAAGTATATATGAGTAAACTTGGTCTGACAGTTACCAATGCTTAATC
AGTGAGGCACCTATCTCAGCGATCTGTCTATTTCGTTCATCCATAGTTGCCTGACTCGGGGG
GGGGGGGCGCTGAGGTCTGCCTCGTGAAGAAGGTGTTGCTGACTCATACCAGGCCTGAATCG
CCCCATCATCCAGCCAGAAAGTGAGGGAGCCACGGTTGATGAGAGCTTTGTTGTAGGTGGAC
CAGTTGGTGATTTTGAACTTTTGCTTTGCCACGGAACGGTCTGCGTTGTCGGGAAGATGCGT
```

-continued

```
GATCTGATCCTTCAACTCAGCAAAAGTTCGATTTATTCAACAAAGCCGCCGTCCCGTCAAGT

CAGCGTAATGCTCTGCCAGTGTTACAACCAATTAACCAATTCTGATTAGAAAAACTCATCGA

GCATCAAATGAAACTGCAATTTATTCATATCAGGATTATCAATACCATATTTTTGAAAAAGC

CGTTTCTGTAATGAAGGAGAAAACTCACCGAGGCAGTTCCATAGGATGGCAAGATCCTGGTA

TCGGTCTGCGATTCCGACTCGTCCAACATCAATACAACCTATTAATTTCCCCTCGTCAAAAA

TAAGGTTATCAAGTGAGAAATCACCATGAGTGACGACTGAATCCGGTGAGAATGGCAAAAGC

TTATGCATTTCTTTCCAGACTTGTTCAACAGGCCAGCCATTACGCTCGTCATCAAAATCACT

CGCATCAACCAAACCGTTATTCATTCGTGATTGCGCCTGAGCGAGACGAAATACGCGATCGC

TGTTAAAAGGACAATTACAAACAGGAATCGAATGCAACCGGCGCAGGAACACTGCCAGCGCA

TCAACAATATTTTCACCTGAATCAGGATATTCTTCTAATACCTGGAATGCTGTTTTCCCGGG

GATCGCAGTGGTGAGTAACCATGCATCATCAGGAGTACGGATAAAATGCTTGATGGTCGGAA

GAGGCATAAATTCCGTCAGCCAGTTTAGTCTGACCATCTCATCTGTAACATCATTGGCAACG

CTACCTTTGCCATGTTTCAGAAACAACTCTGGCGCATCGGGCTTCCCATACAATCGATAGAT

TGTCGCACCTGATTGCCCGACATTATCGCGAGCCCATTTATACCCATATAAATCAGCATCCA

TGTTGGAATTTAATCGCGGCCTCGAGCAAGACGTTTCCCGTTGAATATGGCTCATAACACCC

CTTGTATTACTGTTTATGTAAGCAGACAGTTTTATTGTTCATGATGATATATTTTTATCTTG

TGCAATGTAACATCAGAGATTTTGAGACACAACGTGGATCATCCAGACATGATAAGATACAT

TGATGAGTTTGGACAAACCACAACTAGAATGCAGTGAAAAAAATGCTTTATTTGTGAAATTT

GTGATGCTATTGCTTTATTTGTAACCATTATAAGCTGCAATAAACAAGTTAACAACAACAAT

TGCATTCATTTTATGTTTCAGGTTCAGGGGGAGGTGTGGGAGGTTTTTTAAAGCAAGTAAAA

CCTCTACAAATGTGGTATGGCTGATTATGATCgtcgaggatccggcgccggtttgatccggc gcgcccctaggtCTAGCTGCACGGCACCGACGCCCACTCCGACCACGACGACGAGTAGTACC

GGTCCTGCGCCCGCACCGAGATCGACGCGTTCTTCCGGCAGATCACCGTCGCGCTCGTCTTG

TCGGTGAACACCCGGTCCTTCTTCTCCCGCTTCGACTTGCCCTGCACTTGGACGCAGAACGT

CAGCGAGAAGTACGAGTGCGGCGTCGACCACGTGTCCGGGTACTCCCACGAGACCTCGACCT

GCCGCGAGTTCTTCAGCGGCTTCAGCTGCAGGTTCTTCGGCGGGTCCGGCTTGATGATGTCC

CGGATGAAGAACGACGACGTGTAGTTCTCGTACTTCAGCTTGTGGACCGCGTCGACCATCAC

CTCGATCGGCAGCGACTCCTCCGCCGCCGGGCACGCCGAGTCCTCCTGGCACTCGACCGAGT

ACTCGTACTCCTTGTTGTCGCCCCGCACCCGCTCCGCCGACAGCGTCGCCGCGCCGCAGGTC

ACCCCCTGGGGGTCCGACGAGCCCCGCGACGACTTGACCGAGAACGTCAGGTCCGTGCTGAT

CGTGGTGAGCCACCAGCACGTGAACCGGCCCGAGTAATTCTTCGCCTCGCAGCGCAGGAAGG

TCTTGTTCTTCGGCTCCTTCTGGTCCTTGAGGATGTCCGTGCTCCAGATCCCGTCCTCCTTC

TTGTGTAGCAGGAGGAGGGAGTGGCTCAGGACCTCGCCGCCCTTGTGGCACGTGTACTGGCC

CGCGTCGCCGAACTCCTTGACCTGGATCGTCAGCGTCTTGCCGGAGCCGAGGACCTCGCTGG

ACTGGTCCAGCGTCCACGTGATGCCGTCCTCCTCCGGCGTGTCGCACGTCAGGACGACCATC

TCGCCCGGCGCGTCGGGGTACCAGTCCAGCTCCACCACGTATACGTCCTTCTTGAGCTCCCA

TATGGCGACCAGCGGCGAGGCGAGGAAAACGAGGCTGAACCAGCTGATGACCAGCTGCTGGT

GGCACATttcttctcgacagatccAAACGCTCCTCCGACGTCCCCAGGCAGAATGGCGGTTC

CCTAAACGAGCATTGCTTATATAGACCTCCCATTAGGCACGCCTACCGCCCATTTACGTCAA

TGGAACGCCCATTTGCGTCATTGCCCCTCCCCATTGACGTCAATGGGGATGTACTTGGCAGC
```

```
CATCGCGGGCCATTTACCGCCATTGACGTCAATGGGAGTACTGCCAATGTACCCTGGCGTAC

TTCCAATAGTAATGTACTTGCCAAGTTACTATTAATAGATATTGATGTACTGCCAAGTGGGC

CATTTACCGTCATTGACGTCAATAGGGGGCGTGAGAACGGATATGAATGGGCAATGAGCCAT

CCCATTGACGTCAATGGTGGGTGGTCCTATTGACGTCAATGGGCATTGAGCCAGGCGGGCCA

TTTACCGTAATTGACGTCAATGGGGAGGCGCCATATACGTCAATAGGACCGCCCATATGAC

GTCAATAGGTAAAGACCATGAGGCCCTTTCGTCTCGCGCGTTTCGGTGATGACGGTGAAAAC

CTCTGACACATGCAGCTCCCGGAGACGGTCACAGCTTGTCTGTAAGCGGATGCCGGGAGCAG

ACAAGCCCGTCAGGGCGCGTCAGCGGGTGTTGGCGGGTGTCGGGGCTGGCTTAACTATGCGG

CATCAGAGCAGATTGTACTGAGAGTGCACCATATGCGGTGTGAAATACCGCACAGATGCGTA

AGGAGAAAATACCGCATCAGATTGGCTATTGG
```

SEQ ID NO: 3
- AG157
flanking sequences in lower case; coding sequences underlined
rhesus IL-12 heterodimer expressed; p40 from human CMV
promoter

```
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGcgcgcgtcgaggaattaaacctcgagaagaaATGTGCCACCAGCAGCTGGTGAT

CAGCTGGTTCAGCCTGGTGTTCCTGGCCAGCCCCCTGATGGCCATCTGGGAGCTGAAGAAGG

ACGTATACGTGGTGGAGCTGGACTGGTATCCCGACGCGCCTGGCGAGATGGTGGTGCTGACC

TGCGACACCCCGAGGAGGACGGCATCACCTGGACCCTGGACCAGAGCGGCGAAGTGCTGGG

CAGCGGCAAGACCCTGACGATCCAGGTCAAGGAGTTCGGCGACGCCGGCCAGTACACCTGCC

ACAAGGGCGGCGAGGCCCTGAGCCACAGCCTGCTGCTGCTGCACAAGAAGGAGGACGGGATC

TGGAGCACCGACGTGCTGAAGGACCAGAAGGAGCCCAAGAACAAGACCTTCCTGCGCTGCGA

GGCCAAGAATTACAGCGGCCGGTTCACCTGTTGGTGGCTGACCACCATCAGCACCGACCTGA

CCTTCAGCGTGAAGAGCAGCAGAGGCAGCAGCAACCCCCAGGGCGTGACCTGTGGCGCCGTG

ACCCTGAGCGCCGAGAGTGAGAGGCGACAACAAGGAGTACGAGTACAGCGTGGAGTGCCA

GGAGGACAGCGCCTGCCCTGCCGCCGAGGAGAGACTGCCCATCGAAGTGATGGTGGACGCCA

TCCACAAGCTGAAGTACGAGAACTACACCAGCTCCTTCTTCATCCGGGACATCATCAAGCCC

GACCCCCCCAAGAACCTGCAGCTGAAGCCCCTGAAGAACAGCAGGCAGGTGGAAGTGAGCTG

GGAGTACCCCGACACCTGGAGCACCCCTCACAGCTACTTCAGCCTGACCTTCTGCATCCAAG

TGCAGGGCAAGAGCAAGCGGGAGAAGAAGGACCGGATCTTCACCGATAAGACCAGCGCCACC

GTGATCTGCCGGAAGAACGCCAGCTTCAGCGTGCAGGCCCAGGACAGATACTACAGCAGCAG
```

-continued

<u>CTGGAGCGAGTGGGCCAGCGTGCCTTGCAGCTGATGA</u>acctaggggcgcgccagatctgata tcggatctGCTGTGCCTTCTAGTTGCCAGCCATCTGTTGTTTGCCCCTCCCCGTGCCTTCC

TTGACCCTGGAAGGTGCCACTCCCACTGTCCTTTCCTAATAAAATGAGGAAATTGCATCGCA

TTGTCTGAGTAGGTGTCATTCTATTCTGGGGGGTGGGGTGGGGCAGGACAGCAAGGGGGAGG

ATTGGGAAGACAATAGCAGGCATGCTGGGGATGCGGTGGGCTCTATGGGTACCCAGGTGCTG

AAGAATTGACCCGGTTCCTCCTGGGCCAGAAAGAAGCAGGCACATCCCCTTCTCTGTGACAC

ACCCTGTCCACGCCCCTGGTTCTTAGTTCCAGCCCCACTCATAGGACACTCATAGCTCAGGA

GGGCTCCGCCTTCAATCCCACCCGCTAAAGTACTTGGAGCGGTCTCTCCCTCCCTCATCAGC

CCACCAAACCAAACCTAGCCTCCAAGAGTGGGAAGAAATTAAAGCAAGATAGGCTATTAAGT

GCAGAGGGAGAGAAAATGCCTCCAACATGTGAGGAAGTAATGAGAGAAATCATAGAATTTCT

TCCGCTTCCTCGCTCACTGACTCGCTGCGCTCGGTCGTTCGGCTGCGGCGAGCGGTATCAGC

TCACTCAAAGGCGGTAATACGGTTATCCACAGAATCAGGGGATAACGCAGGAAAGAACATGT

GAGCAAAAGGCCAGCAAAAGGCCAGGAACCGTAAAAAGGCCGCGTTGCTGGCGTTTTTCCAT

AGGCTCCGCCCCCCTGACGAGCATCACAAAAATCGACGCTCAAGTCAGAGGTGGCGAAACCC

GACAGGACTATAAAGATACCAGGCGTTTCCCCCTGGAAGCTCCCTCGTGCGCTCTCCTGTTC

CGACCCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAAGCTGGGCTGTGT

GCACGAACCCCCCGTTCAGCCCGACCGCTGCGCCTTATCCGGTAACTATCGTCTTGAGTCCA

ACCCGGTAAGACACGACTTATCGCCACTGGCAGCAGCCACTGGTAACAGGATTAGCAGAGCG

AGGTATGTAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTTGGTAGCT

CTTGATCCGGCAAACAAACCACCGCTGGTAGCGGTGGTTTTTTTGTTTGCAAGCAGCAGATT

ACGCGCAGAAAAAAAGGATCTCAAGAAGATCCTTTGATCTTTTCTACGGGGTCTGACGCTCA

GTGGAACGAAAACTCACGTTAAGGGATTTTGGTCATGAGATTATCAAAAAGGATCTTCACCT

AGATCCTTTTAAATTAAAAATGAAGTTTTAAATCAATCTAAAGTATATATGAGTAAACTTGG

TCTGACAGTTACCAATGCTTAATCAGTGAGGCACCTATCTCAGCGATCTGTCTATTTCGTTC

ATCCATAGTTGCCTGACTCGGGGGGGGGGGCGCTGAGGTCTGCCTCGTGAAGAAGGTGTTG

CTGACTCATACCAGGCCTGAATCGCCCCATCATCCAGCCAGAAAGTGAGGGAGCCACGGTTG

ATGAGAGCTTTGTTGTAGGTGGACCAGTTGGTGATTTTGAACTTTTGCTTTGCCACGGAACG

GTCTGCGTTGTCGGGAAGATGCGTGATCTGATCCTTCAACTCAGCAAAAGTTCGATTTATTC

AACAAAGCCGCCGTCCCGTCAAGTCAGCGTAATGCTCTGCCAGTGTTACAACCAATTAACCA

ATTCTGATTAGAAAAACTCATCGAGCATCAAATGAAACTGCAATTTATTCATATCAGGATTA

TCAATACCATATTTTTGAAAAAGCCGTTTCTGTAATGAAGGAGAAAACTCACCGAGGCAGTT

CCATAGGATGGCAAGATCCTGGTATCGGTCTGCGATTCCGACTCGTCCAACATCAATACAAC

CTATTAATTTCCCCTCGTCAAAAATAAGGTTATCAAGTGAGAAATCACCATGAGTGACGACT

GAATCCGGTGAGAATGGCAAAAGCTTATGCATTTCTTTCCAGACTTGTTCAACAGGCCAGCC

ATTACGCTCGTCATCAAAATCACTCGCATCAACCAAACCGTTATTCATTCGTGATTGCGCCT

GAGCGAGACGAAATACGCGATCGCTGTTAAAAGGACAATTACAAACAGGAATCGAATGCAAC

CGGCGCAGGAACACTGCCAGCGCATCAACAATATTTTCACCTGAATCAGGATATTCTTCTAA

TACCTGGAATGCTGTTTTCCCGGGGATCGCAGTGGTGAGTAACCATGCATCATCAGGAGTAC

GGATAAAATGCTTGATGGTCGGAAGAGGCATAAATTCCGTCAGCCAGTTTAGTCTGACCATC

TCATCTGTAACATCATTGGCAACGCTACCTTTGCCATGTTTCAGAAACAACTCTGGCGCATC

GGGCTTCCCATACAATCGATAGATTGTCGCACCTGATTGCCCGACATTATCGCGAGCCCATT

TATACCCATATAAATCAGCATCCATGTTGGAATTTAATCGCGGCCTCGAGCAAGACGTTTCC

CGTTGAATATGGCTCATAACACCCCTTGTATTACTGTTTATGTAAGCAGACAGTTTTATTGT

TCATGATGATATATTTTTATCTTGTGCAATGTAACATCAGAGATTTTGAGACACAACGTGGA

TCATCCAGACATGATAAGATACATTGATGAGTTTGGACAAACCACAACTAGAATGCAGTGAA

AAAAATGCTTTATTTGTGAAATTTGTGATGCTATTGCTTTATTTGTAACCATTATAAGCTGC

AATAAACAAGTTAACAACAACAATTGCATTCATTTTATGTTTCAGGTTCAGGGGAGGTGTG

GGAGGTTTTTTAAAGCAAGTAAAACCTCTACAAATGTGGTATGGCTGATTATGATCgtcgag gatcatcTTATCAGCTGGCGTTCAGGTAGCTCATCACTCTGTCGATGGTCACGGCCCTGATC

CGGAAGGCGTGCAGCAGGATGCACAGCTTGATCTTGGTCTTGTAGAAGTCGGGCTCCTCCAG

GCTGCTCTTCTGAGGCACGGTCTCGCTGTTGAAGTTCAGGGCCTGCATCAGCTCGTCGATCA

CGCCCAGGATGTTCTGGTCCAGGAAGATCTGCCTCTTGGGGTCCCTCAGCAGCTTGGCGTTC

ATGGTCTTGAACTCCACCTGGTACATCTTCAGGTCCTCGTAGATGCTCCTCAGGCACAGGGC

CATCATGAAGGAGGTCTTTCTGCTGGCCAGGCAGCTGCCGTTGGTGATGAAGCTGGTCTCCC

TCGAGTTCAGGCACGACTCGTTCTTGATCAGCTCCAGCGGCAGGCACGCCTCCACCGTGCTG

GTCTTGTCCTTCGTGATGTCCTCGTGGTCGATCTCCTCGCTCGTGCACGGGTAGAACTCCAG

GATCTGCCGCGCCTTCTGCAGCGTGTTCGACGCCGCCTTCAGCAGGTTCTGGCTGTGGTGCA

GGCACGGGAACATCTCCGGTCCCGGGTCGCCACCGACAGGTTCCGCGCCAGGCTCAGGTAG

TCGAGCAGGACCAGCGTCGCCACGAGCAGCAGGGAGCGCGCCGGGCACATttctttctagac gtcgacagatccAAACGCTCCTCCGACGTCCCCAGGCAGAATGGCGGTTCCCTAAACGAGCA

TTGCTTATATAGACCTCCCATTAGGCACGCCTACCGCCCATTTACGTCAATGGAACGCCCAT

TTGCGTCATTGCCCCTCCCCATTGACGTCAATGGGGATGTACTTGGCAGCCATCGCGGGCCA

TTTACCGCCATTGACGTCAATGGGAGTACTGCCAATGTACCCTGGCGTACTTCCAATAGTAA

TGTACTTGCCAAGTTACTATTAATAGATATTGATGTACTGCCAAGTGGGCCATTTACCGTCA

TTGACGTCAATAGGGGCGTGAGAACGGATATGAATGGGCAATGAGCCATCCCATTGACGTC

AATGGTGGGTGGTCCTATTGACGTCAATGGGCATTGAGCCAGGCGGGCCATTTACCGTAATT

GACGTCAATGGGGAGGCGCCATATACGTCAATAGGACCGCCCATATGACGTCAATAGGTAA

GACCATGAGGCCCTTTCGTCTCGCGCGTTTCGGTGATGACGGTGAAAACCTCTGACACATGC

AGCTCCCGGAGACGGTCACAGCTTGTCTGTAAGCGGATGCCGGGAGCAGACAAGCCCGTCAG

GGCGCGTCAGCGGGTGTTGGCGGGTGTCGGGCTGGCTTAACTATGCGGCATCAGAGCAGAT

TGTACTGAGAGTGCACCATATGCGGTGTGAAATACCGCACAGATGCGTAAGGAGAAAATACC

GCATCAGATTGGCTATTGG

SEQ ID NO: 4
- AG159
flanking sequences in lower case; coding sequences underlined
rhesus IL-12 heterodimer expressed; p40 from simian CMV
promoter
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

```
AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGgcgcgcgtcgaggaattcgctagaaagaaATGTGCCCGGCGCGCTCCCTGCTGCT

CGTGGCGACGCTGGTCCTGCTCGACTACCTGAGCCTGGCGCGGAACCTGTCGGTGGCGACCC

CGGGACCGGAGATGTTCCCGTGCCTGCACCACAGCCAGAACCTGCTGAAGGCGGCGTCGAAC

ACGCTGCAGAAGGCGCGGCAGATCCTGGAGTTCTACCCGTGCACGAGCGAGGAGATCGACCA

CGAGGACATCACGAAGGACAAGACCAGCACGGTGGAGGCGTGCCTGCCGCTGGAGCTGATCA

AGAACGAGTCGTGCCTGAACTCGAGGGAGACCAGCTTCATCACCAACGGCAGCTGCCTGGCC

AGCAGAAAGACCTCCTTCATGATGGCCCTGTGCCTGAGGAGCATCTACGAGGACCTGAAGAT

GTACCAGGTGGAGTTCAAGACCATGAACGCCAAGCTGCTGAGGGACCCCAAGAGGCAGATCT

TCCTGGACCAGAACATCCTGGGCGTGATCGACGAGCTGATGCAGGCCCTGAACTTCAACAGC

GAGACCGTGCCTCAGAAGAGCAGCCTGGAGGAGCCCGACTTCTACAAGACCAAGATCAAGCT

GTGCATCCTGCTGCACGCCTTCCGGATCAGGGCCGTGACCATCGACAGAGTGATGAGCTACC

TGAACGCCAGCTGATAAgatatcggatctatcggatctGCTGTGCCTTCTAGTTGCCAGCCA

TCTGTTGTTTGCCCCTCCCCCGTGCCTTCCTTGACCCTGGAAGGTGCCACTCCCACTGTCCT

TTCCTAATAAAATGAGGAAATTGCATCGCATTGTCTGAGTAGGTGTCATTCTATTCTGGGGG

GTGGGGTGGGCAGGACAGCAAGGGGGAGGATTGGGAAGACAATAGCAGGCATGCTGGGGAT

GCGGTGGGCTCTATGGGTACCCAGGTGCTGAAGAATTGACCCGGTTCCTCCTGGGCCAGAAA

GAAGCAGGCACATCCCCTTCTCTGTGACACACCCTGTCCACGCCCCTGGTTCTTAGTTCCAG

CCCCACTCATAGGACACTCATAGCTCAGGAGGGCTCCGCCTTCAATCCCACCCGCTAAAGTA

CTTGGAGCGGTCTCTCCCTCCCTCATCAGCCCACCAAACCAAACCTAGCCTCCAAGAGTGGG

AAGAAATTAAAGCAAGATAGGCTATTAAGTGCAGAGGGAGAGAAAATGCCTCCAACATGTGA

GGAAGTAATGAGAGAAATCATAGAATTTCTTCCGCTTCCTCGCTCACTGACTCGCTGCGCTC

GGTCGTTCGGCTGCGGCGAGCGGTATCAGCTCACTCAAAGGCGGTAATACGGTTATCCACAG

AATCAGGGGATAACGCAGGAAAGAACATGTGAGCAAAAGGCCAGCAAAAGGCCAGGAACCGT

AAAAAGGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGTTTCCCC

CTGGAAGCTCCCTCGTGCGCTCTCCTGTTCCGACCCTGCCGCTTACCGGATACCTGTCCGCC

TTTCTCCCTTCGGGAAGCGTGGCGCTTTCTCATAGCTCACGCTGTAGGTATCTCAGTTCGGT

GTAGGTCGTTCGCTCCAAGCTGGGCTGTGTGCACGAACCCCCCGTTCAGCCCGACCGCTGCG

CCTTATCCGGTAACTATCGTCTTGAGTCCAACCCGGTAAGACACGACTTATCGCCACTGGCA

GCAGCCACTGGTAACAGGATTAGCAGAGCGAGGTATGTAGGCGGTGCTACAGAGTTCTTGAA

GTGGTGGCCTAACTACGGCTACACTAGAAGAACAGTATTTGGTATCTGCGCTCTGCTGAAGC

CAGTTACCTTCGGAAAAAGAGTTGGTAGCTCTTGATCCGGCAAACAAACCACCGCTGGTAGC

GGTGGTTTTTTTGTTTGCAAGCAGCAGATTACGCGCAGAAAAAAAGGATCTCAAGAAGATCC
```

-continued

```
TTTGATCTTTTCTACGGGGTCTGACGCTCAGTGGAACGAAAACTCACGTTAAGGGATTTTGG

TCATGAGATTATCAAAAAGGATCTTCACCTAGATCCTTTTAAATTAAAAATGAAGTTTTAAA

TCAATCTAAAGTATATATGAGTAAACTTGGTCTGACAGTTACCAATGCTTAATCAGTGAGGC

ACCTATCTCAGCGATCTGTCTATTTCGTTCATCCATAGTTGCCTGACTCGGGGGGGGGGGC

GCTGAGGTCTGCCTCGTGAAGAAGGTGTTGCTGACTCATACCAGGCCTGAATCGCCCCATCA

TCCAGCCAGAAAGTGAGGGAGCCACGGTTGATGAGAGCTTTGTTGTAGGTGGACCAGTTGGT

GATTTTGAACTTTTGCTTTGCCACGGAACGGTCTGCGTTGTCGGGAAGATGCGTGATCTGAT

CCTTCAACTCAGCAAAAGTTCGATTTATTCAACAAAGCCGCCGTCCCGTCAAGTCAGCGTAA

TGCTCTGCCAGTGTTACAACCAATTAACCAATTCTGATTAGAAAAACTCATCGAGCATCAAA

TGAAACTGCAATTTATTCATATCAGGATTATCAATACCATATTTTTGAAAAAGCCGTTTCTG

TAATGAAGGAGAAAACTCACCGAGGCAGTTCCATAGGATGGCAAGATCCTGGTATCGGTCTG

CGATTCCGACTCGTCCAACATCAATACAACCTATTAATTTCCCCTCGTCAAAAATAAGGTTA

TCAAGTGAGAAATCACCATGAGTGACGACTGAATCCGGTGAGAATGGCAAAAGCTTATGCAT

TTCTTTCCAGACTTGTTCAACAGGCCAGCCATTACGCTCGTCATCAAAATCACTCGCATCAA

CCAAACCGTTATTCATTCGTGATTGCGCCTGAGCGAGACGAAATACGCGATCGCTGTTAAAA

GGACAATTACAAACAGGAATCGAATGCAACCGGCGCAGGAACACTGCCAGCGCATCAACAAT

ATTTTCACCTGAATCAGGATATTCTTCTAATACCTGGAATGCTGTTTTCCCGGGGATCGCAG

TGGTGAGTAACCATGCATCATCAGGAGTACGGATAAAATGCTTGATGGTCGGAAGAGGCATA

AATTCCGTCAGCCAGTTTAGTCTGACCATCTCATCTGTAACATCATTGGCAACGCTACCTTT

GCCATGTTTCAGAAACAACTCTGGCGCATCGGGCTTCCCATACAATCGATAGATTGTCGCAC

CTGATTGCCCGACATTATCGCGAGCCCATTTATACCCATATAAATCAGCATCCATGTTGGAA

TTTAATCGCGGCCTCGAGCAAGACGTTTCCCGTTGAATATGGCTCATAACACCCCTTGTATT

ACTGTTTATGTAAGCAGACAGTTTTATTGTTCATGATGATATATTTTTATCTTGTGCAATGT

AACATCAGAGATTTTGAGACACAACGTGGATCATCCAGACATGATAAGATACATTGATGAGT

TTGGACAAACCACAACTAGAATGCAGTGAAAAAAATGCTTTATTTGTGAAATTTGTGATGCT

ATTGCTTTATTTGTAACCATTATAAGCTGCAATAAACAAGTTAACAACAACAATTGCATTCA

TTTTATGTTTCAGGTTCAGGGGGAGGTGTGGGAGGTTTTTTAAAGCAAGTAAAACCTCTACA

AATGTGGTATGGCTGATTATGATCgtcgaggatccggcgccggtttcgcgcccctaggtTCA

TCAGCTGCAAGGCACGCTGGCCCACTCGCTCCAGCTGCTGCTGTAGTATCTGTCCTGGGCCT

GCACGCTGAAGCTGGCGTTCTTCCGGCAGATCACGGTGGCGCTGGTCTTATCGGTGAAGATC

CGGTCCTTCTTCTCCCGCTTGCTCTTGCCCTGCACTTGGATGCAGAAGGTCAGGCTGAAGTA

GCTGTGAGGGGTGCTCCAGGTGTCGGGGTACTCCCAGCTCACTTCCACCTGCCTGCTGTTCT

TCAGGGGCTTCAGCTGCAGGTTCTTGGGGGGGTCGGGCTTGATGATGTCCCGGATGAAGAAG

GAGCTGGTGTAGTTCTCGTACTTCAGCTTGTGGATGGCGTCCACCATCACTTCGATGGGCAG

TCTCTCCTCGGCGGCAGGGCAGGCGCTGTCCTCCTGGCACTCCACGCTGTACTCGTACTCCT

TGTTGTCGCCTCTCACTCTCTCGGCGCTCAGGGTCACGGCGCCACAGGTCACGCCCTGGGGG

TTGCTGCTGCCTCTGCTGCTCTTCACGCTGAAGGTCAGGTCGGTGCTGATGGTGGTCAGCCA

CCAACAGGTGAACCGGCCGCTGTAATTCTTGGCCTCGCAGCGCAGGAAGGTCTTGTTCTTGG

GCTCCTTCTGGTCCTTCAGCACGTCGGTGCTCCAGATCCCGTCCTCCTTCTTGTGCAGCAGC

AGCAGGCTGTGGCTCAGGGCCTCGCCGCCCTTGTGGCAGGTGTACTGGCCGGCGTCGCCGAA

CTCCTTGACCTGGATCGTCAGGGTCTTGCCGCTGCCCAGCACTTCGCCGCTCTGGTCCAGGG
```

TCCAGGTGATGCCGTCCTCCTCGGGGGTGTCGCAGGTCAGCACCACCATCTCGCCAGGCGCG

TCGGGATACCAGTCCAGCTCCACCACGTATACGTCCTTCTTCAGCTCCCAGATGGCCATCAG

GGGGCTGGCCAGGAACACCAGGCTGAACCAGCTGATCACCAGCTGCTGGTGGCACATttctt ctcgacagatccAAACGCTCCTCCGACGTCCCCAGGCAGAATGGCGGTTCCCTAAACGAGCA

TTGCTTATATAGACCTCCCATTAGGCACGCCTACCGCCCATTTACGTCAATGGAACGCCCAT

TTGCGTCATTGCCCCTCCCCATTGACGTCAATGGGGATGTACTTGGCAGCCATCGCGGGCCA

TTTACCGCCATTGACGTCAATGGGAGTACTGCCAATGTACCCTGGCGTACTTCCAATAGTAA

TGTACTTGCCAAGTTACTATTAATAGATATTGATGTACTGCCAAGTGGGCCATTTACCGTCA

TTGACGTCAATAGGGGCGTGAGAACGGATATGAATGGGCAATGAGCCATCCCATTGACGTC

AATGGTGGGTGGTCCTATTGACGTCAATGGGCATTGAGCCAGGCGGGCCATTTACCGTAATT

GACGTCAATGGGGAGGCGCCATATACGTCAATAGGACCGCCCATATGACGTCAATAGGTAA

GACCATGAGGCCCTTTCGTCTCGCGCGTTTCGGTGATGACGGTGAAAACCTCTGACACATGC

AGCTCCCGGAGACGGTCACAGCTTGTCTGTAAGCGGATGCCGGGAGCAGACAAGCCCGTCAG

GGCGCGTCAGCGGGTGTTGGCGGGTGTCGGGGCTGGCTTAACTATGCGGCATCAGAGCAGAT

TGTACTGAGAGTGCACCATATGCGGTGTGAAATACCGCACAGATGCGTAAGGAGAAAATACC

GCATCAGATTGGCTATTGG

SEQ ID NO: 5
- AG177
flanking sequences in lower case; coding sequences underlined
expresses p19 subunit of human IL-23
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGcgcgcgtcgactctagaaagaaATGCTGGGGAGCCGCGCGGTCATGCTGCTCTT

GCTGCTCCCCTGGACGGCCCAGGGCCGGGCGGTGCCCGGGGGCTCGAGCCCGGCCTGGACGC

AGTGCCAGCAGCTCAGCCAGAAGCTCTGCACCCTGGCCTGGTCGGCCCACCCGCTCGTGGGC

CACATGGACCTCCGGGAGGAGGGCGACGAGGAGACGACCAACGACGTCCCCCACATCCAGTG

CGGCGACGGCTGCGACCCCCAGGGCCTCCGGGACAACTCGCAGTTCTGCCTGCAGCGCATCC

ACCAGGGCCTGATCTTCTACGAGAAGCTGCTCGGCTCGGACATCTTCACGGGGGAGCCGTCG

CTGCTCCCCGACAGCCCGGTGGGCCAGCTCCACGCCTCCCTCCTGGGCCTCTCGCAACTTCT

GCAACCGGAGGGCCACCACTGGGAGACGCAGCAGATCCCGAGCCTCTCGCCCAGCCAGCCGT

GGCAGCGGCTCCTGCTCAGATTCAAGATCTTGCGCTCCCTCCAAGCCTTCGTGGCGGTCGCC

GCCCGGGTCTTCGCCCACGGCGCGGCCACCCTGAGCCCCTGATAAgatatcggatccaGATC

-continued

```
TGCTGTGCCTTCTAGTTGCCAGCCATCTGTTGTTTGCCCCTCCCCCGTGCCTTCCTTGACCC
TGGAAGGTGCCACTCCCACTGTCCTTTCCTAATAAAATGAGGAAATTGCATCGCATTGTCTG
AGTAGGTGTCATTCTATTCTGGGGGGTGGGGTGGGGCAGGACAGCAAGGGGGAGGATTGGGA
AGACAATAGCAGGCATGCTGGGGATGCGGTGGGCTCTATGGGTACCCAGGTGCTGAAGAATT
GACCCGGTTCCTCCTGGGCCAGAAAGAAGCAGGCACATCCCCTTCTCTGTGACACACCCTGT
CCACGCCCCTGGTTCTTAGTTCCAGCCCCACTCATAGGACACTCATAGCTCAGGAGGGCTCC
GCCTTCAATCCCACCCGCTAAAGTACTTGGAGCGGTCTCTCCCTCCCTCATCAGCCCACCAA
ACCAAACCTAGCCTCCAAGAGTGGGAAGAAATTAAAGCAAGATAGGCTATTAAGTGCAGAGG
GAGAGAAAATGCCTCCAACATGTGAGGAAGTAATGAGAGAAATCATAGAATTTCTTCCGCTT
CCTCGCTCACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTTTCCATAGGCTCC
GCCCCCCTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATAGCT
CACGCTGTAGGTATCTCAGTTCGGTGTAGGTCGTTCGCTCCAAGCTGGGCTGTGTGCACGAA
CCCCCCGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGAGGTATG
TAGGCGGTGCTACAGAGTTCTTGAAGTGGTGGCCTAACTACGGCTACACTAGAAGAACAGTA
TTTGGTATCTGCGCTCTGCTGAAGCCAGTTACCTTCGGAAAAAGAGTTGGTAGCTCTTGATC
CGGCAAACAAACCACCGCTGGTAGCGGTGGTTTTTTTGTTTGCAAGCAGCAGATTACGCGCA
GAAAAAAAGGATCTCAAGAAGATCCTTTGATCTTTTCTACGGGGTCTGACGCTCAGTGGAAC
GAAAACTCACGTTAAGGGATTTTGGTCATGAGATTATCAAAAAGGATCTTCACCTAGATCCT
TTTAAATTAAAAATGAAGTTTTAAATCAATCTAAAGTATATATGAGTAAACTTGGTCTGACA
GTTACCAATGCTTAATCAGTGAGGCACCTATCTCAGCGATCTGTCTATTTCGTTCATCCATA
GTTGCCTGACTCGGGGGGGGGGGCGCTGAGGTCTGCCTCGTGAAGAAGGTGTTGCTGACTC
ATACCAGGCCTGAATCGCCCCATCATCCAGCCAGAAAGTGAGGGAGCCACGGTTGATGAGAG
CTTTGTTGTAGGTGGACCAGTTGGTGATTTTGAACTTTTGCTTTGCCACGGAACGGTCTGCG
TTGTCGGGAAGATGCGTGATCTGATCCTTCAACTCAGCAAAAGTTCGATTTATTCAACAAAG
CCGCCGTCCCGTCAAGTCAGCGTAATGCTCTGCCAGTGTTACAACCAATTAACCAATTCTGA
TTAGAAAAACTCATCGAGCATCAAATGAAACTGCAATTTATTCATATCAGGATTATCAATAC
CATATTTTTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAACCTATTAA
TTTCCCCTCGTCAAAAATAAGGTTATCAAGTGAGAAATCACCATGAGTGACGACTGAATCCG
GTGAGAATGGCAAAAGCTTATGCATTTCTTTCCAGACTTGTTCAACAGGCCAGCCATTACGC
TCGTCATCAAAATCACTCGCATCAACCAAACCGTTATTCATTCGTGATTGCGCCTGAGCGAG
ACGAAATACGCGATCGCTGTTAAAAGGACAATTACAAACAGGAATCGAATGCAACCGGCGCA
GGAACACTGCCAGCGCATCAACAATATTTTCACCTGAATCAGGATATTCTTCTAATACCTGG
AATGCTGTTTTCCCGGGGATCGCAGTGGTGAGTAACCATGCATCATCAGGAGTACGGATAAA
ATGCTTGATGGTCGGAAGAGGCATAAATTCCGTCAGCCAGTTTAGTCTGACCATCTCATCTG
TAACATCATTGGCAACGCTACCTTTGCCATGTTTCAGAAACAACTCTGGCGCATCGGGCTTC
```

```
CCATACAATCGATAGATTGTCGCACCTGATTGCCCGACATTATCGCGAGCCCATTTATACCC

ATATAAATCAGCATCCATGTTGGAATTTAATCGCGGCCTCGAGCAAGACGTTTCCCGTTGAA

TATGGCTCATAACACCCCTTGTATTACTGTTTATGTAAGCAGACAGTTTTATTGTTCATGAT

GATATATTTTTATCTTGTGCAATGTAACATCAGAGATTTTGAGACACAACGTGGCTTTCCCC

CCCCCCCCATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCACCTGAC

GTCTAAGAAACCATTATTATCATGACATTAACCTATAAAAATAGGCGTATCACGAGGCCCTT

TCGTCTCGCGCGTTTCGGTGATGACGGTGAAAACCTCTGACACATGCAGCTCCCGGAGACGG

TCACAGCTTGTCTGTAAGCGGATGCCGGGAGCAGACAAGCCCGTCAGGGCGCGTCAGCGGGT

GTTGGCGGGTGTCGGGGCTGGCTTAACTATGCGGCATCAGAGCAGATTGTACTGAGAGTGCA

CCATATGCGGTGTGAAATACCGCACAGATGCGTAAGGAGAAAATACCGCATCAGATTGGCTA

TTGG

SEQ ID NO: 6
- AG180
flanking sequences in lower case; coding sequences underlined
expresses p40 subunit of human IL-12
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGcgcgcgtcgaggaatttcgagaagaaATGTGCCACCAGCAGCTGGTCATCAGCT

GGTTCAGCCTCGTTTTCCTCGCCTCGCCGCTGGTCGCCATATGGGAGCTCAAGAAGGACGTA

TACGTGGTGGAGCTGGACTGGTACCCCGACGCGCCGGGCGAGATGGTCGTCCTGACGTGCGA

CACGCCGGAGGAGGACGGCATCACGTGGACGCTGGACCAGTCCAGCGAGGTCCTCGGCTCCG

GCAAGACGCTGACGATCCAGGTCAAGGAGTTCGGCGACGCGGGCCAGTACACGTGCCACAAG

GGCGGCGAGGTCCTGAGCCACTCCCTCCTCCTGCTACACAAGAAGGAGGACGGGATCTGGAG

CACGGACATCCTCAAGGACCAGAAGGAGCCGAAGAACAAGACCTTCCTGCGCTGCGAGGCGA

AGAATTACTCGGGCCGGTTCACGTGCTGGTGGCTCACCACGATCAGCACGGACCTGACGTTC

TCGGTCAAGTCGTCGCGGGGCTCGTCGGACCCCCAGGGGGTGACCTGCGGCGCGGCGACGCT

GTCGGCGGAGCGGGTGCGGGCGACAACAAGGAGTACGAGTACTCGGTCGAGTGCCAGGAGG

ACTCGGCGTGCCCGGCGGCGGAGGAGTCGCTGCCGATCGAGGTGATGGTCGACGCGGTCCAC

AAGCTGAAGTACGAGAACTACACGTCGTCGTTCTTCATCCGGGACATCATCAAGCCGGACCC

GCCGAAGAACCTGCAGCTGAAGCCGCTGAAGAACTCGCGGCAGGTCGAGGTCTCGTGGGAGT

ACCCGGACACGTGGTCGACGCCGCACTCGTACTTCTCGCTGACGTTCTGCGTCCAAGTGCAG
```

-continued

<u>GGCAAGTCGAAGCGGGAGAAGAAGGACCGGGTGTTCACCGACAAGACGAGCGCGACGGTGAT</u>

<u>CTGCCGGAAGAACGCGTCGATCTCGGTGCGGGCGCAGGACCGGTACTACTCGTCGTCGTGGT</u>

<u>CGGAGTGGGCGTCGGTGCCGTGCAGCTAG</u>acctagggcgcgccagatctgatatcggatct

GCTGTGCCTTCTAGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCATCGCATTGTCTGA

GTAGGTGTCATTCTATTCTGGGGGGTGGGGTGGGGCAGGACAGCAAGGGGGAGGATTGGGAA

GACAATAGCAGGCATGCTGGGGATGCGGTGGGCTCTATGGGTACCCAGGTGCTGAAGAATTG

ACCCGGTTCCTCCTGGGCCAGAAAGAAGCAGGCACATCCCCTTCTCTGTGACACACCCTGTC

CACGCCCCTGGTTCTTAGTTCCAGCCCCACTCATAGGACACTCATAGCTCAGGAGGGCTCCG

CCTTCAATCCCACCCGCTAAAGTACTTGGAGCGGTCTCTCCCTCCCTCATCAGCCCACCAAA

CCAAACCTAGCCTCCAAGAGTGGGAAGAAATTAAAGCAAGATAGGCTATTAAGTGCAGAGGG

AGAGAAAATGCCTCCAACATGTGAGGAAGTAATGAGAGAAATCATAGAATTTCTTCCGCTTC

CTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAGGCTCCG

CCCCCCTGACGAGCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCACGAAC

CCCCCGTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGAACAGTAT

TTGGTATCTGCGCTCTGCTGAAGCCAGTTACCTTCGGAAAAAGAGTTGGTAGCTCTTGATCC

GGCAAACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGATCCTT

TTAAATTAAAAATGAAGTTTTAAATCAATCTAAAGTATATATGAGTAAACTTGGTCTGACAG

TTACCAATGCTTAATCAGTGAGGCACCTATCTCAGCGATCTGTCTATTTCGTTCATCCATAG

TTGCCTGACTCGGGGGGGGGGGCGCTGAGGTCTGCCTCGTGAAGAAGGTGTTGCTGACTCA

TACCAGGCCTGAATCGCCCCATCATCCAGCCAGAAAGTGAGGGAGCCACGGTTGATGAGAGC

TTTGTTGTAGGTGGACCAGTTGGTGATTTTGAACTTTTGCTTTGCCACGGAACGGTCTGCGT

TGTCGGGAAGATGCGTGATCTGATCCTTCAACTCAGCAAAAGTTCGATTTATTCAACAAAGC

CGCCGTCCCGTCAAGTCAGCGTAATGCTCTGCCAGTGTTACAACCAATTAACCAATTCTGAT

TAGAAAAACTCATCGAGCATCAAATGAAACTGCAATTTATTCATATCAGGATTATCAATACC

ATATTTTTGAAAAAGCCGTTTCTGTAATGAAGGAGAAAACTCACCGAGGCAGTTCCATAGGA

TGGCAAGATCCTGGTATCGGTCTGCGATTCCGACTCGTCCAACATCAATACAACCTATTAAT

TTCCCCTCGTCAAAAATAAGGTTATCAAGTGAGAAATCACCATGAGTGACGACTGAATCCGG

TGAGAATGGCAAAAGCTTATGCATTTCTTTCCAGACTTGTTCAACAGGCCAGCCATTACGCT

CGTCATCAAAATCACTCGCATCAACCAAACCGTTATTCATTCGTGATTGCGCCTGAGCGAGA

CGAAATACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATACCTGGA

-continued

```
ATGCTGTTTTCCCGGGGATCGCAGTGGTGAGTAACCATGCATCATCAGGAGTACGGATAAAA

TGCTTGATGGTCGGAAGAGGCATAAATTCCGTCAGCCAGTTTAGTCTGACCATCTCATCTGT

AACATCATTGGCAACGCTACCTTTGCCATGTTTCAGAAACAACTCTGGCGCATCGGGCTTCC

CATACAATCGATAGATTGTCGCACCTGATTGCCCGACATTATCGCGAGCCCATTTATACCCA

TATAAATCAGCATCCATGTTGGAATTTAATCGCGGCCTCGAGCAAGACGTTTCCCGTTGAAT

ATGGCTCATAACACCCCTTGTATTACTGTTTATGTAAGCAGACAGTTTTATTGTTCATGATG

ATATATTTTTATCTTGTGCAATGTAACATCAGAGATTTTGAGACACAACGTGGATCATCCAG

ACATGATAAGATACATTGATGAGTTTGGACAAACCACAACTAGAATGCAGTGAAAAAAATGC

TTTATTTGTGAAATTTGTGATGCTATTGCTTTATTTGTAACCATTATAAGCTGCAATAAACA

AGTTAACAACAACAATTGCATTCATTTTATGTTTCAGGTTCAGGGGGAGGTGTGGGAGGTTT

TTTAAAGCAAGTAAAACCTCTACAAATGTGGTATGGCTGATTATGATCGTCGAGGATCCGGC

GCCGGTTTAAACGTCGACAGATCCAAACGCTCCTCCGACGTCCCCAGGCAGAATGGCGGTTC

CCTAAACGAGCATTGCTTATATAGACCTCCCATTAGGCACGCCTACCGCCCATTTACGTCAA

TGGAACGCCCATTTGCGTCATTGCCCCTCCCCATTGACGTCAATGGGGATGTACTTGGCAGC

CATCGCGGGCCATTTACCGCCATTGACGTCAATGGGAGTACTGCCAATGTACCCTGGCGTAC

TTCCAATAGTAATGTACTTGCCAAGTTACTATTAATAGATATTGATGTACTGCCAAGTGGGC

CATTTACCGTCATTGACGTCAATAGGGGCGTGAGAACGGATATGAATGGGCAATGAGCCAT

CCCATTGACGTCAATGGTGGGTGGTCCTATTGACGTCAATGGGCATTGAGCCAGGCGGGCCA

TTTACCGTAATTGACGTCAATGGGGGAGGCGCCATATACGTCAATAGGACCGCCCATATGAC

GTCAATAGGTAAGACCATGAGGCCCTTTCGTCTCGCGCGTTTCGGTGATGACGGTGAAAACC

TCTGACACATGCAGCTCCCGGAGACGGTCACAGCTTGTCTGTAAGCGGATGCCGGGAGCAGA

CAAGCCCGTCAGGGCGCGTCAGCGGGTGTTGGCGGGTGTCGGGGCTGGCTTAACTATGCGGC

ATCAGAGCAGATTGTACTGAGAGTGCACCATATGCGGTGTGAAATACCGCACAGATGCGTAA

GGAGAAAATACCGCATCAGATTGGCTATTGG
```

```
                                                        SEQ ID NO: 7
- AG184
flanking sequences in lower case; coding sequences underlined
expresses p40 subunit of human IL-12 under control of hCMV and
p19 subunit of human IL-23 under control of siCMV
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGCgcgcgtcgaggaatttcgagaagaaATGTGCCACCAGCAGCTGGTCATCAGCT

GGTTCAGCCTCGTTTTCCTCGCCTCGCCGCTGGTCGCCATATGGGAGCTCAAGAAGGACGTA
```

TACGTGGTGGAGCTGGACTGGTACCCCGACGCGCCGGGCGAGATGGTCGTCCTGACGTGCGA

CACGCCGGAGGAGGACGGCATCACGTGGACGCTGGACCAGTCCAGCGAGGTCCTCGGCTCCG

GCAAGACGCTGACGATCCAGGTCAAGGAGTTCGGCGACGCGGGCCAGTACACGTGCCACAAG

GGCGGCGAGGTCCTGAGCCACTCCCTCCTCCTGCTACACAAGAAGGAGGACGGGATCTGGAG

CACGGACATCCTCAAGGACCAGAAGGAGCCGAAGAACAAGACCTTCCTGCGCTGCGAGGCGA

AGAATTACTCGGGCCGGTTCACGTGCTGGTGGCTCACCACGATCAGCACGGACCTGACGTTC

TCGGTCAAGTCGTCGCGGGGCTCGTCGGACCCCCAGGGGGTGACCTGCGGCGCGGCGACGCT

GTCGGCGGAGCGGGTGCGGGCGACAACAAGGAGTACGAGTACTCGGTCGAGTGCCAGGAGG

ACTCGGCGTGCCCGGCGGCGGAGGAGTCGCTGCCGATCGAGGTGATGGTCGACGCGGTCCAC

AAGCTGAAGTACGAGAACTACACGTCGTCGTTCTTCATCCGGGACATCATCAAGCCGGACCC

GCCGAAGAACCTGCAGCTGAAGCCGCTGAAGAACTCGCGGCAGGTCGAGGTCTCGTGGGAGT

ACCCGGACACGTGGTCGACGCCGCACTCGTACTTCTCGCTGACGTTCTGCGTCCAAGTGCAG

GGCAAGTCGAAGCGGGAGAAGAAGGACCGGGTGTTCACCGACAAGACGAGCGCGACGGTGAT

CTGCCGGAAGAACGCGTCGATCTCGGTGCGGGCGCAGGACCGGTACTACTCGTCGTCGTGGT

CGGAGTGGGCGTCGGTGCCGTGCAGCTAGacctaggggcgcgccagatctgatatcggatct

GCTGTGCCTTCTAGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCATCGCATTGTCTGA

GTAGGTGTCATTCTATTCTGGGGGGTGGGGTGGGCAGGACAGCAAGGGGGAGGATTGGGAA

GACAATAGCAGGCATGCTGGGGATGCGGTGGGCTCTATGGGTACCCAGGTGCTGAAGAATTG

ACCCGGTTCCTCCTGGGCCAGAAAGAAGCAGGCACATCCCCTTCTCTGTGACACACCCTGTC

CACGCCCCTGGTTCTTAGTTCCAGCCCCACTCATAGGACACTCATAGCTCAGGAGGGCTCCG

CCTTCAATCCCACCCGCTAAAGTACTTGGAGCGGTCTCTCCCTCCCTCATCAGCCCACCAAA

CCAAACCTAGCCTCCAAGAGTGGGAAGAAATTAAAGCAAGATAGGCTATTAAGTGCAGAGGG

AGAGAAAATGCCTCCAACATGTGAGGAAGTAATGAGAGAAATCATAGAATTTCTTCCGCTTC

CTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAGGCTCCG

CCCCCCTGACGAGCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCACGAAC

CCCCCGTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGAACAGTAT

TTGGTATCTGCGCTCTGCTGAAGCCAGTTACCTTCGGAAAAAGAGTTGGTAGCTCTTGATCC

GGCAAACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGATCCTT

TTAAATTAAAAATGAAGTTTTAAATCAATCTAAAGTATATATGAGTAAACTTGGTCTGACAG

TTACCAATGCTTAATCAGTGAGGCACCTATCTCAGCGATCTGTCTATTTCGTTCATCCATAG

-continued

```
TTGCCTGACTCGGGGGGGGGGGCGCTGAGGTCTGCCTCGTGAAGAAGGTGTTGCTGACTCA
TACCAGGCCTGAATCGCCCCATCATCCAGCCAGAAAGTGAGGGAGCCACGGTTGATGAGAGC
TTTGTTGTAGGTGGACCAGTTGGTGATTTTGAACTTTTGCTTTGCCACGGAACGGTCTGCGT
TGTCGGAAGATGCGTGATCTGATCCTTCAACTCAGCAAAAGTTCGATTTATTCAACAAAGC
CGCCGTCCCGTCAAGTCAGCGTAATGCTCTGCCAGTGTTACAACCAATTAACCAATTCTGAT
TAGAAAAACTCATCGAGCATCAAATGAAACTGCAATTTATTCATATCAGGATTATCAATACC
ATATTTTTGAAAAAGCCGTTTCTGTAATGAAGGAGAAAACTCACCGAGGCAGTTCCATAGGA
TGGCAAGATCCTGGTATCGGTCTGCGATTCCGACTCGTCCAACATCAATACAACCTATTAAT
TTCCCCTCGTCAAAAATAAGGTTATCAAGTGAGAAATCACCATGAGTGACGACTGAATCCGG
TGAGAATGGCAAAAGCTTATGCATTTCTTTCCAGACTTGTTCAACAGGCCAGCCATTACGCT
CGTCATCAAAATCACTCGCATCAACCAAACCGTTATTCATTCGTGATTGCGCCTGAGCGAGA
CGAAATACGCGATCGCTGTTAAAAGGACAATTACAAACAGGAATCGAATGCAACCGGCGCAG
GAACACTGCCAGCGCATCAACAATATTTTCACCTGAATCAGGATATTCTTCTAATACCTGGA
ATGCTGTTTTCCCGGGGATCGCAGTGGTGAGTAACCATGCATCATCAGGAGTACGGATAAAA
TGCTTGATGGTCGGAAGAGGCATAAATTCCGTCAGCCAGTTTAGTCTGACCATCTCATCTGT
AACATCATTGGCAACGCTACCTTTGCCATGTTTCAGAAACAACTCTGGCGCATCGGGCTTCC
CATACAATCGATAGATTGTCGCACCTGATTGCCCGACATTATCGCGAGCCCATTTATACCCA
TATAAATCAGCATCCATGTTGGAATTTAATCGCGGCCTCGAGCAAGACGTTTCCCGTTGAAT
ATGGCTCATAACACCCCTTGTATTACTGTTTATGTAAGCAGACAGTTTTATTGTTCATGATG
ATATATTTTTATCTTGTGCAATGTAACATCAGAGATTTTGAGACACAACGTGGATCATCCAG
ACATGATAAGATACATTGATGAGTTTGGACAAACCACAACTAGAATGCAGTGAAAAAAATGC
TTTATTTGTGAAATTTGTGATGCTATTGCTTTATTTGTAACCATTATAAGCTGCAATAAACA
AGTTAACAACAACAATTGCATTCATTTTATGTTTCAGGTCAGGGGGAGGTGTGGGAGGTTT
TTTAAAGCAAGTAAAACCTCTACAAATGTGGTATGGCTGATTATGATCgtcgaggatccgat
atcTTATCAGGGGCTCAGGTGGCCGCGCCGTGGGCGAAGACCCGGGCGGCGACCGCCACGA
AGGCTTGGAGGGAGCGCAAGATCTTGAATCTGAGCAGGAGCCGCTGCCACGGCTGGCTGGGC
GAGAGGCTCGGGATCTGCTGCGTCTCCCAGTGGTGGCCCTCCGGTTGCAGAAGTTGCGAGAG
GCCCAGGAGGGAGGCGTGGAGCTGGCCCACCGGGCTGTCCGGGAGCAGCGACGGCTCCCCCG
TGAAGATGTCCGAGCCGAGCAGCTTCTCGTAGAAGATCAGGCCCTGGTGGATGCGCTGCAGG
CAGAACTGCGAGTTGTCCCGGAGGCCCTGGGGGTCGCAGCCGTCGCCGCACTGGATGTGGGG
GACGTCGTTGGTCGTCCTCGTCGCCCTCCTCCCGGAGGTCCATGTGGCCCACGAGCGGGT
GGGCCGACCAGGCCAGGGTGCAGAGCTTCTGGCTGAGCTGCTGGCACTGCGTCCAGGCCGGG
CTCGAGCCCCCGGGCACCGCCCGGCCCTGGGCCGTCCAGGGGAGCAGCAAGAGCAGCATGAC
CGCGCGGCTCCCCAGCATttctttctagagtcaaacgtcgacagatccAAACGCTCCTCCGA
CGTCCCCAGGCAGAATGGCGGTTCCCTAAACGAGCATTGCTTATATAGACCTCCCATTAGGC
ACGCCTACCGCCCATTTACGTCAATGGAACGCCCATTTGCGTCATTGCCCCTCCCCATTGAC
GTCAATGGGATGTACTTGGCAGCCATCGCGGGCCATTTACCGCCATTGACGTCAATGGGAG
TACTGCCAATGTACCCTGGCGTACTTCCAATAGTAATGTACTTGCCAAGTTACTATTAATAG
ATATTGATGTACTGCCAAGTGGGCCATTTACCGTCATTGACGTCAATAGGGGCGTGAGAAC
GGATATGAATGGGCAATGAGCCATCCCATTGACGTCAATGGTGGGTGGTCCTATTGACGTCA
ATGGGCATTGAGCCAGGCGGGCCATTTACCGTAATTGACGTCAATGGGGGAGGCGCCATATA
```

CGTCAATAGGACCGCCCATATGACGTCAATAGGTAAAGACCATGAGGCCCTTTCGTCTCGCG

CGTTTCGGTGATGACGGTGAAAACCTCTGACACATGCAGCTCCCGGAGACGGTCACAGCTTG

TCTGTAAGCGGATGCCGGGAGCAGACAAGCCCGTCAGGGCGCGTCAGCGGGTGTTGGCGGGT

GTCGGGGCTGGCTTAACTATGCGGCATCAGAGCAGATTGTACTGAGAGTGCACCATATGCGG

TGTGAAATACCGCACAGATGCGTAAGGAGAAAATACCGCATCAGATTGGCTATTGG

SEQ ID NO: 8
- AG193
flanking sequences in lower case; coding sequences underlined
expresses murine IL-27 p28

CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGAGGTCTATATAAGCAGAGCTCGTTTAGTGAACCGtcagat cgcctggagacgccatccacgctgttttgacctccatagaagacaccgggaccgatccagcc tccgagggcgcgcgtcgacaagaaATGGGCCAGGTCACCGGGGACCTCGGGTGGCGCCTGTC

GCTCCTGCTCCTGCCCCTCCTCCTGGTCCAAGCGGGGAGCTGGGGCTTCCCCACGGATCCCC

TGAGCCTCCAGGAGCTGCGCAGGGAGTTCACCGTCAGCCTGTACCTCGCCCGGAAGCTGCTC

TCCGAGGTCCAGGGCTACGTCCACAGCTTCGCCGAGTCGCGCCTGCCCGGCGTGAACCTGGA

CCTCCTGCCCCTGGGCTACCACCTCCCCAACGTCTCCCTGACGTTCCAAGCCTGGCACCACC

TCTCCGACTCCGAGCGCCTCTGCTTCCTCGCCACCACGCTCCGGCCGTTCCCGGCCATGCTG

GGCGGGCTGGGGACCCAGGGGACCTGGACCAGCTCCGAGAGGGAGCAGCTGTGGGCCATGAG

GCTGGACCTCCGGGACCTGCACAGGCACCTCCGCTTCCAAGTCCTGGCCGCGGGCTTCAAGT

GCTCCAAGGAGGAGGAGGACAAGGAGGAAGAGGAAGAGGAGGAAGAAGAGGAAAAGAAGCTG

CCCCTCGGGGCCCTGGGCGGCCCCAACCAGGTGTCCTCCCAAGTGTCCTGGCCCCAGCTGCT

CTACACCTACCAGCTCCTCCACTCCCTGGAGCTGGTCCTGAGCCGGGCGGTGCGGGACCTGC

TCCTGCTGTCCCTGCCCCGGCGCCCGGGCTCGGCCTGGGACTCCTAATGAtctagaaGATCT

GCTGTGCCTTCTAGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCATCGCATTGTCTGA

GTAGGTGTCATTCTATTCTGGGGGGTGGGGTGGGCAGGACAGCAAGGGGGAGGATTGGGAA

GACAATAGCAGGCATGCTGGGGATGCGGTGGGCTCTATGGGTACCCAGGTGCTGAAGAATTG

ACCCGGTTCCTCCTGGGCCAGAAAGAAGCAGGCACATCCCCTTCTCTGTGACACACCCTGTC

CACGCCCCTGGTTCTTAGTTCCAGCCCCACTCATAGGACACTCATAGCTCAGGAGGGCTCCG

CCTTCAATCCCACCCGCTAAAGTACTTGGAGCGGTCTCTCCCTCCCTCATCAGCCCACCAAA

CCAAACCTAGCCTCCAAGAGTGGGAAGAAATTAAAGCAAGATAGGCTATTAAGTGCAGAGGG

AGAGAAAATGCCTCCAACATGTGAGGAAGTAATGAGAGAAATCATAGAATTTCTTCCGCTTC

-continued

```
CTCGCTCACTGACTCGCTGCGCTCGGTCGTTCGGCTGCGGCGAGCGGTATCAGCTCACTCAA

AGGCGGTAATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAGGCTCCG

CCCCCCTGACGAGCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGCTTTCTCATAGCTC

ACGCTGTAGGTATCTCAGTTCGGTGTAGGTCGTTCGCTCCAAGCTGGGCTGTGTGCACGAAC

CCCCCGTTCAGCCCGACCGCTGCGCCTTATCCGGTAACTATCGTCTTGAGTCCAACCCGGTA

AGACACGACTTATCGCCACTGGCAGCAGCCACTGGTAACAGGATTAGCAGAGCGAGGTATGT

AGGCGGTGCTACAGAGTTCTTGAAGTGGTGGCCTAACTACGGCTACACTAGAAGAACAGTAT

TTGGTATCTGCGCTCTGCTGAAGCCAGTTACCTTCGGAAAAAGAGTTGGTAGCTCTTGATCC

GGCAAACAAACCACCGCTGGTAGCGGTGGTTTTTTTGTTTGCAAGCAGCAGATTACGCGCAG

AAAAAAAGGATCTCAAGAAGATCCTTTGATCTTTTCTACGGGGTCTGACGCTCAGTGGAACG

AAAACTCACGTTAAGGGATTTTGGTCATGAGATTATCAAAAAGGATCTTCACCTAGATCCTT

TTAAATTAAAAATGAAGTTTTAAATCAATCTAAAGTATATATGAGTAAACTTGGTCTGACAG

TTACCAATGCTTAATCAGTGAGGCACCTATCTCAGCGATCTGTCTATTTCGTTCATCCATAG

TTGCCTGACTCGGGGGGGGGGGCGCTGAGGTCTGCCTCGTGAAGAAGGTGTTGCTGACTCA

TACCAGGCCTGAATCGCCCCATCATCCAGCCAGAAAGTGAGGGAGCCACGGTTGATGAGAGC

TTTGTTGTAGGTGGACCAGTTGGTGATTTTGAACTTTTGCTTTGCCACGGAACGGTCTGCGT

TGTCGGGAAGATGCGTGATCTGATCCTTCAACTCAGCAAAAGTTCGATTTATTCAACAAAGC

CGCCGTCCCGTCAAGTCAGCGTAATGCTCTGCCAGTGTTACAACCAATTAACCAATTCTGAT

TAGAAAAACTCATCGAGCATCAAATGAAACTGCAATTTATTCATATCAGGATTATCAATACC

ATATTTTTGAAAAAGCCGTTTCTGTAATGAAGGAGAAAACTCACCGAGGCAGTTCCATAGGA

TGGCAAGATCCTGGTATCGGTCTGCGATTCCGACTCGTCCAACATCAATACAACCTATTAAT

TTCCCCTCGTCAAAAATAAGGTTATCAAGTGAGAAATCACCATGAGTGACGACTGAATCCGG

TGAGAATGGCAAAAGCTTATGCATTTCTTTCCAGACTTGTTCAACAGGCCAGCCATTACGCT

CGTCATCAAAATCACTCGCATCAACCAAACCGTTATTCATTCGTGATTGCGCCTGAGCGAGA

CGAAATACGCGATCGCTGTTAAAAGGACAATTACAAACAGGAATCGAATGCAACCGGCGCAG

GAACACTGCCAGCGCATCAACAATATTTTCACCTGAATCAGGATATTCTTCTAATACCTGGA

ATGCTGTTTTCCCGGGGATCGCAGTGGTGAGTAACCATGCATCATCAGGAGTACGGATAAAA

TGCTTGATGGTCGGAAGAGGCATAAATTCCGTCAGCCAGTTTAGTCTGACCATCTCATCTGT

AACATCATTGGCAACGCTACCTTTGCCATGTTTCAGAAACAACTCTGGCGCATCGGGCTTCC

CATACAATCGATAGATTGTCGCACCTGATTGCCCGACATTATCGCGAGCCCATTTATACCCA

TATAAATCAGCATCCATGTTGGAATTTAATCGCGGCCTCGAGCAAGACGTTTCCCGTTGAAT

ATGGCTCATAACACCCCTTGTATTACTGTTTATGTAAGCAGACAGTTTTATTGTTCATGATG

ATATATTTTTATCTTGTGCAATGTAACATCAGAGATTTTGAGACACAACGTGGCTTTCCCCC

CCCCCCCATTATTGAAGCATTTATCAGGGTTATTGTCTCATGAGCGGATACATATTTGAATG

TATTTAGAAAAATAAACAAATAGGGGTTCCGCGCACATTTCCCCGAAAAGTGCCACCTGACG

TCTAAGAAACCATTATTATCATGACATTAACCTATAAAAATAGGCGTATCACGAGGCCCTTT

CGTCTCGCGCGTTTCGGTGATGACGGTGAAAACCTCTGACACATGCAGCTCCCGGAGACGGT

CACAGCTTGTCTGTAAGCGGATGCCGGGAGCAGACAAGCCCGTCAGGGCGCGTCAGCGGGTG
```

```
TTGGCGGGTGTCGGGGCTGGCTTAACTATGCGGCATCAGAGCAGATTGTACTGAGAGTGCAC

CATATGCGGTGTGAAATACCGCACAGATGCGTAAGGAGAAAATACCGCATCAGATTGGCTAT

TGG
```

SEQ ID NO: 9
- AG194
flanking sequences in lower case; coding sequences underlined
expresses murine IL-27 EBI3

```
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGtcagat cgcctggagacgccatccacgctgttttgacctccatagaagacaccgggaccgatccagcc tccgcggcacgtgaagaaATGTCGAAGCTCCTGTTCCTGAGCCTGGCGCTCTGGGCCAGCCG

CTCGCCGGGGTATACCGAGACGGCGCTCGTGGCCCTGAGCCAGCCCCGGGTGCAGTGCCACG

CCTCGCGCTACCCCGTGGCCGTGGACTGCTCCTGGACCCCGCTGCAAGCGCCCAACTCCACC

AGGTCCACGTCCTTCATCGCCACGTACCGGCTCGGCGTGGCCACCCAGCAGCAGAGCCAGCC

CTGCCTGCAGCGGAGCCCCCAGGCCTCCCGCTGCACCATCCCCGACGTGCACCTGTTCTCCA

CGGTGCCCTACATGCTCAACGTCACGGCGGTGCACCCGGGCGGCGCCAGCAGCAGCCTCCTG

GCCTTCGTGGCGGAGCGGATCATCAAGCCGGACCCGCCGGAGGGCGTGCGCCTGCGCACGGC

GGGCCAGCGCCTGCAGGTGCTCTGGCACCCCCCGGCCTCCTGGCCCTTCCCGGACATCTTCT

CGCTCAAGTACCGCCTCCGCTACCGGCGCCGAGGCGCCTCCCACTTCCGCCAAGTCGGCCCC

ATCGAGGCCACGACCTTCACCCTCCGGAACTCGAAGCCCCACGCCAAGTACTGCATCCAGGT

GTCGGCGCAGGACCTCACCGACTACGGGAAGCCCAGCGACTGGAGCCTCCCGGGGCAGGTCG

AGAGCGCTCCCCACAAGCCCTAATGAgaattcgcggatatcggttaacggatccaGATCTGC

TGTGCCTTCTAGTTGCCAGCCATCTGTTGTTTGCCCCTCCCCCGTGCCTTCCTTGACCCTGG

AAGGTGCCACTCCCACTGTCCTTTCCTAATAAAATGAGGAAATTGCATCGCATTGTCTGAGT

AGGTGTCATTCTATTCTGGGGGGTGGGGTGGGCAGGACAGCAAGGGGGAGGATTGGGAAGA

CAATAGCAGGCATGCTGGGGATGCGGTGGGCTCTATGGGTACCCAGGTGCTGAAGAATTGAC

CCGGTTCCTCCTGGGCCAGAAAGAAGCAGGCACATCCCCTTCTCTGTGACACACCCTGTCCA

CGCCCCTGGTTCTTAGTTCCAGCCCCACTCATAGGACACTCATAGCTCAGGAGGGCTCCGCC

TTCAATCCCACCCGCTAAAGTACTTGGAGCGGTCTCTCCCTCCCTCATCAGCCCACCAAACC

AAACCTAGCCTCCAAGAGTGGGAAGAAATTAAAGCAAGATAGGCTATTAAGTGCAGAGGGAG

AGAAAATGCCTCCAACATGTGAGGAAGTAATGAGAGAAATCATAGAATTTCTTCCGCTTCCT

CGCTCACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGCAAAAGG
```

-continued

```
CCAGCAAAAGGCCAGGAACCGTAAAAAGGCCGCGTTGCTGGCGTTTTTCCATAGGCTCCGCC
CCCCTGACGAGCATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGCTCAC
GCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAG
ACACGACTTATCGCCACTGGCAGCAGCCACTGGTAACAGGATTAGCAGAGCGAGGTATGTAG
GCGGTGCTACAGAGTTCTTGAAGTGGTGGCCTAACTACGGCTACACTAGAAGAACAGTATTT
GGTATCTGCGCTCTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTT
AAATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAGTT
GCCTGACTCGGGGGGGGGGGCGCTGAGGTCTGCCTCGTGAAGAAGGTGTTGCTGACTCATA
CCAGGCCTGAATCGCCCCATCATCCAGCCAGAAAGTGAGGGAGCCACGGTTGATGAGAGCTT
TGTTGTAGGTGGACCAGTTGGTGATTTTGAACTTTTGCTTTGCCACGGAACGGTCTGCGTTG
TCGGGAAGATGCGTGATCTGATCCTTCAACTCAGCAAAAGTTCGATTTATTCAACAAAGCCG
CCGTCCCGTCAAGTCAGCGTAATGCTCTGCCAGTGTTACAACCAATTAACCAATTCTGATTA
GAAAAACTCATCGAGCATCAAATGAAACTGCAATTTATTCATATCAGGATTATCAATACCAT
ATTTTTGAAAAAGCCGTTTCTGTAATGAAGGAGAAAACTCACCGAGGCAGTTCCATAGGATG
GCAAGATCCTGGTATCGGTCTGCGATTCCGACTCGTCCAACATCAATACAACCTATTAATTT
CCCCTCGTCAAAAATAAGGTTATCAAGTGAGAAATCACCATGAGTGACGACTGAATCCGGTG
AGAATGGCAAAAGCTTATGCATTTCTTTCCAGACTTGTTCAACAGGCCAGCCATTACGCTCG
TCATCAAAATCACTCGCATCAACCAAACCGTTATTCATTCGTGATTGCGCCTGAGCGAGACG
AAATACGCGATCGCTGTTAAAAGGACAATTACAAACAGGAATCGAATGCAACCGGCGCAGGA
ACACTGCCAGCGCATCAACAATATTTTCACCTGAATCAGGATATTCTTCTAATACCTGGAAT
GCTGTTTTCCCGGGGATCGCAGTGGTGAGTAACCATGCATCATCAGGAGTACGGATAAAATG
CTTGATGGTCGGAAGAGGCATAAATTCCGTCAGCCAGTTTAGTCTGACCATCTCATCTGTAA
CATCATTGGCAACGCTACCTTTGCCATGTTTCAGAAACAACTCTGGCGCATCGGGCTTCCCA
TACAATCGATAGATTGTCGCACCTGATTGCCCGACATTATCGCGAGCCCATTTATACCCATA
TAAATCAGCATCCATGTTGGAATTTAATCGCGGCCTCGAGCAAGACGTTTCCCGTTGAATAT
GGCTCATAACACCCCTTGTATTACTGTTTATGTAAGCAGACAGTTTTATTGTTCATGATGAT
ATATTTTTATCTTGTGCAATGTAACATCAGAGATTTTGAGACACAACGTGGCTTTCCCCCCC
CCCCCATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTGACGTC
TAAGAAACCATTATTATCATGACATTAACCTATAAAAATAGGCGTATCACGAGGCCCTTTCG
TCTCGCGCGTTTCGGTGATGACGGTGAAAACCTCTGACACATGCAGCTCCCGGAGACGGTCA
CAGCTTGTCTGTAAGCGGATGCCGGGAGCAGACAAGCCCGTCAGGGCGCGTCAGCGGGTGTT
GGCGGGTGTCGGGGCTGGCTTAACTATGCGGCATCAGAGCAGATTGTACTGAGAGTGCACCA
TATGCGGTGTGAAATACCGCACAGATGCGTAAGGAGAAAATACCGCATCAGATTGGCTATTG
```

G

SEQ ID NO: 10

- AG205
flanking sequences in lower case; coding sequences underlined
expresses murine IL-27 p28 subunit (under control of hCMV) and
murine IL-27 EBI3 subunit (under control of siCMV)

CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGcgcgcgtcgaggaattcgctagtcgacaagaa<u>ATGGGCCAGGTCACCGGGGACC</u>

<u>TCGGGTGGCGCCTGTCGCTCCTGCTCCTGCCCCTCCTCCTGGTCCAAGCGGGGAGCTGGGGC</u>

<u>TTCCCCACGGATCCCCTGAGCCTCCAGGAGCTGCGCAGGGAGTTCACCGTCAGCCTGTACCT</u>

<u>CGCCCGGAAGCTGCTCTCCGAGGTCCAGGGCTACGTCCACAGCTTCGCCGAGTCGCGCCTGC</u>

<u>CCGGCGTGAACCTGGACCTCCTGCCCCTGGGCTACCACCTCCCCAACGTCTCCCTGACGTTC</u>

<u>CAAGCCTGGCACCACCTCTCCGACTCCGAGCGCCTCTGCTTCCTCGCCACCACGCTCCGGCC</u>

<u>GTTCCCGGCCATGCTGGGCGGGCTGGGGACCCAGGGGACCTGGACCAGCTCCGAGAGGGAGC</u>

<u>AGCTGTGGGCCATGAGGCTGGACCTCCGGGACCTGCACAGGCACCTCCGCTTCCAAGTCCTG</u>

<u>GCCGCGGGCTTCAAGTGCTCCAAGGAGGAGGAGGACAAGGAGGAAGAGGAAGAGGAGGAAGA</u>

<u>AGAGGAAAAGAAGCTGCCCCTCGGGGCCCTGGGCGGCCCCAACCAGGTGTCCTCCCAAGTGT</u>

<u>CCTGGCCCCAGCTGCTCTACACCTACCAGCTCCTCCACTCCCTGGAGCTGGTCCTGAGCCGG</u>

<u>GCGGTGCGGGACCTGCTCCTGCTGTCCCTGCCCCGGCGCCCGGGCTCGGCCTGGGACTCCTA</u>

<u>ATGA</u>tctagaagatctgatatcggatctGCTGTGCCTTCTAGTTGCCAGCCATCTGTTGTTT

GCCCCTCCCCCGTGCCTTCCTTGACCCTGGAAGGTGCCACTCCCACTGTCCTTTCCTAATAA

AATGAGGAAATTGCATCGCATTGTCTGAGTAGGTGTCATTCTATTCTGGGGGGTGGGGTGGG

GCAGGACAGCAAGGGGGAGGATTGGGAAGACAATAGCAGGCATGCTGGGGATGCGGTGGGCT

CTATGGGTACCCAGGTGCTGAAGAATTGACCCGGTTCCTCCTGGGCCAGAAAGAAGCAGGCA

CATCCCCTTCTCTGTGACACACCCTGTCCACGCCCCTGGTTCTTAGTTCCAGCCCCACTCAT

AGGACACTCATAGCTCAGGAGGGCTCCGCCTTCAATCCCACCCGCTAAAGTACTTGGAGCGG

TCTCTCCCTCCCTCATCAGCCCACCAAACCAAACCTAGCCTCCAAGAGTGGGAAGAAATTAA

AGCAAGATAGGCTATTAAGTGCAGAGGGAGAGAAAATGCCTCCAACATGTGAGGAAGTAATG

AGAGAAATCATAGAATTTCTTCCGCTTCCTCGCTCACTGACTCGCTGCGCTCGGTCGTTCGG

CTGCGGCGAGCGGTATCAGCTCACTCAAAGGCGGTAATACGGTTATCCACAGAATCAGGGGA

TAACGCAGGAAAGAACATGTGAGCAAAAGGCCAGCAAAAGGCCAGGAACCGTAAAAAGGCCG

CGTTGCTGGCGTTTTTCCATAGGCTCCGCCCCCCTGACGAGCATCACAAAAATCGACGCTCA

```
AGTCAGAGGTGGCGAAACCCGACAGGACTATAAAGATACCAGGCGTTTCCCCCTGGAAGCTC

CCTCGTGCGCTCTCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCCTTATCCGG

TAACTATCGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGTGGTGGCCT

AACTACGGCTACACTAGAAGAACAGTATTTGGTATCTGCGCTCTGCTGAAGCCAGTTACCTT

CGGAAAAAGAGTTGGTAGCTCTTGATCCGGCAAACAAACCACCGCTGGTAGCGGTGGTTTTT

TTGTTTGCAAGCAGCAGATTACGCGCAGAAAAAAAGGATCTCAAGAAGATCCTTTGATCTTT

TCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCTCA

GCGATCTGTCTATTTCGTTCATCCATAGTTGCCTGACTCGGGGGGGGGGGCGCTGAGGTCT

GCCTCGTGAAGAAGGTGTTGCTGACTCATACCAGGCCTGAATCGCCCCATCATCCAGCCAGA

AAGTGAGGGAGCCACGGTTGATGAGAGCTTTGTTGTAGGTGGACCAGTTGGTGATTTTGAAC

TTTTGCTTTGCCACGGAACGGTCTGCGTTGTCGGGAAGATGCGTGATCTGATCCTTCAACTC

AGCAAAAGTTCGATTTATTCAACAAAGCCGCCGTCCCGTCAAGTCAGCGTAATGCTCTGCCA

GTGTTACAACCAATTAACCAATTCTGATTAGAAAAACTCATCGAGCATCAAATGAAACTGCA

ATTTATTCATATCAGGATTATCAATACCATATTTTTGAAAAAGCCGTTTCTGTAATGAAGGA

GAAAACTCACCGAGGCAGTTCCATAGGATGGCAAGATCCTGGTATCGGTCTGCGATTCCGAC

TCGTCCAACATCAATACAACCTATTAATTTCCCCTCGTCAAAAATAAGGTTATCAAGTGAGA

AATCACCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAACCGTT

ATTCATTCGTGATTGCGCCTGAGCGAGACGAAATACGCGATCGCTGTTAAAAGGACAATTAC

AAACAGGAATCGAATGCAACCGGCGCAGGAACACTGCCAGCGCATCAACAATATTTTCACCT

GAATCAGGATATTCTTCTAATACCTGGAATGCTGTTTTCCCGGGGATCGCAGTGGTGAGTAA

CCATGCATCATCAGGAGTACGGATAAAATGCTTGATGGTCGGAAGAGGCATAAATTCCGTCA

GCCAGTTTAGTCTGACCATCTCATCTGTAACATCATTGGCAACGCTACCTTTGCCATGTTTC

AGAAACAACTCTGGCGCATCGGGCTTCCCATACAATCGATAGATTGTCGCACCTGATTGCCC

GACATTATCGCGAGCCCATTTATACCCATATAAATCAGCATCCATGTTGGAATTTAATCGCG

GCCTCGAGCAAGACGTTTCCCGTTGAATATGGCTCATAACACCCCTTGTATTACTGTTTATG

TAAGCAGACAGTTTTATTGTTCATGATGATATATTTTTATCTTGTGCAATGTAACATCAGAG

ATTTTGAGACACAACGTGGATCATCCAGACATGATAAGATACATTGATGAGTTTGGACAAAC

CACAACTAGAATGCAGTGAAAAAAATGCTTTATTTGTGAAATTTGTGATGCTATTGCTTTAT

TTGTAACCATTATAAGCTGCAATAAACAAGTTAACAACAACAATTGCATTCATTTTATGTTT

CAGGTTCAGGGGGAGGTGTGGGAGGTTTTTTAAAGCAAGTAAAACCTCTACAAATGTGGTAT

GGCTGATTATGATCgtcgaggatccgttaaccgatatccgcgaattcTCATTAGGGCTTGTG

GGGAGCGCTCTCGACCTGCCCCGGGAGGCTCCAGTCGCTGGGCTTCCCGTAGTCGGTGAGGT

CCTGCGCCGACACCTGGATGCAGTACTTGGCGTGGGGCTTCGAGTTCCGGAGGGTGAAGGTC

GTGGCCTCGATGGGGCCGACTTGGCGGAAGTGGGAGGCGCCTCGGCGCCGGTAGCGGAGGCG
```

-continued

<u>GTACTTGAGCGAGAAGATGTCCGGGAAGGGCCAGGAGGCCGGGGGGTGCCAGAGCACCTGCA</u>

<u>GGCGCTGGCCCGCCGTGCGCAGGCGCACGCCCTCCGGCGGGTCCGGCTTGATGATCCGCTCC</u>

<u>GCCACGAAGGCCAGGAGGCTGCTGCTGGCGCCGCCCGGGTGCACCGCCGTGACGTTGAGCAT</u>

<u>GTAGGGCACCGTGGAGAACAGGTGCACGTCGGGGATGGTGCAGCGGGAGGCCTGGGGGCTCC</u>

<u>GCTGCAGGCAGGGCTGGCTCTGCTGCTGGGTGGCCACGCCGAGCCGGTACGTGGCGATGAAG</u>

<u>GACGTGGACCTGGTGGAGTTGGGCGCTTGCAGCGGGGTCCAGGAGCAGTCCACGGCCACGGG</u>

<u>GTAGCGCGAGGCGTGGCACTGCACCCGGGGCTGGCTCAGGGCCACGAGCGCCGTCTCGGTAT</u>

<u>ACCCCGGCGAGCGGCTGGCCCAGAGCGCCAGGCTCAGGAACAGGAGCTTCGACAT</u>ttcttca caaacgtcgacagatccAAACGCTCCTCCGACGTCCCCAGGCAGAATGGCGGTTCCCTAAAC

GAGCATTGCTTATATAGACCTCCCATTAGGCACGCCTACCGCCCATTTACGTCAATGGAACG

CCCATTTGCGTCATTGCCCCTCCCCATTGACGTCAATGGGGATGTACTTGGCAGCCATCGCG

GGCCATTTACCGCCATTGACGTCAATGGGAGTACTGCCAATGTACCCTGGCGTACTTCCAAT

AGTAATGTACTTGCCAAGTTACTATTAATAGATATTGATGTACTGCCAAGTGGGCCATTTAC

CGTCATTGACGTCAATAGGGGCGTGAGAACGGATATGAATGGGCAATGAGCCATCCTAAAG

ACCATGAGGCCCTTTCGTCTCGCGCGTTTCGGTGATGACGGTGAAAACCTCTGACACATGCA

GCTCCCGGAGACGGTCACAGCTTGTCTGTAAGCGGATGCCGGGAGCAGACAAGCCCGTCAGG

GCGCGTCAGCGGGTGTTGGCGGGTGTCGGGCTGGCTTAACTATGCGGCATCAGAGCAGATT

GTACTGAGAGTGCACCATATGCGGTGTGAAATACCGCACAGATGCGTAAGGAGAAAATACCG

CATCAGATTGGCTATTGG

SEQ ID NO: 11
- AG197
flanking sequences in lower case; coding sequences underlined
expresses murine IL-27 EBI3 subunit (under control of hCMV)
and murine IL-27 p28 subunit (under control of siCMV)
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGcacgtgaagaa<u>ATGTCGAAGCTCCTGTTCCTGAGCCTGGCGCTCTGGGCCAGCCG</u>

<u>CTCGCCGGGGTATACCGAGACGGCGCTCGTGGCCCTGAGCCAGCCCCGGGTGCAGTGCCACG</u>

<u>CCTCGCGCTACCCCGTGGCCGTGGACTGCTCCTGGACCCCGCTGCAAGCGCCCAACTCCACC</u>

<u>AGGTCCACGTCCTTCATCGCCACGTACCGGCTCGGCGTGGCCACCCAGCAGCAGAGCCAGCC</u>

<u>CTGCCTGCAGCGGAGCCCCCAGGCCTCCCGCTGCACCATCCCCGACGTGCACCTGTTCTCCA</u>

<u>CGGTGCCCTACATGCTCAACGTCACGGCGGTGCACCCGGGCGGCGCCAGCAGCAGCCTCCTG</u>

<u>GCCTTCGTGGCGGAGCGGATCATCAAGCCGGACCCGCCGGAGGGCGTGCGCCTGCGCACGGC</u>

-continued

<u>GGGCCAGCGCCTGCAGGTGCTCTGGCACCCCCGGCCTCCTGGCCCTTCCCGGACATCTTCT</u>

<u>CGCTCAAGTACCGCCTCCGCTACCGGCGCCGAGGCGCCTCCCACTTCCGCCAAGTCGGCCCC</u>

<u>ATCGAGGCCACGACCTTCACCCTCCGGAACTCGAAGCCCCACGCCAAGTACTGCATCCAGGT</u>

<u>GTCGGCGCAGGACCTCACCGACTACGGGAAGCCCAGCGACTGGAGCCTCCCGGGGCAGGTCG</u>

<u>AGAGCGCTCCCCACAAGCCCTAATGA</u>ggaattcgctagaggcgcgccagatctgatatcgga tctGCTGTGCCTTCTAGTTGCCAGCCATCTGTTGTTTGCCCCTCCCCCGTGCCTTCCTTGAC

CCTGGAAGGTGCCACTCCCACTGTCCTTTCCTAATAAAATGAGGAAATTGCATCGCATTGTC

TGAGTAGGTGTCATTCTATTCTGGGGGGTGGGGTGGGGCAGGACAGCAAGGGGGAGGATTGG

GAAGACAATAGCAGGCATGCTGGGGATGCGGTGGGCTCTATGGGTACCCAGGTGCTGAAGAA

TTGACCCGGTTCCTCCTGGGCCAGAAAGAAGCAGGCACATCCCCTTCTCTGTGACACACCCT

GTCCACGCCCCTGGTTCTTAGTTCCAGCCCCACTCATAGGACACTCATAGCTCAGGAGGGCT

CCGCCTTCAATCCCACCCGCTAAAGTACTTGGAGCGGTCTCTCCCTCCCTCATCAGCCCACC

AAACCAAACCTAGCCTCCAAGAGTGGGAAGAAATTAAAGCAAGATAGGCTATTAAGTGCAGA

GGGAGAGAAAATGCCTCCAACATGTGAGGAAGTAATGAGAGAAATCATAGAATTTCTTCCGC

TTCCTCGCTCACTGACTCGCTGCGCTCGGTCGTTCGGCTGCGGCGAGCGGTATCAGCTCACT

CAAAGGCGGTAATACGGTTATCCACAGAATCAGGGGATAACGCAGGAAAGAACATGTGAGCA

AAAGGCCAGCAAAAGGCCAGGAACCGTAAAAAGGCCGCGTTGCTGGCGTTTTTCCATAGGCT

CCGCCCCCCTGACGAGCATCACAAAAATCGACGCTCAAGTCAGAGGTGGCGAAACCCGACAG

GACTATAAAGATACCAGGCGTTTCCCCCTGGAAGCTCCCTCGTGCGCTCTCCTGTTCCGACC

CTGCCGCTTACCGGATACCTGTCCGCCTTTCTCCCTTCGGGAAGCGTGGCGCTTTCTCATAG

CTCACGCTGTAGGTATCTCAGTTCGGTGTAGGTCGTTCGCTCCAAGCTGGGCTGTGTGCACG

AACCCCCCGTTCAGCCCGACCGCTGCGCCTTATCCGGTAACTATCGTCTTGAGTCCAACCCG

GTAAGACACGACTTATCGCCACTGGCAGCAGCCACTGGTAACAGGATTAGCAGAGCGAGGTA

TGTAGGCGGTGCTACAGAGTTCTTGAAGTGGTGGCCTAACTACGGCTACACTAGAAGAACAG

TATTTGGTATCTGCGCTCTGCTGAAGCCAGTTACCTTCGGAAAAAGAGTTGGTAGCTCTTGA

TCCGGCAAACAAACCACCGCTGGTAGCGGTGGTTTTTTTGTTTGCAAGCAGCAGATTACGCG

CAGAAAAAAAGGATCTCAAGAAGATCCTTTGATCTTTTCTACGGGGTCTGACGCTCAGTGGA

ACGAAAACTCACGTTAAGGGATTTTGGTCATGAGATTATCAAAAAGGATCTTCACCTAGATC

CTTTTAAATTAAAAATGAAGTTTTAAATCAATCTAAAGTATATATGAGTAAACTTGGTCTGA

CAGTTACCAATGCTTAATCAGTGAGGCACCTATCTCAGCGATCTGTCTATTTCGTTCATCCA

TAGTTGCCTGACTCGGGGGGGGGGGCGCTGAGGTCTGCCTCGTGAAGAAGGTGTTGCTGAC

TCATACCAGGCCTGAATCGCCCCATCATCCAGCCAGAAAGTGAGGGAGCCACGGTTGATGAG

AGCTTTGTTGTAGGTGGACCAGTTGGTGATTTTGAACTTTTGCTTTGCCACGGAACGGTCTG

CGTTGTCGGGAAGATGCGTGATCTGATCCTTCAACTCAGCAAAAGTTCGATTTATTCAACAA

AGCCGCCGTCCCGTCAAGTCAGCGTAATGCTCTGCCAGTGTTACAACCAATTAACCAATTCT

GATTAGAAAAACTCATCGAGCATCAAATGAAACTGCAATTTATTCATATCAGGATTATCAAT

ACCATATTTTTGAAAAAGCCGTTTCTGTAATGAAGGAGAAAACTCACCGAGGCAGTTCCATA

GGATGGCAAGATCCTGGTATCGGTCTGCGATTCCGACTCGTCCAACATCAATACAACCTATT

AATTTCCCCTCGTCAAAAATAAGGTTATCAAGTGAGAAATCACCATGAGTGACGACTGAATC

CGGTGAGAATGGCAAAAGCTTATGCATTTCTTTCCAGACTTGTTCAACAGGCCAGCCATTAC

GCTCGTCATCAAAATCACTCGCATCAACCAAACCGTTATTCATTCGTGATTGCGCCTGAGCG

```
AGACGAAATACGCGATCGCTGTTAAAAGGACAATTACAAACAGGAATCGAATGCAACCGGCG
CAGGAACACTGCCAGCGCATCAACAATATTTTCACCTGAATCAGGATATTCTTCTAATACCT
GGAATGCTGTTTTCCCGGGGATCGCAGTGGTGAGTAACCATGCATCATCAGGAGTACGGATA
AAATGCTTGATGGTCGGAAGAGGCATAAATTCCGTCAGCCAGTTTAGTCTGACCATCTCATC
TGTAACATCATTGGCAACGCTACCTTTGCCATGTTTCAGAAACAACTCTGGCGCATCGGGCT
TCCCATACAATCGATAGATTGTCGCACCTGATTGCCCGACATTATCGCGAGCCCATTTATAC
CCATATAAATCAGCATCCATGTTGGAATTTAATCGCGGCCTCGAGCAAGACGTTTCCCGTTG
AATATGGCTCATAACACCCCTTGTATTACTGTTTATGTAAGCAGACAGTTTTATTGTTCATG
ATGATATATTTTTATCTTGTGCAATGTAACATCAGAGATTTTGAGACACAACGTGGATCATC
CAGACATGATAAGATACATTGATGAGTTTGGACAAACCACAACTAGAATGCAGTGAAAAAAA
TGCTTTATTTGTGAAATTTGTGATGCTATTGCTTTATTTGTAACCATTATAAGCTGCAATAA
ACAAGTTAACAACAACAATTGCATTCATTTTATGTTTCAGGTTCAGGGGAGGTGTGGGAGG
TTTTTTAAAGCAAGTAAAACCTCTACAAATGTGGTATGGCTGATTATGATCgtcgaggatct
gtttaaactctagaTCATTAGGAGTCCCAGGCCGAGCCCGGGCGCCGGGGCAGGGACAGCAG
GAGCAGGTCCCGCACCGCCCGGCTCAGGACcAGCTCCAGGGAGTGGAGGAGCTGGTAGGTGT
AGAGCAGCTGGGGCCAGGACACTTGGGAGGACACCTGGTTGGGGCCGCCCAGGGCCCCGAGG
GGCAGCTTCTTTTCCTCTTCTTCCTCCTCTTCCTCTTCCTCCTTGTCCTCCTCCTCCTTGGA
GCACTTGAAGCCCGCGGCCAGGACTTGGAAGCGGAGGTGCCTGTGCAGGTCCCGGAGGTCCA
GCCTCATGGCCCACAGCTGCTCCCTCTCGGAGCTGGTCCAGGTCCCCTGGGTCCCCAGCCCG
CCCAGCATGGCCGGGAACGGCCGGAGCGTGGTGGCGAGGAAGCAGAGGCGCTCGGAGTCGGA
GAGGTGGTGCCAGGCTTGGAACGTCAGGGAGACGTTGGGGAGGTGGTAGCCCAGGGGCAGGA
GGTCCAGGTTCACGCCGGGCAGGCGCGACTCGGCGAAGCTGTGGACGTAGCCCTGGACCTCG
GAGAGCAGCTTCCGGGCGAGGTACAGGCTGACGGTGAACTCCCTGCGCAGCTCCTGGAGGCT
CAGGGGaTCcGTGGGGAAGCCCCAGCTCCCCGCTTGGACCAGGAGGAGGGGCAGGAGCAGGA
GCGACAGGCGCCACCCGAGGTCCCCGGTGACCTGGCCCATttcttgtcgacagatccAAACG
CTCCTCCGACGTCCCCAGGCAGAATGGCGGTTCCCTAAACGAGCATTGCTTATATAGACCTC
CCATTAGGCACGCCTACCGCCCATTTACGTCAATGGAACGCCCATTTGCGTCATTGCCCCTC
CCCATTGACGTCAATGGGGATGTACTTGGCAGCCATCGCGGGCCATTTACCGCCATTGACGT
CAATGGGAGTACTGCCAATGTACCCTGGCGTACTTCCAATAGTAATGTACTTGCCAAGTTAC
TATTAATAGATATTGATGTACTGCCAAGTGGGCCATTTACCGTCATTGACGTCAATAGGGGG
CGTGAGAACGGATATGAATGGGCAATGAGCCATCCCATTGACGTCAATGGTGGGTGGTCCTA
TTGACGTCAATGGGCATTGAGCCAGGCGGGCCATTTACCGTAATTGACGTCAATGGGGGAGG
CGCCATATACGTCAATAGGACCGCCCATATGACGTCAATAGGTAAGACCATGAGGCCCTTTC
GTCTCGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCGGGTGT
TGGCGGGTGTCGGGGCTGGCTTAACTATGCGGCATCAGAGCAGATTGTACTGAGAGTGCACC
ATATGCGGTGTGAAATACCGCACAGATGCGTAAGGAGAAAATACCGCATCAGATTGGCTATT
GGCATTATGCC
```

SEQ ID NO: 12
- AG214
flanking sequences in lower case; coding sequences underlined
expresses human IL-27 EBI3

-continued

```
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGaagaaATGACGCCGCAGCTGCTTCTGGCTCTGGTCCTCTGGGCCAGCTGCCCTC

CGTGCAGCGGACGCAAGGGTCCTCCAGCTGCCCTGACCCTGCCCAGAGTGCAGTGCAGAGCC

TCGCGCTACCCCATCGCTGTGGACTGCTCCTGGACCCTTCCACCTGCACCCAACTCCACCTC

CCCTGTCTCCTTCATCGCCACGTACCGGCTCGGCATGGCCGCTAGGGGTCACAGCTGGCCCT

GCCTGCAGCAGACGCCCACATCTACTTCCTGCACCATCACTGACGTGCAGCTGTTCTCCATG

GCTCCCTACGTCCTCAACGTCACGGCGGTGCACCCGTGGGGCTCTTCAAGCAGCTTCGTCCC

TTTCATCACTGAGCACATCATCAAGCCGGACCCACCGGAGGGAGTGCGCCTGTCTCCTCTCG

CGGAGCGCCAGCTGCAGGTGCAGTGGGAGCCCCCAGGTTCCTGGCCCTTCCCGGAGATCTTC

TCGCTCAAGTACTGGATCAGATACAAGCGCCAGGGCGCCGCTAGATTCCACAGAGTCGGCCC

CATCGAGGCCACGTCTTTCATCCTCCGAGCGGTCCGACCCAGAGCCCGATACTACGTGCAGG

TGGCTGCGCAGGACCTCACCGACTACGGGGAGCTTAGCGACTGGAGCCTCCCGGCTACAGCA

ACTATGAGTTTGGGAAAGTAATGAgaattcgcggatatcggttaacggatccaGATCTGCTG

TGCCTTCTAGTTGCCAGCCATCTGTTGTTTGCCCCTCCCCCGTGCCTTCCTTGACCCTGGAA

GGTGCCACTCCCACTGTCCTTTCCTAATAAAATGAGGAAATTGCATCGCATTGTCTGAGTAG

GTGTCATTCTATTCTGGGGGGTGGGGTGGGGCAGGACAGCAAGGGGGAGGATTGGGAAGACA

ATAGCAGGCATGCTGGGGATGCGGTGGGCTCTATGGGTACCCAGGTGCTGAAGAATTGACCC

GGTTCCTCCTGGGCCAGAAAGAAGCAGGCACATCCCCTTCTCTGTGACACACCCTGTCCACG

CCCCTGGTTCTTAGTTCCAGCCCCACTCATAGGACACTCATAGCTCAGGAGGGCTCCGCCTT

CAATCCCACCCGCTAAAGTACTTGGAGCGGTCTCTCCCTCCCTCATCAGCCCACCAAACCAA

ACCTAGCCTCCAAGAGTGGGAAGAAATTAAAGCAAGATAGGCTATTAAGTGCAGAGGGAGAG

AAAATGCCTCCAACATGTGAGGAAGTAATGAGAGAAATCATAGAATTTCTTCCGCTTCCTCG

CTCACTGACTCGCTGCGCTCGGTCGTTCGGCTGCGGCGAGCGGTATCAGCTCACTCAAAGGC

GGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCC

CCTGACGAGCATCACAAAAATCGACGCTCAAGTCAGAGGTGGCGAAACCCGACAGGACTATA

AAGATACCAGGCGTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCTCATAGCTCACGC

TGTAGGTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGTAAGAC
```

ACGACTTATCGCCACTGGCAGCAGCCACTGGTAACAGGATTAGCAGAGCGAGGTATGTAGGC

GGTGCTACAGAGTTCTTGAAGTGGTGGCCTAACTACGGCTACACTAGAAGGACAGTATTTGG

TATCTGCGCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGAACGAAAA

CTCACGTTAAGGGATTTTGGTCATGAGATTATCAAAAAGGATCTTCACCTAGATCCTTTTAA

ATTAAAAATGAAGTTTTAAATCAATCTAAAGTATATATGAGTAAACTTGGTCTGACAGTTAC

CAATGCTTAATCAGTGAGGCACCTATCTCAGCGATCTGTCTATTTCGTTCATCCATAGTTGC

CTGACTCGGGGGGGGGGGCGCTGAGGTCTGCCTCGTGAAGAAGGTGTTGCTGACTCATACC

AGGCCTGAATCGCCCCATCATCCAGCCAGAAAGTGAGGGAGCCACGGTTGATGAGAGCTTTG

TTGTAGGTGGACCAGTTGGTGATTTTGAACTTTTGCTTTGCCACGGAACGGTCTGCGTTGTC

GGGAAGATGCGTGATCTGATCCTTCAACTCAGCAAAAGTTCGATTTATTCAACAAAGCCGCC

GTCCCGTCAAGTCAGCGTAATGCTCTGCCAGTGTTACAACCAATTAACCAATTCTGATTAGA

AAAACTCATCGAGCATCAAATGAAACTGCAATTTATTCATATCAGGATTATCAATACCATAT

TTTTGAAAAAGCCGTTTCTGTAATGAAGGAGAAAACTCACCGAGGCAGTTCCATAGGATGGC

AAGATCCTGGTATCGGTCTGCGATTCCGACTCGTCCAACATCAATACAACCTATTAATTTCC

CCTCGTCAAAAATAAGGTTATCAAGTGAGAAATCACCATGAGTGACGACTGAATCCGGTGAG

AATGGCAAAAGCTTATGCATTTCTTTCCAGACTTGTTCAACAGGCCAGCCATTACGCTCGTC

ATCAAAATCACTCGCATCAACCAAACCGTTATTCATTCGTGATTGCGCCTGAGCGAGACGAA

ATACGCGATCGCTGTTAAAAGGACAATTACAAACAGGAATCGAATGCAACCGGCGCAGGAAC

ACTGCCAGCGCATCAACAATATTTTCACCTGAATCAGGATATTCTTCTAATACCTGGAATGC

TGTTTTCCCGGGGATCGCAGTGGTGAGTAACCATGCATCATCAGGAGTACGGATAAAATGCT

TGATGGTCGGAAGAGGCATAAATTCCGTCAGCCAGTTTAGTCTGACCATCTCATCTGTAACA

TCATTGGCAACGCTACCTTTGCCATGTTTCAGAAACAACTCTGGCGCATCGGGCTTCCCATA

CAATCGATAGATTGTCGCACCTGATTGCCCGACATTATCGCGAGCCCATTTATACCCATATA

AATCAGCATCCATGTTGGAATTTAATCGCGGCCTCGAGCAAGACGTTTCCCGTTGAATATGG

CTCATAACACCCCTTGTATTACTGTTTATGTAAGCAGACAGTTTTATTGTTCATGATGATAT

ATTTTTATCTTGTGCAATGTAACATCAGAGATTTTGAGACACAACGTGGCTTTCCCCCCCCC

CCCATTATTGAAGCATTTATCAGGGTTATTGTCTCATGAGCGGATACATATTTGAATGTATT

TAGAAAAATAAACAAATAGGGGTTCCGCGCACATTTCCCCGAAAAGTGCCACCTGACGTCTA

AGAAACCATTATTATCATGACATTAACCTATAAAAATAGGCGTATCACGAGGCCCTTTCGTC

TCGCGCGTTTCGGTGATGACGGTGAAAACCTCTGACACATGCAGCTCCCGGAGACGGTCACA

GCTTGTCTGTAAGCGGATGCCGGGAGCAGACAAGCCCGTCAGGGCGCGTCAGCGGGTGTTGG

CGGGTGTCGGGGCTGGCTTAACTATGCGGCATCAGAGCAGATTGTACTGAGAGTGCACCATA

TGCGGTGTGAAATACCGCACAGATGCGTAAGGAGAAAATACCGCATCAGATTGGCTATTGG

SEQ ID NO: 13
- AG215
flanking sequences in lower case; coding sequences underlined
expresses human IL-27 p28
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

-continued

```
GCTGACCGCCCAACGACCCCCGCCCATTGACGTCAATAATGACGTATGTTCCCATAGTAACG
CCAATAGGGACTTTCCATTGACGTCAATGGGTGGAGTATTTACGGTAAACTGCCCACTTGGC
AGTACATCAAGTGTATCATATGCCAAGTACGCCCCCTATTGACGTCAATGATGGTAAATGGC
CCGCCTGGCATTATGCCCAGTACATGACCTTATGGGACTTTCCTACTTGGCAGTACATCTAC
GTATTAGTCATCGCTATTACCATGGTGATGCGGTTTTGGCAGTACATCAATGGGCGTGGATA
GCGGTTTGACTCACGGGGATTTCCAAGTCTCCACCCCATTGACGTCAATGGGAGTTTGTTTT
GGCACCAAAATCAACGGGACTTTCCAAAATGTCGTAACAACTCCGCCCCATTGACGCAAATG
GGCGGTAGGCGTGTACGGTGGGAGGTCTATATAAGCAGAGCTCGTTTAGTGAACCGTCAGAT
CGCCTGGAGACGCCATCCACGCTGTTTTGACCTCCATAGAAGACACCGGGACCGATCCAGCC
TCCGCGGGcgcgcgtcgacaagaaATGGGCCAGACGGCGGGGGACCTCGGGTGGCGCCTGTC
GCTTCTGCTACTGCCCCTACTTCTGGTCCAAGCGGGAGTCTGGGGCTTCCCACGTCCACCCG
GCAGACCGCAGCTGAGCCTCCAGGAGCTTCGCAGGGAGTTCACCGTCAGCCTGCACCTCGCC
CGGAAGCTGTTGTCCGAAGTCAGAGGCCAGGCGCACCGGTTCGCCGAGTCGCACCTTCCAGG
CGTGAACCTGTACCTCTTGCCCCTTGGCGAGCAGCTCCCCGACGTCTCCCTGACGTTCCAAG
CCTGGCGACGGCTCTCCGACCCGGAGCGCCTCTGCTTCATCTCGACCACGCTCCAGCCGTTC
CACGCCCTCCTTGGCGGGTTGGGGACCCAGGGGAGGTGGACCAACATGGAGAGGATGCAGCT
GTGGGCCATGAGGCTTGACCTCCGGGACCTGCAGAGGCACCTCCGCTTCCAAGTCCTTGCCG
CTGGCTTCAACCTCCCTGAGGAGGAGGAAGAAGAGGAAGAAGAGGAAGAGGAGGAACGGAAG
GGGCTGCTCCCAGGTGCCCTGGGCTCGGCGCTGCAGGGACCGGCACAGGTGTCTTGGCCCCA
GCTGCTCTCGACCTACCGGCTCCTTCACTCCCTGGAGCTGGTCCTGAGCCGGGCGGTGCGGG
AGCTGCTTCTGTTGTCCAAAGCGGGCCACTCGGTCTGGCCGCTTGGATTCCCCACCCTCTCG
CCCCAGCCGTAATGAggatccaGATCTGCTGTGCCTTCTAGTTGCCAGCCATCTGTTGTTTG
CCCCTCCCCCGTGCCTTCCTTGACCCTGGAAGGTGCCACTCCCACTGTCCTTTCCTAATAAA
ATGAGGAAATTGCATCGCATTGTCTGAGTAGGTGTCATTCTATTCTGGGGGGTGGGGTGGGG
CAGGACAGCAAGGGGGAGGATTGGGAAGACAATAGCAGGCATGCTGGGGATGCGGTGGGCTC
TATGGGTACCCAGGTGCTGAAGAATTGACCCGGTTCCTCCTGGGCCAGAAAGAAGCAGGCAC
ATCCCCTTCTCTGTGACACACCCTGTCCACGCCCCTGGTTCTTAGTTCCAGCCCCACTCATA
GGACACTCATAGCTCAGGAGGGCTCCGCCTTCAATCCCACCCGCTAAAGTACTTGGAGCGGT
CTCTCCCTCCCTCATCAGCCCACCAAACCAAACCTAGCCTCCAAGAGTGGGAAGAAATTAAA
GCAAGATAGGCTATTAAGTGCAGAGGGAGAGAAAATGCCTCCAACATGTGAGGAAGTAATGA
GAGAAATCATAGAATTTCTTCCGCTTCCTCGCTCACTGACTCGCTGCGCTCGGTCGTTCGGC
TGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAAATCGACGCTCAA
GTCAGAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGCGCCTTATCCGGT
AACTATCGTCTTGAGTCCAACCCGGTAAGACACGACTTATCGCCACTGGCAGCAGCCACTGG
TAACAGGATTAGCAGAGCGAGGTATGTAGGCGGTGCTACAGAGTTCTTGAAGTGGTGGCCTA
ACTACGGCTACACTAGAAGAACAGTATTTGGTATCTGCGCTCTGCTGAAGCCAGTTACCTTC
```

```
GGAAAAAGAGTTGGTAGCTCTTGATCCGGCAAACAAACCACCGCTGGTAGCGGTGGTTTTTT

TGTTTGCAAGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCATGAGATTA

TCAAAAGGATCTTCACCTAGATCCTTTTAAATTAAAAATGAAGTTTTAAATCAATCTAAAG

TATATATGAGTAAACTTGGTCTGACAGTTACCAATGCTTAATCAGTGAGGCACCTATCTCAG

CGATCTGTCTATTTCGTTCATCCATAGTTGCCTGACTCGGGGGGGGGGGCGCTGAGGTCTG

CCTCGTGAAGAAGGTGTTGCTGACTCATACCAGGCCTGAATCGCCCCATCATCCAGCCAGAA

AGTGAGGGAGCCACGGTTGATGAGAGCTTTGTTGTAGGTGGACCAGTTGGTGATTTTGAACT

TTTGCTTTGCCACGGAACGGTCTGCGTTGTCGGGAAGATGCGTGATCTGATCCTTCAACTCA

GCAAAAGTTCGATTTATTCAACAAAGCCGCCGTCCCGTCAAGTCAGCGTAATGCTCTGCCAG

TGTTACAACCAATTAACCAATTCTGATTAGAAAAACTCATCGAGCATCAAATGAAACTGCAA

TTTATTCATATCAGGATTATCAATACCATATTTTTGAAAAAGCCGTTTCTGTAATGAAGGAG

AAAACTCACCGAGGCAGTTCCATAGGATGGCAAGATCCTGGTATCGGTCTGCGATTCCGACT

CGTCCAACATCAATACAACCTATTAATTTCCCCTCGTCAAAAATAAGGTTATCAAGTGAGAA

ATCACCATGAGTGACGACTGAATCCGGTGAGAATGGCAAAAGCTTATGCATTTCTTTCCAGA

CTTGTTCAACAGGCCAGCCATTACGCTCGTCATCAAAATCACTCGCATCAACCAAACCGTTA

TTCATTCGTGATTGCGCCTGAGCGAGACGAAATACGCGATCGCTGTTAAAAGGACAATTACA

AACAGGAATCGAATGCAACCGGCGCAGGAACACTGCCAGCGCATCAACAATATTTTCACCTG

AATCAGGATATTCTTCTAATACCTGGAATGCTGTTTTCCCGGGGATCGCAGTGGTGAGTAAC

CATGCATCATCAGGAGTACGGATAAAATGCTTGATGGTCGGAAGAGGCATAAATTCCGTCAG

CCAGTTTAGTCTGACCATCTCATCTGTAACATCATTGGCAACGCTACCTTTGCCATGTTTCA

GAAACAACTCTGGCGCATCGGGCTTCCCATACAATCGATAGATTGTCGCACCTGATTGCCCG

ACATTATCGCGAGCCCATTTATACCCATATAAATCAGCATCCATGTTGGAATTTAATCGCGG

CCTCGAGCAAGACGTTTCCCGTTGAATATGGCTCATAACACCCCTTGTATTACTGTTTATGT

AAGCAGACAGTTTTATTGTTCATGATGATATATTTTTATCTTGTGCAATGTAACATCAGAGA

TTTTGAGACACAACGTGGCTTTCCCCCCCCCCCCATTATTGAAGCATTTATCAGGGTTATTG

TCTCATGAGCGGATACATATTTGAATGTATTTAGAAAAATAAACAAATAGGGGTTCCGCGCA

CATTTCCCCGAAAAGTGCCACCTGACGTCTAAGAAACCATTATTATCATGACATTAACCTAT

AAAAATAGGCGTATCACGAGGCCCTTTCGTCTCGCGCGTTTCGGTGATGACGGTGAAAACCT

CTGACACATGCAGCTCCCGGAGACGGTCACAGCTTGTCTGTAAGCGGATGCCGGGAGCAGAC

AAGCCCGTCAGGGCGCGTCAGCGGGTGTTGGCGGGTGTCGGGGCTGGCTTAACTATGCGGCA

TCAGAGCAGATTGTACTGAGAGTGCACCATATGCGGTGTGAAATACCGCACAGATGCGTAAG

GAGAAAATACCGCATCAGATTGGCTATTGG
```

SEQ ID NO: 14
- AG216
flanking sequences in lower case; coding sequences underlined
expresses human IL-27 p28 subunit (under control of hCMV) and
human IL-27 EBI3 subunit (under control of siCMV)

```
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC
```

-continued

```
AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGcgtcgacaagaaATGGGCCAGACGGCGGGGGACCTCGGGTGGCGCCTGTCGCTTC

TGCTACTGCCCCTACTTCTGGTCCAAGCGGGAGTCTGGGCTTCCCACGTCCACCCGGCAGA

CCGCAGCTGAGCCTCCAGGAGCTTCGCAGGGAGTTCACCGTCAGCCTGCACCTCGCCCGGAA

GCTGTTGTCCGAAGTCAGAGGCCAGGCGCACCGGTTCGCCGAGTCGCACCTTCCAGGCGTGA

ACCTGTACCTCTTGCCCCTTGGCGAGCAGCTCCCCGACGTCTCCCTGACGTTCCAAGCCTGG

CGACGGCTCTCCGACCCGGAGCGCCTCTGCTTCATCTCGACCACGCTCCAGCCGTTCCACGC

CCTCCTTGGCGGGTTGGGGACCCAGGGGAGGTGGACCAACATGGAGAGGATGCAGCTGTGGG

CCATGAGGCTTGACCTCCGGGACCTGCAGAGGCACCTCCGCTTCCAAGTCCTTGCCGCTGGC

TTCAACCTCCCTGAGGAGGAGGAAGAAGAGGAAGAAGAGGAAGAGGAGGAACGGAAGGGGCT

GCTCCCAGGTGCCCTGGGCTCGGCGCTGCAGGGACCGGCACAGGTGTCTTGGCCCCAGCTGC

TCTCGACCTACCGGCTCCTTCACTCCCTGGAGCTGGTCCTGAGCCGGGCGGTGCGGGAGCTG

CTTCTGTTGTCCAAAGCGGGCCACTCGGTCTGGCCGCTTGGATTCCCCACCCTCTCGCCCCA

GCCGTAATGAggatctgatatcggatctGCTGTGCCTTCTAGTTGCCAGCCATCTGTTGTTT

GCCCCTCCCCCGTGCCTTCCTTGACCCTGGAAGGTGCCACTCCCACTGTCCTTTCCTAATAA

AATGAGGAAATTGCATCGCATTGTCTGAGTAGGTGTCATTCTATTCTGGGGGGTGGGGTGGG

GCAGGACAGCAAGGGGGAGGATTGGGAAGACAATAGCAGGCATGCTGGGGATGCGGTGGGCT

CTATGGGTACCCAGGTGCTGAAGAATTGACCCGGTTCCTCCTGGGCCAGAAAGAAGCAGGCA

CATCCCCTTCTCTGTGACACACCCTGTCCACGCCCCTGGTTCTTAGTTCCAGCCCCACTCAT

AGGACACTCATAGCTCAGGAGGGCTCCGCCTTCAATCCCACCCGCTAAAGTACTTGGAGCGG

TCTCTCCCTCCCTCATCAGCCCACCAAACCAAACCTAGCCTCCAAGAGTGGGAAGAAATTAA

AGCAAGATAGGCTATTAAGTGCAGAGGGAGAGAAAATGCCTCCAACATGTGAGGAAGTAATG

AGAGAAATCATAGAATTTCTTCCGCTTCCTCGCTCACTGACTCGCTGCGCTCGGTCGTTCGG

CTGCGGCGAGCGGTATCAGCTCACTCAAAGGCGGTAATACGGTTATCCACAGAATCAGGGGA

TAACGCAGGAAAGAACATGTGAGCAAAAGGCCAGCAAAAGGCCAGGAACCGTAAAAAGGCCG

CGTTGCTGGCGTTTTTCCATAGGCTCCGCCCCCCTGACGAGCATCACAAAAATCGACGCTCA

AGTCAGAGGTGGCGAAACCCGACAGGACTATAAAGATACCAGGCGTTTCCCCCTGGAAGCTC

CCTCGTGCGCTCTCCTGTTCCGACCCTGCCGCTTACCGGATACCTGTCCGCCTTTCTCCCTT

CGGGAAGCGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCCTTATCCGG

TAACTATCGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGTGGTGGCCT

AACTACGGCTACACTAGAAGAACAGTATTTGGTATCTGCGCTCTGCTGAAGCCAGTTACCTT

CGGAAAAAGAGTTGGTAGCTCTTGATCCGGCAAACAAACCACCGCTGGTAGCGGTGGTTTTT
```

-continued

```
TTGTTTGCAAGCAGCAGATTACGCGCAGAAAAAAGGATCTCAAGAAGATCCTTTGATCTTT

TCTACGGGGTCTGACGCTCAGTGGAACGAAAACTCACGTTAAGGGATTTTGGTCATGAGATT

ATCAAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATCTCA

GCGATCTGTCTATTTCGTTCATCCATAGTTGCCTGACTCGGGGGGGGGGGCGCTGAGGTCT

GCCTCGTGAAGAAGGTGTTGCTGACTCATACCAGGCCTGAATCGCCCCATCATCCAGCCAGA

AAGTGAGGGAGCCACGGTTGATGAGAGCTTTGTTGTAGGTGGACCAGTTGGTGATTTTGAAC

TTTTGCTTTGCCACGGAACGGTCTGCGTTGTCGGGAAGATGCGTGATCTGATCCTTCAACTC

AGCAAAAGTTCGATTTATTCAACAAAGCCGCCGTCCCGTCAAGTCAGCGTAATGCTCTGCCA

GTGTTACAACCAATTAACCAATTCTGATTAGAAAAACTCATCGAGCATCAAATGAAACTGCA

ATTTATTCATATCAGGATTATCAATACCATATTTTTGAAAAAGCCGTTTCTGTAATGAAGGA

GAAAACTCACCGAGGCAGTTCCATAGGATGGCAAGATCCTGGTATCGGTCTGCGATTCCGAC

TCGTCCAACATCAATACAACCTATTAATTTCCCCTCGTCAAAAATAAGGTTATCAAGTGAGA

AATCACCATGAGTGACGACTGAATCCGGTGAGAATGGCAAAAGCTTATGCATTTCTTTCCAG

ACTTGTTCAACAGGCCAGCCATTACGCTCGTCATCAAAATCACTCGCATCAACCAAACCGTT

ATTCATTCGTGATTGCGCCTGAGCGAGACGAAATACGCGATCGCTGTTAAAAGGACAATTAC

AAACAGGAATCGAATGCAACCGGCGCAGGAACACTGCCAGCGCATCAACAATATTTTCACCT

GAATCAGGATATTCTTCTAATACCTGGAATGCTGTTTTCCCGGGGATCGCAGTGGTGAGTAA

CCATGCATCATCAGGAGTACGGATAAAATGCTTGATGGTCGGAAGAGGCATAAATTCCGTCA

GCCAGTTTAGTCTGACCATCTCATCTGTAACATCATTGGCAACGCTACCTTTGCCATGTTTC

AGAAACAACTCTGGCGCATCGGGCTTCCCATACAATCGATAGATTGTCGCACCTGATTGCCC

GACATTATCGCGAGCCCATTTATACCCATATAAATCAGCATCCATGTTGGAATTTAATCGCG

GCCTCGAGCAAGACGTTTCCCGTTGAATATGGCTCATAACACCCCTTGTATTACTGTTTATG

TAAGCAGACAGTTTTATTGTTCATGATGATATATTTTTATCTTGTGCAATGTAACATCAGAG

ATTTTGAGACACAACGTGGATCATCCAGACATGATAAGATACATTGATGAGTTTGGACAAAC

CACAACTAGAATGCAGTGAAAAAAATGCTTTATTTGTGAAATTTGTGATGCTATTGCTTTAT

TTGTAACCATTATAAGCTGCAATAAACAAGTTAACAACAACAATTGCATTCATTTTATGTTT

CAGGTTCAGGGGGAGGTGTGGGAGGTTTTTTAAAGCAAGTAAAACCTCTACAAATGTGGTAT

GGCTGATTATGATCgtcgaggatcccTCATTACTTTCCCAAACTCATAGTTGCTGTAGCCGG

GAGGCTCCAGTCGCTAAGCTCCCCGTAGTCGGTGAGGTCCTGCGCAGCCACCTGCACGTAGT

ATCGGGCTCTGGGTCGGACCGCTCGGAGGATGAAAGACGTGGCCTCGATGGGGCCGACTCTG

TGGAATCTAGCGGCGCCCTGGCGCTTGTATCTGATCCAGTACTTGAGCGAGAAGATCTCCGG

GAAGGGCCAGGAACCTGGGGGCTCCCACTGCACCTGCAGCTGGCGCTCCGCGAGAGGAGACA

GGCGCACTCCCTCCGGTGGGTCCGGCTTGATGATGTGCTCAGTGATGAAAGGGACGAAGCTG

CTTGAAGAGCCCCACGGGTGCACCGCCGTGACGTTGAGGACGTAGGGAGCCATGGAGAACAG

CTGCACGTCAGTGATGGTGCAGGAAGTAGATGTGGGCGTCTGCTGCAGGCAGGGCCAGCTGT

GACCCCTAGCGGCCATGCCGAGCCGGTACGTGGCGATGAAGGAGACAGGGGAGGTGGAGTTG

GGTGCAGGTGGAAGGGTCCAGGAGCAGTCCACAGCGATGGGTAGCGCGAGGCTCTGCACTG

CACTCTGGGCAGGGTCAGGGCAGCTGGAGGACCCTTGCGTCCGCTGCACGGAGGGCAGCTGG

CCCAGAGGACCAGAGCCAGAAGCAGCTGCGGCGTCATttcttgtttaaacgtcgacagatcc

AAACGCTCCTCCGACGTCCCCAGGCAGAATGGCGGTTCCCTAAACGAGCATTGCTTATATAG
```

ACCTCCCATTAGGCACGCCTACCGCCCATTTACGTCAATGGAACGCCCATTTGCGTCATTGC

CCCTCCCCATTGACGTCAATGGGATGTACTTGGCAGCCATCGCGGGCCATTTACCGCCATT

GACGTCAATGGGAGTACTGCCAATGTACCCTGGCGTACTTCCAATAGTAATGTACTTGCCAA

GTTACTATTAATAGATATTGATGTACTGCCAAGTGGGCCATTTACCGTCATTGACGTCAATA

GGGGGCGTGAGAACGGATATGAATGGGCAATGAGCCATCCCATTGACGTCAATGGTGGGTGG

TCCTATTGACGTCAATGGGCATTGAGCCAGGCGGGCCATTTACCGTAATTGACGTCAATGGG

GGAGGCGCCATATACGTCAATAGGACCGCCCATATGACGTCAATAGGTAAGACCATGAGGCC

CTTTCGTCTCGCGCGTTTCGGTGATGACGGTGAAAACCTCTGACACATGCAGCTCCCGGAGA

CGGTCACAGCTTGTCTGTAAGCGGATGCCGGGAGCAGACAAGCCCGTCAGGGCGCGTCAGCG

GGTGTTGGCGGGTGTCGGGGCTGGCTTAACTATGCGGCATCAGAGCAGATTGTACTGAGAGT

GCACCATATGCGGTGTGAAATACCGCACAGATGCGTAAGGAGAAAATACCGCATCAGATTGG

CTATTGGCATTATGCC

SEQ ID NO: 15
- AG217
flanking sequences in lower case; coding sequences underlined
expresses human IL-27 EBI3 subunit (under control of hCMV)and
human IL-27 p28 subunit (under control of siCMV)
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGgcgcgcgtcgaaagaa<u>ATGACGCCGCAGCTGCTTCTGGCTCTGGTCCTCTGGGCC</u>

<u>AGCTGCCCTCCGTGCAGCGGACGCAAGGGTCCTCAGCTGCCCTGACCCTGCCCAGAGTGCA</u>

<u>GTGCAGAGCCTCGCGCTACCCCATCGCTGTGGACTGCTCCTGGACCCTTCCACCTGCACCCA</u>

<u>ACTCCACCTCCCCTGTCTCCTTCATCGCCACGTACCGGCTCGGCATGGCCGCTAGGGGTCAC</u>

<u>AGCTGGCCCTGCCTGCAGCAGACGCCCACATCTACTTCCTGCACCATCACTGACGTGCAGCT</u>

<u>GTTCTCCATGGCTCCCTACGTCCTCAACGTCACGGCGGTGCACCCGTGGGGCTCTTCAAGCA</u>

<u>GCTTCGTCCCTTTCATCACTGAGCACATCATCAAGCCGGACCCACCGGAGGGAGTGCGCCTG</u>

<u>TCTCCTCTCGCGGAGCGCCAGCTGCAGGTGCAGTGGGAGCCCCCAGGTTCCTGGCCCTTCCC</u>

<u>GGAGATCTTCTCGCTCAAGTACTGGATCAGATACAAGCGCCAGGGCGCCGCTAGATTCCACA</u>

<u>GAGTCGGCCCCATCGAGGCCACGTCTTTCATCCTCCGAGCGGTCCGACCCAGAGCCCGATAC</u>

<u>TACGTGCAGGTGGCTGCGCAGGACCTCACCGACTACGGGGAGCTTAGCGACTGGAGCCTCCC</u>

<u>GGCTACAGCAACTATGAGTTTGGGAAAGTAATGA</u>ggaattcgctagcggcgcgccagatctg atatcggatctGCTGTGCCTTCTAGTTGCCAGCCATCTGTTGTTTGCCCCTCCCCCGTGCCT

TCCTTGACCCTGGAAGGTGCCACTCCCACTGTCCTTTCCTAATAAAATGAGGAAATTGCATC

-continued

```
GCATTGTCTGAGTAGGTGTCATTCTATTCTGGGGGGTGGGGTGGGGCAGGACAGCAAGGGGG

AGGATTGGGAAGACAATAGCAGGCATGCTGGGGATGCGGTGGGCTCTATGGGTACCCAGGTG

CTGAAGAATTGACCCGGTTCCTCCTGGGCCAGAAAGAAGCAGGCACATCCCCTTCTCTGTGA

CACACCCTGTCCACGCCCCTGGTTCTTAGTTCCAGCCCCACTCATAGGACACTCATAGCTCA

GGAGGGCTCCGCCTTCAATCCCACCCGCTAAAGTACTTGGAGCGGTCTCTCCCTCCCTCATC

AGCCCACCAAACCAAACCTAGCCTCCAAGAGTGGGAAGAAATTAAAGCAAGATAGGCTATTA

AGTGCAGAGGGAGAGAAAATGCCTCCAACATGTGAGGAAGTAATGAGAGAAATCATAGAATT

TCTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTT

TCTCATAGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAG

AAGAACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGACGC

TCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCG

TTCATCCATAGTTGCCTGACTCGGGGGGGGGGGCGCTGAGGTCTGCCTCGTGAAGAAGGTG

TTGCTGACTCATACCAGGCCTGAATCGCCCCATCATCCAGCCAGAAAGTGAGGGAGCCACGG

TTGATGAGAGCTTTGTTGTAGGTGGACCAGTTGGTGATTTTGAACTTTTGCTTTGCCACGGA

ACGGTCTGCGTTGTCGGGAAGATGCGTGATCTGATCCTTCAACTCAGCAAAAGTTCGATTTA

TTCAACAAAGCCGCCGTCCCGTCAAGTCAGCGTAATGCTCTGCCAGTGTTACAACCAATTAA

CCAATTCTGATTAGAAAAACTCATCGAGCATCAAATGAAACTGCAATTTATTCATATCAGGA

TTATCAATACCATATTTTTGAAAAAGCCGTTTCTGTAATGAAGGAGAAAACTCACCGAGGCA

GTTCCATAGGATGGCAAGATCCTGGTATCGGTCTGCGATTCCGACTCGTCCAACATCAATAC

AACCTATTAATTTCCCCTCGTCAAAAATAAGGTTATCAAGTGAGAAATCACCATGAGTGACG

ACTGAATCCGGTGAGAATGGCAAAAGCTTATGCATTTCTTTCCAGACTTGTTCAACAGGCCA

GCCATTACGCTCGTCATCAAAATCACTCGCATCAACCAAACCGTTATTCATTCGTGATTGCG

CCTGAGCGAGACGAAATACGCGATCGCTGTTAAAAGGACAATTACAAACAGGAATCGAATGC

AACCGGCGCAGGAACACTGCCAGCGCATCAACAATATTTTCACCTGAATCAGGATATTCTTC

TAATACCTGGAATGCTGTTTTCCCGGGGATCGCAGTGGTGAGTAACCATGCATCATCAGGAG

TACGGATAAAATGCTTGATGGTCGGAAGAGGCATAAATTCCGTCAGCCAGTTTAGTCTGACC

ATCTCATCTGTAACATCATTGGCAACGCTACCTTTGCCATGTTTCAGAAACAACTCTGGCGC

ATCGGGCTTCCCATACAATCGATAGATTGTCGCACCTGATTGCCCGACATTATCGCGAGCCC
```

-continued

ATTTATACCCATATAAATCAGCATCCATGTTGGAATTTAATCGCGGCCTCGAGCAAGACGTT

TCCCGTTGAATATGGCTCATAACACCCCTTGTATTACTGTTTATGTAAGCAGACAGTTTTAT

TGTTCATGATGATATATTTTTATCTTGTGCAATGTAACATCAGAGATTTTGAGACACAACGT

GGATCATCCAGACATGATAAGATACATTGATGAGTTTGGACAAACCACAACTAGAATGCAGT

GAAAAAAATGCTTTATTTGTGAAATTTGTGATGCTATTGCTTTATTTGTAACCATTATAAGC

TGCAATAAACAAGTTAACAACAACAATTGCATTCATTTTATGTTTCAGGTTCAGGGGGAGGT

GTGGGAGGTTTTTTAAAGCAAGTAAAACCTCTACAAATGTGGTATGGCTGATTATGATCgtc gaggatccggcgccgtttaaacTCATTACGGCTGGGGCGAGAGGGTGGGGAATCCAAGCGGC

CAGACCGAGTGGCCCGCTTTGGACAACAGAAGCAGCTCCCGCACCGCCCGGCTCAGGACCAG

CTCCAGGGAGTGAAGGAGCCGGTAGGTCGAGAGCAGCTGGGGCCAAGACACCTGTGCCGGTC

CCTGCAGCGCCGAGCCCAGGGCACCTGGGAGCAGCCCCTTCCGTTCCTCCTCTTCCTCTTCT

TCCTCTTCTTCCTCCTCCTCAGGGAGGTTGAAGCCAGCGGCAAGGACTTGGAAGCGGAGGTG

CCTCTGCAGGTCCCGGAGGTCAAGCCTCATGGCCCACAGCTGCATCCTCTCCATGTTGGTCC

ACCTCCCCTGGGTCCCCAACCCGCCAAGGAGGGCGTGGAACGGCTGGAGCGTGGTCGAGATG

AAGCAGAGGCGCTCCGGGTCGGAGAGCCGTCGCCAGGCTTGGAACGTCAGGGAGACGTCGGG

GAGCTGCTCGCCAAGGGGCAAGAGGTACAGGTTCACGCCTGGAAGGTGCGACTCGGCGAACC

GGTGCGCCTGGCCTCTGACTTCGGACAACAGCTTCCGGGCGAGGTGCAGGCTGACGGTGAAC

TCCCTGCGAAGCTCCTGGAGGCTCAGCTGCGGTCTGCCGGGTGGACGTGGGAAGCCCCAGAC

TCCCGCTTGGACCAGAAGTAGGGGCAGTAGCAGAAGCGACAGGCGCCACCCGAGGTCCCCCG

CCGTCTGGCCCATttcttgtcgacagatccAAACGCTCCTCCGACGTCCCCAGGCAGAATGG

CGGTTCCCTAAACGAGCATTGCTTATATAGACCTCCCATTAGGCACGCCTACCGCCCATTTA

CGTCAATGGAACGCCCATTTGCGTCATTGCCCCTCCCCATTGACGTCAATGGGGATGTACTT

GGCAGCCATCGCGGGCCATTTACCGCCATTGACGTCAATGGGAGTACTGCCAATGTACCCTG

GCGTACTTCCAATAGTAATGTACTTGCCAAGTTACTATTAATAGATATTGATGTACTGCCAA

GTGGGCATTTACCGTCATTGACGTCAATAGGGGGCGTGAGAACGGATATGAATGGGCAATG

AGCCATCCCATTGACGTCAATGGTGGGTGGTCCTATTGACGTCAATGGGCATTGAGCCAGGC

GGGCCATTTACCGTAATTGACGTCAATGGGGGAGGCGCCATATACGTCAATAGGACCGCCCA

TATGACGTCAATAGGTAAGACCATGAGGCCCTTTCGTCTCGCGCGTTTCGGTGATGACGGTG

AAAACCTCTGACACATGCAGCTCCCGGAGACGGTCACAGCTTGTCTGTAAGCGGATGCCGGG

AGCAGACAAGCCCGTCAGGGCGCGTCAGCGGGTGTTGGCGGGTGTCGGGGCTGGCTTAACTA

TGCGGCATCAGAGCAGATTGTACTGAGAGTGCACCATATGCGGTGTGAAATACCGCACAGAT

GCGTAAGGAGAAAATACCGCATCAGATTGGCTATTGGCATTATGCC

SEQ ID NO: 16
- human IL-23 (p19) nucleotide sequence wildtype
GenBank NM_016584.
Atgctggggagcagagctgtaatgctgctgttgctgctgccctggacagctcagggcagagc tgtgcctgggggcagcagccctgcctggactcagtgccagcagctttcacagaagctctgca cactggcctggagtgcacatccactagtgggacacatggatctaagagaagagggagatgaa gagactacaaatgatgttccccatatccagtgtggagatggctgtgaccccaaggactcag ggacaacagtcagttctgcttgcaaaggatccaccagggtctgatttttatgagaagctgc taggatcggatattttcacaggggagccttctctgctccctgatagccctgtgggccagctt catgcctccctactgggcctcagccaactcctgcagcctgagggtcaccactgggagactca -continued gcagattccaagcctcagtcccagccagccatggcagcgtctccttctccgcttcaaaatcc ttcgcagcctccaggcctttgtggctgtagccgcccgggtctttgcccatggagcagcaacc ctgagtccctaa SEQ ID NO: 17
- human IL-23 (p19) protein sequence
GenBank NP_057668.

M L G S R A V M L L L L P W T A Q G R A

V P G G S S P A W T Q C Q Q L S Q K L C T

L A W S A H P L V G H M D L R E E G D E E

T T N D V P H I Q C G D G C D P Q G L R D

N S Q F C L Q R I H Q G L I F Y E K L L G

S D I F T G E P S L L P D S P V G Q L H A

S L L G L S Q L L Q P E G H H W E T Q Q I

P S L S P S Q P W Q R L L L R F K I L R S

L Q A F V A V A A R V F A H G A A T L S P
.

SEQ ID NO: 18
- murine p28 nucleotide sequence wildtype
GenBank NM_145636.
Atgggccaggtgacaggagaccttggctggcggctcagcctgttgctgctaccttgcttct ggtacaagctggttcctgggggttcccaacagaccccctgagccttcaagagctgcgcaggg aattcacagtcagcctgtaccttgccaggaagctgctctctgaggttcagggctatgtccac agctttgctgaatctcgattgccaggagtgaacctggacctcctgcccctgggataccatct tcccaatgtttccctgactttccaggcatggcatcacctctctgactctgagagactctgct tcctcgctaccacacttcggccctccctgccatgctgggagggctggggacccaggggacc tggaccagctcagagagggagcagctgtgggccatgaggctggatctccgggacctgcacag gcacctccgctttcaggtgctggctgcaggattcaaatgttcaaaggaggaggaggacaagg aggaagaggaagaggaggaagaagaagaaaagaagctgcccctaggggctctgggtggcccc aatcaggtgtcatcccaagtgtcctggccccagctgctctatacctaccagctccttcactc cctggagcttgtcctgtctcgggctgttcgggacctgctgctgctgtccctgcccaggcgcc caggctcagcctgggattcctaa SEQ ID NO: 19
- murine p28 protein sequence
MGQVTGDLGWRLSLLLLPLLLVQAGSWGFPTDPLSLQELRREFTVSLYLARKLLSEVQGYVH

SFAESRLPGVNLDLLPLGYHLPNVSLTFQAWHHLSDSERLCFLATTLRPFPAMLGGLGTQGT

WTSSEREQLWAMRLDLRDLHRHLRFQVLAAGFKCSKEEEDKEEEEEEEEEKKLPLGALGGP

NQVSSQVSWPQLLYTYQLLHSLELVLSRAVRDLLLLSLPRRPGSAWDS

SEQ ID NO: 20
- murine EBI3 nucleotide sequence wildtype
Genbank NM_015766
Atgtccaagctgctcttcctgtcacttgccctctgggccagccgctcccctggttacactga aacagctctcgtggctctaagccagcccagagtgcaatgccatgcttctcggtatcccgtgg ccgtggactgctcctggactcctctccaggctcccaactccaccagatccacgtccttcatt gccacttacaggctcggtgtggccacccagcagcagagccagccctgcctacaacggagccc ccaggcctcccgatgcaccatcccgacgtgcacctgttctccacggtgccctacatgctaa atgtcactgcagtgcacccaggcggcgccagcagcagcctcctagcctttgtggctgagcga -continued

```
atcatcaagccggaccctccggaaggcgtgcgcctgcgcacagcgggacagcgcctgcaggt gctctggcatcccctgcttcctggcccttcccggacatcttctctctcaagtaccgactcc gctaccggcgccgaggagcctctcacttccgccaggtgggacccattgaagccacgactttc accctcaggaactcgaaacccatgccaagtattgcatccaggtgtcagctcaggacctcac agattatgggaaaccaagtgactggagcctccctgggcaagtagaaagtgcaccccataagc cc
```

SEQ ID NO: 21
- murine EBI3 protein sequence wildtype
Genbank NP_056581

M S K L L F L S L A L W A S R S P G Y T E

T A L V A L S Q P R V Q C H A S R Y P V A

V D C S W T P L Q A P N S T R S T S F I A

T Y R L G V A T Q Q Q S Q P C L Q R S P Q

A S R C T I P D V H L F S T V P Y M L N V

T A V H P G G A S S S L L A F V A E R I I

K P D P P E G V R L R T A G Q R L Q V L W

H P P A S W P F P D I F S L K Y R L R Y R

R R G A S H F R Q V G P I E A T T F T L R

N S K P H A K Y C I Q V S A Q D L T D Y G

K P S D W S L P G Q V E S A P H K P

SEQ ID NO: 22
- human EBI3 nucleotide sequence wildtype
Genbank CCDS12123.1 (also, NM_005755)

```
ATGACCCCGCAGCTTCTCCTGGCCCTTGTCCTCTGGGCCAGCTGCCCGCCCTGCAGTGGAAG

GAAAGGGCCCCCAGCAGCTCTGACACTGCCCCGGGTGCAATGCCGAGCCTCTCGGTACCCGA

TCGCCGTGGATTGCTCCTGGACCCTGCCGCCTGCTCCAAACTCCACCAGCCCCGTGTCCTTC

ATTGCCACGTACAGGCTCGGCATGGCTGCCCGGGGCCACAGCTGGCCCTGCCTGCAGCAGAC

GCCAACGTCCACCAGCTGCACCATCACGGATGTCCAGCTGTTCTCCATGGCTCCCTACGTGC

TCAATGTCACCGCCGTCCACCCCTGGGGCTCCAGCAGCAGCTTCGTGCCTTTCATAACAGAG

CACATCATCAAGCCCGACCCTCCAGAAGGCGTGCGCCTAAGCCCCCTCGCTGAGCGCCAGCT

ACAGGTGCAGTGGGAGCCTCCCGGGTCCTGGCCCTTCCCAGAGATCTTCTCACTGAAGTACT

GGATCCGTTACAAGCGTCAGGGAGCTGCGCGCTTCCACCGGGTGGGGCCCATTGAAGCCACG

TCCTTCATCCTCAGGGCTGTGCGGCCCCGAGCCAGGTACTACGTCCAAGTGGCGGCTCAGGA

CCTCACAGACTACGGGGAACTGAGTGACTGGAGTCTCCCCGCCACTGCCACAATGAGCCTGG

GCAAG
```

SEQ ID NO: 23
- human EBI3 protein sequence

M T P Q L L L A L V L W A S C P P C S G R

K G P P A A L T L P R V Q C R A S R Y P I

A V D C S W T L P P A P N S T S P V S F I

A T Y R L G M A A R G H S W P C L Q Q T P

T S T S C T I T D V Q L F S M A P Y V L N

V T A V H P W G S S S S F V P F I T E H I

I K P D P P E G V R L S P L A E R Q L Q V

Q W E P P G S W P F P E I F S L K Y W I R

```
Y  K  R  Q  G  A  A  R  F  H  R  V  G  P  I  E  A  T  S  F  I

L  R  A  V  R  P  R  A  R  Y  Y  V  Q  V  A  A  Q  D  L  T  D

Y  G  E  L  S  D  W  S  L  P  A  T  A  T  M  S  L  G  K
```

SEQ ID NO: 24 human IL-27 p28 nucleotide sequence
Genbank NM_145659.

```
Atgggccagacggcaggcgaccttggctggcggctcagcctgttgctgcttcccttgctcct ggttcaagctggtgtctggggattccaaggcccccagggaggccccagctgagcctgcagg agctgcggagggagttcacagtcagcctgcatctcgccaggaagctgctctccgaggttcgg ggccaggccaccgctttgcggaatctcacctgccaggagtgaacctgtacctcctgcccct gggagagcagctccctgatgtttccctgaccttccaggcctggcgccgcctctctgacccgg agcgtctctgcttcatctccaccacgcttcagcccttccatgccctgctgggagggctgggg acccagggccgctggaccaacatggagaggatgcagctgtgggccatgaggctggacctccg cgatctgcagaggcacctccgcttccaggtgctggctgcaggattcaacctcccggaggagg aggaggaggaagaggaggaggaggaggaggagaggaaggggctgctcccaggggcactgggc agcgccttacagggcccggcccaggtgtcctggccccagctcctctccacctaccgcctgct gcactccttggagctcgtcttatctcgggccgtgcgggagttgctgctgctgtccaaggctg ggcactcagtctggcccttggggttcccaacattgagcccccagccctga
```

SEQ ID NO: 25 human IL-27 p28 protein sequence
Genbank NP_663634.

```
M  G  Q  T  A  G  D  L  G  W  R  L  S  L  L  L  L  P  L  L  L

V  Q  A  G  V  W  G  F  P  R  P  P  G  R  P  Q  L  S  L  Q  E

L  R  R  E  F  T  V  S  L  H  L  A  R  K  L  L  S  E  V  R  G

Q  A  H  R  F  A  E  S  H  L  P  G  V  N  L  Y  L  L  P  L  G

E  Q  L  P  D  V  S  L  T  F  Q  A  W  R  R  L  S  D  P  E  R

L  C  F  I  S  T  T  L  Q  P  F  H  A  L  L  G  G  L  G  T  Q

G  R  W  T  N  M  E  R  M  Q  L  W  A  M  R  L  D  L  R  D  L

Q  R  H  L  R  F  Q  V  L  A  A  G  F  N  L  P  E  E  E  E  E

E  E  E  E  E  E  E  R  K  G  L  L  P  G  A  L  G  S  A  L

Q  G  P  A  Q  V  S  W  P  Q  L  L  S  T  Y  R  L  L  H  S  L

E  L  V  L  S  R  A  V  R  E  L  L  L  L  S  K  A  G  H  S  V

W  P  L  G  F  P  T  L  S  P  Q  P  *
```

SEQ ID NO: 26

- human IL-23 p19
RNA improved nucleotide sequence

```
ATGCTGGGGAGCCGCGCGGTCATGCTGCTCTTGCTGCTCCCCTGGACGGCCCAGGGCCGGGC

GGTGCCCGGGGGCTCGAGCCCGGCCTGGACGCAGTGCCAGCAGCTCAGCCAGAAGCTCTGCA

CCCTGGCCTGGTCGGCCCACCCGCTCGTGGGCCACATGGACCTCCGGGAGGAGGGCGACGAG

GAGACGACCAACGACGTCCCCCACATCCAGTGCGGCGACGGCTGCGACCCCCAGGGCCTCCG

GGACAACTCGCAGTTCTGCCTGCAGCGCATCCACCAGGGCCTGATCTTCTACGAGAAGCTGC

TCGGCTCGGACATCTTCACGGGGGAGCCGTCGCTGCTCCCCGACAGCCCGGTGGGCCAGCTC

CACGCCTCCCTCCTGGGCCTCTCGCAACTTCTGCAACCGGAGGGCCACCACTGGGAGACGCA

GCAGATCCCGAGCCTCTCGCCCAGCCAGCCGTGGCAGCGGCTCCTGCTCAGATTCAAGATCT
```

```
TGCGCTCCCTCCAAGCCTTCGTGGCGGTCGCCGCCCGGGTCTTCGCCCACGGCGCGGCCACC

CTGAGCCCCTGATAA
```

SEQ ID NO: 27
- murine IL-27 p28
RNA improved nucleotide sequence
```
ATGGGCCAGGTCACCGGGGACCTCGGGTGGCGCCTGTCGCTCCTGCTCCTGCCCCTCCTCCT

GGTCCAAGCGGGGAGCTGGGGCTTCCCCACGGATCCCCTGAGCCTCCAGGAGCTGCGCAGGG

AGTTCACCGTCAGCCTGTACCTCGCCCGGAAGCTGCTCTCCGAGGTCCAGGGCTACGTCCAC

AGCTTCGCCGAGTCGCGCCTGCCCGGCGTGAACCTGGACCTCCTGCCCCTGGGCTACCACCT

CCCCAACGTCTCCCTGACGTTCCAAGCCTGGCACCACCTCTCCGACTCCGAGCGCCTCTGCT

TCCTCGCCACCACGCTCCGGCCGTTCCCGGCCATGCTGGGCGGGCTGGGGACCCAGGGGACC

TGGACCAGCTCCGAGAGGGAGCAGCTGTGGGCCATGAGGCTGGACCTCCGGGACCTGCACAG

GCACCTCCGCTTCCAAGTCCTGGCCGCGGGCTTCAAGTGCTCCAAGGAGGAGGAGGACAAGG

AGGAAGAGGAAGAGGAGGAAGAAGAGGAAAAGAAGCTGCCCCTCGGGGCCCTGGGCGGCCCC

AACCAGGTGTCCTCCCAAGTGTCCTGGCCCCAGCTGCTCTACACCTACCAGCTCCTCCACTC

CCTGGAGCTGGTCCTGAGCCGGGCGGTGCGGGACCTGCTCCTGCTGTCCCTGCCCCGGCGCC

CGGGCTCGGCCTGGGACTCCTAATGA
```

SEQ ID NO: 28
- murine IL-27 EBI3
RNA improved nucleotide sequence
```
ATGTCGAAGCTCCTGTTCCTGAGCCTGGCGCTCTGGGCCAGCCGCTCGCGGGGTATACCGA

GACGGCGCTCGTGGCCCTGAGCCAGCCCCGGGTGCAGTGCCACGCCTCGCGCTACCCCGTGG

CCGTGGACTGCTCCTGGACCCCGCTGCAAGCGCCCAACTCCACCAGGTCCACGTCCTTCATC

GCCACGTACCGGCTCGGCGTGGCCACCCAGCAGCAGAGCCAGCCCTGCCTGCAGCGGAGCCC

CCAGGCCTCCCGCTGCACCATCCCCGACGTGCACCTGTTCTCCACGGTGCCCTACATGCTCA

ACGTCACGGCGGTGCACCCGGGCGGCGCCAGCAGCAGCCTCCTGGCCTTCGTGGCGGAGCGG

ATCATCAAGCCGGACCCGCCGGAGGGCGTGCGCCTGCGCACGGCGGGCCAGCGCCTGCAGGT

GCTCTGGCACCCCCCGGCCTCCTGGCCCTTCCCGGACATCTTCTCGCTCAAGTACCGCCTCC

GCTACCGGCGCCGAGGCGCCTCCCACTTCCGCCAAGTCGGCCCCATCGAGGCCACGACCTTC

ACCCTCCGGAACTCGAAGCCCCACGCCAAGTACTGCATCCAGGTGTCGGCGCAGGACCTCAC

CGACTACGGGAAGCCCAGCGACTGGAGCCTCCCGGGGCAGGTCGAGAGCGCTCCCCACAAGC

CCTAATGA
```

SEQ ID NO: 29
- human IL-27 p28
RNA improved nucleotide sequence
```
ATGGGCCAGACGGCGGGGGACCTCGGGTGGCGCCTGTCGCTTCTGCTACTGCCCCTACTTCT

GGTCCAAGCGGGAGTCTGGGGCTTCCCACGTCCACCCGGCAGACCGCAGCTGAGCCTCCAGG

AGCTTCGCAGGGAGTTCACCGTCAGCCTGCACCTCGCCCGGAAGCTGTTGTCCGAAGTCAGA

GGCCAGGCGCACCGGTTCGCCGAGTCGCACCTTCCAGGCGTGAACCTGTACCTCTTGCCCCT

TGGCGAGCAGCTCCCCGACGTCTCCCTGACGTTCCAAGCCTGGCGACGGCTCTCCGACCCGG

AGCGCCTCTGCTTCATCTCGACCACGCTCCAGCCGTTCCACGCCCTCCTTGGCGGGTTGGGG

ACCCAGGGGAGGTGGACCAACATGGAGAGGATGCAGCTGTGGGCCATGAGGCTTGACCTCCG

GGACCTGCAGAGGCACCTCCGCTTCCAAGTCCTTGCCGCTGGCTTCAACCTCCTGAGGAGG

AGGAAGAAGAGGAAGAAGAGGAAGAGGAGGAACGAAGGGGCTGCTCCCAGGTGCCCTGGGC

TCGGCGCTGCAGGGACCGGCACAGGTGTCTTGGCCCCAGCTGCTCTCGACCTACCGGCTCCT
```

SEQ ID NO: 30
- human IL-27 EBI3
RNA improved nucleotide sequence
ATGACGCCGCAGCTGCTTCTGGCTCTGGTCCTCTGGGCCAGCTGCCCTCCGTGCAGCGGACG

CAAGGGTCCTCCAGCTGCCCTGACCCTGCCCAGAGTGCAGTGCAGAGCCTCGCGCTACCCCA

TCGCTGTGGACTGCTCCTGGACCCTTCCACCTGCACCCAACTCCACCTCCCCTGTCTCCTTC

ATCGCCACGTACCGGCTCGGCATGGCCGCTAGGGGTCACAGCTGGCCCTGCCTGCAGCAGAC

GCCCACATCTACTTCCTGCACCATCACTGACGTGCAGCTGTTCTCCATGGCTCCCTACGTCC

TCAACGTCACGGCGGTGCACCCGTGGGGCTCTTCAAGCAGCTTCGTCCCTTTCATCACTGAG

CACATCATCAAGCCGGACCCACCGGAGGGAGTGCGCCTGTCTCCTCTCGCGGAGCGCCAGCT

GCAGGTGCAGTGGGAGCCCCCAGGTTCCTGGCCCTTCCCGGAGATCTTCTCGCTCAAGTACT

GGATCAGATACAAGCGCCAGGGCGCCGCTAGATTCCACAGAGTCGGCCCCATCGAGGCCACG

TCTTTCATCCTCCGAGCGGTCCGACCCAGAGCCCGATACTACGTGCAGGTGGCTGCGCAGGA

CCTCACCGACTACGGGGAGCTTAGCGACTGGAGCCTCCCGGCTACAGCAACTATGAGTTTGG

GAAAGTAATGA

SEQ ID NO: 31
- CMVkan vector backbone
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGCGCGCGTCGACGCTAGCGGCGCGCCGCGGCCGCCAATTGAGATCTGCTGTGCCT

TCTAGTTGCCAGCCATCTGTTGTTTGCCCCTCCCCCGTGCCTTCCTTGACCCTGGAAGGTGC

CACTCCCACTGTCCTTTCCTAATAAAATGAGGAAATTGCATCGCATTGTCTGAGTAGGTGTC

ATTCTATTCTGGGGGGTGGGGTGGGGCAGGACAGCAAGGGGGAGGATTGGGAAGACAATAGC

AGGCATGCTGGGGATGCGGTGGGCTCTATGGGTACCCAGGTGCTGAAGAATTGACCCGGTTC

CTCCTGGGCCAGAAAGAAGCAGGCACATCCCCTTCTCTGTGACACACCCTGTCCACGCCCCT

GGTTCTTAGTTCCAGCCCCACTCATAGGACACTCATAGCTCAGGAGGGCTCCGCCTTCAATC

CCACCCGCTAAAGTACTTGGAGCGGTCTCTCCCTCCCTCATCAGCCCACCAAACCAAACCTA

GCCTCCAAGAGTGGGAAGAAATTAAAGCAAGATAGGCTATTAAGTGCAGAGGGAGAGAAAAT

GCCTCCAACATGTGAGGAAGTAATGAGAGAAATCATAGAATTTCTTCCGCTTCCTCGCTCAC

TGACTCGCTGCGCTCGGTCGTTCGGCTGCGGCGAGCGGTATCAGCTCACTCAAAGGCGGTAA

TACGGTTATCCACAGAATCAGGGGATAACGCAGGAAAGAACATGTGAGCAAAAGGCCAGCAA

```
-continued
AAGGCCAGGAACCGTAAAAAGGCCGCGTTGCTGGCGTTTTTCCATAGGCTCCGCCCCCTGA

CGAGCATCACAAAAATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGACCCTGCCGCTTACC

GGATACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCCCGTTC

AGCCCGACCGCTGCGCCTTATCCGGTAACTATCGTCTTGAGTCCAACCCGGTAAGACACGAC

TTATCGCCACTGGCAGCAGCCACTGGTAACAGGATTAGCAGAGCGAGGTATGTAGGCGGTGC

TACAGAGTTCTTGAAGTGGTGGCCTAACTACGGCTACACTAGAAGAACAGTATTTGGTATCT

GCGCTCTGCTGAAGCCAGTTACCTTCGGAAAAAGAGTTGGTAGCTCTTGATCCGGCAAACAA

ACCACCGCTGGTAGCGGTGGTTTTTTTGTTTGCAAGCAGCAGATTACGCGCAGAAAAAAAGG

ATCTCAAGAAGATCCTTTGATCTTTTCTACGGGGTCTGACGCTCAGTGGAACGAAAACTCAC

GTTAAGGGATTTTGGTCATGAGATTATCAAAAAGGATCTTCACCTAGATCCTTTTAAATTAA

AAATGAAGTTTTAAATCAATCTAAAGTATATATGAGTAAACTTGGTCTGACAGTTACCAATG

CTTAATCAGTGAGGCACCTATCTCAGCGATCTGTCTATTTCGTTCATCCATAGTTGCCTGAC

TCGGGGGGGGGGGCGCTGAGGTCTGCCTCGTGAAGAAGGTGTTGCTGACTCATACCAGGCC

TGAATCGCCCCATCATCCAGCCAGAAAGTGAGGGAGCCACGGTTGATGAGAGCTTTGTTGTA

GGTGGACCAGTTGGTGATTTTGAACTTTTGCTTTGCCACGGAACGGTCTGCGTTGTCGGAA

GATGCGTGATCTGATCCTTCAACTCAGCAAAAGTTCGATTTATTCAACAAAGCCGCCGTCCC

GTCAAGTCAGCGTAATGCTCTGCCAGTGTTACAACCAATTAACCAATTCTGATTAGAAAAAC

TCATCGAGCATCAAATGAAACTGCAATTTATTCATATCAGGATTATCAATACCATATTTTTG

AAAAAGCCGTTTCTGTAATGAAGGAGAAAACTCACCGAGGCAGTTCCATAGGATGGCAAGAT

CCTGGTATCGGTCTGCGATTCCGACTCGTCCAACATCAATACAACCTATTAATTTCCCCTCG

TCAAAAATAAGGTTATCAAGTGAGAAATCACCATGAGTGACGACTGAATCCGGTGAGAATGG

CAAAAGCTTATGCATTTCTTTCCAGACTTGTTCAACAGGCCAGCCATTACGCTCGTCATCAA

AATCACTCGCATCAACCAAACCGTTATTCATTCGTGATTGCGCCTGAGCGAGACGAAATACG

CGATCGCTGTTAAAAGGACAATTACAAACAGGAATCGAATGCAACCGGCGCAGGAACACTGC

CAGCGCATCAACAATATTTTCACCTGAATCAGGATATTCTTCTAATACCTGGAATGCTGTTT

TCCCGGGGATCGCAGTGGTGAGTAACCATGCATCATCAGGAGTACGGATAAAATGCTTGATG

GTCGGAAGAGGCATAAATTCCGTCAGCCAGTTTAGTCTGACCATCTCATCTGTAACATCATT

GGCAACGCTACCTTTGCCATGTTTCAGAAACAACTCTGGCGCATCGGGCTTCCCATACAATC

GATAGATTGTCGCACCTGATTGCCCGACATTATCGCGAGCCCATTTATACCCATATAAATCA

GCATCCATGTTGGAATTTAATCGCGGCCTCGAGCAAGACGTTTCCCGTTGAATATGGCTCAT

AACACCCCTTGTATTACTGTTTATGTAAGCAGACAGTTTTATTGTTCATGATGATATATTTT

TATCTTGTGCAATGTAACATCAGAGATTTTGAGACACAACGTGGCTTTCCCCCCCCCCCAT

TATTGAAGCATTTATCAGGGTTATTGTCTCATGAGCGGATACATATTTGAATGTATTTAGAA

AAATAAACAAATAGGGGTTCCGCGCACATTTCCCCGAAAAGTGCCACCTGACGTCTAAGAAA

CCATTATTATCATGACATTAACCTATAAAAATAGGCGTATCACGAGGCCCTTTCGTCTCGCG

CGTTTCGGTGATGACGGTGAAAACCTCTGACACATGCAGCTCCCGGAGACGGTCACAGCTTG

TCTGTAAGCGGATGCCGGGAGCAGACAAGCCCGTCAGGGCGCGTCAGCGGGTGTTGGCGGGT
```

GTCGGGGCTGGCTTAACTATGCGGCATCAGAGCAGATTGTACTGAGAGTGCACCATATGCGG

TGTGAAATACCGCACAGATGCGTAAGGAGAAAATACCGCATCAGATTGGCTATTGG

SEQ ID NO: 32
- DP dual promoter expression vector backbone
CCTGGCCATTGCATACGTTGTATCCATATCATAATATGTACATTTATATTGGCTCATGTCCA

ACATTACCGCCATGTTGACATTGATTATTGACTAGTTATTAATAGTAATCAATTACGGGGTC

ATTAGTTCATAGCCCATATATGGAGTTCCGCGTTACATAACTTACGGTAAATGGCCCGCCTG

GCTGACCGCCCAACGACCCCCGCCCATTGACGTCAATAATGACGTATGTTCCCATAGTAACG

CCAATAGGGACTTTCCATTGACGTCAATGGGTGGAGTATTTACGGTAAACTGCCCACTTGGC

AGTACATCAAGTGTATCATATGCCAAGTACGCCCCCTATTGACGTCAATGATGGTAAATGGC

CCGCCTGGCATTATGCCCAGTACATGACCTTATGGGACTTTCCTACTTGGCAGTACATCTAC

GTATTAGTCATCGCTATTACCATGGTGATGCGGTTTTGGCAGTACATCAATGGGCGTGGATA

GCGGTTTGACTCACGGGGATTTCCAAGTCTCCACCCCATTGACGTCAATGGGAGTTTGTTTT

GGCACCAAAATCAACGGGACTTTCCAAAATGTCGTAACAACTCCGCCCCATTGACGCAAATG

GGCGGTAGGCGTGTACGGTGGGAGGTCTATATAAGCAGAGCTCGTTTAGTGAACCGTCAGAT

CGCCTGGAGACGCCATCCACGCTGTTTTGACCTCCATAGAAGACACCGGGACCGATCCAGCC

TCCGCGGGCGCGCGTCGAGGAATTCGCTAGCGGCGCGCCAGATCTGATATCGGATCTGCTGT

GCCTTCTAGTTGCCAGCCATCTGTTGTTTGCCCCTCCCCCGTGCCTTCCTTGACCCTGGAAG

GTGCCACTCCCACTGTCCTTTCCTAATAAAATGAGGAAATTGCATCGCATTGTCTGAGTAGG

TGTCATTCTATTCTGGGGGGTGGGGTGGGGCAGGACAGCAAGGGGGAGGATTGGGAAGACAA

TAGCAGGCATGCTGGGGATGCGGTGGGCTCTATGGGTACCCAGGTGCTGAAGAATTGACCCG

GTTCCTCCTGGGCCAGAAAGAAGCAGGCACATCCCCTTCTCTGTGACACACCCTGTCCACGC

CCCTGGTTCTTAGTTCCAGCCCCACTCATAGGACACTCATAGCTCAGGAGGGCTCCGCCTTC

AATCCCACCCGCTAAAGTACTTGGAGCGGTCTCTCCCTCCCTCATCAGCCCACCAAACCAAA

CCTAGCCTCCAAGAGTGGGAAGAAATTAAAGCAAGATAGGCTATTAAGTGCAGAGGGAGAGA

AAATGCCTCCAACATGTGAGGAAGTAATGAGAGAAATCATAGAATTTCTTCCGCTTCCTCGC

TCACTGACTCGCTGCGCTCGGTCGTTCGGCTGCGGCGAGCGGTATCAGCTCACTCAAAGGCG

GTAATACGGTTATCCACAGAATCAGGGGATAACGCAGGAAAGAACATGTGAGCAAAAGGCCA

GCAAAAGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGACTATAA

AGATACCAGGCGTTTCCCCCTGGAAGCTCCCTCGTGCGCTCTCCTGTTCCGACCCTGCCGCT

TACCGGATACCTGTCCGCCTTTCTCCCTTCGGGAAGCGTGGCGCTTTCTCATAGCTCACGCT

GTAGGTATCTCAGTTCGGTGTAGGTCGTTCGCTCCAAGCTGGGCTGTGTGCACGAACCCCCC

GTTCAGCCCGACCGCTGCGCCTTATCCGGTAACTATCGTCTTGAGTCCAACCCGGTAAGACA

CGACTTATCGCCACTGGCAGCAGCCACTGGTAACAGGATTAGCAGAGCGAGGTATGTAGGCG

GTGCTACAGAGTTCTTGAAGTGGTGGCCTAACTACGGCTACACTAGAAGAACAGTATTTGGT

ATCTGCGCTCTGCTGAAGCCAGTTACCTTCGGAAAAAGAGTTGGTAGCTCTTGATCCGGCAA

ACAAACCACCGCTGGTAGCGGTGGTTTTTTTGTTTGCAAGCAGCAGATTACGCGCAGAAAAA

AAGGATCTCAAGAAGATCCTTTGATCTTTTCTACGGGGTCTGACGCTCAGTGGAACGAAAAC

TCACGTTAAGGGATTTTGGTCATGAGATTATCAAAAAGGATCTTCACCTAGATCCTTTTAAA

TTAAAAATGAAGTTTTAAATCAATCTAAAGTATATATGAGTAAACTTGGTCTGACAGTTACC

-continued

```
AATGCTTAATCAGTGAGGCACCTATCTCAGCGATCTGTCTATTTCGTTCATCCATAGTTGCC

TGACTCGGGGGGGGGGGCGCTGAGGTCTGCCTCGTGAAGAAGGTGTTGCTGACTCATACCA

GGCCTGAATCGCCCCATCATCCAGCCAGAAAGTGAGGGAGCCACGGTTGATGAGAGCTTTGT

TGTAGGTGGACCAGTTGGTGATTTTGAACTTTTGCTTTGCCACGGAACGGTCTGCGTTGTCG

GGAAGATGCGTGATCTGATCCTTCAACTCAGCAAAAGTTCGATTTATTCAACAAAGCCGCCG

TCCCGTCAAGTCAGCGTAATGCTCTGCCAGTGTTACAACCAATTAACCAATTCTGATTAGAA

AAACTCATCGAGCATCAAATGAAACTGCAATTTATTCATATCAGGATTATCAATACCATATT

TTTGAAAAAGCCGTTTCTGTAATGAAGGAGAAAACTCACCGAGGCAGTTCCATAGGATGGCA

AGATCCTGGTATCGGTCTGCGATTCCGACTCGTCCAACATCAATACAACCTATTAATTTCCC

CTCGTCAAAAATAAGGTTATCAAGTGAGAAATCACCATGAGTGACGACTGAATCCGGTGAGA

ATGGCAAAAGCTTATGCATTTCTTTCCAGACTTGTTCAACAGGCCAGCCATTACGCTCGTCA

TCAAAATCACTCGCATCAACCAAACCGTTATTCATTCGTGATTGCGCCTGAGCGAGACGAAA

TACGCGATCGCTGTTAAAAGGACAATTACAAACAGGAATCGAATGCAACGGCGCAGGAACA

CTGCCAGCGCATCAACAATATTTTCACCTGAATCAGGATATTCTTCTAATACCTGGAATGCT

GTTTTCCCGGGGATCGCAGTGGTGAGTAACCATGCATCATCAGGAGTACGGATAAAATGCTT

GATGGTCGGAAGAGGCATAAATTCCGTCAGCCAGTTTAGTCTGACCATCTCATCTGTAACAT

CATTGGCAACGCTACCTTTGCCATGTTTCAGAAACAACTCTGGCGCATCGGGCTTCCCATAC

AATCGATAGATTGTCGCACCTGATTGCCCGACATTATCGCGAGCCCATTTATACCCATATAA

ATCAGCATCCATGTTGGAATTTAATCGCGGCCTCGAGCAAGACGTTTCCCGTTGAATATGGC

TCATAACACCCCTTGTATTACTGTTTATGTAAGCAGACAGTTTTATTGTTCATGATGATATA

TTTTTATCTTGTGCAATGTAACATCAGAGATTTTGAGACACAACGTGGATCATCCAGACATG

ATAAGATACATTGATGAGTTTGGACAAACCACAACTAGAATGCAGTGAAAAAAATGCTTTAT

TTGTGAAATTTGTGATGCTATTGCTTTATTTGTAACCATTATAAGCTGCAATAAACAAGTTA

ACAACAACAATTGCATTCATTTTATGTTTCAGGTTCAGGGGAGGTGTGGGAGGTTTTTTAA

AGCAAGTAAAACCTCTACAAATGTGGTATGGCTGATTATGATCGTCGAGGATCCGGCGCCGT

TTAAACGTCGACAGATCCAAACGCTCCTCCGACGTCCCCAGGCAGAATGGCGGTTCCCTAAA

CGAGCATTGCTTATATAGACCTCCCATTAGGCACGCCTACCGCCCATTTACGTCAATGGAAC

GCCCATTTGCGTCATTGCCCCTCCCCATTGACGTCAATGGGGATGTACTTGGCAGCCATCGC

GGGCCATTTACCGCCATTGACGTCAATGGGAGTACTGCCAATGTACCCTGGCGTACTTCCAA

TAGTAATGTACTTGCCAAGTTACTATTAATAGATATTGATGTACTGCCAAGTGGGCCATTTA

CCGTCATTGACGTCAATAGGGGGCGTGAGAACGGATATGAATGGGCAATGAGCCATCCCATT

GACGTCAATGGTGGGTGGTCCTATTGACGTCAATGGGCATTGAGCCAGGCGGGCCATTTACC

GTAATTGACGTCAATGGGGAGGCGCCATATACGTCAATAGGACCGCCCATATGACGTCAAT

AGGTAAGACCATGAGGCCCTTTCGTCTCGCGCGTTTCGGTGATGACGGTGAAAACCTCTGAC

ACATGCAGCTCCCGGAGACGGTCACAGCTTGTCTGTAAGCGGATGCCGGGAGCAGACAAGCC

CGTCAGGGCGCGTCAGCGGGTGTTGGCGGGTGTCGGGGCTGGCTTAACTATGCGGCATCAGA

GCAGATTGTACTGAGAGTGCACCATATGCGGTGTGAAATACCGCACAGATGCGTAAGGAGAA

AATACCGCATCAGATTGGCTATTGGCATTATGCC
```

SEQ ID NO: 33
Human improved IL-12 p40 nucleic acid sequence

```
ATGTGCCACCAGCAGCTGGTCATCAGCTGGTTCAGCCTCGTTTTCCTCGCCTCGCCGCTGGT

CGCCATATGGGAGCTCAAGAAGGACGTATACGTGGTGGAGCTGGACTGGTACCCCGACGCGC
```

-continued

CGGGCGAGATGGTCGTCCTGACGTGCGACACGCCGGAGGAGGACGGCATCACGTGGACGCTG

GACCAGTCCAGCGAGGTCCTCGGCTCCGGCAAGACGCTGACGATCCAGGTCAAGGAGTTCGG

CGACGCGGGCCAGTACACGTGCCACAAGGGCGGCGAGGTCCTGAGCCACTCCCTCCTCCTGC

TACACAAGAAGGAGGACGGGATCTGGAGCACGGACATCCTCAAGGACCAGAAGGAGCCGAAG

AACAAGACCTTCCTGCGCTGCGAGGCGAAGAATTACTCGGGCCGGTTCACGTGCTGGTGGCT

CACCACGATCAGCACGGACCTGACGTTCTCGGTCAAGTCGTCGCGGGGCTCGTCGGACCCCC

AGGGGGTGACCTGCGGCGCGGCGACGCTGTCGGCGGAGCGGGTGCGGGGCGACAACAAGGAG

TACGAGTACTCGGTCGAGTGCCAGGAGGACTCGGCGTGCCCGGCGGCGGAGGAGTCGCTGCC

GATCGAGGTGATGGTCGACGCGGTCCACAAGCTGAAGTACGAGAACTACACGTCGTCGTTCT

TCATCCGGGACATCATCAAGCCGGACCCGCCGAAGAACCTGCAGCTGAAGCCGCTGAAGAAC

TCGCGGCAGGTCGAGGTCTCGTGGGAGTACCCGGACACGTGGTCGACGCCGCACTCGTACTT

CTCGCTGACGTTCTGCGTCCAAGTGCAGGGCAAGTCGAAGCGGGAGAAGAAGGACCGGGTGT

TCACCGACAAGACGAGCGCGACGGTGATCTGCCGGAAGAACGCGTCGATCTCGGTGCGGGCG

CAGGACCGGTACTACTCGTCGTCGTGGTCGGAGTGGGCGTCGGTGCCGTGCAGCTAG

SEQ ID NO: 34
Human improved IL-12 p35 nucleic acid sequence
ATGTGCCCGGCGCGCTCCCTGCTGCTCGTGGCGACGCTGGTCCTGCTCGACCACCTGAGCCT

GGCGCGGAACCTGCCGGTGGCGACGCCGGACCCGGGGATGTTCCCGTGCCTGCACCACAGCC

AGAACCTGCTGCGGGCGGTGTCGAACATGCTGCAGAAGGCGCGGCAGACGCTGGAGTTCTAC

CCGTGCACGAGCGAGGAGATCGACCACGAGGACATCACGAAGGACAAGACCAGCACGGTGGA

GGCGTGCCTGCCGCTGGAGCTGACGAAGAACGAGTCGTGCCTGAACTCGAGGGAGACGTCGT

TCATCACGAACGGGTCGTGCCTGGCGTCGCGGAAGACGTCGTTCATGATGGCGCTGTGCCTG

TCGTCGATCTACGAGGACCTGAAGATGTACCAGGTGGAGTTCAAGACGATGAACGCGAAGCT

GCTGATGGACCCGAAGCGGCAGATCTTCCTCGACCAGAACATGCTGGCGGTGATCGACGAGC

TCATGCAGGCGCTCAACTTCAACAGCGAGACGGTGCCGCAGAAGTCGTCGCTCGAGGAGCCG

GACTTCTACAAGACGAAGATCAAGCTCTGCATCCTGCTGCACGCTTTCCGGATCCGGGCGGT

GACGATCGACCGGGTGATGTCGTACCTGAACGCTTCGTAA

What is claimed is:

1. A method of promoting the stability and secretion of an IL-12 family member heterodimer that comprises a first subunit and a second subunit, wherein the second subunit is an IL-12 p40 subunit, comprising expressing the first subunit and the p40 subunit in a cell at a ratio in the range of 1:3 to about 1:15.

2. The method of claim 1, wherein the first subunit is an IL-12 p35 subunit.

3. The method of claim 2, wherein the p35 subunit shares at least 95% nucleic acid sequence identity with SEQ ID NO:34 and the p40 subunit shares at least 95% nucleic acid sequence identity with SEQ ID NO:33.

4. The method of claim 2, wherein the p35 subunit and the p40 subunit are expressed at the ratio in the range of 1:3 to about 1:15 by cotransfecting the cell with a first nucleic acid encoding the p35 subunit and a second nucleic acid encoding the p40 subunit at the ratio in the range of about 1:3 to about 1:15.

5. The method of claim 2, wherein the p35 subunit and the p40 subunit are expressed at the ratio in the range of 1:3 to about 1:15 by transfecting the cell with a single plasmid comprising a first nucleic acid encoding the p35 subunit under the control of a first promoter and a second nucleic acid encoding the p40 subunit under the control of a second promoter, wherein the first promoter and the second promoter are of relative expression strengths to allow expression of the p35 subunit and the p40 subunits at the ratio in the range of 1:3 to about 1:15.

6. The method of claim 5, wherein the first promoter is a simian CMV promoter and the second promoter is a human CMV promoter.

7. The method of claim 2, wherein the p35 subunit and the p40 subunit are expressed at the ratio in the range of 1:3 to 1:15 by transfecting the cell with a bicistronic nucleic acid encoding the p35 subunit and the p40 subunit, wherein the nucleic acid encoding the p35 subunit and the nucleic acid encoding the p40 subunit are separated by an internal ribosomal entry site.

8. The method of claim 1, wherein the first subunit is an IL-23 p19 subunit.

9. The method of claim 8, wherein the p19 subunit shares at least 95% nucleic acid sequence identity with SEQ ID NO:26 and the p40 subunit shares at least 95% nucleic acid sequence identity with SEQ ID NO:33.

* * * * *